United States Patent
Hagstrom et al.

(10) Patent No.: US 11,773,446 B2
(45) Date of Patent: Oct. 3, 2023

(54) METHODS FOR ASSESSMENT OF MULTIPLE SCLEROSIS ACTIVITY

(71) Applicant: OCTAVE BIOSCIENCE, INC., Menlo Park, CA (US)

(72) Inventors: William A. Hagstrom, Seattle, WA (US); Melinda Thomas, Palo Alto, CA (US); Michael G. Walker, Carlsbad, CA (US); Robert Schmidt, Carlsbad, CA (US)

(73) Assignee: OCTAVE BIOSCIENCE, INC., Menlo Park, CA (US)

( * ) Notice: Subject to any disclaimer, the term of this patent is extended or adjusted under 35 U.S.C. 154(b) by 1174 days.

(21) Appl. No.: 16/093,626

(22) PCT Filed: Apr. 14, 2017

(86) PCT No.: PCT/US2017/027810
§ 371 (c)(1),
(2) Date: Oct. 13, 2018

(87) PCT Pub. No.: WO2017/181147
PCT Pub. Date: Oct. 19, 2017

(65) Prior Publication Data
US 2019/0127798 A1    May 2, 2019

Related U.S. Application Data

(60) Provisional application No. 62/462,302, filed on Feb. 22, 2017, provisional application No. 62/323,541, filed on Apr. 15, 2016.

(51) Int. Cl.
| | |
|---|---|
| C12Q 1/6883 | (2018.01) |
| G16H 50/30 | (2018.01) |
| G16H 50/20 | (2018.01) |
| G16B 40/20 | (2019.01) |
| G16B 40/10 | (2019.01) |
| G06F 17/18 | (2006.01) |

(52) U.S. Cl.
CPC .......... *C12Q 1/6883* (2013.01); *G06F 17/18* (2013.01); *G16B 40/20* (2019.02); *G16H 50/20* (2018.01); *G16H 50/30* (2018.01); *C12Q 2600/106* (2013.01); *C12Q 2600/112* (2013.01); *C12Q 2600/158* (2013.01); *G16B 40/10* (2019.02)

(58) Field of Classification Search
None
See application file for complete search history.

(56) References Cited

U.S. PATENT DOCUMENTS

2015/0377909 A1*  12/2015  Cavet .................... G01N 33/53
                                                        702/19
2016/0040236 A1    2/2016   Hosur et al.

FOREIGN PATENT DOCUMENTS

WO    2007/056332 A2    5/2007

OTHER PUBLICATIONS

Kingsmore. Multiplexed protein measurement: technologies and applications of protein and antibody arrays. Nature Reviews Drug Discovery 2006, advanced online publication, pp. 1-11 (Year: 2006).*
Wingerchuk et al. Multiple Sclerosis: Current and Emerging Disease-Modifying Therapies and Treatment Strategies. Mayo Clin Proc . 2014, 89(2), pp. 225-240 (Year: 2014).*
Murray. Diagnosis and treatment of multiple sclerosis. BMJ 2006, vol. 332, p. 525-527 (Year: 2006).*
Goldenberg. Multiple Sclerosis Review. P&T 2012, vol. 37, No. 3, pp. 175-184 (Year: 2012).*
Mockler et al. Applications of DNA tiling arrays for whole-genome analysis. Genomics 2005, vol. 85, pp. 1-15 (Year: 2005).*
PCT International Search Report and Written Opinion, PCT/US2017/027810, dated Sep. 8, 2017, 24 Pages.
Kesarwani, P., et al., "Redox Regulation of T-Cell Function: From Molecular Mechanisms to Significance in Human Health and Disease," Antioxidants & Redox Signaling, 2013, vol. 18, No. 12, pp. 1497-1534.
Mitsui, T., et al., "In situ hybridization of myoglobin mRNA: results on the skeletal muscles of normal subjects and patients with neul•omuscular diseases," Acta Neuropathol., 1993, vol. 86, pp. 313-318.
Andreassen et al., "Concentrations of the Acute Phase Reactants High-Sensitive C-Reactive Protein and YKL-40 and of Interleukin-6 Before and After Treatment in Patients with Acromegaly and Growth Hormone Deficiency," Clinical Endoctrinology, 2007, 67, pp. 909-916.
Baranzini, "Prognostic Biomarkers of IFNb Therapy in Multiple Sclerosis Patients," Multiple Sclerosis Journal, 2015, vol. 21, No. 7, Jun. 6, 2015, pp. 894-904.
Brettschneider et al., "Axonal Damage Markers in the Cerebrospinal Fluid of Patients with Clinically Isolated Syndrome Improve Predicting Conversion to Definite Multiple Sclerosis," Multiple Sclerosis, 2006, 12: 143-148.
Mathieu et al., "IL-23/IL-1b Ratio as a Biomarker of Disease Activity in Multiple Sclerosis," Neurology; 62nd Annual Meeting of the American Academy of Neurology; Toronto, Canada, Apr. 10-17, 2010, vol. 74, No. 9, Suppl 2.
Radetti et al., "Influence of Growth Hormone on a New Marker of Cartilage Metabolism (Chondrex)," Calcified Tissue International, New York, NY, vol. 67, No. 1, Mar. 12, 2014, pp. 45-46.
Supplementary European Search Report, Application No. EP17783336, dated May 26, 2020, 17 pages.
Yin et al., "Protein Biomarkers of New-Onset Cardiovascular Disease," Arterioscler Thromb Vase Biol, Apr. 1, 2014, pp. 939-945.

\* cited by examiner

*Primary Examiner* — Olivia M. Wise
(74) *Attorney, Agent, or Firm* — Goodwin Procter LLP

(57) ABSTRACT

Markers useful for determining multiple sclerosis activity in a human subject are provided, along with kits for measuring quantitative expression values of the markers. Also provided are computer systems and software embodiments of predictive models for scoring and determining multiple sclerosis activity in human subjects based on the quantitative expression values of the markers.

11 Claims, 6 Drawing Sheets

Training Data
230A

| Individual | Marker A | Marker B |
|---|---|---|
| 1 | A1 | B1 |
| 2 | A2 | B2 |
| 3 | A3 | B3 |
| 4 | A4 | B4 |

| Indication |
|---|
| Positive Result |
| Positive Result |
| Negative Result |
| Negative Result |

FIG. 3

METHODS FOR ASSESSMENT OF MULTIPLE SCLEROSIS ACTIVITY

CROSS REFERENCE TO RELATED APPLICATIONS

This application is the National Stage Entry of International Application No. PCT/US2017/027810, filed Apr. 14, 2017, which claims the benefit of U.S. Provisional Application No. 62/323,541, filed Apr. 15, 2016, and U.S. Provisional Application No. 62/462,302, filed Feb. 22, 2017, the entire disclosures of which are hereby incorporated by reference in their entirety for all purposes.

BACKGROUND

Field of the Invention

The invention relates to predictive models for assessment of multiple sclerosis activity in an individual based on biomarker expression measurements from a sample obtained from the individual. The invention further relates to the methods of use of the predictive models, and to computer systems, software, and kits for the implementation of such predictive models.

Description of the Related Art

Multiple Sclerosis (MS) is a chronic debilitating disease with highly variable outcomes. Currently there are few tools outside of magnetic resonance imaging (MRI) to directly assess disease activity. While useful, MRI reflects historic damage but not the dynamic biological processes that underlie MS.

The field is in need of tools to accurately determine multiple sclerosis activity in an individual including diagnosing MS, tracking disease activity, identifying early evidence of relapse, and determining effectiveness of treatment response. A non-invasive blood test that could reliably determine MS activity would have significant clinical utility. Herein the development and validation of predictive models that can predict MS activity in an individual using quantitative expression levels of markers in a blood sample obtained from the individual is described.

SUMMARY

In some embodiments, the invention relates to diagnosing MS in an individual according to a prediction generated based on expression values of one or more markers in a test sample obtained from the individual. In other embodiments, the invention relates to assessing therapeutic response in an individual diagnosed with multiple sclerosis according to a prediction generated based on expression values of one or more markers in a test sample obtained from the individual. In yet other embodiments, the invention relates to assessing disease activity in an individual diagnosed with multiple sclerosis according to a prediction generated based on expression values of one or more markers in a test sample obtained from the individual. In other embodiments, the invention relates to assessing relapse and flare in an individual diagnosed with multiple sclerosis according to a prediction generated based on expression values of one or more markers in a test sample obtained from the individual. In other embodiments, the invention relates to assessing remission in an individual diagnosed with multiple sclerosis according to a prediction generated based on expression values of one or more markers in a test sample obtained from the individual.

In various embodiments of the invention, the prediction model is trained using one of random forest (RF), stochastic gradient boosting (GBM), Lasso, or extreme gradient boosting (XGB) machine learning techniques. The prediction model can be applied to a test sample obtained from the individual in order to generate an assessment that can be used to guide the diagnosis of multiple sclerosis in an individual, assessment of a therapeutic response in an individual diagnosed with multiple sclerosis, assessment of disease activity in an individual diagnosed with multiple sclerosis, assessment of relapse and flare in an individual diagnosed with multiple sclerosis, or assessment of remission in an individual diagnosed with multiple sclerosis.

Disclosed herein is a method for assessing multiple sclerosis activity in an individual, the method comprising: obtaining a dataset comprising quantitative expression values for a plurality of biomarkers from a test sample from the individual, wherein the plurality of biomarkers comprise two or more biomarkers as shown in one or more of set 1, set 2, set 3, set 4, and set 5, wherein set 1 comprises PON1, Myoglobin, PAI1, TIMP1, SDF1, IL6Rbeta, Cystatin B, IgE, MIP3beta, and VCAM1, wherein set 2 comprises MDC, VEGF, Ficolin 3, IgA, Factor VII, IL6R, RAGE, FIB1C, ITAC, and GH, wherein set 3 comprises HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2, wherein set 4 comprises IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3, and wherein set 5 comprises AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1; applying a predictive model on the obtained dataset to generate a score; and determining multiple sclerosis activity in the individual based on the score.

In some embodiments, the dataset comprises quantitative expression values for PON1, Myoglobin, PAI1, TIMP1, SDF1, IL6Rbeta, Cystatin B, IgE, MIP3beta, and VCAM1, wherein the multiple sclerosis activity in the individual is a state of quiescence or exacerbation, wherein a performance of the predictive model is characterized by an area under the curve (AUC) ranging from 0.60 to 0.99, and wherein determining multiple sclerosis activity in the individual based on the score comprises comparing the generated score to a distribution of scores, the distribution of scores corresponding to individuals previously diagnosed with multiple sclerosis that have been clinically classified as being in one of a state of quiescence or exacerbation; and classifying the individual as being in one of the state of quiescence or exacerbation based on the comparison.

In some scenarios, the dataset comprises quantitative expression values for ten or more biomarkers. In some scenarios, at least five of the ten or more biomarkers are selected from biomarkers in set 1. In some scenarios, the dataset comprises quantitative expression values for twenty or more biomarkers. In some scenarios, at least ten of the twenty or more biomarkers are selected from biomarkers in set 1 and set 2. In some scenarios, the dataset comprises quantitative expression values for forty or more biomarkers. In some scenarios, at least twenty of the forty or more biomarkers are selected from biomarkers in set 1, set 2, and set 3. In some scenarios, the dataset comprises quantitative expression values for sixty or more biomarkers. In some scenarios, at least thirty of the sixty or more biomarkers are selected from biomarkers in set 1, set 2, set 3, and set 4.

In some embodiments, the predictive model is trained using one of a random forest algorithm, a gradient boosting algorithm, and a Lasso algorithm. In one scenario, performance of the predictive model is characterized by an area under the curve (AUC) ranging from 0.60 to 0.99. In one scenario, performance of the predictive model is characterized by an area under the curve (AUC) ranging from 0.70 to 0.99. In one scenario, performance of the predictive model is characterized by an area under the curve (AUC) ranging from 0.80 to 0.99.

In some embodiments, the step of obtaining the dataset comprises carrying out a multiplex immunoassay on the test sample from the individual. In some embodiments, obtaining the dataset from the test sample comprises obtaining the test sample and processing the test sample to experimentally determine the dataset. In some embodiments, obtaining the dataset from the test sample comprises receiving the dataset from a third party that has processed the test sample to experimentally determine the dataset.

In various embodiments, the quantitative expression values for the plurality of biomarkers are adjusted based on at least one of age and gender of the individual. In one scenario, the individual is a human. In one scenario, the test sample from the individual is a blood sample.

In some scenarios, determining multiple sclerosis activity comprises determining a state of multiple sclerosis in the individual, wherein the state is quiescence or exacerbation. In some scenarios, determining multiple sclerosis activity comprises diagnosing the individual with multiple sclerosis.

In various embodiments, determining multiple sclerosis activity in the individual based on the score comprises: comparing the generated score to a distribution of scores, the distribution of scores corresponding to individuals that have been previously classified in one of a plurality of categories of multiple sclerosis activity. In some embodiments, the previous classification of individuals in the category of multiple sclerosis activity is based on clinical standards.

Also disclosed herein is a method for generating a predictive model for predicting multiple sclerosis activity, the method comprising: obtaining training data derived from a plurality of individuals, the training data comprising: for each individual from the plurality of individuals: quantitative expression values of a plurality of biomarkers derived from a test sample obtained from the individual, wherein the plurality of biomarkers comprise two or more biomarkers selected from a group consisting of biomarkers from set 1, set 2, set 3, set 4, and set 5, wherein set 1 comprises PON1, Myoglobin, PAI1, TIMP1, SDF1, IL6Rbeta, Cystatin B, IgE, MIP3beta, and VCAM1, wherein set 2 comprises MDC, VEGF, Ficolin 3, IgA, Factor VII, IL6R, RAGE, FIB1C, ITAC, and GH, wherein set 3 comprises HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2, wherein set 4 comprises IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3, and wherein set 5 comprises AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1; and an indication as to the multiple sclerosis activity of the individual; training the predictive model using the obtained training data, wherein the predictive model is trained on inputs comprising the quantitative expression values of the plurality of biomarkers and on ground truth data comprising the indication.

In one scenario, the plurality of biomarkers comprise ten or more biomarkers. In one scenario, at least five of the ten or more biomarkers are selected from biomarkers in set 1. In one scenario, the plurality of biomarkers comprise twenty or more biomarkers. In one scenario, at least ten of the twenty or more biomarkers are selected from biomarkers in set 1 and set 2. In one scenario, the plurality of biomarkers comprise forty or more biomarkers. In one scenario, at least twenty of the forty or more biomarkers are selected from biomarkers in set 1, set 2, and set 3. In one scenario, the plurality of biomarkers comprise sixty or more biomarkers. In one scenario, at least thirty of the sixty or more biomarkers are selected from biomarkers in set 1, set 2, set 3, and set 4.

In some embodiments, biomarkers in set 1, set 2, set 3, set 4, and set 5 are ranked based on an importance of each biomarker for determining multiple sclerosis activity, wherein biomarkers in set 1 are ranked higher than biomarkers in set 2, wherein biomarkers in set 2 are ranked higher than biomarkers in set 3, wherein biomarkers in set 3 are ranked higher than biomarkers in set 4, and wherein biomarkers in set 4 are ranked higher than biomarkers in set 5.

In some embodiments, training the prediction model comprises training the prediction model using one of a random forest algorithm, gradient boosting algorithm, and Lasso algorithm.

In various embodiments, each individual of the plurality of individuals is a human. In some embodiments, the test sample obtained from the individual is a blood sample. In some embodiments, the predictive model determines a state of multiple sclerosis in an individual, wherein the state is quiescence or exacerbation. In some embodiments, the predictive model determines whether to diagnose the individual with multiple sclerosis.

Also disclosed herein is a system for determining multiple sclerosis activity in an individual, the system comprising: a storage memory for storing a dataset comprising quantitative expression values for a plurality of biomarkers from a test sample from the individual, wherein the plurality of biomarkers comprise two or more biomarkers as shown in one or more of set 1, set 2, set 3, set 4, and set 5, wherein set 1 comprises PON1, Myoglobin, PAI1, TIMP1, SDF1, IL6Rbeta, Cystatin B, IgE, MIP3beta, and VCAM1, wherein set 2 comprises MDC, VEGF, Ficolin 3, IgA, Factor VII, IL6R, RAGE, FIB1C, ITAC, and GH, wherein set 3 comprises HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2, wherein set 4 comprises IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3, and wherein set 5 comprises AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1; and a processor communicatively coupled to the storage memory for determining a score by applying the stored dataset as input to a predictive model, wherein the score is predictive of an assessment of multiple sclerosis activity in the individual.

In some embodiments, the dataset comprises quantitative expression values for PON1, Myoglobin, PAI1, TIMP1, SDF1, IL6Rbeta, Cystatin B, IgE, MIP3beta, and VCAM1, wherein the multiple sclerosis activity in the individual is a state of quiescence or exacerbation, wherein a performance of the predictive model is characterized by an area under the curve (AUC) ranging from 0.60 to 0.99, and wherein the assessment of multiple sclerosis activity in the individual is determined by comparing the determined score to a distribution of scores, the distribution of scores corresponding to individuals previously diagnosed with multiple sclerosis that have been clinically classified as being in one of a state of quiescence or exacerbation.

In one scenario, the dataset comprises quantitative expression values for ten or more biomarkers. In one scenario, at least five of the ten or more biomarkers are selected from biomarkers in set 1. In one scenario, the dataset comprises quantitative expression values for twenty or more biomarkers. In one scenario, at least ten of the twenty or more biomarkers are selected from biomarkers in set 1 and set 2. In one scenario, the dataset comprises quantitative expression values for forty or more biomarkers. In one scenario, at least twenty of the forty or more biomarkers are selected from biomarkers in set 1, set 2, and set 3. In one scenario, the dataset comprises quantitative expression values for sixty or more biomarkers. In one scenario, at least thirty of the sixty or more biomarkers are selected from biomarkers in set 1, set 2, set 3, and set 4.

In various embodiments, the predictive model is trained using one of a random forest algorithm, a gradient boosting algorithm, and a Lasso algorithm. In some embodiments, the performance of the predictive model is characterized by an area under the curve (AUC) ranging from 0.60 to 0.99. In some embodiments, the performance of the predictive model is characterized by an area under the curve (AUC) ranging from 0.70 to 0.99. In some embodiments, the performance of the predictive model is characterized by an area under the curve (AUC) ranging from 0.80 to 0.99.

In various embodiments, the dataset is obtained from a multiplex immunoassay performed on the test sample from the individual. In some embodiments, the dataset is experimentally determined by processing the test sample. In some embodiments, the dataset is received from a third party that has processed the test sample to experimentally determine the dataset.

In various embodiments, the quantitative expression values for the plurality of biomarkers are adjusted based on at least one of age and gender of the individual. In one scenario, the individual is a human. In one scenario, the test sample from the individual is a blood sample. In one embodiment, the assessment of multiple sclerosis activity indicates a state of multiple sclerosis in the individual, wherein the state is quiescence or exacerbation. In one embodiment, the assessment of multiple sclerosis activity indicates a diagnosis of multiple sclerosis.

In some embodiments, the assessment of multiple sclerosis activity in the individual is determined by comparing the determined score to a distribution of scores, the distribution of scores corresponding to individuals that have been previously classified in one of a plurality of categories of multiple sclerosis activity. In some embodiments, the previous classification of individuals in the category of multiple sclerosis activity is based on clinical standards.

Also disclosed herein is a non-transitory computer-readable medium storing computer code that, when executed by a processor of a computer, causes the processor to: obtain a dataset comprising quantitative expression values for a plurality of biomarkers from a test sample from the individual, wherein the plurality of biomarkers comprise two or more biomarkers as shown in one or more of set 1, set 2, set 3, set 4, and set 5, wherein set 1 comprises PON1, Myoglobin, PAI1, TIMP1, SDF1, IL6Rbeta, Cystatin B, IgE, MIP3beta, and VCAM1, wherein set 2 comprises MDC, VEGF, Ficolin 3, IgA, Factor VII, IL6R, RAGE, FIB1C, ITAC, and GH, wherein set 3 comprises HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2, wherein set 4 comprises IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3, and wherein set 5 comprises AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1; and apply a predictive model on the obtained dataset to generate a score; and determine multiple sclerosis activity in the individual based on the score.

In various embodiments, the dataset comprises quantitative expression values for PON1, Myoglobin, PAI1, TIMP1, SDF1, IL6Rbeta, Cystatin B, IgE, MIP3beta, and VCAM1, wherein the multiple sclerosis activity in the individual is a state of quiescence or exacerbation, wherein a performance of the predictive model is characterized by an area under the curve (AUC) ranging from 0.60 to 0.99, and wherein the computer code that causes the processor to determine multiple sclerosis activity in the individual based on the score further comprises computer code that causes the processor to: compare the generated score to a distribution of scores, the distribution of scores corresponding to individuals previously diagnosed with multiple sclerosis that have been clinically classified as being in one of a state of quiescence or exacerbation; and classify the individual as being in one of the state of quiescence or exacerbation based on the comparison.

In one scenario, the dataset comprises quantitative expression values for ten or more biomarkers. In one scenario, at least five of the ten or more biomarkers are selected from biomarkers in set 1.

In one scenario, the dataset comprises quantitative expression values for twenty or more biomarkers. In one scenario, at least ten of the twenty or more biomarkers are selected from biomarkers in set 1 and set 2. In one scenario, the dataset comprises quantitative expression values for forty or more biomarkers. In one scenario, at least twenty of the forty or more biomarkers are selected from biomarkers in set 1, set 2, and set 3. In one scenario, the dataset comprises quantitative expression values for sixty or more biomarkers. In one scenario, at least thirty of the sixty or more biomarkers are selected from biomarkers in set 1, set 2, set 3, and set 4.

In various embodiments, the predictive model is trained using one of a random forest algorithm, a gradient boosting algorithm, and a Lasso algorithm. In one scenario, performance of the predictive model is characterized by an area under the curve (AUC) ranging from 0.60 to 0.99. In one scenario, performance of the predictive model is characterized by an area under the curve (AUC) ranging from 0.70 to 0.99. In one scenario, performance of the predictive model is characterized by an area under the curve (AUC) ranging from 0.80 to 0.99.

In various embodiments, the obtained dataset is experimentally determined by processing the test sample. In some embodiments, the obtained dataset is received from a third party that has processed the test sample to experimentally determine the dataset. In some embodiments, the quantitative expression values for the plurality of biomarkers are adjusted based on at least one of age and gender of the individual.

In one embodiment, the individual is a human. In some embodiments, the test sample from the individual is a blood sample. In some embodiments, the assessment of multiple sclerosis activity in the individual is an indication of a state of multiple sclerosis in the individual, wherein the state is quiescence or exacerbation. In some embodiments, the assessment of multiple sclerosis activity in the individual is a diagnosis of multiple sclerosis in the individual.

In various embodiments, the computer code that causes the processor to determine multiple sclerosis activity in the individual based on the score further comprises computer code that causes the processor to compare the generated score to a distribution of scores, the distribution of scores corresponding to individuals that have been previously classified in one of a plurality of categories of multiple sclerosis activity. In some embodiments, the previous classification of individuals in the category of multiple sclerosis activity is based on clinical standards.

Also disclosed herein is a kit for diagnosing multiple sclerosis in an individual, the kit comprising: a set of reagents for determining, from a test sample obtained from the individual, quantitative expression values for a plurality of biomarkers from a test sample from the individual, wherein the plurality of biomarkers comprise two or more biomarkers as shown in one or more of set 1, set 2, set 3, set 4, and set 5, wherein set 1 comprises PON1, Myoglobin, PAI1, TIMP1, SDF1, IL6Rbeta, Cystatin B, IgE, MIP3beta, and VCAM1, wherein set 2 comprises MDC, VEGF, Ficolin 3, IgA, Factor VII, IL6R, RAGE, FIB1C, ITAC, and GH, wherein set 3 comprises HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2, wherein set 4 comprises IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3, and wherein set 5 comprises AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1; instructions for using the set of reagents to determine the quantitative expression values of the test sample, wherein the instructions further comprise instructions for determining a score from the quantitative expression values, wherein the score is predictive of an assessment of multiple sclerosis activity in the individual.

In some embodiments, the set of reagents comprises reagents for determining quantitative expression values for PON1, Myoglobin, PAI1, TIMP1, SDF1, IL6Rbeta, Cystatin B, IgE, MIP3beta, and VCAM1, wherein the multiple sclerosis activity in the individual is a state of quiescence or exacerbation, wherein a performance of the predictive model is characterized by an area under the curve (AUC) ranging from 0.60 to 0.99, and wherein the assessment of multiple sclerosis activity in the individual is determined by comparing the determined score to a distribution of scores, the distribution of scores corresponding to individuals previously diagnosed with multiple sclerosis that have been clinically classified as being in one of a state of quiescence or exacerbation.

In one scenario, the set of reagents comprise reagents for determining quantitative expression values for ten or more biomarkers. In one scenario, at least five of the ten or more biomarkers are selected from biomarkers in set 1. In one scenario, the set of reagents comprise reagents for determining quantitative expression values for twenty or more biomarkers. In one scenario, at least ten of the twenty or more biomarkers are selected from biomarkers in set 1 and set 2. In one scenario, the set of reagents comprise reagents for determining quantitative expression values for forty or more biomarkers. In one scenario, at least twenty of the forty or more biomarkers are selected from biomarkers in set 1, set 2, and set 3. In one scenario, the set of reagents comprise reagents for determining quantitative expression values for sixty or more biomarkers. In one scenario, at least thirty of the sixty or more biomarkers are selected from biomarkers in set 1, set 2, set 3, and set 4.

In some embodiments, the instructions further comprise instructions for applying a predictive model to generate the assessment of multiple sclerosis activity, the predictive model trained using one of a random forest algorithm, a gradient boosting algorithm, and a Lasso algorithm. In some embodiments, the performance of the predictive model is characterized by an area under the curve (AUC) ranging from 0.60 to 0.99. In some embodiments, the performance of the predictive model is characterized by an area under the curve (AUC) ranging from 0.70 to 0.99. In some embodiments, the performance of the predictive model is characterized by an area under the curve (AUC) ranging from 0.80 to 0.99.

In various embodiments, the set of reagents are for performing a multiplex immunoassay on the test sample from the individual and wherein the quantitative expression values of the plurality of biomarkers are obtained from the performed multiplex immunoassay.

In some embodiments, the instructions further comprise instructions for adjusting the quantitative expression values for the plurality of biomarkers based on at least one of age and gender of the individual.

In one embodiment, the individual is a human. In one embodiment, the test sample from the individual is a blood sample. In one embodiment, the assessment of multiple sclerosis activity is an indication of a state of multiple sclerosis in the individual, wherein the state is quiescence or exacerbation. In one embodiment, the assessment of multiple sclerosis activity is a diagnosis of multiple sclerosis in the individual.

In some embodiments, the assessment of multiple sclerosis activity in the individual is determined by comparing the determined score to a distribution of scores, the distribution of scores corresponding to individuals that have been previously classified in one of a plurality of categories of multiple sclerosis activity. In some embodiments, the previous classification of individuals in the category of multiple sclerosis activity is based on clinical standards.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 3 illustrates an example set of training data, in accordance with an embodiment.

DETAILED DESCRIPTION

I. Definitions

Figure 1:
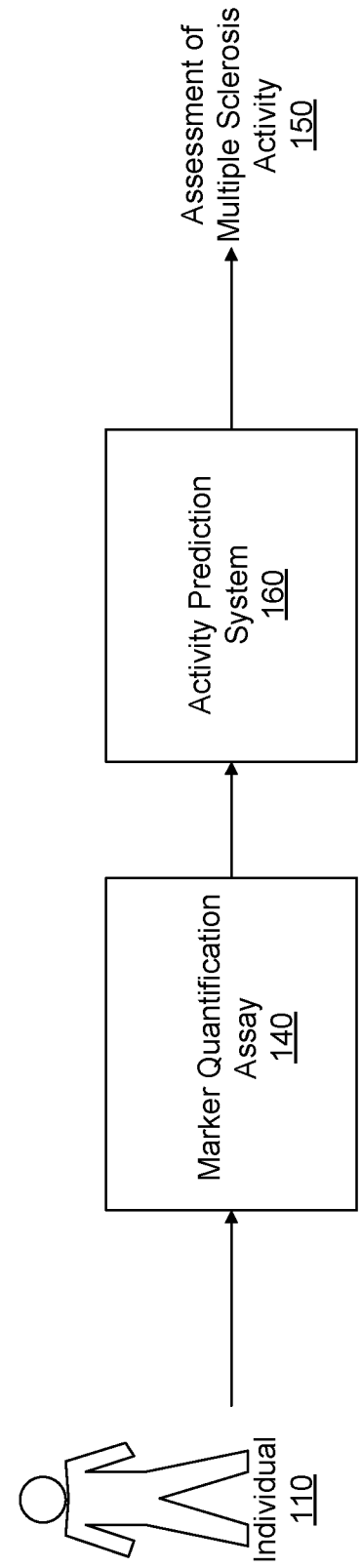
FIG. 1 depicts an overview of an environment for assessing MS activity in an individual via an activity prediction system, in accordance with an embodiment.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

The term "multiple sclerosis" or "MS" encompasses all forms of multiple sclerosis including relapsing-remitting multiple sclerosis (RRMS), secondary progressive multiple sclerosis (SPMS), primary-progressive multiple sclerosis (PPMS), and progressive relapsing multiple sclerosis (PRMS).

The terms "marker," "markers," "biomarker," and "biomarkers" encompass, without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants, in circumstances in which such mutations, variations in copy number and/or transcript variants are useful for generating a predictive model, or are useful in predictive models developed using related markers (e.g., non-mutated versions of the proteins or nucleic acids, alternative transcripts, etc.).

The term "multiple sclerosis activity" encompasses, without limitation, the presence or absence of multiple sclerosis in an individual, a state (e.g., quiescent vs exacerbation) of multiple sclerosis in an individual, a relapse or flare event associated with MS, a response of an individual diagnosed with multiple sclerosis to a therapy, a degree of multiple sclerosis disability, and a risk (e.g., likelihood) of the individual developing multiple sclerosis at a subsequent time.

The term "antibody" is used in the broadest sense and specifically covers monoclonal antibodies (including full length monoclonal antibodies), polyclonal antibodies, multispecific antibodies (e.g., bispecific antibodies), and antibody fragments that are antigen-binding so long as they exhibit the desired biological activity, e.g., an antibody or an antigen-binding fragment thereof.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide").

The term "mammal" encompasses both humans and non-humans and includes but is not limited to humans, non-human primates, canines, felines, murines, bovines, equines, and porcines.

The term "sample" can include a single cell or multiple cells or fragments of cells or an aliquot of body fluid, such as a blood sample, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female.

The term "obtaining a dataset associated with a sample" encompasses obtaining a set of data determined from at least one sample. Obtaining a dataset encompasses obtaining a sample, and processing the sample to experimentally determine the data. The phrase also encompasses receiving a set of data, e.g., from a third party that has processed the sample to experimentally determine the dataset. Additionally, the phrase encompasses mining data from at least one database or at least one publication or a combination of databases and publications. A dataset can be obtained by one of skill in the art via a variety of known ways including stored on a storage memory.

It must be noted that, as used in the specification and the appended claims, the singular forms "a," "an," and "the" include plural referents unless the context clearly dictates otherwise.

II. Methods of Assessing Multiple Sclerosis Activity in an Individual

Disclosed herein are methods for assessing MS activity in an individual. As one example, one such method may include the steps of: obtaining a dataset including quantitative expression values for one or more markers from a test sample obtained from the individual; applying a predictive model on the obtained dataset to generate an assessment of MS activity in the individual. Such a method can be computer-implemented using a processor or may be embodied in a kit that includes reagents for obtaining the dataset and/or instructions for generating an assessment of MS activity.

Also disclosed herein are methods for generating a predictive model that can be used to assess MS activity in an individual. As one example, one such method may include the steps of obtaining training data derived from multiple individuals, where the training data includes quantitative expression values of one or more markers from test samples obtained from each of the multiple individuals as well as indications as to the MS activity in each of the multiple individuals; and training a predictive model using the obtained training data. Specifically, the predictive model can be trained on inputs that include the quantitative expression values and ground truth data that includes the indications as to the MS activity.

Overall, described herein is a robust, stepwise process for identifying a panel or panels of biomarkers that are strongly predictive of MS. Univariate and multivariate analysis of specific biomarkers as described herein demonstrate the ability to predict MS activity in an individual. Given the diverse pathology of the disease as well as diverse outcomes that result from treatment of the disease, the methods of the present teachings may be useful in the clinical assessment of MS in individual subjects Biomarkers used for the assessment of MS activity in an individual are identified through an identification and ranking process. An exemplary process includes obtaining test samples, such as blood samples, from a population of individuals (e.g., population in the Accelerated Cure Project (ACP)), as described herein. The test samples are analyzed to obtain a dataset that includes expression values of biomarkers. For example, expression values of biomarkers can be obtained by applying the test samples to a multi-plex immunoassay.

In some embodiments, test samples can be derived through a variety of methods, including prospective, retrospective, cross-sectional, or longitudinal studies that involve interventions or observations of the representative subjects or populations from one or more time points. Test samples can be obtained from a single study or multiple studies. Subject and population data can generally include data pertaining to the subjects' disease status and/or clinical assessments, which can be used, in addition to biomarker data obtained from test samples, for building, training, and validating a predictive model (e.g., algorithms) for use in the present teachings.

In some embodiments, predictive models are built using expression values of a single biomarker (e.g., univariate prediction). In some embodiments, predictive models are built using expression values of two or more biomarkers (e.g., multivariate prediction). In some embodiments, predictive models are built based on expression values of biomarkers that are identified to be most important for predicting MS activity in an individual. For example, various methods, such as random forest (RF), gradient boosting (GBM), extreme gradient boosting (XBM), and/or least absolute shrinkage and selection operator (LASSO) can be used to determine the importance of each individual biomarker. Various predictive models can be built based on a variety of criteria such as the biomarker rankings. For example, individual predictive models can be built using expression values of a top 80, top 60, top 40, top 20, top 10, or even top 2 biomarkers. Other criteria to be considered when building a model includes any improvement in a predictive model's performance when the biomarker is added to the predictive model. Predictive models can include various machine learning models such as decision tree, an ensemble (e.g., bagging, boosting, random forest), linear regression, Naïve Bayes, neural network, or logistic regression.

Predictive models are trained using training data to better predict MS activity in an individual. Specifically, a predictive model can be trained using training data that includes quantitative expression levels of the selected biomarkers (e.g., 2, 10, 20, 40, 60, or 80 biomarkers that are input to the predictive model) as well as ground truth data that includes an indication as to the MS activity (e.g., quiescent or exacerbated state of MS) in the individual.

Trained predictive models can be evaluated and/or selected based on various performance and/or accuracy criteria, such as are described herein. The predictive ability of a model can be evaluated according to its ability to provide a quality metric, e.g. area under the curve (AUC) or accuracy, of a particular value, or range of values. In some embodiments, a desired quality threshold is a predictive model that will classify a sample with an accuracy of at least about 0.6, at least about 0.65, at least about 0.7, at least about 0.75, at least about 0.8, at least about 0.85, at least about 0.9, at least about 0.95, or higher. As an alternative measure, a desired quality threshold can refer to a predictive model that will classify a sample with an AUC (area under the curve) of at least about 0.6, at least about 0.65, at least about 0.7, at least about 0.75, at least about 0.8, at least about 0.85, at least about 0.9, or higher. Classification can be made according to predictive modeling methods that set a threshold for determining the probability that a sample belongs to a given class. The probability preferably is at least 50%, or at least 60% or at least 70% or at least 80% or higher.

Trained predictive models can be stored and subsequently retrieved when needed. For example, during execution, a trained predictive model is selected and applied to expression values of biomarkers from a test sample obtained from an individual of interest. The predictive model can output an assessment of MS activity in the individual of interest.

III. Multiple Sclerosis Activity in an Individual

As used hereafter in this disclosure, MS activity refers can refer to any one of the presence of multiple sclerosis in an individual, a state (e.g., quiescent vs exacerbation) of multiple sclerosis in an individual, a response of an individual diagnosed with multiple sclerosis to a therapy, a degree of multiple sclerosis disability, and a risk (e.g., likelihood) of the individual developing multiple sclerosis at a subsequent time.

Methods described herein focus on assessing MS activity in an individual by applying quantitative expression levels of biomarkers as input to a trained prediction model. In various embodiments, the assessment of MS activity is used to further train the prediction model and/or is validated. Results corresponding to an individual of interest may be compared to results of individuals that have been previously classified in one of two or more categories. For example, individuals may be previously categorized such as a positive diagnosis of MS, a categorization in a quiescent or exacerbated state, a categorization in a level of disability according to the expanded disability status scale (EDSS), an identified clinical response to a therapy, and a clinical identification of a risk of developing MS. Categorization of previously individuals may occur based on clinical standards.

Clinical diagnosis of MS can occur through various methods. As an example, a clinical diagnosis of MS can be made through magnetic resonance imaging (MRI) of the brain and spinal cord to identify lesions or plaques that form as a result of MS. The McDonald criteria can be employed in making the diagnosis. Clinical diagnosis of MS can also occur through a lumbar puncture (spinal tap) that observes abnormalities in antibody concentrations in the spinal fluid due to the presence of MS. Clinical diagnosis of MS can also occur through evoked potential tests, where electrical signals produced by neurons of the nervous system are recorded in response to a stimulus. An impaired transmission is indicative of the presence of MS.

Clinical categorization of a patient previously diagnosed with MS in a quiescent state versus an exacerbated state can depend on a variety of factors. Namely, a patient can be clinically categorized in an exacerbated state after presenting with a new disease that is related to MS such as optic neuritis. As another example, a patient is clinically categorized in an exacerbated state if the patient presents with significant worsening of symptoms. Examples may include a worsening of balance and/or mobility, vision, pain in the eye, fatigue, and/or heart-related problems. Patients previously diagnosed with MS can be clinically categorized in a quiescent state if the patient does not present with a new disease or a change or worsening of symptoms.

Determination that a patient previously diagnosed with MS is responding to a therapy can be dependent on a variety of clinical variables. For example, a response to therapy can be determined based on the occurrence or lack of a relapse. A patient can be deemed responsive to a therapy if relapses do not occur. A response to therapy can also be determined based on a total number of relapses, a time to a first relapse, the patient's EDSS score, a change in the patient's EDSS score (e.g., an increase in the score corresponds to a lack of response to therapy), a change in MRI status (e.g., the development of additional lesions or plaques corresponds to a lack of response to therapy).

Patients can be clinically categorized in a level of disability. For example, the EDSS can be used to determine a severity of MS in a patient. Therefore, patients are categorized in categories that correspond to an EDSS score between 1.0 and 10.0 in 0.5 point intervals. Generally, EDSS scores of 1.0 to 4.5 refer to patients with MS who are able to walk without any aid. EDSS scores of 5.0 to 9.5 refer to patients with MS whose ability to walk is impaired, with a higher score corresponding to a higher degree of impairment.

IV. Markers

In some embodiments, one or more markers are detected from a sample obtained from an individual. The sample can be obtained by the individual or by a third party, e.g., a medical professional. Examples of medical professionals include physicians, emergency medical technicians, nurses, first responders, psychologists, medical physics personnel, nurse practitioners, surgeons, dentists, and any other obvious medical professional as would be known to one skilled in the art. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe. The bodily fluid can then be tested to determine values of one or more markers. The values of one or more markers can be indicated as a numerical value. The numerical values can be obtained, for example, by experimentally obtaining measures from a sample obtained from an individual by an assay (e.g., an immunoassay) performed in a laboratory, or alternatively, obtaining a dataset from a service provider such as a laboratory, or from a database or a server on which the dataset has been stored, e.g., on a storage memory.

In an embodiment, the quantity of one or more markers can be one or more quantitative expression values of: 6Ckine, Adiponectin, Adrenomedullin (ADM), Alpha-1 Antitrypsin (AAT), Alpha-1-Microglobulin (A1Micro), Alpha-2-Macroglobulin (A2Macro), Alpha-Fetoprotein (AFP), Amphiregulin (AR), Angiogenin, Angiopoietin 1 (ANG-1), Angiopoietin 2 (ANG-2), Angiotensin Converting Enzyme (ACE), Antileukoproteinase (ALP), Antithrombin III (ATIII), Apolipoprotein A (Apo-A), Apolipoprotein D (Apo-D), Apolipoprotein E (Apo-E), AXL Receptor Tyrosine Kinase (AXL), B-cell activating factor (BAFF), B Lymphocyte Chemoattractant (BLC), Beta-Amyloid (1-40) (AB-40), Beta-Amyloid (1-42) (AB-42), Beta-2 Microglobulin (B2M), Betacellulin (BTC), Brain Derived Neurotrophic Factor (BDNF), C-Reactive Protein (CRP), Cadherin 1 (E-Cad), Calbindin, Cancer Antigen 125 (CA-125), Cancer Antigen 15-3 (CA 15-3), Cancer Antigen 19-9 (CA 19-9), Carbonic anhydrase 9 (CA-9), Carcinoembryonic Antigen (CEA), Carcinoembryonic antigen related cell adhesion molecule 1 (CEACAM1), Cathepsin D, CD40 Ligand (CD40-L), CD163, Ceruloplasmin, Chemokine CC-4 (HCC-4), Chromogranin A (CgA), Ciliary Neurotrophic Factor (CNTF), Clusterin (CLU), Complement C3 (C3), Complement Factor H (CFH), Complement Factor H Related Protein 1 (CFHR1), Cystatin B, CystatinC, Decorin, Dickkopf related protein 1 (DKK-1), Dopamine beta hydroxylase (DBH), E-Selectin, EN-RAGE, Eotaxin-1, Eotaxin-2, Eotaxin-3, Epidermal Growth Factor (EGF), Epidermal Growth Factor Receptor (EGFR), Epiregulin (EPR), Epithelial Derived Neutrophil Activating Protein 78 (ENA-78), Erythropoietin (EPO), Factor VII, Fas Ligand (FasL), FASLG Receptor (FAS), Ferritin (FRTN), Fibrinogen, Fibulin 1C (Fib1C), Ficolin 3, Follicle Stimulating Hormone (FSH), Gastric inhibitory polypeptide (GIP), Gelsolin, Glucagon Like Peptide-1 (GLP-1), Glycogen phosphorylase isoenzyme BB (GPBB), Granulocyte Colony Stimulating Factor (GCSF), Granulocyte Macrophage Colony Stimulating Factor (GM-CSF), Growth differentiation factor 15 (GDF-15), Growth Hormone (GH), Growth Regulated alpha protein (GROalpha), Haptoglobin, Heat Shock protein 70 (HSP-70), Heparin Binding EGF Like Growth Factor (HB-EGF), Hepatocyte Growth Factor (HGF), Human Chorionic Gonadotropin beta (hCG), Immunoglobulin A (IgA), Immunoglobulin E (IgE), Immunoglobulin M (IgM), Insulin, Insulin like Growth Factor Binding Protein 2 (IGFBP2), Intercellular Adhesion Molecule 1 (ICAM-1), Interferon alpha (IFN-alpha), Interferon gamma (IFN-gamma), Interferon gamma Induced Protein 10 (IP-10), Interferon inducible T cell alpha chemoattractant (ITAC), Interleukin 1 alpha (IL-1alpha), Interleukin 1 beta (IL-1beta), Interleukin 1 receptor antagonist (IL1ra), Interleukin 2 (IL-2), Interleukin 2 receptor alpha (IL2receptoralpha), Interleukin 3 (IL-3), Interleukin 4 (IL-4), Interleukin 5 (IL-5), Interleukin 6 (IL-6), Interleukin 6 receptor (IL6r), Interleukin 6 receptor subunit beta (IL6Rbeta), Interleukin 7 (IL-7), Interleukin 8 (IL-8), Interleukin 10 (IL-10), Interleukin 12 Subunit p40 (IL12p40), Interleukin 12 Subunit p70 (IL12p70), Interleukin 13 (IL13), Interleukin 15 (IL15), Interleukin 16 (IL16), Interleukin 17 (IL17), Interleukin 18 (IL18), Interleukin 18 binding protein (IL18bp), Interleukin 22 (IL22), Interleukin 23 (IL23), Interleukin 31 (IL31), Kidney Injury Molecule 1 (KIM-1), Lactoferrin (LTF), Latency Associated Peptide of Transforming Growth Factor beta 1 (LAP TGF b1), Leptin, Leptin Receptor (Leptin R), Leucine rich alpha 2 glycoprotein (LRG1), Luteinizing Hormone (LH), Macrophage Colony Stimulating Factor 1 (M-CSF), Macrophage Derived Chemokine (MDC), Macrophage Inflammatory Protein 1 alpha (MIP1-alpha), Macrophage Inflammatory Protein 1 beta (MIP1-beta), Macrophage Inflammatory Protein 3 alpha (MIP3-alpha), Macrophage Inflammatory Protein 3 beta (MIP3-beta), Macrophage Migration Inhibitory Factor (MIF), Macrophage Stimulating Protein (MSP), Mast stem cell growth factor receptor (SCFR), Matrix Metalloproteinase 1 (MMP-1), Matrix Metalloproteinase 2 (MMP-2), Matrix Metalloproteinase 3 (MMP-3), Matrix Metalloproteinase 7 (MMP-7), Matrix Metalloproteinase 9 (MMP-9), Matrix Metalloproteinase 9 total (MMP-9 total), Matrix Metalloproteinase 10 (MMP-10), Microalbumin, Monocyte Chemotactic Protein 1 (MCP-1), Monocyte Chemotactic Protein 2 (MCP-2), Monocyte Chemotactic Protein 3 (MCP-3), Monocyte Chemotactic Protein 4 (MCP-4), Monokine Induced by Gamma Interferon (MIG), Myeloid Progenitor Inhibitory Factor 1 (MPIF-1), Myeloperoxidase (MPO), Myoglobin, Nerve Growth Factor beta (NGF-beta), Neurofilament heavy polypeptide (NF-H), Neuron Specific Enolase (NSE), Neuronal Cell Adhesion Molecule (NrCAM), Neuropilin-1, Neutrophil Activating Peptide 2 (NAP-2), Omentin, Osteocalcin, Osteopontin, Osteoprotegerin (OPG), P-Selectin, Pancreatic Polypeptide (PPP), Pancreatic secretory trypsin inhibitor (TATI), Paraoxonase-1 (PON1), Pepsinogen-I (PGI), Periostin, Pigment Epithelium Derived Factor (PEDF), Placenta Growth Factor (PLGF), Plasminogen Activator Inhibitor 1 (PAI-1), Platelet endothelial cell adhesion molecule (PECAM-1), Platelet Derived Growth Factor BB (PDGF-BB), Prolactin (PRL), Prostate Specific Antigen Free (PSA-f), Protein DJ-1 (DJ-1), Pulmonary and Activation Regulated Chemokine (PARC), Pulmonary surfactant associated protein D (SP-D), Receptor for advanced glycosylation end products (RAGE), Resistin, S100 calcium binding protein B (S100B), Serum Amyloid A Protein (SAA), Serum Amyloid P Component (SAP), Sex Hormone Binding Globulin (SHBG), Sortilin, ST2, Stem Cell Factor (SCF), Stromal cell derived factor 1 (SDF-1), Superoxide Dismutase 1 soluble (SOD-1), T Cell Specific Protein RANTES (RANTES), T Lymphocyte Secreted Protein I 309 (I309), Tamm Horsfall Urinary Glycoprotein (THP), Tenascin C (TN-C), Tetranectin, Thrombin Activatable ibrinolysis (TAFI), Thrombospondin-1, Thymus and activation regulated chemokine (TARC), Thyroid Stimulating Hormone (TSH), Thyroxine Binding Globulin (TBG), Tissue Inhibitor of Metalloproteinases 1 (TIMP-1), Tissue Inhibitor of Metalloproteinases 2 (TIMP-2), TNF Related Apoptosis Inducing Ligand Receptor 3 (TRAIL-R3), Transferrin receptor protein 1 (TFR1), Transforming Growth Factor beta 3 (TGF-beta3), Tumor Necrosis Factor alpha (TNF-alpha), Tumor Necrosis Factor beta (TNF-beta), Tumor necrosis factor ligand superfamily member 12 (Tweak), Tumor necrosis factor ligand superfamily member 13 (APRIL), Tumor Necrosis Factor Receptor I (TNF-RI), Tumor necrosis factor receptor 2 (TNFR2), Vascular Cell Adhesion Molecule 1 (VCAM-1), Vascular Endothelial Growth Factor (VEGF), Visceral adipose tissue derived serpin A12 (Vaspin), Visfatin, Vitamin D Binding Protein (VDBP), Vitronectin, von Willebrand Factor (vWF), or YKL-40, resulting from evaluation of a sample. Markers can also include those listed in the Tables and Figures.

In an embodiment, a marker's quantitative expression value can be included in a dataset associated with a sample obtained from a subject. In various embodiments, a dataset includes quantitative expression values of two markers. In some embodiments, the dataset includes quantitative expression values of three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, sixty, or eighty markers. As an example, a dataset can include the expression values for PON1, Myoglobin, PAI1, TIMP1, SDF1, IL6Rbeta, Cystatin B, IgE, MIP3beta, and VCAM1. Other combinations are described in more detail in the Examples section below.

In an embodiment, one or more markers can be divided into sets. For example, markers may be partitioned into a set 1, set 2, set 3, set 4, and set 5. In other examples, markers may be partitioned into more or fewer sets. In various embodiments, the sets are ranked according to the importance of the markers in each set for predicting multiple sclerosis activity in an individual. For example, markers in set 1 are ranked higher than biomarkers in set 2, markers in set 2 are ranked higher than markers in set 3, markers in set 3 are ranked higher than markers in set 4, and markers in set 4 are ranked higher than markers in set 5. In an embodiment, a set can include one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s).

In some embodiments, set 1 and set 2 each include 10 biomarkers, whereas set 3, set 4, and set 5 each include 20 biomarkers. Specifically, set 1 may include the markers of PON1, Myoglobin, PAI1, TIMP1, SDF1, IL6Rbeta, Cystatin B, IgE, MIP3beta, and VCAM1. Set 2 may include the markers of MDC, VEGF, Ficolin 3, IgA, Factor VII, IL6R, RAGE, FIB1C, ITAC, and GH. Set 3 may include the markers of HBEGF, NrCAM, GROalpha, GDF15, SCFR, Ecad, Angiogenin, Sortilin, AAT, IgM, PARC, SP-D, BAFF, ADM, PEDF, IL1ra, TBG, Microalbumin, Leptin, and Eotaxin 2. Set 4 may include the markers of IGFBP2, Resistin, Cathepsin D, E-Selectin, YKL40, IL22, IL8, CA 15-3, LeptinR, IGFBP2, MCP1, PRL, Tetranectin, CEACAM1, 6Ckine, SAP, CFHR1, HCC-4, and C3. Set 5 may include the markers of AFP, ANG-1, IL18, Gelsolin, TN-C, Vitronectin, B2M, TATI, MMP3, Omentin, IL 18bp, ApoD, MCP-4, Apo-E, ST2, Thrombospondin 1, GIP, MMP7, ICAM-1, and DKK1.

V. Assays

Examples of assays for one or more markers include DNA assays, microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, immunoprecipitation, and the assays described in the Examples section below. The information from the assay can be quantitative and sent to a computer system of the invention. The information can also be qualitative, such as observing patterns or fluorescence, which can be translated into a quantitative measure by a user or automatically by a reader or computer system. In an embodiment, the individual can also provide information other than assay information to a computer system, such as race, height, weight, age, gender, eye color, hair color, family medical history and any other information that may be useful for predicting multiple sclerosis activity in the individual.

Various immunoassays designed to quantitate markers can be used in screening including multiplex assays. Measuring the concentration of a target marker in a sample or fraction thereof can be accomplished by a variety of specific assays. For example, a conventional sandwich type assay can be used in an array, ELISA, RIA, etc. format. Other immunoassays include Ouchterlony plates that provide a simple determination of antibody binding. Additionally, Western blots can be performed on protein gels or protein spots on filters, using a detection system specific for the markers as desired, conveniently using a labeling method.

Protein based analysis, using an antibody as described above that specifically binds to a polypeptide (e.g. marker), can be used to quantify the marker level in a test sample obtained from an individual. For multiplex analysis of markers, arrays containing one or more marker affinity reagents, e.g. antibodies can be generated. Such an array can be constructed comprising antibodies against markers. Detection can utilize one or a panel of marker affinity reagents, e.g. a panel or cocktail of affinity reagents specific for one, two, three, four, five or more markers.

VI. Prediction Model

V.A. System Overview

FIG. 1 depicts an overview of an environment for assessing MS activity in an individual, in accordance with an embodiment. The environment provides context in order to introduce a marker quantification assay 140 and an activity prediction system 160.

The marker quantification assay 140 determines quantitative expression values of one or more biomarkers from a test sample obtained from the individual 110. As described above, the assay 140 may be an immunoassay, and more specifically, a multi-plex immunoassay. Therefore, the expression levels of various biomarkers can be obtained in a single run using a single test sample obtained from the individual 110. The quantified expression values of the biomarkers are provided to the activity prediction system 160.

Figure 2:
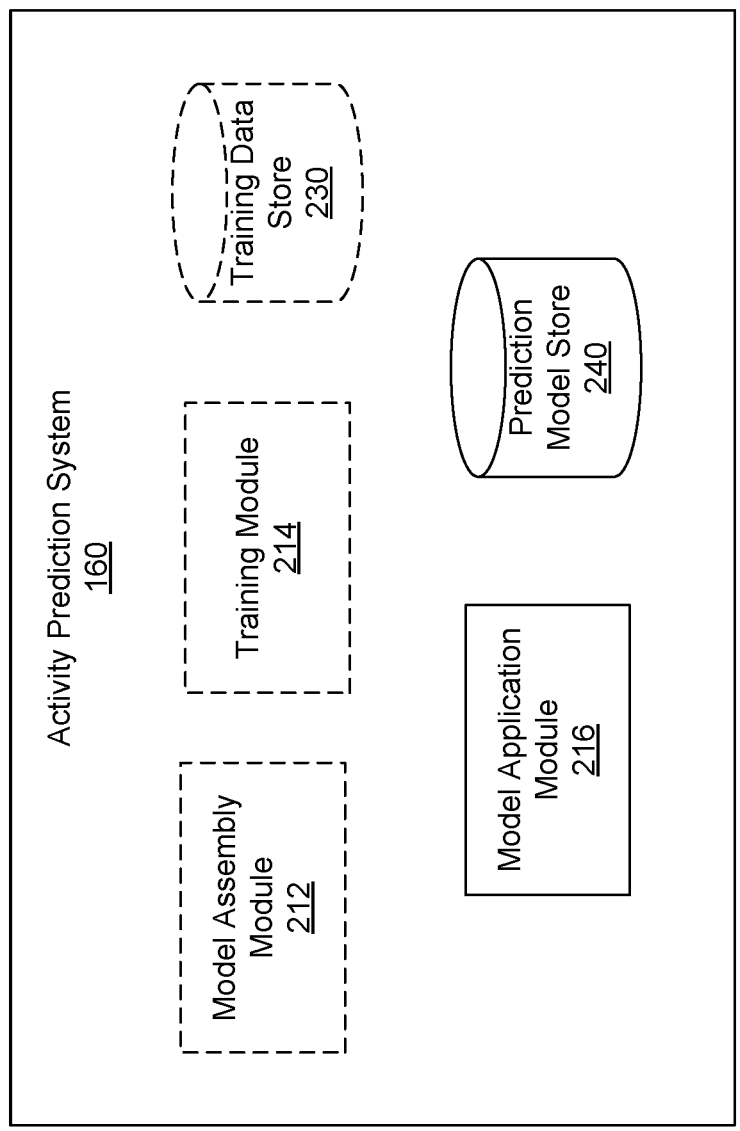
FIG. 2 depicts a block diagram illustrating the computer logic components of the activity prediction system, in accordance with an embodiment.

The activity prediction system 160 includes one or more computer models, embodied in a computer 600 as discussed below with respect to FIG. 6, which analyzes the received biomarker expression values to generate an assessment of MS activity 150 in the individual 110. Reference is now made to FIG. 2 which depicts a block diagram illustrating the computer logic components of the activity prediction system 160, in accordance with an embodiment. Specifically, the activity prediction system 160 may include a model assembly module 212, a training module 214, a model application module 216, as well as a training data store 230 and a prediction model store 240.

Each of the components of the activity prediction system 160 is hereafter described in reference to two phases: 1) a training phase and 2) an execution phase. More specifically, the training phase refers to the building and training of one or more prediction models based on training data that includes quantitative expression values of biomarkers obtained from individuals with known MS activity. Therefore, the one or more prediction models are trained to predict MS activity in an individual based on quantitative biomarker expression values. During the execution phase, a prediction model can be applied quantitative biomarker expression values from a test sample obtained from an individual of interest in order to generate a prediction of MS activity in the individual of interest.

In some embodiments, the components of the activity prediction system 160 are applied during one of the training phase and the execution phase. For example, the model assembly module 212 and training module 214 (dotted lines) are applied during the training phase whereas the model application module 216 (solid lines) is applied during the execution phase.

V.B. Building and Training a Prediction Model

During the training phase, the model assembly module 212 builds one or more predictive models based on expression values of biomarkers. In various embodiments, the model assembly module 212 adjusts the quantitative expression values of each biomarker prior to building the predictive models. For example, the quantitative expression values of each biomarker may be adjusted according to the age, the gender, or other personal characteristics of the individual from whom the sample was obtained. The variable effects of different personal characteristics can be mitigated in order to produce a prediction model that reflects the influence of individual biomarker values on the predicted output.

To identify a set of biomarkers that are to be used to build a model, the model assembly module 212 may begin with a list of candidate biomarkers that may be deemed promising for predicting MS activity in an individual. In one embodiment, candidate biomarkers may be biomarkers identified through a literature curation process. In some embodiments, candidate biomarkers may be biomarkers whose expression values in test samples obtained from individuals that are positive for MS activity (e.g., presence of MS, in an exacerbated state, and the like) are statistically significant in comparison to expression values of biomarkers in test samples obtained from individuals that are negative for the MS activity. As an example, a total of 215 candidate biomarkers are shown in Table 2 below.

In one embodiment, the model assembly module 212 builds a predictive model that considers the expression values of all candidate biomarkers. In another embodiment, the model assembly module 212 partitions the candidate biomarkers and constructs a predictive model from a subset of the candidate biomarkers. As an example, the model assembly module 212 can rank the candidate biomarkers based on their importance and select a subset of candidate biomarkers for building the predictive model given the rankings. For example, candidate biomarkers that are determined to be highly correlated with MS activity would be deemed highly important and highly ranked. In one embodiment, the model assembly module 212 selects biomarkers above a threshold ranking to be used in constructing the predictive model.

In some embodiments, the importance of each candidate biomarker is determined by using a method including one of random forest (RF), gradient boosting (GBM), extreme gradient boosting (XGB), or LASSO algorithms. For example, if using random forest algorithms, the model assembly module 212 may generate a variable importance plot that depicts the importance of each candidate biomarker. Specifically, the random forest algorithm may provide, for each candidate biomarker, 1) a mean decrease in model accuracy and 2) a mean decrease in a Gini coefficient which is a measure of how much each candidate biomarker contributes to the homogeneity of nodes and leaves in the random forest. In one scenario, the importance of each candidate biomarker is dependent on one or both of the mean decrease in model accuracy and mean decrease in Gini coefficient. Each of GBM, XGB, and LASSO, can also be used to rank the importance of each candidate biomarker based on an influence value, as described below in the Examples. Therefore, the model assembly module 212 can generate a ranking of each of candidate biomarkers using one of the methods including RF, GBM, XGB, or LASSO.

In some embodiments, in generating a ranking of candidate biomarkers using an analysis method, the model assembly module 212 generates rankings in an iterative fashion. As an example, the model assembly module 212 may generate an initial ranking of N candidate biomarkers. The model assembly module 212 may fix the rankings of candidate biomarkers ranked below a threshold and re-ranks the candidate biomarkers above the threshold. The model assembly module 212 may iterate this process. For example, if N=215 candidate biomarkers, the model assembly module 212 fixes the ranking of candidate biomarkers from rank 81 to rank 215 while re-ranking biomarkers ranked in the top 80. In various embodiments, a candidate biomarker may be ranked significantly differently in the first ranking in comparison to its re-ranking. In the next iteration, reranked candidate biomarkers between ranks 61 and 80 are fixed while candidate biomarkers in the top 60 are reranked. This iterative ranking process may continue for the top 40, top 20, top 10, top 5, and top 2 candidate biomarkers.

In various embodiments, in order to minimize bias in a ranking of candidate biomarkers from a single analysis method, the model assembly module 212 can generate a ranking of candidate biomarkers by combining rankings generated by multiple analysis methods. For example, the model assembly module 212 may generate a first ranking of candidate biomarkers using RF, a second ranking of candidate biomarkers using GBM, a third ranking of candidate biomarkers using XGB, and a fourth ranking of candidate biomarkers using LASSO. In one embodiment, the final ranking of biomarkers can be an average of the ranking of each biomarker from two, three, four, or more different rankings. In some embodiments, additional rankings using additional or the same analysis methods may be generated. The final ranking of candidate biomarkers may be dependent on the ranking of each candidate biomarker in each of the first, second, third, and fourth rankings. In one embodiment, each of the first, second, third, and fourth rankings are assigned weights that are considered in generating the final rankings of candidate biomarkers. For example, the final rankings may be a weighted sum of the rankings of biomarkers from two, three, four, or more different rankings.

The model assembly module 212 constructs one or more predictive models, each predictive model receiving, as input, one or more biomarkers. In one embodiment, the one or more biomarkers are selected from a ranking of the candidate biomarkers. As one example, the model assembly module 212 constructs a predictive model that receives, as input, two biomarkers that are ranked in the top 80 of the candidate biomarkers.

In some embodiments, the model assembly module 212 constructs a predictive model for more than two biomarkers. For example, a predictive model is constructed to receive, as input, the top 80 biomarkers in the ranking. In some embodiments, the model assembly module 212 constructs a predictive model for the top 60, top 40, top 20, or top 10 biomarkers in the ranking. In further embodiments, the model assembly module 212 constructs a predictive model for the top 2 biomarkers in the ranking.

The model assembly module 212 may provide the constructed predictive models to the training module 214 to train each of the predictive models.

The training module 214 trains each of the predictive models using training data that is stored in the training data store 230. In some embodiments, the training module 214 retrieves the training data and randomly partitions the training data into a training set and a validation set. As an example, 80% of the training data may be partitioned into the training set and the other 20% can be partitioned into the validation set. Other proportions of training set and validation set may be implemented. As such, the training set is used to train the predictive models whereas the validation set is used to validate the predictive models.

Reference is now made to FIG. 3, which illustrates an example set of training data 230A, in accordance with an embodiment. As shown in FIG. 3, the training data 230A may include data corresponding to multiple individuals (e.g., column 1 depicting individual 1, 2, 3, 4 . . . ). For each individual, the training data 230A includes quantitative expression values of different markers from a test sample obtained from the individual. In some embodiments, the quantitative expression values are determined by the marker quantification assay 140 shown in FIG. 1. Although FIG. 3 depicts 4 individuals and 2 different markers (marker A and marker B), the training data 230A may include tens, hundreds, or thousands of individuals as well as tens, hundreds, or thousands of markers.

As depicted in FIG. 3, a test sample obtained from individual 1 can correspond to a quantified expression value of "A1" for marker A, a quantified expression value of "B1" for marker B, and so on. Similarly, a test sample obtained from individual 2 can correspond to a quantified expression value of "A2" for marker A, a quantified expression value of "B2" for marker B, and so on. Individuals 3 and 4 have corresponding marker values as shown in FIG. 3.

The training data 230A can also include a positive or negative indication as to MS activity in each individual. Each indication may be a clinical result (e.g., a clinical diagnosis) that has classified the patient in a category, as described above in the section entitled "Multiple Sclerosis Activity in an Individual." For example, if MS activity corresponds to the presence of MS in individual 1, a positive result can correspond to a positive diagnosis of MS in individual 1 based on an MRI image obtained from individual 1. Similarly, an indication of a negative result (e.g., individual 3 or individual 4) corresponds to a negative diagnosis of MS in the individual based on a corresponding MRI image.

In various embodiments, the training data 230A may further include personal characteristics of the individual (e.g., sex, age, and the like). Therefore, in some embodiments, the quantitative expression values of biomarkers in the training data 230A can be adjusted based on the personal characteristics of the individual.

The training module 214 may identify model parameters that are then tuned during training to optimize the performance (e.g., minimize prediction error) of each predictive model. As an example, the training module 214 identifies model parameters using a cross validation process. In some embodiments, the cross validation may be a 10-fold 5-repeat cross validation process. Specifically, the training module 214 may retrieve a portion of the training set and further partition the portion into 10 subsamples such that 9 subsamples are used to train and identify model parameters. The training module 214 may repeat the subsampling 5 times to minimize the impact of randomness that may arise due to subsampling. The one holdout subsample is used to generate a measure of model performance given the identified model parameters. Therefore, given the average model performance across the multiple cross validation runs, the best model parameters are selected to be further tuned through the training phase.

Each predictive model is iteratively trained using, as input, the quantitative expression values of the markers for each individual. For example, one iteration involves providing input training data that includes the quantitative expression value A1 for Marker A from individual 1, quantitative expression value A2 for Marker B from individual 1, and so on. Each predictive model can be trained on ground truth data that includes the indication (e.g., the positive or negative result). Over training iterations, each predictive model is trained (e.g., the parameters are tuned) to minimize a prediction error between a prediction of MS activity outputted by the predictive model and the ground truth data.

The training module 214 can further validate each prediction model using the validation set (e.g., 20% of training data). For each sample corresponding to an individual in the validation set, the prediction model outputs a prediction of MS activity in the individual. The prediction is a quantitative measure of a relative likelihood that the sample belongs to one of two classes in question. The quantitative measure is used to compute the area under the curve (AUC), or the measure of the model's overall performance across the validation set. The trained predictive models are stored in the prediction model store 240 such that they can be appropriately retrieved at a subsequent time (e.g., execution phase).

V.C. Applying a Prediction Model

Returning to FIG. 2, during the execution phase, the marker application module 216 receives quantitative biomarker expression values from a test sample obtained from an individual of interest. As an example, the individual may not have been previously diagnosed with MS and therefore, the marker application module 216 retrieves and applies a trained prediction model to determine whether the individual to be diagnosed with MS based on the quantitative biomarker expression values.

Specifically, the model application module 216 retrieves the appropriate prediction model from the prediction model store 240. For example, the prediction model store 240 may include prediction models that predict different types of MS activity (e.g., positive/negative diagnosis of MS, a state of MS (e.g., quiescent vs exacerbated), a therapeutic response, a positive identification of a flare or relapse of MS, and the like). Therefore, the model application module 216 may identify the appropriate prediction model and applies the prediction model to generate the assessment of MS activity in the individual. The assessment of MS activity can be presented on a display, such as the display 618 depicted in FIG. 6 of an example computer 600. The assessment of MS activity in the individual may be informative for determining a course of treatment for the individual.

In various embodiments, the assessment of MS activity is a predicted score outputted by the prediction model. The score may be informative of the MS activity in the individual.

In one embodiment, the MS activity corresponds to the presence or absence of multiple sclerosis in an individual. Therefore, the assessment (e.g., predicted score) provided by the prediction model can be used to assess the MS activity. As an example, the assessment can be used to determine whether the individual is to be diagnosed with MS. In various embodiments, the assessment (e.g., predicted score) corresponding to the individual is compared to a distribution of predicted scores obtained from the prediction model that correspond to healthy patients (e.g., not clinically diagnosed with MS). In this scenario, the individual is positive for MS activity (e.g., diagnosed with MS) if the individual's predicted score is significantly different (e.g., p-value<0.05) in comparison to the distribution of predicted scores of healthy patients. In various embodiments, the individual can be subsequently treated for MS. In other words, the assessment can guide the treatment of the individual.

In one embodiment, the MS activity corresponds to a state (e.g., quiescent vs exacerbation) of MS in an individual. Therefore, the assessment (e.g., predicted score) provided by the prediction model can be used to assess the MS activity. In various embodiments, the assessment (e.g., predicted score) corresponding to the individual is compared to one or two distributions of predicted scores obtained from the prediction model. For example, a first distribution of predicted scores may correspond to individuals previously determined to be in a quiescent state (e.g., clinically determined to be in a quiescent state). A second distribution of predicted scores may correspond to individuals previously determined to be in an exacerbated state (e.g., clinically determined to be in an exacerbated state). In this scenario, the individual may be classified as being in a quiescent state if the individual's predicted score is not significantly different (e.g., p-value>0.05) than the distribution of predicted scores corresponding to individuals previously determined to be in a quiescent state. Alternatively, the individual may be classified as being in an exacerbated state if the individual's predicted score is not significantly different (e.g., p-value>0.05) than the distribution of predicted scores corresponding to individuals previously determined to be in an exacerbated state. In various embodiments, the subsequent treatment of an individual previously diagnosed with MS can be tailored depending on the predicted state of MS in the individual.

In one embodiment, the MS activity corresponds to a response to a therapy of an individual diagnosed with multiple sclerosis. Therefore, the assessment (e.g., predicted score) provided by the prediction model can be used to assess the MS activity. In various embodiments, the assessment (e.g., predicted score) corresponding to the individual is compared to one or two distributions of predicted scores obtained from the prediction model. For example, a first distribution of predicted scores may correspond to individuals previously determined to be responsive to the therapy (e.g., clinically determined to be responsive to the therapy). A second distribution of predicted scores may correspond to individuals previously determined to be non-responsive to the therapy (e.g., clinically determined to be non-responsive to the therapy). In this scenario, the individual may be classified as responsive to a therapy if the individual's predicted score is not significantly different (e.g., p-value>0.05) than the distribution of predicted scores corresponding to individuals previously determined to be responsive to the therapy. Alternatively, the individual may be classified as non-responsive to a therapy if the individual's predicted score is not significantly different (e.g., p-value>0.05) than the distribution of predicted scores corresponding to individuals previously determined to be non-responsive to the therapy. In various embodiments, the subsequent treatment of the individual can be tailored depending on the predicted responsiveness or non-responsiveness to the therapy. For example, the dosing regimen (e.g., time or dose quantity) can be altered. As another example, a different therapy may be provided.

In one embodiment, the MS activity corresponds to a degree of MS disability in an individual diagnosed with multiple sclerosis. In one embodiment, the degree of MS disability corresponds to the EDSS. Therefore, the assessment (e.g., predicted score) provided by the prediction model can be used to assess the MS activity. In various embodiments, the assessment (e.g., predicted score) corresponding to the individual is compared to multiple distributions of predicted scores obtained from the prediction model. Each distribution of predicted scores may correspond to a group of individuals that have been clinically categorized in a degree of disability. For example, a first distribution of predicted scores may correspond to individuals clinically categorized with a score of 1 on the EDSS. Additional distributions of predicted scores may correspond to groups of individuals that have been clinically categorized with a score of 1.5, 2.0, 2.5, 3.0, 3.5, 4.0, 4.5, 5.0, 5.5, 6.0, 6.5, 7.0, 7.5, 8.0, 8.5, 9.0, 9.5, and 10.0. In one scenario, the individual may be classified with one of the EDSS scores if the individual's predicted score is not significantly different (e.g., p-value>0.05) from one group and is significantly different (e.g., p-value<0.05) in comparison to all other groups. The individual may be treated according to clinical protocols based on the categorization.

In one embodiment, the MS activity corresponds to a risk (e.g., likelihood) of the individual developing MS at a subsequent time. Therefore, the assessment (e.g., predicted score) provided by the prediction model can be used to assess the MS activity. In various embodiments, the assessment (e.g., predicted score) corresponding to the individual is compared to multiple distributions of predicted scores. Each distribution of predicted scores may correspond to a group of individuals in a risk group that have been clinically categorized with a particular risk of developing MS. As an example, the risk groups may be divided into a high risk group, medium risk group, and low risk group. In one scenario, the individual may be classified in a risk group if the individual's predicted score is not significantly different (e.g., p-value>0.05) from one group and is significantly different (e.g., p-value<0.05) in comparison to other groups. Therefore, the individual can undertake changes in lifestyle and/or treatments based on the prediction of a risk/likelihood of developing MS.

VII. Therapeutic Agents and Compositions for Therapeutic Agents

In one embodiment of the invention, a therapeutic agent is provided to an individual prior to and/or subsequent to obtaining the sample from the individual and determining quantitative expression values of one or more markers in the obtained sample. As one example, a predictive model that receives the quantitative expression values predicts that an individual is to be diagnosed with multiple sclerosis and a therapeutic agent is to be provided. In another example, the predictive model predicts that a provided therapeutic agent is demonstrating therapeutic efficacy against a multiple in a previously diagnosed individual.

In various embodiments the therapeutic agent is a biologic, e.g. a cytokine, antibody, soluble cytokine receptor, anti-sense oligonucleotide, siRNA, etc. Such biologic agents encompass muteins and derivatives of the biological agent, which derivatives can include, for example, fusion proteins, PEGylated derivatives, cholesterol conjugated derivatives, and the like as known in the art. Also included are antagonists of cytokines and cytokine receptors, e.g. traps and monoclonal antagonists, e.g. IL-1Ra, IL-1 Trap, sIL-4Ra, etc. Also included are biosimilar or bioequivalent drugs to the active agents set forth herein.

Therapeutic agents for multiple sclerosis include corticosteroids, plasma exchange, ocrelizumab (Ocrevus®), IFN-β (Avonex®, Betaseron®, Rebif®), Glatiramer acetate (Copaxone®), anti-VLA4 (Tysabri, natalizumab), dimethyl fumarate (Tecfidera®), teriflunomide (Aubagio®), fingolimod (Gilenya®), anti-CD52 antibody (e.g., alemtuzumab), methotrexate, cladribine, simvastatin, and cyclophosphamide. In addition or alternative to therapeutic agents, other treatments for multiple sclerosis include lifestyle changes such as physical therapy or a change in diet. The method also provide for combination therapy of one or more therapeutic agents and/or additional treatments, where the combination can provide for additive or synergistic benefits.

A pharmaceutical composition administered to an individual includes an active agent such as the therapeutic agent described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients. Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

Such a pharmaceutical composition may be administered for prophylactic (e.g., before diagnosis of a patient with multiple sclerosis) or for treatment (e.g., after diagnosis of a patient with multiple sclerosis) purposes. Preventing, prophylaxis or prevention of a disease or disorder as used in the context of this invention refers to the administration of a composition to prevent the occurrence or onset of multiple sclerosis or some or all of the symptoms of multiple sclerosis or to lessen the likelihood of the onset of a disease or disorder. Treating, treatment, or therapy of multiple sclerosis shall mean slowing, stopping or reversing the disease's progression by administration of treatment according to the present invention. In the preferred embodiment, treating multiple sclerosis means reversing the disease's progression, ideally to the point of eliminating the disease itself.

VII. Computer Implementation

The methods of the invention, including the methods of assessing multiple sclerosis activity in an individual, are, in some embodiments, performed on a computer.

For example, the building and execution of a predictive model and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and execution and results of a predictive model of this invention. Such data can be used for a variety of purposes, such as patient monitoring, treatment considerations, and the like. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

VI.A. Example Computer

Figure 6:
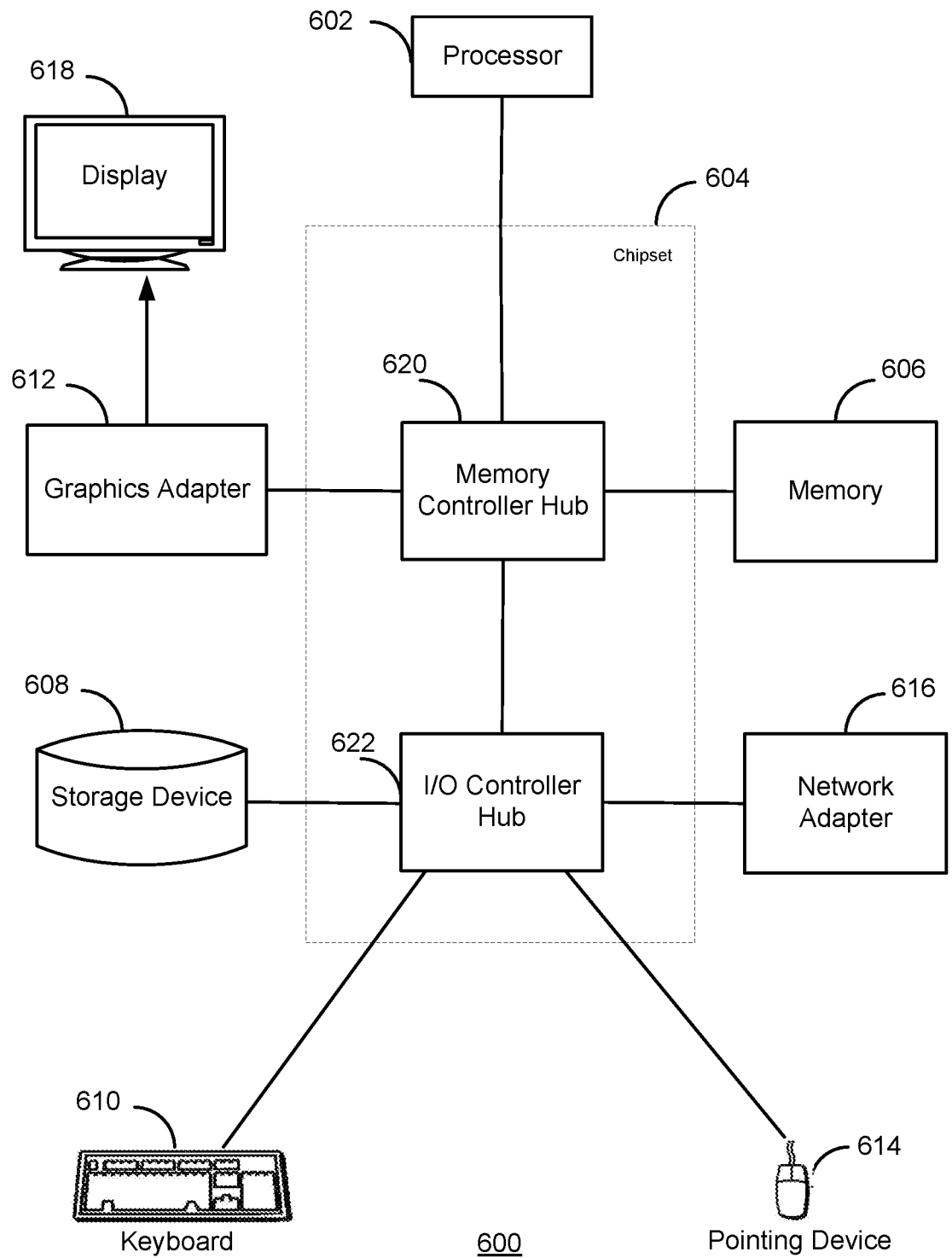
FIG. 6 illustrates an example computer for implementing the entities shown in FIGS. 1 and 2.

FIG. 6 illustrates an example computer 600 for implementing the entities shown in FIGS. 1 and 3. The computer 600 includes at least one processor 602 coupled to a chipset 604. The chipset 604 includes a memory controller hub 620 and an input/output (I/O) controller hub 622. A memory 606 and a graphics adapter 612 are coupled to the memory controller hub 620, and a display 618 is coupled to the graphics adapter 612. A storage device 608, an input device 614, and network adapter 616 are coupled to the I/O controller hub 622. Other embodiments of the computer 600 have different architectures.

The storage device 608 is a non-transitory computer-readable storage medium such as a hard drive, compact disk read-only memory (CD-ROM), DVD, or a solid-state memory device. The memory 606 holds instructions and data used by the processor 602. The input interface 614 is a touch-screen interface, a mouse, track ball, or other type of pointing device, a keyboard 610, or some combination thereof, and is used to input data into the computer 600. In some embodiments, the computer 600 may be configured to receive input (e.g., commands) from the input interface 614 via gestures from the user. The graphics adapter 612 displays images and other information on the display 618. The network adapter 616 couples the computer 600 to one or more computer networks.

The computer 600 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 608, loaded into the memory 606, and executed by the processor 602.

The types of computers 600 used by the entities of FIG. 1 can vary depending upon the embodiment and the processing power required by the entity. For example, the presentation identification system 160 can run in a single computer 600 or multiple computers 600 communicating with each other through a network such as in a server farm. The computers 600 can lack some of the components described above, such as graphics adapters 612, and displays 618.

VI.B. Kit Implementation

Also disclosed herein are kits for assessing multiple sclerosis activity in an individual. Such kits can include reagents for detecting expression levels of one or markers and instructions for assessing multiple sclerosis activity based on the detected expression levels.

The detection reagents can be provided as part of a kit. Thus, the invention further provides kits for detecting the presence of a panel of specific markers of interest in a biological sample. A kit can comprise a set of reagents for generating a dataset via at least one protein detection assay that is associated with a sample from the individual. The set of reagents enable the detection of quantitative expression levels of one or more markers from set 1, set 2, set 3, set 4, and set 5 as set forth in Table 3. In certain aspects, the reagents include one or more antibodies that bind to one or more of the markers. The antibodies may be monoclonal antibodies or polyclonal antibodies. In some aspects, the reagents can include reagents for performing ELISA including buffers and detection agents.

A kit can include instructions for use of a set of reagents. For example, a kit can include instructions for performing at least one marker detection assay such as an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, and an immunoassay selected from RIA, immunofluorescence, immunochemiluminescence, immunoelectrochemiluminescence, immunoelectrophoretic, a competitive immunoassay, and immunoprecipitation.

In addition to the above components, the subject kits will further include instructions for practicing the subject methods. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that can be present is a website address which can be used via the internet to access the information at a removed site. Any convenient means can be present in the kits.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers (e.g., p-values, area under the curve) used but some experimental error and deviation should, of course, be allowed for.

Example 1: Demographic Data

Baseline demographic characteristics of test samples obtained from 125 individuals in the Accelerated Cure Project (ACP) registry are shown in Table 1.

Figure 4:
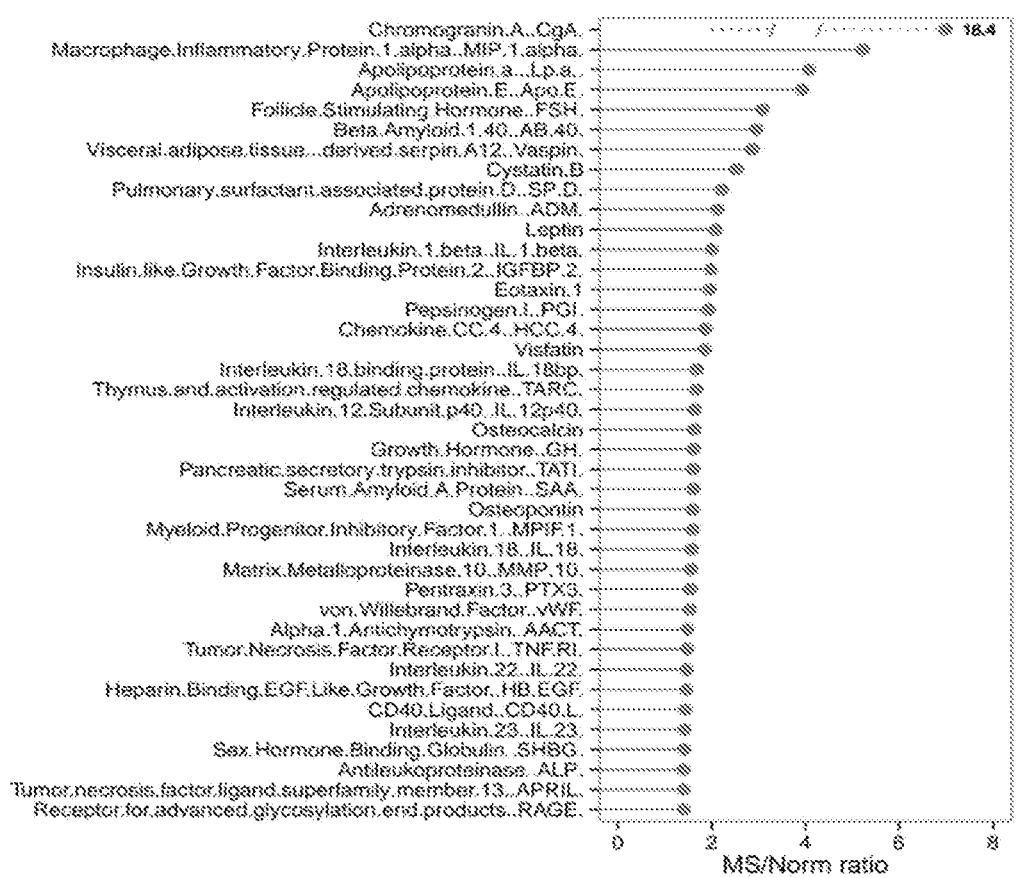
FIG. 4 depicts identified markers that are upregulated in MS patients.
Figure 5:
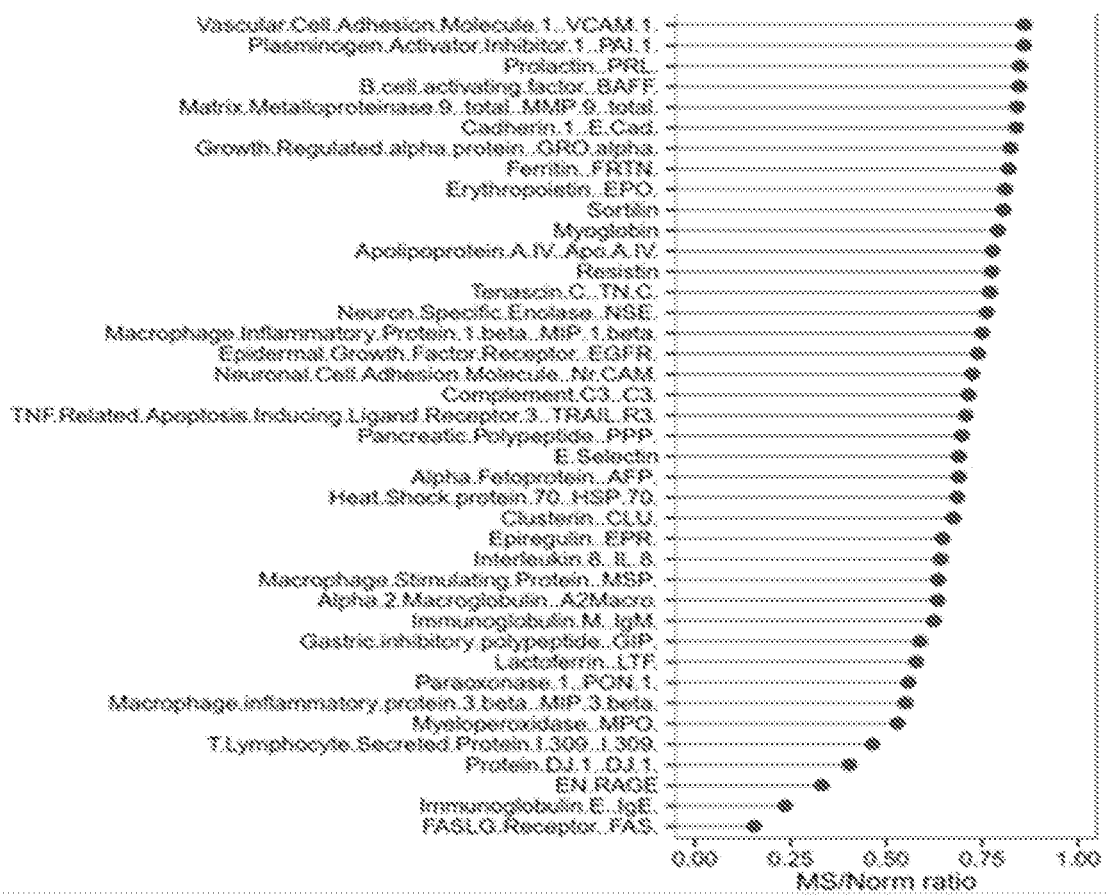
FIG. 5 depicts identified markers that are downregulated in MS patients.

Example 2: Feasibility of Assays in Determining Correlation Between Expression Values of Markers and Presence of MS Blood serum samples were obtained from 8-12 individual samples from MS and healthy individuals. Samples obtained from MS individuals were pooled and samples obtained from healthy individuals were similarly pooled. Quantitative expression values of a total of 220 biomarkers were assessed in the pooled MS samples and pooled healthy samples by multiplex luminex analysis (Rules Based Medicine). FIG. 4 and FIG. 5 illustrate the feasibility of correlating upregulated and downregulated quantitative expression values of biomarkers with the presence of MS in comparison to the absence of MS. Specifically, FIG. 4 depicts the top 40 identified biomarkers that are upregulated in MS patients in comparison to healthy individuals. FIG. 5 depicts the top 40 identified biomarkers that are downregulated in MS patients in comparison to healthy individuals.

Example 3: Univariate Analysis of One Biomarker for Predicting a Quiescent or Exacerbated State of MS in an Individual Univariate analyses was performed to obtain measures of potential predictive utility for each of 199 analytes. Table 2 depicts the univariate analysis of single biomarkers for predicting a state (e.g., quiescent or exacerbated) of MS in an individual. Specifically, table 2 includes:
  P-value for a T-test comparing the quantified level of a biomarker determined from the Exacerbation subgroup (N=60) in comparison to the Quiescent subgroup (N=65)
  Predictive metric (e.g., Area under the curve (AUC)) of a single-analyte logistic regression model
For the logistic regression model, quantitative expression values for a biomarker were fit to a logistic regression. The predictive ability of the logistic regression was evaluated using the fitted values and reported as the AUC metric.

These measures provide quantitative indications of each biomarker's ability to distinguish sample groups of interest (exacerbation vs quiescent). A p-value<0.05 is generally accepted as a statistically significant threshold for identifying biomarkers that are upregulated/downregulated. An AUC value>0.60 is a reasonable threshold for identifying promising biomarkers using the univariate logistic regression model.

Example 4: Multivariate Analyses of Two Biomarkers for Predicting a Quiescent or Exacerbated State of MS in an Individual Multivariate analyses were conducted to obtain measures of potential predictive utility for pairs of biomarkers. Specifically, pairs of biomarkers were selected from the ranked biomarker list of 80 total biomarkers shown in Table 3. The ranking of biomarkers is described below in reference to Example 6.

For each pair of biomarkers, two predictive models were constructed using the quantitative expression values of each pair of biomarkers. The two predictive models include: 1) a logistic regression model and 2) a random forest model. The predictive ability of each model was evaluated using the fitted expression values and reported as an AUC metric. For each model, an AUC greater than a threshold value of 0.6 is considered predictive. The evaluated predictive ability of each predictive model based on a pair of biomarkers is described in further detail below in reference to Examples 9-87.

Example 5: Multivariate Analysis of 10/20/40/60/80 Biomarkers for Predicting a Quiescence or Exacerbated State of MS in an Individual Multivariate analyses were conducted to obtain measures of potential predictive utility for N biomarkers shown in Table 3, where N biomarkers is one of 10, 20, 40, 60, or 80 total biomarkers. Overall, the multivariate analyses included ranking candidate biomarkers based on each candidate biomarker's importance as discussed in Example 6 below. Predictive models using one of random forest (RF), gradient boosting (GBM), extreme gradient boosting (GBM), or least absolute shrinkage and selection operator (LASSO) were built including biomarkers that were selected based on their respective rankings. Each predictive model was trained using as is discussed in Example 7 below. Each predictive model was validated through the reporting of a mean AUC metric as described in Example 8 below.

Example 6: Assessing Analyte Importance

For each of the four methods (random forest (RF), gradient boosting (GBM), least absolute shrinkage and selection operator (LASSO), and extreme gradient boosting (XGB)), two independent model building runs were executed to determine analyte importance (ranking). Each independent model building run iteratively identified the Top 80/60/40/20/10 biomarkers.

Each of the multivariate classification methods (RF, GBM, LASSO, and XGB) provides one or more quantitative measures for assessing and ranking the importance of every biomarker (variable) included in a model produced by that method. For example, RF provides, for each variable: (a) the mean decrease in model accuracy, and (b) the mean decrease in Gini index, which is a measure of variable importance based on node purity at node splits involving the variable in question as the trees of the random forest model are being built. These method-specific measures are used to rank analytes by importance.

For each method, the biomarkers are iteratively trimmed to the top 80/60/40/20/10. At each iteration, a new model is built using the shorter list of biomarkers. In other words, we first build a model using all analytes and select the Top 80 ranked by the method. Then we build a model using only the Top 80 and we select the Top 60 (which could differ in composition from the 60 top analytes in the first model). Then we build a model using only the Top 60 and we select the Top 40. Then we build a model using only the Top 40 and we select the Top 20. Then we build a model using only the Top 20 and we select the Top 10.

Each method independently generates a ranking of top biomarkers. After computing the Top N biomarker lists for each of the methods, the biomarkers are sorted by a number of Top N appearances (e.g., total number of times an analyte is ranked in the Top 80/60/40/20/10 across both runs of all four methods) as a simple but reasonable way of ordering analytes by average importance. To break ties (same number of Top N appearances), the mean Rank of the biomarker's appearances on the Top N lists is used. For example, as shown in Table 3, the most important analyte (in the aggregate multivariate analysis), Paraoxonase 1 (PON1), appears on all 32 Top N lists (it is in the Top 80, 40, 20, and 10 for each of two runs of all four methods). The second and third most important analytes each appear on 30 of the 32 Top N lists. The tie is broken using Mean Rank which is 6.3 for the second most important analyte and 8.3 for the third most important analyte.

Example 7: Building a Prediction Model

The goal of building a predictive model is to create a model for predicting an assessment of MS activity in a previously unseen sample from an individual.

Separate prediction models were built for 1) a set of biomarkers (e.g., top 10/20/40/60/80) and 2) a method. In other words, a predictive model was built for the top 10 biomarkers using RF algorithms. Additionally, independent predictive models were built for the top 20, top 40, top 60, and top 80 biomarkers using RF algorithms. Independent predictive models were also built for the top 10/20/40/60/80 for each of GBM, LASSO, and XGB algorithms.

Specifically, as shown in Table 3, biomarkers that rank in the top 10 are categorized in Set 1. Biomarkers ranked between rank 11 and rank 20, inclusive, are categorized in Set 2. Biomarkers ranked between rank 21 and rank 40, inclusive, are categorized in Set 3. Biomarkers ranked between rank 41 and rank 60, inclusive, are categorized in Set 4. Biomarkers ranked between rank 61 and rank 80, inclusive, are categorized in Set 5.

A subset (80%) of training samples were randomly selected, while holding aside the remaining samples (20%) for testing and validation. The biomarker values were adjusted for age and sex of the individual that the test sample was obtained from. Additionally, biomarker values were scaled across all samples in the training set.

For each predictive model, cross validation (e.g., 10-fold, 5-repeat) was performed to select certain model parameters. Specifically, each of the multivariate classification methods offers parameters which can be tuned in order to optimize the performance of the model produced by that method. For example, RF offers the mtry parameter, which determines the number of variables that are randomly selected as candidates at each node split during the building of a tree. We use cross-validation as a technique for selecting the best value of mtry among a set of possible values. The cross-validation is performed using 10 folds of the training subset which means that the training subset is randomly partitioned into 10 subsamples of roughly equal size. For each of these 10 subsamples we train a model using 9 subsamples, and then validate the model using the one subsample that was held aside. By aggregating the results across the 10 mutually exclusive subsamples, a measure of model performance for a given value of the mtry parameter is obtained. For each candidate value for mtry, this validation process is repeated 5 times so as to reduce the impact of randomness involved in the subsampling step. Based on the average model performance of the 5 cross-validation runs, the best performing value of mtry is chosen, and that parameter value is used in subsequent model training using the full training subset.

Example 8: Validating a Prediction Model

Each prediction model was validated using the remaining 20% of the training samples. Four hundred independent iterations were conducted using the training samples. Within one iteration, a prediction model is validated by making predictions for each of the samples in the testing set (in that iteration). The performance of each prediction model is reported as the area under the curve (AUC) of the testing set.

Use of statistical values such as the AUC, and specifically the AUC as it relates to a receiver operating characteristic (ROC) curve, encompassing all potential threshold or cut-off point values is generally used to quantify predictive model performance. Acceptable degrees of accuracy can be defined. In certain embodiments of the present teachings, an acceptable degree of accuracy can be one in which the AUC for the ROC curve is 0.60 or higher.

In general, defining the degree of accuracy for the relevant predictive model or test (e.g., cut-off points on a ROC curve), defining an acceptable AUC value, and determining the acceptable ranges in relative concentration of what constitutes an effective amount of the biomarkers of the present teachings, allows one of skill in the art to use the biomarkers of the present teachings to determine MS activity in individuals with a pre-determined level of predictability and performance.

Each prediction was a quantitative measure of the relative likelihood that a sample belongs to one of the two classes in question (e.g. Exacerbation vs. Quiescence). These quantitative predictions are used in the computation of AUC, which is a measure of a model's overall performance across the entire set of testing samples. The mean AUC across the 400 iterations is reported for each of the methods for each of the Top 80/40/20/10 analyte lists as shown in Table 83.

Example 9: Two Biomarker Combinations Including Paraoxonase 1 (PON1)

The ability of the predictive models to determine the state (e.g., quiescent or exacerbation) of MS in an individual using expression values of PON1 and one other biomarker from Table 3 was assessed. Summary statistics, including a maximum AUC across the two methods, are depicted in Table 4. All two biomarker combinations including PON1 result in a maximum AUC above the threshold value, indicating that at least one of the predictive models is predictive of a state of MS in an individual when considering two biomarker combinations, wherein one of the two biomarkers is PON1.

Example 10: Two Biomarker Combinations Including Myoglobin

The ability of the predictive models to determine the state (e.g., quiescent or exacerbation) of MS in an individual using expression values of Myoglobin and one other biomarker from Table 3 was assessed. Summary statistics, including a maximum AUC across the two methods, are depicted in Table 5. All two biomarker combinations including Myoglobin result in a maximum AUC above the threshold value, indicating that at least one of the predictive models is predictive of a state of MS in an individual when considering two biomarker combinations, wherein one of the two biomarkers is Myoglobin.

Example 11: Two Biomarker Combinations Including Plasminogen Activator Inhibitor 1 (PAI-1)

The ability of the predictive models to determine the state (e.g., quiescent or exacerbation) of MS in an individual using expression values of PAI-1 and one other biomarker from Table 3 was assessed. Summary statistics, including a maximum AUC across the two methods, are depicted in Table 6. All two biomarker combinations including PAI-1 result in a maximum AUC above the threshold value, indicating that at least one of the predictive models is predictive of a state of MS in an individual when considering two biomarker combinations, wherein one of the two biomarkers is PAI-1.

Example 12: Two Biomarker Combinations Including Tissue Inhibitor of Metalloproteinases 1 (TIMP1)

The ability of the predictive models to determine the state (e.g., quiescent or exacerbation) of MS in an individual using expression values of TIMP1 and one other biomarker from Table 3 was assessed. Summary statistics, including a maximum AUC across the two methods, are depicted in Table 7. A majority of biomarker combinations including TIMP1 result in a maximum AUC above the threshold value, indicating that at least one of the predictive models is predictive of a state of MS in an individual when considering two biomarker combinations, wherein one of the two biomarkers is TIMP1.

Example 13: Two Biomarker Combinations Including Stromal Cell Derived Factor 1 (SDF1)

The ability of the predictive models to determine the state (e.g., quiescent or exacerbation) of MS in an individual using expression values of SDF1 and one other biomarker from Table 3 was assessed. Summary statistics, including a maximum AUC across the two methods, are depicted in Table 8. A majority of biomarker combinations including SDF1 result in a maximum AUC above the threshold value, indicating that at least one of the predictive models is predictive of a state of MS in an individual when considering two biomarker combinations, wherein one of the two biomarkers is SDF1.

Example 14: Two Biomarker Combinations Including Interleukin 6 Receptor Subunit Beta (IL6Rbeta)

The ability of the predictive models to determine the state (e.g., quiescent or exacerbation) of MS in an individual using expression values of IL6Rbeta and one other biomarker from Table 3 was assessed. Summary statistics, including a maximum AUC across the two methods, are depicted in Table 9. All two biomarker combinations including IL6Rbeta result in a maximum AUC above the threshold value, indicating that at least one of the predictive models is predictive of a state of MS in an individual when considering two biomarker combinations, wherein one of the two biomarkers is IL6Rbeta.

Example 15: Two Biomarker Combinations Including Cystatin B

The ability of the predictive models to determine the state (e.g., quiescent or exacerbation) of MS in an individual using expression values of Cystatin B and one other biomarker from Table 3 was assessed. Summary statistics, including a maximum AUC across the two methods, are depicted in Table 10. All two biomarker combinations including Cystatin B result in a maximum AUC above the threshold value, indicating that at least one of the predictive models is predictive of a state of MS in an individual when considering two biomarker combinations, wherein one of the two biomarkers is Cystatin B.

Example 16: Two Biomarker Combinations Including Immunoglobulin E (IgE)

The ability of the predictive models to determine the state (e.g., quiescent or exacerbation) of MS in an individual using expression values of IgE and one other biomarker from Table 3 was assessed. Summary statistics, including a maximum AUC across the two methods, are depicted in Table 11. All two biomarker combinations including IgE result in a maximum AUC above the threshold value, indicating that at least one of the predictive models is predictive of a state of MS in an individual when considering two biomarker combinations, wherein one of the two biomarkers is IgE.

Example 17: Two Biomarker Combinations Including Macrophage Inflammatory Protein 3 Beta (MIP3beta)

The ability of the predictive models to determine the state (e.g., quiescent or exacerbation) of MS in an individual using expression values of MIP3beta and one other biomarker from Table 3 was assessed. Summary statistics, including a maximum AUC across the two methods, are depicted in Table 12. A majority of biomarker combinations including MIP3beta result in a maximum AUC above the threshold value, indicating that at least one of the predictive models is predictive of a state of MS in an individual when considering two biomarker combinations, wherein one of the two biomarkers is MIP3beta.

Example 18: Two Biomarker Combinations Including Vascular Cell Adhesion Molecule 1 (VCAM1)

The ability of the predictive models to determine the state (e.g., quiescent or exacerbation) of MS in an individual using expression values of VCAM1 and one other biomarker from Table 3 was assessed. Summary statistics, including a maximum AUC across the two methods, are depicted in Table 13. All biomarker combinations including VCAM1 result in a maximum AUC above the threshold value, indicating that at least one of the predictive models is predictive of a state of MS in an individual when considering two biomarker combinations, wherein one of the two biomarkers is VCAM1.

Example 19: Two Biomarker Combinations Including Macrophage Derived Chemokine (MDC)

The ability of the predictive models to determine the state (e.g., quiescent or exacerbation) of MS in an individual using expression values of MDC and one other biomarker from Table 3 was assessed. Summary statistics, including a maximum AUC across the two methods, are depicted in Table 14. All biomarker combinations including MDC result in a maximum AUC above the threshold value, indicating that at least one of the predictive models is predictive of a state of MS in an individual when considering two biomarker combinations, wherein one of the two biomarkers is MDC.

Example 20: Two Biomarker Combinations Including Vascular Endothelial Growth Factor (VEGF)

The ability of the predictive models to determine the state (e.g., quiescent or exacerbation) of MS in an individual using expression values of VEGF and one other biomarker from Table 3 was assessed. Summary statistics, including a maximum AUC across the two methods, are depicted in Table 15. A majority of biomarker combinations including VEGF result in a maximum AUC above the threshold value, indicating that at least one of the predictive models is predictive of a state of MS in an individual when considering two biomarker combinations, wherein one of the two biomarkers is VEGF.

Example 21: Two Biomarker Combinations Including Ficolin 3

The ability of the predictive models to determine the state (e.g., quiescent or exacerbation) of MS in an individual using expression values of Ficolin 3 and one other biomarker from Table 3 was assessed. Summary statistics, including a maximum AUC across the two methods, are depicted in Table 16. All biomarker combinations including Ficolin 3 result in a maximum AUC above the threshold value, indicating that at least one of the predictive models is predictive of a state of MS in an individual when considering two biomarker combinations, wherein one of the two biomarkers is Ficolin 3.

Example 22: Two Biomarker Combinations Including Immunoglobulin a (IgA)

The ability of the predictive models to determine the state (e.g., quiescent or exacerbation) of MS in an individual using expression values of IgA and one other biomarker from Table 3 was assessed. Summary statistics, including a maximum AUC across the two methods, are depicted in Table 17. A majority of biomarker combinations including IgA result in a maximum AUC above the threshold value, indicating that at least one of the predictive models is predictive of a state of MS in an individual when considering two biomarker combinations, wherein one of the two biomarkers is IgA.

Example 23: Two Biomarker Combinations Including Factor VII

The ability of the predictive models to determine the state (e.g., quiescent or exacerbation) of MS in an individual using expression values of Factor VII and one other biomarker from Table 3 was assessed. Summary statistics, including a maximum AUC across the two methods, are depicted in Table 18. A majority of biomarker combinations including Factor VII result in a maximum AUC above the threshold value, indicating that at least one of the predictive models is predictive of a state of MS in an individual when considering two biomarker combinations, wherein one of the two biomarkers is Factor VII.

Example 24: Two Biomarker Combinations Including Interleukin 6 Receptor (IL6R)

The ability of the predictive models to determine the state (e.g., quiescent or exacerbation) of MS in an individual using expression values of IL6R and one other biomarker from Table 3 was assessed. Summary statistics, including a maximum AUC across the two methods, are depicted in Table 19. A majority of biomarker combinations including IL6R result in a maximum AUC above the threshold value, indicating that at least one of the predictive models is predictive of a state of MS in an individual when considering two biomarker combinations, wherein one of the two biomarkers is IL6R.

Example 25: Two Biomarker Combinations Including Receptor for Advanced Glycosylation End Products (RAGE)

The ability of the predictive models to determine the state (e.g., quiescent or exacerbation) of MS in an individual using expression values of RAGE and one other biomarker from Table 3 was assessed. Summary statistics, including a maximum AUC across the two methods, are depicted in Table 20. A majority of biomarker combinations including RAGE result in a maximum AUC above the threshold value, indicating that at least one of the predictive models is predictive of a state of MS in an individual when considering two biomarker combinations, wherein one of the two biomarkers is RAGE.

Example 26: Two Biomarker Combinations Including Fibulin 1C (FIB1C)

The ability of the predictive models to determine the state (e.g., quiescent or exacerbation) of MS in an individual using expression values of FIB1C and one other biomarker from Table 3 was assessed. Summary statistics, including a maximum AUC across the two methods, are depicted in Table 21. A significant number of biomarker combinations including FIB1C result in a maximum AUC above the threshold value, indicating that at least one of the predictive models is predictive of a state of MS in an individual when considering two biomarker combinations, wherein one of the two biomarkers is FIB1C.

Example 27: Two Biomarker Combinations Including Interferon Inducible T Cell Alpha Chemoattractant (ITAC)

The ability of the predictive models to determine the state (e.g., quiescent or exacerbation) of MS in an individual using expression values of ITAC and one other biomarker from Table 3 was assessed. Summary statistics, including a maximum AUC across the two methods, are depicted in Table 22. A significant number of biomarker combinations including ITAC result in a maximum AUC above the threshold value, indicating that at least one of the predictive models is predictive of a state of MS in an individual when considering two biomarker combinations, wherein one of the two biomarkers is ITAC.

Example 28: Two Biomarker Combinations Including Growth Hormone (GH)

The ability of the predictive models to determine the state (e.g., quiescent or exacerbation) of MS in an individual using expression values of GH and one other biomarker from Table 3 was assessed. Summary statistics, including a maximum AUC across the two methods, are depicted in Table 23. A majority of biomarker combinations including GH result in a maximum AUC above the threshold value, indicating that at least one of the predictive models is predictive of a state of MS in an individual when considering two biomarker combinations, wherein one of the two biomarkers is GH.

Example 29: Two Biomarker Combinations Including Heparin Binding EGF Like Growth Factor (HBEGF)

The ability of the predictive models to determine the state (e.g., quiescent or exacerbation) of MS in an individual using expression values of HBEGF and one other biomarker from Table 3 was assessed. Summary statistics, including a maximum AUC across the two methods, are depicted in Table 24. A majority of biomarker combinations including HBEGF result in a maximum AUC above the threshold value, indicating that at least one of the predictive models is predictive of a state of MS in an individual when considering two biomarker combinations, wherein one of the two biomarkers is HBEGF.

Example 30: Two Biomarker Combinations Including Neuronal Cell Adhesion Molecule (NrCAM)

The ability of the predictive models to determine the state (e.g., quiescent or exacerbation) of MS in an individual using expression values of NrCAM and one other biomarker from Table 3 was assessed. Summary statistics, including a maximum AUC across the two methods, are depicted in Table 25. A majority of biomarker combinations including NrCAM result in a maximum AUC above the threshold value, indicating that at least one of the predictive models is predictive of a state of MS in an individual when considering two biomarker combinations, wherein one of the two biomarkers is NrCAM.

Example 31: Two Biomarker Combinations Including Growth Regulated Alpha Protein (GROalpha)

The ability of the predictive models to determine the state (e.g., quiescent or exacerbation) of MS in an individual using expression values of GROalpha and one other biomarker from Table 3 was assessed. Summary statistics, including a maximum AUC across the two methods, are depicted in Table 26. A significant number of biomarker combinations including GROalpha result in a maximum AUC above the threshold value, indicating that at least one of the predictive models is predictive of a state of MS in an individual when considering two biomarker combinations, wherein one of the two biomarkers is GROalpha.

Example 32: Two Biomarker Combinations Including Growth Differentiation Factor 15 (GDF15)

The ability of the predictive models to determine the state (e.g., quiescent or exacerbation) of MS in an individual using expression values of GDF15 and one other biomarker from Table 3 was assessed. Summary statistics, including a maximum AUC across the two methods, are depicted in Table 27. A significant number of biomarker combinations including GDF15 result in a maximum AUC above the threshold value, indicating that at least one of the predictive models is predictive of a state of MS in an individual when considering two biomarker combinations, wherein one of the two biomarkers is GDF15.

Example 33: Two Biomarker Combinations Including Mast Stem Cell Growth Factor Receptor (SCFR)

The ability of the predictive models to determine the state (e.g., quiescent or exacerbation) of MS in an individual using expression values of SCFR and one other biomarker from Table 3 was assessed. Summary statistics, including a maximum AUC across the two methods, are depicted in Table 28. A significant number of biomarker combinations including SCFR result in a maximum AUC above the threshold value, indicating that at least one of the predictive models is predictive of a state of MS in an individual when considering two biomarker combinations, wherein one of the two biomarkers is SCFR.

Example 34: Two Biomarker Combinations Including Cadherin 1 (Ecad)

The ability of the predictive models to determine the state (e.g., quiescent or exacerbation) of MS in an individual using expression values of Ecad and one other biomarker from Table 3 was assessed. Summary statistics, including a maximum AUC across the two methods, are depicted in Table 29. A significant number of biomarker combinations including Ecad result in a maximum AUC above the threshold value, indicating that at least one of the predictive models is predictive of a state of MS in an individual when considering two biomarker combinations, wherein one of the two biomarkers is Ecad.

Example 35: Two Biomarker Combinations Including Angiogenin

The ability of the predictive models to determine the state (e.g., quiescent or exacerbation) of MS in an individual using expression values of Angiogenin and one other biomarker from Table 3 was assessed. Summary statistics, including a maximum AUC across the two methods, are depicted in Table 30. A significant number of biomarker combinations including Angiogenin result in a maximum AUC above the threshold value, indicating that at least one of the predictive models is predictive of a state of MS in an individual when considering two biomarker combinations, wherein one of the two biomarkers is Angiogenin.

Example 36: Two Biomarker Combinations Including Sortilin

The ability of the predictive models to determine the state (e.g., quiescent or exacerbation) of MS in an individual using expression values of Sortilin and one other biomarker from Table 3 was assessed. Summary statistics, including a maximum AUC across the two methods, are depicted in Table 31. A significant number of biomarker combinations including Sortilin result in a maximum AUC above the threshold value, indicating that at least one of the predictive models is predictive of a state of MS in an individual when considering two biomarker combinations, wherein one of the two biomarkers is Sortilin.

Example 37: Two Biomarker Combinations Including Alpha 1 Antitrypsin (AAT)

The ability of the predictive models to determine the state (e.g., quiescent or exacerbation) of MS in an individual using expression values of AAT and one other biomarker from Table 3 was assessed. Summary statistics, including a maximum AUC across the two methods, are depicted in Table 32. A significant number of biomarker combinations including AAT result in a maximum AUC above the threshold value, indicating that at least one of the predictive models is predictive of a state of MS in an individual when considering two biomarker combinations, wherein one of the two biomarkers is AAT.

Example 38: Two Biomarker Combinations Including Immunoglobulin M (IgM)

The ability of the predictive models to determine the state (e.g., quiescent or exacerbation) of MS in an individual using expression values of IgM and one other biomarker from Table 3 was assessed. Summary statistics, including a maximum AUC across the two methods, are depicted in Table 33. A significant number of biomarker combinations including IgM result in a maximum AUC above the threshold value, indicating that at least one of the predictive models is predictive of a state of MS in an individual when considering two biomarker combinations, wherein one of the two biomarkers is IgM.

Example 39: Two Biomarker Combinations Including Pulmonary and Activation Regulated Chemokine (PARC)

The ability of the predictive models to determine the state (e.g., quiescent or exacerbation) of MS in an individual using expression values of PARC and one other biomarker from Table 3 was assessed. Summary statistics, including a maximum AUC across the two methods, are depicted in Table 34. A significant number of biomarker combinations including PARC result in a maximum AUC above the threshold value, indicating that at least one of the predictive models is predictive of a state of MS in an individual when considering two biomarker combinations, wherein one of the two biomarkers is PARC.

Example 40: Two Biomarker Combinations Including Pulmonary Surfactant Associated Protein D (SP-D)

The ability of the predictive models to determine the state (e.g., quiescent or exacerbation) of MS in an individual using expression values of SP-D and one other biomarker from Table 3 was assessed. Summary statistics, including a maximum AUC across the two methods, are depicted in Table 35. A significant number of biomarker combinations including SP-D result in a maximum AUC above the threshold value, indicating that at least one of the predictive models is predictive of a state of MS in an individual when considering two biomarker combinations, wherein one of the two biomarkers is SP-D.

Example 41: Two Biomarker Combinations Including B Cell Activating Factor (BAFF)

The ability of the predictive models to determine the state (e.g., quiescent or exacerbation) of MS in an individual using expression values of BAFF and one other biomarker from Table 3 was assessed. Summary statistics, including a maximum AUC across the two methods, are depicted in Table 36. A significant number of biomarker combinations including BAFF result in a maximum AUC above the threshold value, indicating that at least one of the predictive models is predictive of a state of MS in an individual when considering two biomarker combinations, wherein one of the two biomarkers is BAFF.

Example 42: Two Biomarker Combinations Including Adrenomedullin (ADM)

The ability of the predictive models to determine the state (e.g., quiescent or exacerbation) of MS in an individual using expression values of ADM and one other biomarker from Table 3 was assessed. Summary statistics, including a maximum AUC across the two methods, are depicted in Table 37. A majority of biomarker combinations including ADM result in a maximum AUC above the threshold value, indicating that at least one of the predictive models is predictive of a state of MS in an individual when considering two biomarker combinations, wherein one of the two biomarkers is ADM.

Example 43: Two Biomarker Combinations Including Pigment Epithelium Derived Factor (PEDF)

The ability of the predictive models to determine the state (e.g., quiescent or exacerbation) of MS in an individual using expression values of PEDF and one other biomarker from Table 3 was assessed. Summary statistics, including a maximum AUC across the two methods, are depicted in Table 38. A majority of biomarker combinations including PEDF result in a maximum AUC above the threshold value, indicating that at least one of the predictive models is predictive of a state of MS in an individual when considering two biomarker combinations, wherein one of the two biomarkers is PEDF.

Example 44: Two Biomarker Combinations Including Interleukin 1 Receptor Antagonist (IL1ra)

The ability of the predictive models to determine the state (e.g., quiescent or exacerbation) of MS in an individual using expression values of IL1ra and one other biomarker from Table 3 was assessed. Summary statistics, including a maximum AUC across the two methods, are depicted in Table 39. A significant number of biomarker combinations including IL1ra result in a maximum AUC above the threshold value, indicating that at least one of the predictive models is predictive of a state of MS in an individual when considering two biomarker combinations, wherein one of the two biomarkers is IL1ra.

Example 45: Two Biomarker Combinations Including Thyroxine Binding Globulin (TBG)

The ability of the predictive models to determine the state (e.g., quiescent or exacerbation) of MS in an individual using expression values of TBG and one other biomarker from Table 3 was assessed. Summary statistics, including a maximum AUC across the two methods, are depicted in Table 40. A significant number of biomarker combinations including TBG result in a maximum AUC above the threshold value, indicating that at least one of the predictive models is predictive of a state of MS in an individual when considering two biomarker combinations, wherein one of the two biomarkers is TBG.

Example 46: Two Biomarker Combinations Including Microalbumin

The ability of the predictive models to determine the state (e.g., quiescent or exacerbation) of MS in an individual using expression values of Microalbumin and one other biomarker from Table 3 was assessed. Summary statistics, including a maximum AUC across the two methods, are depicted in Table 41. A significant number of biomarker combinations including Microalbumin result in a maximum AUC above the threshold value, indicating that at least one of the predictive models is predictive of a state of MS in an individual when considering two biomarker combinations, wherein one of the two biomarkers is Microalbumin.

Example 47: Two Biomarker Combinations Including Leptin

The ability of the predictive models to determine the state (e.g., quiescent or exacerbation) of MS in an individual using expression values of Leptin and one other biomarker from Table 3 was assessed. Summary statistics, including a maximum AUC across the two methods, are depicted in Table 42. A majority of biomarker combinations including Leptin result in a maximum AUC above the threshold value, indicating that at least one of the predictive models is predictive of a state of MS in an individual when considering two biomarker combinations, wherein one of the two biomarkers is Leptin.

Example 48: Two Biomarker Combinations Including Eotaxin 2

The ability of the predictive models to determine the state (e.g., quiescent or exacerbation) of MS in an individual using expression values of Eotaxin 2 and one other biomarker from Table 3 was assessed. Summary statistics, including a maximum AUC across the two methods, are depicted in Table 43. A significant number of biomarker combinations including Eotaxin 2 result in a maximum AUC above the threshold value, indicating that at least one of the predictive models is predictive of a state of MS in an individual when considering two biomarker combinations, wherein one of the two biomarkers is Eotaxin 2.

Example 49: Two Biomarker Combinations Including Insulin Like Growth Factor Binding Protein 2 (IGFBP2)

The ability of the predictive models to determine the state (e.g., quiescent or exacerbation) of MS in an individual using expression values of IGFBP2 and one other biomarker from Table 3 was assessed. Summary statistics, including a maximum AUC across the two methods, are depicted in Table 44. A significant number of biomarker combinations including IGFBP2 result in a maximum AUC above the threshold value, indicating that at least one of the predictive models is predictive of a state of MS in an individual when considering two biomarker combinations, wherein one of the two biomarkers is IGFBP2.

Example 50: Two Biomarker Combinations Including Resistin

The ability of the predictive models to determine the state (e.g., quiescent or exacerbation) of MS in an individual using expression values of Resistin and one other biomarker from Table 3 was assessed. Summary statistics, including a maximum AUC across the two methods, are depicted in Table 45. A significant number of biomarker combinations including Resistin result in a maximum AUC above the threshold value, indicating that at least one of the predictive models is predictive of a state of MS in an individual when considering two biomarker combinations, wherein one of the two biomarkers is Resistin.

Example 51: Two Biomarker Combinations Including Cathepsin D

The ability of the predictive models to determine the state (e.g., quiescent or exacerbation) of MS in an individual using expression values of Cathepsin D and one other biomarker from Table 3 was assessed. Summary statistics, including a maximum AUC across the two methods, are depicted in Table 46. A majority of biomarker combinations including Cathepsin D result in a maximum AUC above the threshold value, indicating that at least one of the predictive models is predictive of a state of MS in an individual when considering two biomarker combinations, wherein one of the two biomarkers is Cathepsin D.

Example 52: Two Biomarker Combinations Including E-Selectin

The ability of the predictive models to determine the state (e.g., quiescent or exacerbation) of MS in an individual using expression values of E-Selectin and one other biomarker from Table 3 was assessed. Summary statistics, including a maximum AUC across the two methods, are depicted in Table 47. A majority of biomarker combinations including E-Selectin result in a maximum AUC above the threshold value, indicating that at least one of the predictive models is predictive of a state of MS in an individual when considering two biomarker combinations, wherein one of the two biomarkers is E-Selectin.

Example 53: Two Biomarker Combinations Including YKL40

The ability of the predictive models to determine the state (e.g., quiescent or exacerbation) of MS in an individual using expression values of YKL40 and one other biomarker from Table 3 was assessed. Summary statistics, including a maximum AUC across the two methods, are depicted in Table 48. A significant number of biomarker combinations including YKL40 result in a maximum AUC above the threshold value, indicating that at least one of the predictive models is predictive of a state of MS in an individual when considering two biomarker combinations, wherein one of the two biomarkers is YKL40.

Example 54: Two Biomarker Combinations Including Interleukin 22 (IL22)

The ability of the predictive models to determine the state (e.g., quiescent or exacerbation) of MS in an individual using expression values of IL22 and one other biomarker from Table 3 was assessed. Summary statistics, including a maximum AUC across the two methods, are depicted in Table 49. A significant number of biomarker combinations including IL22 result in a maximum AUC above the threshold value, indicating that at least one of the predictive models is predictive of a state of MS in an individual when considering two biomarker combinations, wherein one of the two biomarkers is IL22.

Example 55: Two Biomarker Combinations Including Carcinoembryonic Antigen (CEA)

The ability of the predictive models to determine the state (e.g., quiescent or exacerbation) of MS in an individual using expression values of CEA and one other biomarker from Table 3 was assessed. Summary statistics, including a maximum AUC across the two methods, are depicted in Table 50. A significant number of biomarker combinations including CEA result in a maximum AUC above the threshold value, indicating that at least one of the predictive models is predictive of a state of MS in an individual when considering two biomarker combinations, wherein one of the two biomarkers is CEA.

Example 56: Two Biomarker Combinations Including Interleukin 8 (IL8)

The ability of the predictive models to determine the state (e.g., quiescent or exacerbation) of MS in an individual using expression values of IL8 and one other biomarker from Table 3 was assessed. Summary statistics, including a maximum AUC across the two methods, are depicted in Table 51. A significant number of biomarker combinations including IL8 result in a maximum AUC above the threshold value, indicating that at least one of the predictive models is predictive of a state of MS in an individual when considering two biomarker combinations, wherein one of the two biomarkers is IL8.

Example 57: Two Biomarker Combinations Including Cancer Antigen 15-3 (CA 15-3)

The ability of the predictive models to determine the state (e.g., quiescent or exacerbation) of MS in an individual using expression values of CA 15-3 and one other biomarker from Table 3 was assessed. Summary statistics, including a maximum AUC across the two methods, are depicted in Table 52. A significant number of biomarker combinations including CA 15-3 result in a maximum AUC above the threshold value, indicating that at least one of the predictive models is predictive of a state of MS in an individual when considering two biomarker combinations, wherein one of the two biomarkers is CA 15-3.

Example 58: Two Biomarker Combinations Including Leptin Receptor (LeptinR)

The ability of the predictive models to determine the state (e.g., quiescent or exacerbation) of MS in an individual using expression values of LeptinR and one other biomarker from Table 3 was assessed. Summary statistics, including a maximum AUC across the two methods, are depicted in Table 53. A significant number of biomarker combinations including LeptinR result in a maximum AUC above the threshold value, indicating that at least one of the predictive models is predictive of a state of MS in an individual when considering two biomarker combinations, wherein one of the two biomarkers is LeptinR.

Example 59: Two Biomarker Combinations Including Insulin

The ability of the predictive models to determine the state (e.g., quiescent or exacerbation) of MS in an individual using expression values of Insulin and one other biomarker from Table 3 was assessed. Summary statistics, including a maximum AUC across the two methods, are depicted in Table 54. A significant number of biomarker combinations including Insulin result in a maximum AUC above the threshold value, indicating that at least one of the predictive models is predictive of a state of MS in an individual when considering two biomarker combinations, wherein one of the two biomarkers is Insulin.

Example 60: Two Biomarker Combinations Including Monocyte Chemotactic Protein 1 (MCP1)

The ability of the predictive models to determine the state (e.g., quiescent or exacerbation) of MS in an individual using expression values of MCP1 and one other biomarker from Table 3 was assessed. Summary statistics, including a maximum AUC across the two methods, are depicted in Table 55. A significant number of biomarker combinations including MCP1 result in a maximum AUC above the threshold value, indicating that at least one of the predictive models is predictive of a state of MS in an individual when considering two biomarker combinations, wherein one of the two biomarkers is MCP1.

Example 61: Two Biomarker Combinations Including Prolactin (PRL)

The ability of the predictive models to determine the state (e.g., quiescent or exacerbation) of MS in an individual using expression values of PRL and one other biomarker from Table 3 was assessed. Summary statistics, including a maximum AUC across the two methods, are depicted in Table 56. A significant number of biomarker combinations including PRL result in a maximum AUC above the threshold value, indicating that at least one of the predictive models is predictive of a state of MS in an individual when considering two biomarker combinations, wherein one of the two biomarkers is PRL.

Example 62: Two Biomarker Combinations Including Tetranectin

The ability of the predictive models to determine the state (e.g., quiescent or exacerbation) of MS in an individual using expression values of Tetranectin and one other biomarker from Table 3 was assessed. Summary statistics, including a maximum AUC across the two methods, are depicted in Table 57. A significant number of biomarker combinations including Tetranectin result in a maximum AUC above the threshold value, indicating that at least one of the predictive models is predictive of a state of MS in an individual when considering two biomarker combinations, wherein one of the two biomarkers is Tetranectin.

Example 63: Two Biomarker Combinations Including Carcinoembryonic Antigen Related Cell Adhesion Molecule 1 (CEACAM1)

The ability of the predictive models to determine the state (e.g., quiescent or exacerbation) of MS in an individual using expression values of CEACAM1 and one other biomarker from Table 3 was assessed. Summary statistics, including a maximum AUC across the two methods, are depicted in Table 58. A significant number of biomarker combinations including CEACAM1 result in a maximum AUC above the threshold value, indicating that at least one of the predictive models is predictive of a state of MS in an individual when considering two biomarker combinations, wherein one of the two biomarkers is CEACAM1.

Example 64: Two Biomarker Combinations Including 6Ckine

The ability of the predictive models to determine the state (e.g., quiescent or exacerbation) of MS in an individual using expression values of 6Ckine and one other biomarker from Table 3 was assessed. Summary statistics, including a maximum AUC across the two methods, are depicted in Table 59. A significant number of biomarker combinations including 6Ckine result in a maximum AUC above the threshold value, indicating that at least one of the predictive models is predictive of a state of MS in an individual when considering two biomarker combinations, wherein one of the two biomarkers is 6Ckine.

Example 65: Two Biomarker Combinations Including Serum Amyloid P Component (SAP)

The ability of the predictive models to determine the state (e.g., quiescent or exacerbation) of MS in an individual using expression values of SAP and one other biomarker from Table 3 was assessed. Summary statistics, including a maximum AUC across the two methods, are depicted in Table 60. A significant number of biomarker combinations including SAP result in a maximum AUC above the threshold value, indicating that at least one of the predictive models is predictive of a state of MS in an individual when considering two biomarker combinations, wherein one of the two biomarkers is SAP.

Example 66: Two Biomarker Combinations Including Complement Factor H Related Protein 1 (CFHR1)

The ability of the predictive models to determine the state (e.g., quiescent or exacerbation) of MS in an individual using expression values of CFHR1 and one other biomarker from Table 3 was assessed. Summary statistics, including a maximum AUC across the two methods, are depicted in Table 61. A significant number of biomarker combinations including CFHR1 result in a maximum AUC above the threshold value, indicating that at least one of the predictive models is predictive of a state of MS in an individual when considering two biomarker combinations, wherein one of the two biomarkers is CFHR1.

Example 67: Two Biomarker Combinations Including Chemokine CC-4 (HCC-4)

The ability of the predictive models to determine the state (e.g., quiescent or exacerbation) of MS in an individual using expression values of HCC-4 and one other biomarker from Table 3 was assessed. Summary statistics, including a maximum AUC across the two methods, are depicted in Table 62. A significant number of biomarker combinations including HCC-4 result in a maximum AUC above the threshold value, indicating that at least one of the predictive models is predictive of a state of MS in an individual when considering two biomarker combinations, wherein one of the two biomarkers is HCC-4.

Example 68: Two Biomarker Combinations Including Complement C3 (C3)

The ability of the predictive models to determine the state (e.g., quiescent or exacerbation) of MS in an individual using expression values of C3 and one other biomarker from Table 3 was assessed. Summary statistics, including a maximum AUC across the two methods, are depicted in Table 63. A significant number of biomarker combinations including C3 result in a maximum AUC above the threshold value, indicating that at least one of the predictive models is predictive of a state of MS in an individual when considering two biomarker combinations, wherein one of the two biomarkers is C3.

Example 69: Two Biomarker Combinations Including Alpha Fetoprotein (AFP)

The ability of the predictive models to determine the state (e.g., quiescent or exacerbation) of MS in an individual using expression values of AFP and one other biomarker from Table 3 was assessed. Summary statistics, including a maximum AUC across the two methods, are depicted in Table 64. A significant number of biomarker combinations including AFP result in a maximum AUC above the threshold value, indicating that at least one of the predictive models is predictive of a state of MS in an individual when considering two biomarker combinations, wherein one of the two biomarkers is AFP.

Example 70: Two Biomarker Combinations Including Angiopoietin 1 (ANG-1)

The ability of the predictive models to determine the state (e.g., quiescent or exacerbation) of MS in an individual using expression values of ANG-1 and one other biomarker from Table 3 was assessed. Summary statistics, including a maximum AUC across the two methods, are depicted in Table 65. A significant number of biomarker combinations including ANG-1 result in a maximum AUC above the threshold value, indicating that at least one of the predictive models is predictive of a state of MS in an individual when considering two biomarker combinations, wherein one of the two biomarkers is ANG-1.

Example 71: Two Biomarker Combinations Including Interleukin 18 (IL18)

The ability of the predictive models to determine the state (e.g., quiescent or exacerbation) of MS in an individual using expression values of IL18 and one other biomarker from Table 3 was assessed. Summary statistics, including a maximum AUC across the two methods, are depicted in Table 66. A significant number of biomarker combinations including IL18 result in a maximum AUC above the threshold value, indicating that at least one of the predictive models is predictive of a state of MS in an individual when considering two biomarker combinations, wherein one of the two biomarkers is IL18.

Example 72: Two Biomarker Combinations Including Gelsolin

The ability of the predictive models to determine the state (e.g., quiescent or exacerbation) of MS in an individual using expression values of Gelsolin and one other biomarker from Table 3 was assessed. Summary statistics, including a maximum AUC across the two methods, are depicted in Table 67. A significant number of biomarker combinations including Gelsolin result in a maximum AUC above the threshold value, indicating that at least one of the predictive models is predictive of a state of MS in an individual when considering two biomarker combinations, wherein one of the two biomarkers is Gelsolin.

Example 73: Two Biomarker Combinations Including Tenascin C (TN-C)

The ability of the predictive models to determine the state (e.g., quiescent or exacerbation) of MS in an individual using expression values of TN-C and one other biomarker from Table 3 was assessed. Summary statistics, including a maximum AUC across the two methods, are depicted in Table 68. A significant number of biomarker combinations including TN-C result in a maximum AUC above the threshold value, indicating that at least one of the predictive models is predictive of a state of MS in an individual when considering two biomarker combinations, wherein one of the two biomarkers is TN-C.

Example 74: Two Biomarker Combinations Including Vitronectin

The ability of the predictive models to determine the state (e.g., quiescent or exacerbation) of MS in an individual using expression values of Vitronectin and one other biomarker from Table 3 was assessed. Summary statistics, including a maximum AUC across the two methods, are depicted in Table 69. A significant number of biomarker combinations including Vitronectin result in a maximum AUC above the threshold value, indicating that at least one of the predictive models is predictive of a state of MS in an individual when considering two biomarker combinations, wherein one of the two biomarkers is Vitronectin.

Example 75: Two Biomarker Combinations Including Beta 2 Microglobulin (B2M)

The ability of the predictive models to determine the state (e.g., quiescent or exacerbation) of MS in an individual using expression values of B2M and one other biomarker from Table 3 was assessed. Summary statistics, including a maximum AUC across the two methods, are depicted in Table 70. A significant number of biomarker combinations including B2M result in a maximum AUC above the threshold value, indicating that at least one of the predictive models is predictive of a state of MS in an individual when considering two biomarker combinations, wherein one of the two biomarkers is B2M.

Example 76: Two Biomarker Combinations Including Pancreatic Secretory Trypsin Inhibitor (TATI)

The ability of the predictive models to determine the state (e.g., quiescent or exacerbation) of MS in an individual using expression values of TATI and one other biomarker from Table 3 was assessed. Summary statistics, including a maximum AUC across the two methods, are depicted in Table 71. A significant number of biomarker combinations including TATI result in a maximum AUC above the threshold value, indicating that at least one of the predictive models is predictive of a state of MS in an individual when considering two biomarker combinations, wherein one of the two biomarkers is TATI.

Example 77: Two Biomarker Combinations Including Matrix Metalloproteinase 3 (MMP3)

The ability of the predictive models to determine the state (e.g., quiescent or exacerbation) of MS in an individual using expression values of MMP3 and one other biomarker from Table 3 was assessed. Summary statistics, including a maximum AUC across the two methods, are depicted in Table 72. A significant number of biomarker combinations including MMP3 result in a maximum AUC above the threshold value, indicating that at least one of the predictive models is predictive of a state of MS in an individual when considering two biomarker combinations, wherein one of the two biomarkers is MMP3.

Example 78: Two Biomarker Combinations Including Omentin

The ability of the predictive models to determine the state (e.g., quiescent or exacerbation) of MS in an individual using expression values of Omentin and one other biomarker from Table 3 was assessed. Summary statistics, including a maximum AUC across the two methods, are depicted in Table 73. A significant number of biomarker combinations including Omentin result in a maximum AUC above the threshold value, indicating that at least one of the predictive models is predictive of a state of MS in an individual when considering two biomarker combinations, wherein one of the two biomarkers is Omentin.

Example 79: Two Biomarker Combinations Including Interleukin 18 Binding Protein (IL 18bp)

The ability of the predictive models to determine the state (e.g., quiescent or exacerbation) of MS in an individual using expression values of IL 18bp and one other biomarker from Table 3 was assessed. Summary statistics, including a maximum AUC across the two methods, are depicted in Table 74. A significant number of biomarker combinations including IL 18bp result in a maximum AUC above the threshold value, indicating that at least one of the predictive models is predictive of a state of MS in an individual when considering two biomarker combinations, wherein one of the two biomarkers is IL 18bp.

Example 80: Two Biomarker Combinations Including Apolipoprotein D (ApoD)

The ability of the predictive models to determine the state (e.g., quiescent or exacerbation) of MS in an individual using expression values of ApoD and one other biomarker from Table 3 was assessed. Summary statistics, including a maximum AUC across the two methods, are depicted in Table 75. A significant number of biomarker combinations including ApoD result in a maximum AUC above the threshold value, indicating that at least one of the predictive models is predictive of a state of MS in an individual when considering two biomarker combinations, wherein one of the two biomarkers is ApoD.

Example 81: Two Biomarker Combinations Including Monocyte Chemotactic Protein 4 (MCP-4)

The ability of the predictive models to determine the state (e.g., quiescent or exacerbation) of MS in an individual using expression values of MCP-4 and one other biomarker from Table 3 was assessed. Summary statistics, including a maximum AUC across the two methods, are depicted in Table 76. A significant number of biomarker combinations including MCP-4 result in a maximum AUC above the threshold value, indicating that at least one of the predictive models is predictive of a state of MS in an individual when considering two biomarker combinations, wherein one of the two biomarkers is MCP-4.

Example 82: Two Biomarker Combinations Including Apolipoprotein E (Apo-E)

The ability of the predictive models to determine the state (e.g., quiescent or exacerbation) of MS in an individual using expression values of Apo-E and one other biomarker from Table 3 was assessed. Summary statistics, including a maximum AUC across the two methods, are depicted in Table 77. A significant number of biomarker combinations including Apo-E result in a maximum AUC above the threshold value, indicating that at least one of the predictive models is predictive of a state of MS in an individual when considering two biomarker combinations, wherein one of the two biomarkers is Apo-E.

Example 83: Two Biomarker Combinations Including ST2

The ability of the predictive models to determine the state (e.g., quiescent or exacerbation) of MS in an individual using expression values of ST2 and one other biomarker from Table 3 was assessed. Summary statistics, including a maximum AUC across the two methods, are depicted in Table 78. A significant number of biomarker combinations including ST2 result in a maximum AUC above the threshold value, indicating that at least one of the predictive models is predictive of a state of MS in an individual when considering two biomarker combinations, wherein one of the two biomarkers is ST2.

Example 84: Two Biomarker Combinations Including Thrombospondin 1

The ability of the predictive models to determine the state (e.g., quiescent or exacerbation) of MS in an individual using expression values of Thrombospondin 1 and one other biomarker from Table 3 was assessed. Summary statistics, including a maximum AUC across the two methods, are depicted in Table 79. A significant number of biomarker combinations including Thrombospondin 1 result in a maximum AUC above the threshold value, indicating that at least one of the predictive models is predictive of a state of MS in an individual when considering two biomarker combinations, wherein one of the two biomarkers is Thrombospondin 1.

Example 85: Two Biomarker Combinations Including Gastric Inhibitory Polypeptide (GIP)

The ability of the predictive models to determine the state (e.g., quiescent or exacerbation) of MS in an individual using expression values of GIP and one other biomarker from Table 3 was assessed. Summary statistics, including a maximum AUC across the two methods, are depicted in Table 80. A significant number of biomarker combinations including GIP result in a maximum AUC above the threshold value, indicating that at least one of the predictive models is predictive of a state of MS in an individual when considering two biomarker combinations, wherein one of the two biomarkers is GIP.

Example 86: Two Biomarker Combinations Including Matrix Metalloproteinase 7 (MMP7)

The ability of the predictive models to determine the state (e.g., quiescent or exacerbation) of MS in an individual using expression values of MMP7 and one other biomarker from Table 3 was assessed. Summary statistics, including a maximum AUC across the two methods, are depicted in Table 81. A significant number of biomarker combinations including MMP7 result in a maximum AUC above the threshold value, indicating that at least one of the predictive models is predictive of a state of MS in an individual when considering two biomarker combinations, wherein one of the two biomarkers is MMP7.

Example 87: Two Biomarker Combinations Including Intercellular Adhesion Molecule 1 (ICAM-1)

The ability of the predictive models to determine the state (e.g., quiescent or exacerbation) of MS in an individual using expression values of ICAM-1 and one other biomarker from Table 3 was assessed. Summary statistics, including a maximum AUC across the two methods, are depicted in Table 82. A significant number of biomarker combinations including ICAM-1 result in a maximum AUC above the threshold value, indicating that at least one of the predictive models is predictive of a state of MS in an individual when considering two biomarker combinations, wherein one of the two biomarkers is ICAM-1.

Example 88: Additional Biomarker Combinations

The ability of the predictive model to determine the state (e.g., quiescent or exacerbation) of MS in an individual using expression values of additional biomarker combinations from Table 3 was assessed. Specifically, biomarker combinations were as follows: 1) 10 biomarkers from set 1, 2) 10 biomarkers from set 1 and 10 biomarkers from set 2, 3) 10 biomarkers from set 1, 10 biomarkers from set 2, and 20 biomarkers from set 3, 4) 10 biomarkers from set 1, 10 biomarkers from set 2, 20 biomarkers from set 3, and 20 biomarkers from set 4, and 5) 10 biomarkers from set 1, 10 biomarkers from set 2, 20 biomarkers from set 3, 20 biomarkers from set 4, and 20 biomarkers from set 5.

Three methods were used for the assessment of the predictive model: random forest, gradient boosting, and LASSO. For all analyses, the area under the curve (AUC) was the primary accuracy metric used. For each analysis, the mean AUC is depicted in Table 83. AUCs greater than a threshold value of 0.6 are considered predictive. As shown in Table 83, each combination of biomarkers (e.g., N=10, 20, 40, 60, or 80 total biomarkers) yields an AUC above the threshold value, indicating that the predictive model is predictive of a state of MS in an individual.

In particular, when the predictive model was assessed using a random forest method, the highest mean AUC (mean AUC=0.857) was observed for N=20 total biomarkers (biomarkers from set 1 and set 2). When the predictive model was assessed using a gradient boosting method, the highest mean AUC (mean AUC=0.873) was observed for N=40 total biomarkers (biomarkers from set 1, set 2, and set 3). When the predictive model was assessed using a LASSO method, the highest mean AUC (mean AUC=0.829) was observed for N=60 total biomarkers (biomarkers from set 1, set 2, set 3, and set 4).

Methods

General Study Design and Study Population

Test samples were obtained from subjects as a part of the Accelerated Cure Project (ACP), which includes 10 leading MS clinics across the United States. The study was approved at the institutional review board at all participating centers and all patients gave written informed consent. Eligible subjects included in the ACP study included individuals with at least one central nervous system demyelinating event characteristic of MS, transverse myelitis (TM), acute disseminated encephalomyelitis (ADEM), neuromyelitis optica (NMO), and optic neuritis (ON). Subjects were ineligible if the individual presented with clinical or radiological evidence of stroke, meningitis, neoplastic, peripheral nervous system or primary muscle disease, or other well characterized and defined diseases of the nervous system with the exception of MS, TM, ADEM, NMO, ON. Ineligible subjects also included individuals with a history of blood borne pathogens, history of allogeneic bone marrow transplant, and individuals who weigh less than 37 pounds due to limits on blood collection.

Blood Collection

Blood serum samples were collected accorded to sample processing instructions provided by the Accelerated Cure Project. Specifically, blood (up to 110 mL) was drawn into tiger top SST tubes, inverted 5 times, and left to sit in an upright position for 30-60 minutes to allow clotting. Tubes were centrifuged at 3,000 RPM (approximately 1000×g) for 10 minutes. Serum was then transferred in 0.5 mL aliquots into 1.0 mL cryovials using a plastic pipette. Cryovials were stored frozen at the collection site at −70 to −80° C. until shipment to SeraCare. Samples were batched at least monthly and shipped frozen on dry ice using overnight delivery. Cryovials were stored frozen at SeraCare at −80° C.

Marker Quantification

Multiplex analysis was performed using multiplex luminex analysis (Rules-Based Medicine (Austin, TX)), which uses Multi-Analyte Profiles (MAPs) based on powerful Luminex xMAP® technology to discover biomarker expression values within very small sample volumes.

Statistical Modeling

Logistic Regression

Logistic Regression is the traditional predictive modeling method of choice for dichotomous response variables; e.g., positive diagnosis vs negative diagnosis. It can be used to model both linear and non-linear aspects of the data variables. A series of logistic regression models were fit to the quantitative expression values of one or more biomarkers. Specifically, logistic regression models were generated for one biomarker (univariate), two biomarkers, or the top 10, top 20, top 40, top 60, or top 80 biomarkers as described above.

Random Forest (RF)

Random Forest models are based upon the idea of creating hundreds of regression trees as models. Each regression tree model is created with a uniform number of terminal nodes ("leaves") at the end of the branches of the tree. To estimate the regression value of a new individual, or to assign the individual to a class, quantitative expression levels of biomarkers from a test sample obtained from the individual is evaluated within each of the regression tree models. The output prediction (i.e., regression value if continuous data, classification if binary data) from all trees is then averaged to create the final regression value or class prediction. In the case of regression values, averaging may be obtained by a weighted average; in class prediction, simply by voting.

The Random Forest methodology was as follows. First, a bootstrap sample (i.e., a sample with replacement) was drawn from the original data. Then a regression tree was "grown" from each bootstrap sample; i.e., at each node one randomly samples p of the n biomarkers measured, and selects the best biomarker and the best value of that biomarker to split the data into pure subsets from those biomarkers. Data from "training" subjects were used to build the tree models. Then, new data was predicted by aggregating the predictions of the various regression trees thus derived. Then, new data was predicted by aggregating the predictions of the various regression trees thus derived. For each subject sample k, where the k subject samples were different from those used in training the model (i.e., all k samples are "out of the bag"), the response estimates was averaged over the trees, given as $\hat{y}_k$. The random forest prediction algorithm was then given by the equation:

$$\widehat{PE}_f = E_{XY}(Y - \bar{h}(X))^2 = \frac{1}{k}\sum(y_k - \hat{y}_k)^2$$

where $\widehat{PE}_f$ was a test set estimate of the generalization error of $PE_f$, and $$\bar{h}(X) = \left(\frac{1}{L}\right)\sum h(x; \theta_l)$$

was the random forest prediction. The collection of tree predictors was given by $h(x; \theta_l)$, l=1, ..., L, where $\theta_l$ is a random vector. Y represented the actual ground truth (e.g., the indication).

The variable importance was then estimated. In every regression tree thus grown in the random forest, one calculated the prediction error for that tree, $$PE_t = \frac{1}{K}\sum(y_k - \hat{y}_k)^2,$$

as predicted by the lth tree predictor, $h(x; \theta_l)$. One then randomly permuted the values of a biomarker variable i in the "out of bag" cases, and computed the prediction error as predicted by the lth tree predictor. Importance (Imp) was given as the variable i for $Imp_i = PE_t i - PE_t$ for the ith biomarker for lth tree. The variable importance of the ith variable was computed $I_i =$ $$\frac{\overline{Imp}_i}{SE(Imp_i)}$$

where $\overline{Imp}_i$ was the average and standard area of importance of ith variable over all L trees.

Gradient Boosting

Boosted Trees models are based upon the idea of computing a sequence of trees, where each successive tree is built by predicting the residuals of the preceding tree. Put another way, boosting will generate a sequence of classifiers, where each consecutive classifier in the sequence is an "expert" in classifying observations that were not well classified by those preceding it. Gradient boosting is described in further detail by Friedman, Jerome H. "Greedy function approximation: a gradient boosting machine." *Annals of statistics* (2001): 1189-1232, which is hereby incorporated by reference in its entirety.

The variable importance input variables for a GBM model is as follows. For an output $\hat{F}(x)$, the relative influence $I_j$ or input variable $x_j$ is estimated as:

$$\hat{I}_j^2(T) = \Sigma_{t=1}^{J-1} \hat{i}_t^2 1(v_t = j) \quad (1)$$

where the summation is over the non-terminal nodes t of the J-terminal node tree T, $v_t$ is the splitting variable associated with node t, and $\hat{i}_t^2$ is the corresponding empirical improvement in squared-error as a result of the split. For a collection of decision trees $\{T_m\}_1^M$ obtained through boosting, Equation 1 above can be generalized by its overage over all of the trees in the sequence as:

$$\hat{I}_j^2 = \frac{1}{M} \sum_{m=1}^{M} \hat{I}_j^2(T_m) \quad (2)$$

The importance of each input variable (e.g., biomarker) can be ranked according to their respective relative influence $I_j$.

Extreme Gradient Boosting (XGB)

XGB is an independent implementation of boosted trees and is hence similar in approach to the GBM method. XGB uses additional regularization within its model in order to limit overfitting of the data (regularization is a way of penalizing model complexity, so as to avoid highly complex models that fit the training data well but don't generalize well to new data). XGB is described in further detail by Chen et al (Tianqi Chen and Carlos Guestrin. 2016. XGBoost: A Scalable Tree Boosting System. In *Proceedings of the 22nd ACM SIGKDD International Conference on Knowledge Discovery and Data Mining* (KDD '16). ACM, New York, NY, USA, 785-794), which is hereby incorporated by reference in its entirety.

The variable importance of input variables for a XGB model is similar to the GBM model. Specifically, the input variables can be ranked according to a "gain" where gain is the improvement in accuracy brought by an input feature to the branches it is on. The idea is that before adding a new split on a feature X to the branch, there were some wrongly classified elements. After adding the split on this feature, there are two new branches, and each of these branches is more accurate (one branch saying if your observation is on this branch then it should be classified as 1, and the other branch saying the exact opposite).

Least Absolute Shrinkage and Selection Operator (LASSO)

Penalized regression model methods are a set of statistical techniques that select subsets of variables to include in a model and determine stable coefficients for the variables. These methods are particularly useful when variables are correlated, and include ridge regression, Lasso, Elastic Net, and other methods. All of these methods have the characteristic that they shrink (penalize) the coefficients in the regression model.

Least Absolute Shrinkage and Selection Operator (LASSO or Lasso) was used to prioritize biomarkers (based on R2 values) and to obtain a Lasso model. The "lasso" in this model minimized the residual sum of the square, subject to the sum of the absolute value of the coefficients being less than a constant. See R. Tibshirani, J. Royal Stat. Soc., series B 1996, 58(1):267-288. The Lasso method produced interpretable models, such as subset selection, and exhibited the stability of ridge regression (a statistical method that shrinks and stabilizes coefficients in regression models with multicollinearity). See W. Mendenhall and T. Sincich, A Second Course in Statistics: Regression Analysis, 6th edition 2003, Pearson Prentice Hall, Inc., Upper Saddle River, NJ.

Discussion of Methods

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation.

Additional Embodiments

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Tables

TABLE 1

| Phase 1 Cohort Phase I-Accelerated Cure Project (ACP) Cohort | |
| --- | --- |
| Total Samples (N) | 125 |
| Female | 94 |
| Male | 31 |
| Age range | 20-60 years old |
| Years since diagnosis | 0-10 |
| Current State | |
| Exacerbation | 60 |
| Quiescent | 65 |

TABLE 2

| Univariate Analysis of Identified Biomarker Candidates | | |
| --- | --- | --- |
| Analyte | P-value | AUC |
| 1  6Ckine | 0.052563 | 0.607949 |
| 2  Adiponectin | 0.781103 | 0.565641 |

TABLE 2-continued

Univariate Analysis of Identified Biomarker Candidates

| Analyte | P-value | AUC |
|---|---|---|
| 3 Adrenomedullin (ADM) | 0.031053 | 0.621538 |
| 4 Alpha-1 Antitrypsin (AAT) | 0.142885 | 0.546667 |
| 5 Alpha-1-Microglobulin (A1Micro) | 0.50261 | 0.528718 |
| 6 Alpha-2-Macroglobulin (A2Macro) | 0.396704 | 0.503333 |
| 7 Alpha-Fetoprotein (AFP) | 0.095375 | 0.546923 |
| 8 Amphiregulin (AR) | 0.795756 | 0.495256 |
| 9 Angiogenin | 0.319132 | 0.582308 |
| 10 Angiopoietin 1 (ANG-1) | 0.601165 | 0.539103 |
| 11 Angiopoietin 2 (ANG-2) | 0.132375 | 0.559615 |
| 12 Angiotensin Converting Enzyme (ACE) | 0.355858 | 0.555128 |
| 13 Antileukoproteinase (ALP) | 0.252867 | 0.547821 |
| 14 Antithrombin III (ATIII) | 0.487011 | 0.543077 |
| 15 Apolipoprotein A (Apo-A) | 0.179049 | 0.482308 |
| 16 Apolipoprotein D (Apo-D) | 0.514727 | 0.551026 |
| 17 Apolipoprotein E (Apo-E) | 0.025992 | 0.599744 |
| 18 AXL Receptor Tyrosine Kinase (AXL) | 0.615571 | 0.500128 |
| 19 B-cell activating factor (BAFF) | 0.776797 | 0.492436 |
| 20 B Lymphocyte Chemoattractant (BLC) | 0.490296 | 0.490513 |
| 21 Beta-Amyloid (1-40) (AB-40) | 0.24407 | 0.569744 |
| 22 Beta-Amyloid (1-42) (AB-42) | 0.457162 | 0.547564 |
| 23 Beta-2 Microglobulin (B2M) | 0.249675 | 0.560256 |
| 24 Betacellulin (BTC) | NA | NA |
| 25 Brain Derived Neurotrophic Factor (BDNF) | 0.800508 | 0.533462 |
| 26 C-Reactive Protein (CRP) | 0.117169 | 0.548846 |
| 27 Cadherin 1 (E-Cad) | 0.728647 | 0.550513 |
| 28 Calbindin | 0.978126 | 0.508205 |
| 29 Cancer Antigen 125 (CA-125) | 0.940383 | 0.479103 |
| 30 Cancer Antigen 15-3 (CA 15-3) | 0.452502 | 0.54141 |
| 31 Cancer Antigen 19-9 (CA 19-9) | 0.656405 | 0.503333 |
| 32 Carbonic anhydrase 9 (CA-9) | 0.240729 | 0.542436 |
| 33 Carcinoembryonic Antigen (CEA) | 0.307703 | 0.563205 |
| 34 Carcinoembryonic antigen related cell adhesion molecule 1 (CEACAM1) | 0.183887 | 0.564872 |
| 35 Cathepsin D | 0.027467 | 0.620513 |
| 36 CD40 Ligand (CD40-L) | 0.686825 | 0.517692 |
| 37 CD163 | 0.299555 | 0.546154 |
| 38 Ceruloplasmin | 0.785238 | 0.54359 |
| 39 Chemokine CC-4 (HCC-4) | 0.723205 | 0.495256 |
| 40 Chromogranin A (CgA) | 0.986027 | 0.537436 |
| 41 Ciliary Neurotrophic Factor (CNTF) | 0.146877 | 0.553718 |
| 42 Clusterin (CLU) | 0.864157 | 0.491154 |
| 43 Complement C3 (C3) | 0.399032 | 0.513205 |
| 44 Complement Factor H (CFH) | 0.043004 | 0.581282 |
| 45 Complement Factor H Related Protein 1 (CFHR1) | 0.956458 | 0.502949 |
| 46 Cystatin B | 0.029893 | 0.641282 |
| 47 CystatinC | 0.135032 | 0.572051 |
| 48 Decorin | 0.416237 | 0.547692 |
| 49 Dickkopf related protein 1 (DKK-1) | 0.429032 | 0.488333 |
| 50 Dopamine beta hydroxylase (DBH) | 0.800301 | 0.527821 |
| 51 E-Selectin | 0.010997 | 0.632179 |
| 52 EN-RAGE | 0.671174 | 0.54141 |
| 53 Eotaxin-1 | 0.957069 | 0.501923 |
| 54 Eotaxin-2 | 0.498705 | 0.572308 |
| 55 Eotaxin-3 | 0.341768 | 0.509487 |
| 56 Epidermal Growth Factor (EGF) | 0.923961 | 0.514615 |
| 57 Epidermal Growth Factor Receptor (EGFR) | 0.974963 | 0.503846 |
| 58 Epiregulin (EPR) | 0.871179 | 0.475641 |
| 59 Epithelial Derived Neutrophil Activating Protein 78 (ENA-78) | 0.817716 | 0.520769 |
| 60 Erythropoietin (EPO) | 0.892677 | 0.453974 |
| 61 Factor VII | 0.062994 | 0.578718 |
| 62 Fas Ligand (FasL) | 0.181567 | 0.545385 |
| 63 FASLG Receptor (FAS) | 0.737959 | 0.502051 |
| 64 Ferritin (FRTN) | 0.74802 | 0.535128 |
| 65 Fibrinogen | 0.581972 | 0.488077 |
| 66 Fibulin 1C (Fib1C) | 0.417486 | 0.577821 |
| 67 Ficolin 3 | 0.050576 | 0.613333 |
| 68 Follicle Stimulating Hormone (FSH) | 0.928345 | 0.529744 |
| 69 Gastric inhibitory polypeptide (GIP) | 0.125713 | 0.588077 |
| 70 Gelsolin | 0.438391 | 0.466923 |
| 71 Glucagon Like Peptide-1 (GLP-1) | 0.863589 | 0.512051 |
| 72 Glycogen phosphorylase isoenzyme BB (GPBB) | 0.243271 | 0.517051 |
| 73 Granulocyte Colony Stimulating Factor (GCSF) | 0.415708 | 0.507051 |
| 74 Granulocyte Macrophage Colony Stimulating Factor (GM-CSF) | NA | NA |
| 75 Growth differentiation factor 15 (GDF-15) | 0.411947 | 0.459872 |
| 76 Growth Hormone (GH) | 0.326537 | 0.605769 |
| 77 Growth Regulated alpha protein (GROalpha) | 0.499583 | 0.535769 |

TABLE 2-continued

Univariate Analysis of Identified Biomarker Candidates

| Analyte | P-value | AUC |
| --- | --- | --- |
| 78 Haptoglobin | 0.130474 | 0.581538 |
| 79 Heat Shock protein 70 (HSP-70) | 0.933051 | 0.482308 |
| 80 Heparin Binding EGF Like Growth Factor (HB-EGF) | 0.350227 | 0.529487 |
| 81 Hepatocyte Growth Factor (HGF) | 0.612673 | 0.493846 |
| 82 Human Chorionic Gonadotropin beta (hCG) | 0.303706 | 0.528077 |
| 83 Immunoglobulin A (IgA) | 0.05694 | 0.583846 |
| 84 Immunoglobulin E (IgE) | 0.121457 | 0.582692 |
| 85 Immunoglobulin M (IgM) | 0.509751 | 0.541538 |
| 86 Insulin | 0.074983 | 0.607949 |
| 87 Insulin like Growth Factor Binding Protein 2 (IGFBP2) | 0.232107 | 0.565897 |
| 88 Intercellular Adhesion Molecule 1 (ICAM-1) | 0.539951 | 0.494103 |
| 89 Interferon alpha (IFN-alpha) | NA | NA |
| 90 Interferon gamma (IFN-gamma) | NA | NA |
| 91 Interferon gamma Induced Protein 10 (IP-10) | 0.351582 | 0.521667 |
| 92 Interferon inducible T cell alpha chemoattractant (ITAC) | 0.578611 | 0.562051 |
| 93 Interleukin 1 alpha (IL-1alpha) | NA | NA |
| 94 Interleukin 1 beta (IL-1beta) | NA | NA |
| 95 Interleukin 1 receptor antagonist (IL1ra) | 0.011251 | 0.584103 |
| 96 Interleukin 2 (IL-2) | NA | NA |
| 97 Interleukin 2 receptor alpha (IL2receptoralpha) | 0.366795 | 0.562051 |
| 98 Interleukin 3 (IL-3) | 0.230016 | 0.543718 |
| 99 Interleukin 4 (IL-4) | NA | NA |
| 100 Interleukin 5 (IL-5) | NA | NA |
| 101 Interleukin 6 (IL-6) | 0.351258 | 0.497692 |
| 102 Interleukin 6 receptor (IL6r) | 0.117127 | 0.580256 |
| 103 Interleukin 6 receptor subunit beta (IL6Rbeta) | 0.00971 | 0.630385 |
| 104 Interleukin 7 (IL-7) | 0.335385 | 0.501538 |
| 105 Interleukin 8 (IL-8) | 0.966306 | 0.543846 |
| 106 Interleukin 10 (IL-10) | 0.076322 | 0.572308 |
| 107 Interleukin 12 Subunit p40 (IL12p40) | 0.874175 | 0.522179 |
| 108 Interleukin 12 Subunit p70 (IL12p70) | NA | NA |
| 109 Interleukin 13 (IL13) | 0.417776 | 0.490513 |
| 110 Interleukin 15 (IL15) | 0.108857 | 0.563333 |
| 111 Interleukin 16 (IL16) | 0.855117 | 0.518974 |
| 112 Interleukin 17 (IL17) | NA | NA |
| 113 Interleukin 18 (IL18) | 0.013593 | 0.627564 |
| 114 Interleukin 18 binding protein (IL18bp) | 0.09585 | 0.580513 |
| 115 Interleukin 22 (IL22) | 0.232761 | 0.569615 |
| 116 Interleukin 23 (IL23) | NA | NA |
| 117 Interleukin 31 (IL31) | 0.28503 | 0.534103 |
| 118 Kidney Injury Molecule 1 (KIM-1) | 0.194814 | 0.482179 |
| 119 Lactoferrin (LTF) | 0.28361 | 0.552308 |
| 120 Latency Associated Peptide of Transforming Growth Factor beta 1 (LAP TGF b1) | 0.691925 | 0.516795 |
| 121 Leptin | 0.03778 | 0.598846 |
| 122 Leptin Receptor (Leptin R) | 0.246461 | 0.586282 |
| 123 Leucine rich alpha 2 glycoprotein (LRG1) | 0.537216 | 0.505385 |
| 124 Luteinizing Hormone (LH) | 0.299057 | 0.532179 |
| 125 Macrophage Colony Stimulating Factor 1 (M-CSF) | 0.701042 | 0.491538 |
| 126 Macrophage Derived Chemokine (MDC) | 0.016395 | 0.625897 |
| 127 Macrophage Inflammatory Protein 1 alpha (MIP1-alpha) | 0.030048 | 0.564744 |
| 128 Macrophage Inflammatory Protein 1 beta (MIP1-beta) | 0.980452 | 0.502436 |
| 129 Macrophage Inflammatory Protein 3 alpha (MIP3-alpha) | 0.754238 | 0.550513 |
| 130 Macrophage Inflammatory Protein 3 beta (MIP3-beta) | 0.044677 | 0.620769 |
| 131 Macrophage Migration Inhibitory Factor (MIF) | 0.318299 | 0.470897 |
| 132 Macrophage Stimulating Protein (MSP) | 0.217264 | 0.514487 |
| 133 Mast stem cell growth factor receptor (SCFR) | 0.070457 | 0.595513 |
| 134 Matrix Metalloproteinase 1 (MMP-1) | 0.785116 | 0.550513 |
| 135 Matrix Metalloproteinase 2 (MMP-2) | 0.271719 | 0.535385 |
| 136 Matrix Metalloproteinase 3 (MMP-3) | 0.216694 | 0.542692 |
| 137 Matrix Metalloproteinase 7 (MMP-7) | 0.303586 | 0.557821 |
| 138 Matrix Metalloproteinase 9 (MMP-9) | 0.650263 | 0.500128 |
| 139 Matrix Metalloproteinase 9 total (MMP-9 total) | 0.939975 | 0.507308 |
| 140 Matrix Metalloproteinase 10 (MMP-10) | 0.352371 | 0.578462 |
| 141 Microalbumin | 0.195335 | 0.448077 |
| 142 Monocyte Chemotactic Protein 1 (MCP-1) | 0.12657 | 0.584103 |
| 143 Monocyte Chemotactic Protein 2 (MCP-2) | 0.427973 | 0.49 |
| 144 Monocyte Chemotactic Protein 3 (MCP-3) | NA | NA |
| 145 Monocyte Chemotactic Protein 4 (MCP-4) | 0.693488 | 0.542949 |
| 146 Monokine Induced by Gamma Interferon (MIG) | 0.610324 | 0.534872 |
| 147 Myeloid Progenitor Inhibitory Factor 1 (MPIF-1) | 0.278631 | 0.488974 |
| 148 Myeloperoxidase(MPO) | 0.93055 | 0.521795 |
| 149 Myoglobin | 0.056264 | 0.625256 |
| 150 Nerve Growth Factor beta (NGF-beta) | NA | NA |
| 151 Neurofilament heavy polypeptide (NF-H) | 0.29952 | 0.532179 |
| 152 Neuron Specific Enolase (NSE) | 0.246881 | 0.449744 |

TABLE 2-continued

Univariate Analysis of Identified Biomarker Candidates

| Analyte | P-value | AUC |
|---|---|---|
| 153 Neuronal Cell Adhesion Molecule (NrCAM) | 0.043976 | 0.605 |
| 154 Neuropilin-1 | 0.525837 | 0.531795 |
| 155 Neutrophil Activating Peptide 2 (NAP-2) | 0.900622 | 0.51141 |
| 156 Omentin | 0.655919 | 0.524359 |
| 157 Osteocalcin | 0.999932 | 0.495 |
| 158 Osteopontin | 0.97764 | 0.510256 |
| 159 Osteoprotegerin (OPG) | 0.281271 | 0.54359 |
| 160 P-Selectin | 0.573835 | 0.506026 |
| 161 Pancreatic Polypeptide (PPP) | 0.279735 | 0.528205 |
| 162 Pancreatic secretory trypsin inhibitor (TATI) | 0.744834 | 0.534487 |
| 163 Paraoxonase-1 (PON1) | 0.001273 | 0.645897 |
| 164 Pepsinogen-I (PGI) | 0.490286 | 0.527179 |
| 165 Periostin | 0.410303 | 0.480513 |
| 166 Pigment Epithelium Derived Factor (PEDF) | 0.002423 | 0.641282 |
| 167 Placenta Growth Factor (PLGF) | 0.063951 | 0.572564 |
| 168 Plasminogen Activator Inhibitor 1 (PAI-1) | 0.12149 | 0.587436 |
| 169 Platelet endothelial cell adhesion molecule (PECAM-1) | 0.839889 | 0.491282 |
| 170 Platelet Derived Growth Factor BB (PDGF-BB) | 0.430758 | 0.535641 |
| 171 Prolactin (PRL) | 0.278799 | 0.562821 |
| 172 Prostate Specific Antigen Free (PSA-f) | 0.285199 | 0.51859 |
| 173 Protein DJ-1 (DJ-1) | 0.241978 | 0.529231 |
| 174 Pulmonary and Activation Regulated Chemokine (PARC) | 0.088935 | 0.592436 |
| 175 Pulmonary surfactant associated protein D (SP-D) | 0.057952 | 0.584615 |
| 176 Receptor for advanced glycosylation end products (RAGE_ | 0.008763 | 0.614744 |
| 177 Resistin | 0.300862 | 0.555385 |
| 178 S100 calcium binding protein B (S100B) | 0.304565 | 0.556026 |
| 179 Serum Amyloid A Protein (SAA) | 0.226538 | 0.523077 |
| 180 Serum Amyloid P Component (SAP) | 0.077886 | 0.575897 |
| 181 Sex Hormone Binding Globulin (SHBG) | 0.076998 | 0.576795 |
| 182 Sortilin | 0.369815 | 0.536154 |
| 183 ST2 | 0.906613 | 0.496795 |
| 184 Stem Cell Factor (SCF) | 0.157098 | 0.542949 |
| 185 Stromal cell derived factor 1 (SDF-1) | 0.014087 | 0.631282 |
| 186 Superoxide Dismutase 1 soluble (SOD-1) | 0.955132 | 0.502308 |
| 187 T Cell Specific Protein RANTES (RANTES) | 0.515373 | 0.544231 |
| 188 T Lymphocyte Secreted Protein I 309 (I309) | 0.222034 | 0.50641 |
| 189 Tamm Horsfall Urinary Glycoprotein (THP) | 0.863214 | 0.527051 |
| 190 Tenascin C (TN-C) | 0.347787 | 0.525641 |
| 191 Tetranectin | 0.759074 | 0.518077 |
| 192 Thrombin Activatable Fibrinolysis (TAFI) | 0.669463 | 0.529231 |
| 193 Thrombospondin-1 | 0.731679 | 0.52641 |
| 194 Thymus and activation regulated chemokine (TARC) | 0.243371 | 0.546795 |
| 195 Thyroid Stimulating Hormone (TSH) | 0.36033 | 0.495513 |
| 196 Thyroxine Binding Globulin (TBG) | 0.193485 | 0.586154 |
| 197 Tissue Inhibitor of Metalloproteinases 1 (TIMP-1) | 0.51884 | 0.562436 |
| 198 Tissue Inhibitor of Metalloproteinases 2 (TIMP-2) | 0.993488 | 0.51141 |
| 199 TNF Related Apoptosis Inducing Ligand Receptor 3 (TRAIL-R3) | 0.113077 | 0.565 |
| 200 Transferrin receptor protein 1 (TFR1) | 0.856601 | 0.516667 |
| 201 Transforming Growth Factor beta 3 (TGF-beta3) | NA | NA |
| 202 Tumor Necrosis Factor alpha (TNF-alpha) | 0.312678 | 0.538718 |
| 203 Tumor Necrosis Factor beta (TNF-beta) | NA | NA |
| 204 Tumor necrosis factor ligand superfamily member 12 (Tweak) | 0.951312 | 0.509359 |
| 205 Tumor necrosis factor ligand superfamily member 13 (APRIL) | 0.235847 | 0.557436 |
| 206 Tumor Necrosis Factor Receptor I (TNF-RI) | 0.329747 | 0.548718 |
| 207 Tumor necrosis factor receptor 2 (TNFR2) | 0.245271 | 0.546667 |
| 208 Vascular Cell Adhesion Molecule 1 (VCAM-1) | 0.009169 | 0.618718 |
| 209 Vascular Endothelial Growth Factor (VEGF) | 0.032693 | 0.600513 |
| 210 Visceral adipose tissue derived serpin A12 (Vaspin) | 0.227509 | 0.519487 |
| 211 Visfatin | 0.591463 | 0.524615 |
| 212 Vitamin D Binding Protein (VDBP) | 0.833476 | 0.526154 |
| 213 Vitronectin | 0.571112 | 0.499231 |
| 214 von Willebrand Factor (vWF) | 0.313429 | 0.534872 |
| 215 YKL-40 | 0.803751 | 0.521026 |

TABLE 3

Ranked Biomarker List

| Biomarker Number | Biomarker Set | Accession Number(s) | Biomarker |
|---|---|---|---|
| 1 | 1 | NM_000446 | Paraoxonase 1 (PON1) |
| 2 | 1 | NM_203377 | Myoglobin |

TABLE 3-continued

Ranked Biomarker List

| Biomarker Number | Biomarker Set | Accession Number(s) | Biomarker |
|---|---|---|---|
| 3 | 1 | NM_000602 | Plasminogen Activator Inhibitor (PAI1) |
| 4 | 1 | NM_003254 | Tissue Inhibitor of Metalloproteinases 1 (TIMP1) |
| 5 | 1 | NM_000609 | Stromal Cell Derived Factor 1 (SDF1) |
| 6 | 1 | NM_002184 | Interleukin 6 Receptor Subunit Beta (IL6Rbeta) |
| 7 | 1 | NM_000100 | Cystatin B |
| 8 | 1 | NG_001019, P01854 | Immunoglobulin E (IgE) |
| 9 | 1 | NM_006274 | Macrophage Inflammatory Protein 3 beta (MIP3beta) |
| 10 | 1 | NM_001078 | Vascular Cell Adhesion Molecule 1 (VCAM1) |
| 11 | 2 | NM_002990 | Macrophage Derived Chemokine (MDC) |
| 12 | 2 | NM_001025366 | Vascular Endothelial Growth Factor (VEGF) |
| 13 | 2 | NM_003665 | Ficolin 3 |
| 14 | 2 | NG_001019, P01876 | Immunoglobulin A (IgA) |
| 15 | 2 | NM_000131 | Factor VII |
| 16 | 2 | NM_000565 | Interleukin 6 Receptor (IL6R) |
| 17 | 2 | NM_001136 | Receptor for Advanced Glycosylation End Products (RAGE) |
| 18 | 2 | NM_006486 | Fibulin 1C (FIB1C) |
| 19 | 2 | NM_001302123 | Interferon Inducible T Cell Alpha Chemoattractant (ITAC) |
| 20 | 2 | NM_000515 | Growth Hormone (GH) |
| 21 | 3 | NM_001945 | Heparin Binding EGF Like Growth Factor (HBEGF) |
| 22 | 3 | NM_001037132 | Neuronal Cell Adhesion Molecule (NrCAM) |
| 23 | 3 | NM_001511 | Growth Regulated Alpha Protein (GROalpha) |
| 24 | 3 | NM_004864 | Growth Differentiation Factor 15 (GDF15) |
| 25 | 3 | NM_000222 | Mast Stem Cell Growth Factor Receptor (SCFR) |
| 26 | 3 | NM_004360 | Cadherin 1 (Ecad) |
| 27 | 3 | NM_001097577 | Angiogenin |
| 28 | 3 | NM_002959 | Sortilin |
| 29 | 3 | NM_001002235 | Alpha 1 Antitrypsin (AAT) |
| 30 | 3 | NG_001019, P01871 | Immunoglobulin M (IgM) |
| 31 | 3 | NM_002988 | Pulmonary and Activation Regulated Chemokine (PARC) |
| 32 | 3 | NM_003019 | Pulmonary Surfactant Associated Protein D (SP-D) |
| 33 | 3 | NM_001145645 | B Cell Activating Factor (BAFF) |
| 34 | 3 | NM_001124 | Adrenomedullin (ADM) |
| 35 | 3 | NM_002615 | Pigment Epithelium Derived Factor (PEDF) |
| 36 | 3 | NM_173841 | Interleukin 1 Receptor Antagonist (IL1ra) |
| 37 | 3 | NM_000354 | Thyroxine Binding Globulin (TBG) |
| 38 | 3 | NM_000477 | Microalbumin |
| 39 | 3 | NM_000230 | Leptin |
| 40 | 3 | NM_002986 | Eotaxin 2 |
| 41 | 4 | NM_000597 | Insulin like Growth Factor Binding Protein 2 (IGFBP2) |
| 42 | 4 | NM_020415 | Resistin |
| 43 | 4 | NM_001909 | Cathepsin D |
| 44 | 4 | NM_000450 | E-Selectin |
| 45 | 4 | NM_001276 | YKL40 |
| 46 | 4 | NM_020525 | Interleukin 22 (IL22) |
| 47 | 4 | NM_004363 | Cacinoembryonic Antigen (CEA) |
| 48 | 4 | NM_000584 | Interleukin 8 (IL8) |
| 49 | 4 | NM_002456 | Cancer Antigen 15-3 (CA 15-3) |
| 50 | 4 | NM_002303 | Leptin Receptor (LeptinR) |
| 51 | 4 | NM_000207 | Insulin |
| 52 | 4 | NM_002982 | Monocyte Chemotactic Protein 1 (MCP1) |
| 53 | 4 | NM_000948 | Prolactin (PRL) |
| 54 | 4 | NM_003278 | Tetranectin |
| 55 | 4 | NM_001712 | Carcinoembryonic Antigen Related Cell Adhesion Molecule 1 (CEACAM1) |
| 56 | 4 | NM_002989 | 6Ckine |
| 57 | 4 | NM_001639 | Serum Amyloid P Component (SAP) |
| 58 | 4 | NM_002113 | Complement Factor H Related Protein 1 (CFHR1) |
| 59 | 4 | NM_004590 | Chemokine CC-4 (HCC-4) |
| 60 | 4 | NM-000064 | Complement C3 (C3) |
| 61 | 5 | NM_001134 | Alpha Fetoprotein (AFP) |
| 62 | 5 | NM_001146, NM_139290 | Angiopoietin 1 (ANG-1) |
| 63 | 5 | NM_001562 | Interleukin 18 (IL18) |
| 64 | 5 | NM_000177 | Gelsolin |
| 65 | 5 | NM_002160 | Tenascin C (TN-C) |
| 66 | 5 | NM_000638 | Vitronectin |
| 67 | 5 | NM_004048 | Beta 2 Microglobulin (B2M) |
| 68 | 5 | NM.003122 | Pancreatic Secretory Trypsin Inhibitor (TATI) |
| 69 | 5 | NM_002422 | Matrix Metalloproteinase 3 (MMP3) |
| 70 | 5 | NM_017625 | Omentin |
| 71 | 5 | NM_173042 | Interleukin 18 Binding Protein (IL 18bp) |
| 72 | 5 | NM_001647 | Apolipoprotein D (ApoD) |
| 73 | 5 | NM_005408 | Monocyte Chemotactic Protein 4 (MCP-4) |

TABLE 3-continued

Ranked Biomarker List

| Biomarker Number | Biomarker Set | Accession Number(s) | Biomarker |
|---|---|---|---|
| 74 | 5 | NM_000041 | Apolipoprotein E (Apo-E) |
| 75 | 5 | NM_016232 | ST2 |
| 76 | 5 | NM_003246 | Thrombospondin 1 |
| 77 | 5 | NM_004123 | Gastric Inhibitory Polypeptide (GIP) |
| 78 | 5 | NM_002423 | Matrix Metalloproteinase 7 (MMP7) |
| 79 | 5 | NM_000201 | Intercellular Adhesion Molecule 1 (ICAM-1) |
| 80 | 5 | NM_012242 | Dickkopf Related Protein 1 (DKK1) |

TABLE 4

2 Biomarker Multivariate Analysis. Combination of Paraoxonase 1 (PON1) and Analyte 2

| Analyte 2 | AUC by random forest | AUC by logistic regression | Maximum AUC |
|---|---|---|---|
| Myoglobin | 0.52 | 0.68 | 0.68 |
| Plasminogen Activator Inhibitor (PAI1) | 0.57 | 0.66 | 0.66 |
| Tissue Inhibitor of Metalloproteinases 1 (TIMP1) | 0.59 | 0.65 | 0.65 |
| Stromal Cell Derived Factor 1 (SDF1) | 0.54 | 0.70 | 0.70 |
| Interleukin 6 Receptor Subunit Beta (IL6Rbeta) | 0.60 | 0.72 | 0.72 |
| Cystatin B | 0.64 | 0.70 | 0.70 |
| Immunoglobulin E (IgE) | 0.55 | 0.68 | 0.68 |
| Macrophage Inflammatory Protein 3 beta (MIP3beta) | 0.58 | 0.70 | 0.70 |
| Vascular Cell Adhesion Molecule 1 (VCAM1) | 0.58 | 0.69 | 0.69 |
| Macrophage Derived Chemokine (MDC) | 0.63 | 0.71 | 0.71 |
| Vascular Endothelial Growth Factor (VEGF) | 0.49 | 0.69 | 0.69 |
| Ficolin 3 | 0.57 | 0.70 | 0.70 |
| Immunoglobulin A (IgA) | 0.54 | 0.70 | 0.70 |
| Factor VII | 0.69 | 0.70 | 0.70 |
| Interleukin 6 Receptor (IL6R) | 0.55 | 0.67 | 0.67 |
| Receptor for Advanced Glycosylation End Products (RAGE) | 0.48 | 0.69 | 0.69 |
| Fibulin 1C (FIB1C) | 0.52 | 0.66 | 0.66 |
| Interferon Inducble T Cell Alpha Chemoattractant (ITAC) | 0.60 | 0.65 | 0.65 |
| Growth Hormone (GH) | 0.54 | 0.67 | 0.67 |
| Heparin Binding EGF Like Growth Factor (HBEGF) | 0.63 | 0.66 | 0.66 |
| Neuronal Cell Adhesion Molecule (NrCAM) | 0.44 | 0.68 | 0.68 |
| Growth Regulated Alpha Protein (GROalpha) | 0.54 | 0.64 | 0.64 |
| Growth Differentation Factor 15 (GDF15) | 0.58 | 0.65 | 0.65 |
| Mast Stem Cell Growth Factor Receptor (SCFR) | 0.56 | 0.68 | 0.68 |
| Cadherin 1 (Ecad) | 0.61 | 0.65 | 0.65 |
| Angiogenin | 0.55 | 0.66 | 0.66 |
| Sortilin | 0.60 | 0.66 | 0.66 |
| Alpha 1 Antitrypsin (AAT) | 0.54 | 0.66 | 0.66 |
| Immunoglobulin M (IgM) | 0.56 | 0.64 | 0.64 |
| Pulmonary and Activation Regulated Chemokine (PARC) | 0.68 | 0.67 | 0.68 |
| Pulmonary Surfactant Associated Protein D (SP-D) | 0.52 | 0.65 | 0.65 |
| B Cell Activating Factor (BAFF) | 0.59 | 0.67 | 0.67 |
| Adrenomedullin (ADM) | 0.63 | 0.68 | 0.68 |
| Pigment Epithelium Derived Factor (PEDF) | 0.62 | 0.74 | 0.74 |
| Interleukin 1 Receptor Antagonist (IL1ra) | 0.49 | 0.70 | 0.70 |
| Thyrosine Binding Globulin (TBG) | 0.55 | 0.67 | 0.67 |
| Microalbumin | 0.56 | 0.64 | 0.64 |
| Leptin | 0.57 | 0.68 | 0.68 |
| Eotaxin 2 | 0.60 | 0.64 | 0.64 |
| Insulin like Growth Factor Binding Protein 2 (IGFBP2) | 0.46 | 0.66 | 0.66 |
| Resistin | 0.52 | 0.66 | 0.66 |
| Cathepsin D | 0.60 | 0.70 | 0.70 |
| E-Selectin | 0.52 | 0.69 | 0.69 |
| YKL40 | 0.53 | 0.66 | 0.66 |
| Interleukin 22 (IL22) | 0.53 | 0.67 | 0.67 |
| Cacinoembryoinc Antigen (CEA) | 0.46 | 0.64 | 0.64 |
| Interleukin 8 (IL8) | 0.59 | 0.64 | 0.64 |
| Cancer Antigen 15-3 (CA 15-3) | 0.58 | 0.65 | 0.65 |
| Leptin Receptor (LeptinR) | 0.55 | 0.65 | 0.65 |
| Insulin | 0.58 | 0.68 | 0.68 |
| Monocyte Chemotactic Protein 1 (MCP1) | 0.61 | 0.69 | 0.69 |
| Prolactin (PRL) | 0.51 | 0.65 | 0.65 |
| Tetranectin | 0.47 | 0.65 | 0.65 |
| Carcinoembryonic Antigen Related Cell Adhesion Molecule 1 (CEACAM1) | 0.61 | 0.65 | 0.65 |
| 6Ckine | 0.52 | 0.66 | 0.66 |
| Serum Amyloid P Component (SAP) | 0.59 | 0.69 | 0.69 |

TABLE 4-continued

2 Biomarker Multivariate Analysis. Combination of Paraoxonase 1 (PON1) and Analyte 2

| Analyte 2 | AUC by random forest | AUC by logistic regression | Maximum AUC |
|---|---|---|---|
| Complement Factor H Related Protein 1 (CFHR1) | 0.53 | 0.65 | 0.65 |
| Chemokine CC-4 (HCC-4) | 0.58 | 0.65 | 0.65 |
| Complement C3 (C3) | 0.56 | 0.67 | 0.67 |
| Alpha Fetoprotein (AFP) | 0.56 | 0.68 | 0.68 |
| Angiopoietin 1 (ANG-1) | 0.51 | 0.64 | 0.64 |
| Interleukin 18 (IL18) | 0.62 | 0.68 | 0.68 |
| Gelsolin | 0.65 | 0.66 | 0.66 |
| Tenascin C (TN-C) | 0.59 | 0.66 | 0.66 |
| Vitronectin | 0.55 | 0.68 | 0.68 |
| Beta 2 Microglobulin (B2M) | 0.60 | 0.66 | 0.66 |
| Pancreatic Secretory Trypsin Inhibitor (TATI) | 0.55 | 0.64 | 0.64 |
| Matrix Metailoproteinase 3 (MMP3) | 0.60 | 0.66 | 0.66 |
| Omentin | 0.58 | 0.65 | 0.65 |
| Interleukin 18 Binding Protein (IL 18bp) | 0.57 | 0.65 | 0.65 |
| Apolipoprotein D (ApoD) | 0.57 | 0.65 | 0.65 |
| Monoctye Chemotactic Protein 4 (MCP-4) | 0.54 | 0.65 | 0.65 |
| Apolipoprotein E (Apo-E) | 0.60 | 0.69 | 0.69 |
| ST2 | 0.54 | 0.64 | 0.64 |
| Thrombospondin 1 | 0.50 | 0.65 | 0.65 |
| Gastric Inhibitory Polypeptide (GIP) | 0.56 | 0.67 | 0.67 |
| Matrix Metalloproteinase 7 (MMP7) | 0.53 | 0.66 | 0.66 |
| Intercellular Adhesion Molecule 1 (ICAM-1) | 0.51 | 0.65 | 0.65 |
| Dickkopf Related Protein 1 (DKK1) | 0.53 | 0.66 | 0.66 |

TABLE 5

2 Biomarker Multivariate Analysis. Combination of Myoglobin and Analyte 2

| Analyte 2 | AUC by random forest | AUC by logistic regression | Maximum AUC |
|---|---|---|---|
| Plasminogen Activator Inhibitor (PAI1) | 0.52 | 0.63 | 0.63 |
| Tissue Inhibitor of Metalloproteinases 1 (TIMP1) | 0.61 | 0.62 | 0.62 |
| Stromal Cell Derived Factor 1 (SDF1) | 0.52 | 0.65 | 0.65 |
| Interleukin 6 Receptor Subunit Beta (IL6Rbeta) | 0.48 | 0.67 | 0.67 |
| Cystatin B | 0.66 | 0.72 | 0.72 |
| Immunoglobulin E (IgE) | 0.57 | 0.64 | 0.64 |
| Macrophage Inflammatory Protein 3 beta (MIP3beta) | 0.62 | 0.67 | 0.67 |
| Vascular Cell Adhesion Molecule 1 (VCAM1) | 0.51 | 0.63 | 0.63 |
| Macrophage Derived Chemokine (MDC) | 0.62 | 0.65 | 0.65 |
| Vascular Endothelial Growth Factor (VEGF) | 0.51 | 0.65 | 0.65 |
| Ficolin 3 | 0.52 | 0.64 | 0.64 |
| Immunoglobulin A (IgA) | 0.55 | 0.65 | 0.65 |
| Factor VII | 0.60 | 0.62 | 0.62 |
| Interleukin 6 Receptor (IL6R) | 0.49 | 0.61 | 0.61 |
| Receptor for Advanced Glycosylation End Products (RAGE) | 0.58 | 0.63 | 0.63 |
| Fibulin 1C (FIB1C) | 0.52 | 0.62 | 0.62 |
| Interferon Inducble T Cell Alpha Chemoattractant (ITAC) | 0.56 | 0.61 | 0.61 |
| Growth Hormone (GH) | 0.49 | 0.64 | 0.64 |
| Heparin Binding EGF Like Growth Factor (HBEGF) | 0.55 | 0.63 | 0.63 |
| Neuronal Cell Adhesion Molecule (NrCAM) | 0.52 | 0.67 | 0.67 |
| Growth Regulated Alpha Protein (GROalpha) | 0.54 | 0.62 | 0.62 |
| Growth Differentation Factor 15 (GDF15) | 0.60 | 0.62 | 0.62 |
| Mast Stem Cell Growth Factor Receptor (SCFR) | 0.51 | 0.62 | 0.62 |
| Cadherin 1 (Ecad) | 0.67 | 0.62 | 0.67 |
| Angiogenin | 0.49 | 0.63 | 0.63 |
| Sortilin | 0.49 | 0.62 | 0.62 |
| Alpha 1 Antitrypsin (AAT) | 0.47 | 0.62 | 0.62 |
| Immunoglobulin M (IgM) | 0.59 | 0.61 | 0.61 |
| Pulmonary and Activation Regulated Chemokine (PARC) | 0.61 | 0.67 | 0.67 |
| Pulmonary Surfactant Associated Protein D (SP-D) | 0.51 | 0.62 | 0.62 |
| B Cell Activating Factor (BAFF) | 0.53 | 0.63 | 0.63 |
| Adrenomedullin (ADM) | 0.56 | 0.66 | 0.66 |
| Pigment Epithelium Derived Factor (PEDF) | 0.57 | 0.69 | 0.69 |
| Interleukin 1 Receptor Antagonist (IL1ra) | 0.62 | 0.70 | 0.70 |
| Thyrosine Binding Globulin (TBG) | 0.57 | 0.62 | 0.62 |
| Microalbumin | 0.61 | 0.62 | 0.62 |
| Leptin | 0.54 | 0.66 | 0.66 |
| Eotaxin 2 | 0.67 | 0.63 | 0.67 |
| Insulin like Growth Factor Binding Protein 2 (IGFBP2) | 0.62 | 0.61 | 0.62 |

TABLE 5-continued

2 Biomarker Multivariate Analysis. Combination of Myoglobin and Analyte 2

| Analyte 2 | AUC by random forest | AUC by logistic regression | Maximum AUC |
|---|---|---|---|
| Resistin | 0.54 | 0.66 | 0.66 |
| Cathepsin D | 0.64 | 0.66 | 0.66 |
| E-Selectin | 0.51 | 0.68 | 0.68 |
| YKL40 | 0.53 | 0.62 | 0.62 |
| Interleukin 22 (IL22) | 0.56 | 0.62 | 0.62 |
| Cacinoembryonic Antigen (CEA) | 0.54 | 0.64 | 0.64 |
| Interleukin 8 (IL8) | 0.64 | 0.62 | 0.64 |
| Cancer Antigen 15-3 (CA 15-3) | 0.49 | 0.63 | 0.63 |
| Leptin Receptor (LeptinR) | 0.47 | 0.64 | 0.64 |
| Insulin | 0.49 | 0.65 | 0.65 |
| Monocyte Chemotactic Protein 1 (MCP1) | 0.56 | 0.65 | 0.65 |
| Prolactin (PRL) | 0.51 | 0.63 | 0.63 |
| Tetranectin | 0.57 | 0.62 | 0.62 |
| Carcinoembryonic Antigen Related Cell Adhesion Molecule 1 (CEACAM1) | 0.59 | 0.62 | 0.62 |
| 6Ckine | 0.49 | 0.65 | 0.65 |
| Serum Amyloid P Component (SAP) | 0.53 | 0.62 | 0.62 |
| Complement Factor H Related Protein 1 (CFHR1) | 0.54 | 0.63 | 0.63 |
| Chemokine CC-4 (HCC-4) | 0.57 | 0.62 | 0.62 |
| Complement C3 (C3) | 0.58 | 0.61 | 0.61 |
| Alpha Fetoprotein (AFP) | 0.61 | 0.65 | 0.65 |
| Angiopoietin 1 (ANG-1) | 0.57 | 0.62 | 0.62 |
| Interleukin 18 (IL18) | 0.58 | 0.68 | 0.68 |
| Gelsolin | 0.54 | 0.61 | 0.61 |
| Tenascin C (TN-C) | 0.47 | 0.62 | 0.62 |
| Vitronectin | 0.60 | 0.62 | 0.62 |
| Beta 2 Microglobulin (B2M) | 0.56 | 0.64 | 0.64 |
| Pancreatic Secretory Trypsin Inhibitor (TATI) | 0.56 | 0.62 | 0.62 |
| Matrix Metalloproteinase 3 (MMP3) | 0.60 | 0.63 | 0.63 |
| Omentin | 0.57 | 0.62 | 0.62 |
| Interleukin 18 Binding Protein (IL 18bp) | 0.53 | 0.66 | 0.66 |
| Apolipoprotein D (ApoD) | 0.58 | 0.62 | 0.62 |
| Monoctye Chemotactic Protein 4 (MCP-4) | 0.50 | 0.63 | 0.63 |
| Apolipoprotein E (Apo-E) | 0.48 | 0.64 | 0.64 |
| ST2 | 0.52 | 0.63 | 0.63 |
| Thrombospondin 1 | 0.52 | 0.62 | 0.62 |
| Gastric Inhibitory Polypeptide (GIP) | 0.48 | 0.62 | 0.62 |
| Matrix Metalloproteinase 7 (MMP7) | 0.52 | 0.61 | 0.61 |
| Intercellular Adhesion Molecule 1 (ICAM-1) | 0.53 | 0.64 | 0.64 |
| Dickkopf Related Protein 1 (DKK1) | 0.53 | 0.61 | 0.61 |

TABLE 6

2 Biomarker Multivariate Analysis. Combination of Plasminogen Activator Inhibitor (PAI1) and Analyte 2

| Analyte 2 | AUC by random forest | AUC by logistic regression | Maximum AUC |
|---|---|---|---|
| Tissue Inhibitor of Metalloproteinases 1 (TIMP1) | 0.70 | 0.64 | 0.70 |
| Stromal Cell Derived Factor 1 (SDF1) | 0.57 | 0.64 | 0.64 |
| Interleukin 6 Receptor Subunit Beta (IL6Rbeta) | 0.60 | 0.65 | 0.65 |
| Cystatin B | 0.61 | 0.66 | 0.66 |
| Immunoglobulin E (IgE) | 0.54 | 0.64 | 0.64 |
| Macrophage Inflammatory Protein 3 beta (MIP3beta) | 0.66 | 0.64 | 0.66 |
| Vascular Cell Adhesion Molecule 1 (VCAM1) | 0.56 | 0.64 | 0.64 |
| Macrophage Derived Chemokine (MDC) | 0.65 | 0.65 | 0.65 |
| Vascular Endothelial Growth Factor (VEGF) | 0.55 | 0.61 | 0.61 |
| Ficolin 3 | 0.62 | 0.63 | 0.63 |
| Immunoglobulin A (IgA) | 0.53 | 0.64 | 0.64 |
| Factor VII | 0.60 | 0.63 | 0.63 |
| Interleukin 6 Receptor (IL6R) | 0.55 | 0.59 | 0.59 |
| Receptor for Advanced Glycosylation End Products (RAGE) | 0.60 | 0.64 | 0.64 |
| Fibulin 1C (FIB1C) | 0.49 | 0.59 | 0.59 |
| Interferon Inducble T Cell Alpha Chemoattractant (ITAC) | 0.54 | 0.58 | 0.58 |
| Growth Hormone (GH) | 0.55 | 0.62 | 0.62 |
| Heparin Binding EGF Like Growth Factor (HBEGF) | 0.52 | 0.62 | 0.62 |
| Neuronal Cell Adhesion Molecule (NrCAM) | 0.54 | 0.65 | 0.65 |
| Growth Regulated Alpha Protein (GROalpha) | 0.49 | 0.59 | 0.59 |
| Growth Differentiation Factor 15 (GDF15) | 0.59 | 0.59 | 0.59 |
| Mast Stem Cell Growth Factor Receptor (SCFR) | 0.56 | 0.62 | 0.62 |

TABLE 6-continued

2 Biomarker Multivariate Analysis. Combination of Plasminogen Activator Inhibitor (PAI1) and Analyte 2

| Analyte 2 | AUC by random forest | AUC by logistic regression | Maximum AUC |
|---|---|---|---|
| Cadherin 1 (Ecad) | 0.48 | 0.59 | 0.59 |
| Angiogenin | 0.57 | 0.61 | 0.61 |
| Sortilin | 0.49 | 0.61 | 0.61 |
| Alpha 1 Antitrypsin (AAT) | 0.56 | 0.59 | 0.59 |
| Immunoglobulin M (IgM) | 0.56 | 0.59 | 0.59 |
| Pulmonary and Activation Regulated Chemokine (PARC) | 0.61 | 0.63 | 0.63 |
| Pulmonary Surfactant Associated Protein D (SP-D) | 0.54 | 0.59 | 0.59 |
| B Cell Activating Factor (BAFF) | 0.52 | 0.60 | 0.60 |
| Adrenomedullin (ADM) | 0.57 | 0.64 | 0.64 |
| Pigment Epithelium Derived Factor (PEDF) | 0.60 | 0.68 | 0.68 |
| Interleukin 1 Receptor Antagonist (IL1ra) | 0.52 | 0.64 | 0.64 |
| Thyrosine Binding Globulin (TBG) | 0.49 | 0.62 | 0.62 |
| Microalbumin | 0.59 | 0.58 | 0.59 |
| Leptin | 0.47 | 0.64 | 0.64 |
| Eotaxin 2 | 0.56 | 0.58 | 0.58 |
| Insulin like Growth Factor Binding Protein 2 (IGFBP2) | 0.50 | 0.59 | 0.59 |
| Resistin | 0.54 | 0.61 | 0.61 |
| Cathepsin D | 0.60 | 0.66 | 0.66 |
| E-Selectin | 0.50 | 0.64 | 0.64 |
| YKL40 | 0.52 | 0.59 | 0.59 |
| Interleukin 22 (IL22) | 0.54 | 0.61 | 0.61 |
| Cacinoembryonic Antigen (CEA) | 0.52 | 0.60 | 0.60 |
| Interleukin 8 (IL8) | 0.60 | 0.59 | 0.60 |
| Cancer Antigen 15-3 (CA 15-3) | 0.54 | 0.59 | 0.59 |
| Leptin Receptor (LeptinR) | 0.49 | 0.60 | 0.60 |
| Insulin | 0.58 | 0.64 | 0.64 |
| Monocyte Chemotactic Protein 1 (MCP1) | 0.55 | 0.65 | 0.65 |
| Prolactin (PRL) | 0.53 | 0.58 | 0.58 |
| Tetranectin | 0.58 | 0.59 | 0.59 |
| Carcinoembryonic Antigen Related Cell Adhesion Molecule 1 (CEACAM1) | 0.50 | 0.58 | 0.58 |
| 6Ckine | 0.60 | 0.64 | 0.64 |
| Serum Amyloid P Component (SAP) | 0.64 | 0.62 | 0.64 |
| Complement Factor H Related Protein 1 (CFHR1) | 0.51 | 0.59 | 0.59 |
| Chemokine CC-4 (HCC-4) | 0.48 | 0.58 | 0.58 |
| Complement C3 (C3) | 0.55 | 0.59 | 0.59 |
| Alpha Fetoprotein (AFP) | 0.52 | 0.58 | 0.58 |
| Angiopoietin 1 (ANG-1) | 0.54 | 0.59 | 0.59 |
| Interleukin 18 (IL18) | 0.68 | 0.65 | 0.68 |
| Gelsolin | 0.52 | 0.60 | 0.60 |
| Tenascin C (TN-C) | 0.54 | 0.60 | 0.60 |
| Vitronectin | 0.62 | 0.60 | 0.62 |
| Beta 2 Microglobulin (B2M) | 0.57 | 0.61 | 0.61 |
| Pancreatic Secretory Trypsin Inhibitor (TATI) | 0.60 | 0.59 | 0.60 |
| Matrix Metalloproteinase 3 (MMP3) | 0.67 | 0.62 | 0.67 |
| Omentin | 0.58 | 0.60 | 0.60 |
| Interleukin 18 Binding Protein (IL 18bp) | 0.53 | 0.60 | 0.60 |
| Apolipoprotein D (ApoD) | 0.60 | 0.60 | 0.60 |
| Monoctye Chemotactic Protein 4 (MCP-4) | 0.53 | 0.58 | 0.58 |
| Apolipoprotein E (Apo-E) | 0.57 | 0.64 | 0.64 |
| ST2 | 0.51 | 0.59 | 0.59 |
| Thrombospondin 1 | 0.57 | 0.61 | 0.61 |
| Gastric Inhibitory Polypeptide (GIP) | 0.56 | 0.61 | 0.61 |
| Matrix Metalloproteinase 7 (MMP7) | 0.61 | 0.61 | 0.61 |
| Intercellular Adhesion Molecule 1 (ICAM-1) | 0.53 | 0.59 | 0.59 |
| Dickkopf Related Protein 1 (DKK1) | 0.50 | 0.62 | 0.62 |

TABLE 7

2 Biomarker Multivariate Analysis. Combination of Tissue Inhibitor of Metalloproteinases 1 (TIMP1) and Analyte 2

| Analyte 2 | AUC by random forest | AUC by logistic regression | Maximum AUC |
|---|---|---|---|
| Stromal Cell Derived Factor 1 (SDF1) | 0.65 | 0.67 | 0.67 |
| Interleukin 6 Receptor Subunit Beta (IL6Rbeta) | 0.59 | 0.63 | 0.63 |
| Cystatin B | 0.60 | 0.64 | 0.64 |
| Immunoglobulin E (IgE) | 0.65 | 0.63 | 0.65 |
| Macrophage Inflammatory Protein 3 beta (MIP3beta) | 0.64 | 0.62 | 0.64 |

TABLE 7-continued

2 Biomarker Multivariate Analysis. Combination of Tissue Inhibitor of
Metalloproteinases 1 (TIMP1) and Analyte 2

| Analyte 2 | AUC by random forest | AUC by logistic regression | Maximum AUC |
|---|---|---|---|
| Vascular Cell Adhesion Molecule 1 (VCAM1) | 0.66 | 0.62 | 0.66 |
| Macrophage Derived Chemokine (MDC) | 0.62 | 0.63 | 0.63 |
| Vascular Endothelial Growth Factor (VEGF) | 0.57 | 0.62 | 0.62 |
| Ficolin 3 | 0.66 | 0.62 | 0.66 |
| Immunoglobulin A (IgA) | 0.53 | 0.59 | 0.59 |
| Factor VII | 0.60 | 0.59 | 0.60 |
| Interleukin 6 Receptor (IL6R) | 0.60 | 0.60 | 0.60 |
| Receptor for Advanced Glycosylation End Products (RAGE) | 0.67 | 0.63 | 0.67 |
| Fibulin 1C (FIB1C) | 0.62 | 0.56 | 0.62 |
| Interferon Inducble T Cell Alpha Chemoattractant (ITAC) | 0.64 | 0.56 | 0.64 |
| Growth Hormone (GH) | 0.59 | 0.60 | 0.60 |
| Heparin Binding EGF Like Growth Factor (HBEGF) | 0.67 | 0.53 | 0.67 |
| Neuronal Cell Adhesion Molecule (NrCAM) | 0.63 | 0.59 | 0.63 |
| Growth Regulated Alpha Protein (GROalpha) | 0.61 | 0.57 | 0.61 |
| Growth Differentiation Factor 15 (GDF15) | 0.68 | 0.59 | 0.68 |
| Mast Stem Cell Growth Factor Receptor (SCFR) | 0.55 | 0.60 | 0.60 |
| Cadherin 1 (Ecad) | 0.65 | 0.58 | 0.65 |
| Angiogenin | 0.63 | 0.58 | 0.63 |
| Sortilin | 0.60 | 0.54 | 0.60 |
| Alpha 1 Antitrypsin (AAT) | 0.67 | 0.56 | 0.67 |
| Immunoglobulin M (IgM) | 0.63 | 0.55 | 0.63 |
| Pulmonary and Activation Regulated Chemokine (PARC) | 0.68 | 0.59 | 0.68 |
| Pulmonary Surfactant Associated Protein D (SP-D) | 0.58 | 0.56 | 0.58 |
| B Cell Activating Factor (BAFF) | 0.60 | 0.60 | 0.60 |
| Adrenomedullin (ADM) | 0.62 | 0.63 | 0.63 |
| Pigment Epithelium Derived Factor (PEDF) | 0.65 | 0.64 | 0.65 |
| Interleukin 1 Receptor Antagonist (IL1ra) | 0.59 | 0.59 | 0.59 |
| Thyrosine Binding Globulin (TBG) | 0.56 | 0.59 | 0.59 |
| Microalbumin | 0.71 | 0.57 | 0.71 |
| Leptin | 0.53 | 0.60 | 0.60 |
| Eotaxin 2 | 0.66 | 0.58 | 0.66 |
| Insulin like Growth Factor Binding Protein 2 (IGFBP2) | 0.65 | 0.57 | 0.65 |
| Resistin | 0.55 | 0.55 | 0.55 |
| Cathepsin D | 0.59 | 0.62 | 0.62 |
| E-Selectin | 0.61 | 0.63 | 0.63 |
| YKL40 | 0.57 | 0.56 | 0.57 |
| Interleukin 22 (IL22) | 0.54 | 0.57 | 0.57 |
| Cacinoembryonic Antigen (CEA) | 0.57 | 0.58 | 0.58 |
| Interleukin 8 (IL8) | 0.60 | 0.56 | 0.60 |
| Cancer Antigen 15-3 (CA 15-3) | 0.64 | 0.56 | 0.64 |
| Leptin Receptor (LeptinR) | 0.58 | 0.60 | 0.60 |
| Insulin | 0.64 | 0.60 | 0.64 |
| Monocyte Chemotactic Protein 1 (MCP1) | 0.57 | 0.59 | 0.59 |
| Prolactin (PRL) | 0.62 | 0.56 | 0.62 |
| Tetranectin | 0.57 | 0.58 | 0.58 |
| Carcinoembryonic Antigen Related Cell Adhesion Molecule 1 (CEACAM1) | 0.65 | 0.58 | 0.65 |
| 6Ckine | 0.66 | 0.61 | 0.66 |
| Serum Amyloid P Component (SAP) | 0.69 | 0.58 | 0.69 |
| Complement Factor H Related Protein 1 (CFHR1) | 0.60 | 0.55 | 0.60 |
| Chemokine CC-4 (HCC-4) | 0.62 | 0.54 | 0.62 |
| Complement C3 (C3) | 0.64 | 0.46 | 0.64 |
| Alpha Fetoprotein (AFP) | 0.59 | 0.60 | 0.60 |
| Angiopoietin 1 (ANG-1) | 0.62 | 0.56 | 0.62 |
| Interleukin 18 (IL18) | 0.67 | 0.65 | 0.67 |
| Gelsolin | 0.61 | 0.56 | 0.61 |
| Tenascin C (TN-C) | 0.64 | 0.55 | 0.64 |
| Vitronectin | 0.69 | 0.55 | 0.69 |
| Beta 2 Microglobulin (B2M) | 0.60 | 0.56 | 0.60 |
| Pancreatic Secretory Trypsin Inhibitor (TATI) | 0.63 | 0.56 | 0.63 |
| Matrix Metalloproteinase 3 (MMP3) | 0.65 | 0.56 | 0.65 |
| Omentin | 0.58 | 0.57 | 0.58 |
| Interleukin 18 Binding Protein (IL 18bp) | 0.59 | 0.60 | 0.60 |
| Apolipoprotein D (ApoD) | 0.70 | 0.57 | 0.70 |
| Monoctye Chemotactic Protein 4 (MCP-4) | 0.60 | 0.56 | 0.60 |
| Apolipoprotein E (Apo-E) | 0.71 | 0.61 | 0.71 |
| ST2 | 0.64 | 0.56 | 0.64 |
| Thrombospondin 1 | 0.67 | 0.56 | 0.67 |
| Gastric Inhibitory Polypeptide (GIP) | 0.58 | 0.58 | 0.58 |
| Matrix Metalloproteinase 7 (MMP7) | 0.61 | 0.56 | 0.61 |
| Intercellular Adhesion Molecule 1 (ICAM-1) | 0.57 | 0.57 | 0.57 |
| Dickkopf Related Protein 1 (DKK1) | 0.57 | 0.53 | 0.57 |

TABLE 8

2 Biomarker Multivariate Analysis. Combination of Stromel Cell Derived Factor 1 (SDF1) and Analyte 2

| Analyte 2 | AUC by random forest | AUC by logistic regression | Maximum AUC |
|---|---|---|---|
| Interleukin 6 Receptor Subunit Beta (IL6Rbeta) | 0.53 | 0.68 | 0.68 |
| Cystatin B | 0.59 | 0.68 | 0.68 |
| Immunoglobulin E (IgE) | 0.65 | 0.69 | 0.69 |
| Macrophage Inflammatory Protein 3 beta (MIP3beta) | 0.62 | 0.67 | 0.67 |
| Vascular Cell Adhesion Molecule 1 (VCAM1) | 0.56 | 0.68 | 0.68 |
| Macrophage Derived Chemokine (MDC) | 0.61 | 0.70 | 0.70 |
| Vascular Endothelial Growth Factor (VEGF) | 0.57 | 0.66 | 0.66 |
| Ficolin 3 | 0.52 | 0.64 | 0.64 |
| Immunoglobulin A (IgA) | 0.50 | 0.69 | 0.69 |
| Factor VII | 0.56 | 0.65 | 0.65 |
| Interleukin 6 Receptor (IL6R) | 0.47 | 0.65 | 0.65 |
| Receptor for Advanced Glycosylation End Products (RAGE) | 0.55 | 0.66 | 0.66 |
| Fibulin 1C (FIB1C) | 0.52 | 0.64 | 0.64 |
| Interferon Inducble T Cell Alpha Chemoattractant (ITAC) | 0.54 | 0.64 | 0.64 |
| Growth Hormone (GH) | 0.59 | 0.66 | 0.66 |
| Heparin Binding EGF Like Growth Factor (HBEGF) | 0.58 | 0.66 | 0.66 |
| Neuronal Cell Adhesion Molecule (NrCAM) | 0.60 | 0.64 | 0.64 |
| Growth Regulated Alpha Protein (GROalpha) | 0.60 | 0.63 | 0.63 |
| Growth Differentiation Factor 15 (GDF15) | 0.68 | 0.64 | 0.68 |
| Mast Stem Cell Growth Factor Receptor (SCFR) | 0.51 | 0.66 | 0.66 |
| Cadherin 1 (Ecad) | 0.51 | 0.64 | 0.64 |
| Angiogenin | 0.50 | 0.64 | 0.64 |
| Sortilin | 0.50 | 0.65 | 0.65 |
| Alpha 1 Antitrypsin (AAT) | 0.57 | 0.64 | 0.64 |
| Immunoglobulin M (IgM) | 0.56 | 0.63 | 0.63 |
| Pulmonary and Activation Regulated Chemokine (PARC) | 0.59 | 0.68 | 0.68 |
| Pulmonary Surfactant Associated Protein D (SP-D) | 0.52 | 0.63 | 0.63 |
| B Cell Activating Factor (BAFF) | 0.52 | 0.65 | 0.65 |
| Adrenomedullin (ADM) | 0.52 | 0.66 | 0.66 |
| Pigment Epithelium Derived Factor (PEDF) | 0.54 | 0.68 | 0.68 |
| Interleukin 1 Receptor Antagonist (IL1ra) | 0.56 | 0.68 | 0.68 |
| Thyrosine Binding Globulin (TBG) | 0.49 | 0.65 | 0.65 |
| Microalbumin | 0.63 | 0.63 | 0.63 |
| Leptin | 0.62 | 0.66 | 0.66 |
| Eotaxin 2 | 0.48 | 0.63 | 0.63 |
| Insulin like Growth Factor Binding Protein 2 (IGFBP2) | 0.47 | 0.63 | 0.63 |
| Resistin | 0.49 | 0.66 | 0.66 |
| Cathepsin D | 0.53 | 0.68 | 0.68 |
| E-Selectin | 0.51 | 0.69 | 0.69 |
| YKL40 | 0.52 | 0.63 | 0.63 |
| Interleukin 22 (IL22) | 0.50 | 0.66 | 0.66 |
| Cacinoembryonic Antigen (CEA) | 0.52 | 0.63 | 0.63 |
| Interleukin 8 (IL8) | 0.56 | 0.64 | 0.64 |
| Cancer Antigen 15-3 (CA 15-3) | 0.54 | 0.63 | 0.63 |
| Leptin Receptor (LeptinR) | 0.55 | 0.64 | 0.64 |
| Insulin | 0.54 | 0.66 | 0.66 |
| Monocyte Chemotactic Protein 1 (MCP1) | 0.55 | 0.66 | 0.66 |
| Prolactin (PRL) | 0.55 | 0.65 | 0.65 |
| Tetranectin | 0.55 | 0.64 | 0.64 |
| Carcinoembryonic Antigen Related Cell Adhesion Molecule 1 (CEACAM1) | 0.57 | 0.64 | 0.64 |
| 6Ckine | 0.51 | 0.67 | 0.67 |
| Serum Amyloid P Component (SAP) | 0.44 | 0.64 | 0.64 |
| Complement Factor H Related Protein 1 (CFHR1) | 0.52 | 0.63 | 0.63 |
| Chemokine CC-4 (HCC-4) | 0.52 | 0.63 | 0.63 |
| Complement C3 (C3) | 0.47 | 0.64 | 0.64 |
| Alpha Fetoprotein (AFP) | 0.50 | 0.64 | 0.64 |
| Angiopoietin 1 (ANG-1) | 0.55 | 0.63 | 0.63 |
| Interleukin 18 (IL18) | 0.55 | 0.69 | 0.69 |
| Gelsolin | 0.59 | 0.64 | 0.64 |
| Tenascin C (TN-C) | 0.50 | 0.64 | 0.64 |
| Vitronectin | 0.44 | 0.63 | 0.63 |
| Beta 2 Microglobulin (B2M) | 0.53 | 0.63 | 0.63 |
| Pancreatic Secretory Trypsin Inhibitor (TATI) | 0.53 | 0.64 | 0.64 |
| Matrix Metalloproteinase 3 (MMP3) | 0.65 | 0.64 | 0.65 |
| Omentin | 0.52 | 0.63 | 0.63 |
| Interleukin 18 Binding Protein (IL 18bp) | 0.56 | 0.67 | 0.67 |
| Apolipoprotein D (ApoD) | 0.63 | 0.63 | 0.63 |
| Monoctye Chemotactic Protein 4 (MCP-4) | 0.60 | 0.66 | 0.66 |
| Apolipoprotein E (Apo-E) | 0.46 | 0.67 | 0.67 |
| ST2 | 0.46 | 0.63 | 0.63 |
| Thrombospondin 1 | 0.51 | 0.64 | 0.64 |
| Gastric Inhibitory Polypeptide (GIP) | 0.56 | 0.65 | 0.65 |
| Matrix Metalloproteinase 7 (MMP7) | 0.60 | 0.67 | 0.67 |

TABLE 8-continued

2 Biomarker Multivariate Analysis. Combination of Stromel Cell Derived Factor 1 (SDF1) and Analyte 2

| Analyte 2 | AUC by random forest | AUC by logistic regression | Maximum AUC |
|---|---|---|---|
| Intercellular Adhesion Molecule 1 (ICAM-1) | 0.52 | 0.63 | 0.63 |
| Dickkopf Related Protein 1 (DKK1) | 0.59 | 0.66 | 0.66 |

TABLE 9

2 Biomarker Multivariate Analysis. Combination of Interleukin 6 Receptor Subunit Beta (IL6Rbeta) and Analyte 2

| Analyte 2 | AUC by random forest | AUC by logistic regression | Maximum AUC |
|---|---|---|---|
| Cystatin B | 0.52 | 0.66 | 0.66 |
| Immunoglobulin E (IgE) | 0.50 | 0.68 | 0.68 |
| Macrophage Inflammatory Protein 3 beta (MIP3beta) | 0.57 | 0.69 | 0.69 |
| Vascular Cell Adhesion Molecule 1 (VCAM1) | 0.49 | 0.66 | 0.66 |
| Macrophage Derived Chemokine (MDC) | 0.52 | 0.68 | 0.68 |
| Vascular Endothelial Growth Factor (VEGF) | 0.56 | 0.66 | 0.66 |
| Ficolin 3 | 0.51 | 0.66 | 0.66 |
| Immunoglobulin A (IgA) | 0.57 | 0.67 | 0.67 |
| Factor VII | 0.53 | 0.65 | 0.65 |
| Interleukin 6 Receptor (IL6R) | 0.58 | 0.65 | 0.65 |
| Receptor for Advanced Glycosylation End Products (RAGE) | 0.50 | 0.69 | 0.69 |
| Fibulin 1C (FIB1C) | 0.52 | 0.63 | 0.63 |
| Interferon Inducble T Cell Alpha Chemoattractant (ITAC) | 0.71 | 0.62 | 0.71 |
| Growth Hormone (GH) | 0.54 | 0.66 | 0.66 |
| Heparin Binding EGF Like Growth Factor (HBEGF) | 0.47 | 0.63 | 0.63 |
| Neuronal Cell Adhesion Molecule (NrCAM) | 0.59 | 0.68 | 0.68 |
| Growth Regulated Alpha Protein (GROalpha) | 0.53 | 0.64 | 0.64 |
| Growth Differentiation Factor 15 (GDF15) | 0.60 | 0.64 | 0.64 |
| Mast Stem Cell Growth Factor Receptor (SCFR) | 0.55 | 0.66 | 0.66 |
| Cadherin 1 (Ecad) | 0.48 | 0.63 | 0.63 |
| Angiogenin | 0.46 | 0.63 | 0.63 |
| Sortilin | 0.51 | 0.65 | 0.65 |
| Alpha 1 Antitrypsin (AAT) | 0.49 | 0.66 | 0.66 |
| Immunoglobulin M (IgM) | 0.52 | 0.63 | 0.63 |
| Pulmonary and Activation Regulated Chemokine (PARC) | 0.50 | 0.66 | 0.66 |
| Pulmonary Surfactant Associated Protein D (SP-D) | 0.50 | 0.63 | 0.63 |
| B Cell Activating Factor (BAFF) | 0.51 | 0.66 | 0.66 |
| Adrenomedullin (ADM) | 0.46 | 0.68 | 0.68 |
| Pigment Epithelium Derived Factor (PEDF) | 0.50 | 0.68 | 0.68 |
| Interleukin 1 Receptor Antagonist (IL1ra) | 0.50 | 0.69 | 0.69 |
| Thyrosine Binding Globulin (TBG) | 0.61 | 0.64 | 0.64 |
| Microalbumin | 0.61 | 0.67 | 0.67 |
| Leptin | 0.54 | 0.66 | 0.66 |
| Eotaxin 2 | 0.60 | 0.64 | 0.64 |
| Insulin like Growth Factor Binding Protein 2 (IGFBP2) | 0.51 | 0.63 | 0.63 |
| Resistin | 0.51 | 0.64 | 0.64 |
| Cathepsin D | 0.48 | 0.64 | 0.64 |
| E-Selectin | 0.59 | 0.65 | 0.65 |
| YKL40 | 0.61 | 0.63 | 0.63 |
| Interleukin 22 (IL22) | 0.45 | 0.64 | 0.64 |
| Cacinoembryonic Antigen (CEA) | 0.56 | 0.65 | 0.65 |
| Interleukin 8 (IL8) | 0.55 | 0.63 | 0.63 |
| Cancer Antigen 15-3 (CA 15-3) | 0.56 | 0.63 | 0.63 |
| Leptin Receptor (LeptinR) | 0.57 | 0.64 | 0.64 |
| Insulin | 0.53 | 0.66 | 0.66 |
| Monocyte Chemotactic Protein 1 (MCP1) | 0.54 | 0.65 | 0.65 |
| Prolactin (PRL) | 0.58 | 0.64 | 0.64 |
| Tetranectin | 0.53 | 0.64 | 0.64 |
| Carcinoembryonic Antigen Related Cell Adhesion Molecule 1 (CEACAM1) | 0.50 | 0.65 | 0.65 |
| 6Ckine | 0.53 | 0.64 | 0.64 |
| Serum Amyloid P Component (SAP) | 0.55 | 0.66 | 0.66 |
| Complement Factor H Related Protein 1 (CFHR1) | 0.55 | 0.63 | 0.63 |
| Chemokine CC-4 (HCC-4) | 0.50 | 0.63 | 0.63 |
| Complement C3 (C3) | 0.50 | 0.63 | 0.63 |
| Alpha Fetoprotein (AFP) | 0.51 | 0.67 | 0.67 |
| Angiopoietin 1 (ANG-1) | 0.52 | 0.63 | 0.63 |
| Interleukin 18 (IL18) | 0.57 | 0.68 | 0.68 |
| Gelsolin | 0.57 | 0.63 | 0.63 |

TABLE 9-continued

2 Biomarker Multivariate Analysis. Combination of Interleukin 6 Receptor Subunit Beta (IL6Rbeta) and Analyte 2

| Analyte 2 | AUC by random forest | AUC by logistic regression | Maximum AUC |
|---|---|---|---|
| Tenascin C (TN-C) | 0.55 | 0.64 | 0.64 |
| Vitronectin | 0.54 | 0.63 | 0.63 |
| Beta 2 Microglobulin (B2M) | 0.54 | 0.65 | 0.65 |
| Pancreatic Secretory Trypsin Inhibitor (TATI) | 0.51 | 0.63 | 0.63 |
| Matrix Metalloproteinase 3 (MMP3) | 0.65 | 0.65 | 0.65 |
| Omentin | 0.59 | 0.63 | 0.63 |
| Interleukin 18 Binding Protein (IL 18bp) | 0.51 | 0.66 | 0.66 |
| Apolipoprotein D (ApoD) | 0.62 | 0.63 | 0.63 |
| Monoctye Chemotactic Protein 4 (MCP-4) | 0.54 | 0.63 | 0.63 |
| Apolipoprotein E (Apo-E) | 0.51 | 0.68 | 0.68 |
| ST2 | 0.52 | 0.63 | 0.63 |
| Thrombospondin 1 | 0.50 | 0.63 | 0.63 |
| Gastric Inhibitory Polypeptide (GIP) | 0.46 | 0.65 | 0.65 |
| Matrix Metalloproteinase 7 (MMP7) | 0.49 | 0.64 | 0.64 |
| Intercellular Adhesion Molecule 1 (ICAM-1) | 0.54 | 0.63 | 0.63 |
| Dickkopf Related Protein 1 (DKK1) | 0.63 | 0.64 | 0.64 |

TABLE 10

2 Biomarker Multivariate Analysis. Combination of Cystatin B and Analyte 2

| Analyte 2 | AUC by random forest | AUC by logistic regression | Maximum AUC |
|---|---|---|---|
| Immunoglobulin E (IgE) | 0.61 | 0.67 | 0.67 |
| Macrophage Inflammatory Protein 3 beta (MIP3beta) | 0.74 | 0.64 | 0.74 |
| Vascular Cell Adhesion Molecule 1 (VCAM1) | 0.66 | 0.68 | 0.68 |
| Macrophage Derived Chemokine (MDC) | 0.59 | 0.64 | 0.64 |
| Vascular Endothelial Growth Factor (VEGF) | 0.63 | 0.69 | 0.69 |
| Ficolin 3 | 0.58 | 0.64 | 0.64 |
| Immunoglobulin A (IgA) | 0.53 | 0.65 | 0.65 |
| Factor VII | 0.65 | 0.65 | 0.65 |
| Interleukin 6 Receptor (IL6R) | 0.50 | 0.65 | 0.65 |
| Receptor for Advanced Glycosylation End Products (RAGE) | 0.65 | 0.67 | 0.67 |
| Fibulin 1C (FIB1C) | 0.64 | 0.64 | 0.64 |
| Interferon Inducble T Cell Alpha Chemoattractant (ITAC) | 0.66 | 0.64 | 0.66 |
| Growth Hormone (GH) | 0.54 | 0.64 | 0.64 |
| Heparin Binding EGF Like Growth Factor (HBEGF) | 0.62 | 0.64 | 0.64 |
| Neuronal Cell Adhesion Molecule (NrCAM) | 0.68 | 0.68 | 0.68 |
| Growth Regulated Alpha Protein (GROalpha) | 0.63 | 0.64 | 0.64 |
| Growth Differentiation Factor 15 (GDF15) | 0.64 | 0.63 | 0.64 |
| Mast Stem Cell Growth Factor Receptor (SCFR) | 0.58 | 0.65 | 0.65 |
| Cadherin 1 (Ecad) | 0.64 | 0.64 | 0.64 |
| Angiogenin | 0.59 | 0.63 | 0.63 |
| Sortilin | 0.61 | 0.63 | 0.63 |
| Alpha 1 Antitrypsin (AAT) | 0.66 | 0.67 | 0.67 |
| Immunoglobulin M (IgM) | 0.69 | 0.65 | 0.69 |
| Pulmonary and Activation Regulated Chemokine (PARC) | 0.62 | 0.65 | 0.65 |
| Pulmonary Surfactant Associated Protein D (SP-D) | 0.58 | 0.64 | 0.64 |
| B Cell Activating Factor (BAFF) | 0.63 | 0.64 | 0.64 |
| Adrenomedullin (ADM) | 0.60 | 0.67 | 0.67 |
| Pigment Epithelium Derived Factor (PEDF) | 0.61 | 0.66 | 0.66 |
| Interleukin 1 Receptor Antagonist (IL1ra) | 0.58 | 0.64 | 0.64 |
| Thyrosine Binding Globulin (TBG) | 0.53 | 0.64 | 0.64 |
| Microalbumin | 0.67 | 0.64 | 0.67 |
| Leptin | 0.48 | 0.64 | 0.64 |
| Eotaxin 2 | 0.64 | 0.64 | 0.64 |
| Insulin like Growth Factor Binding Protein 2 (IGFBP2) | 0.63 | 0.63 | 0.63 |
| Resistin | 0.55 | 0.64 | 0.64 |
| Cathepsin D | 0.63 | 0.64 | 0.64 |
| E-Selectin | 0.58 | 0.66 | 0.66 |
| YKL40 | 0.58 | 0.64 | 0.64 |
| Interleukin 22 (IL22) | 0.52 | 0.63 | 0.63 |
| Cacinoembryonic Antigen (CEA) | 0.56 | 0.63 | 0.63 |
| Interleukin 8 (IL8) | 0.64 | 0.65 | 0.65 |
| Cancer Antigen 15-3 (CA 15-3) | 0.54 | 0.64 | 0.64 |
| Leptin Receptor (LeptinR) | 0.56 | 0.64 | 0.64 |
| Insulin | 0.63 | 0.65 | 0.65 |
| Monocyte Chemotactic Protein 1 (MCP1) | 0.66 | 0.65 | 0.66 |

TABLE 10-continued

| 2 Biomarker Multivariate Analysis. Combination of Cystatin B and Analyte 2 | | | |
|---|---|---|---|
| Analyte 2 | AUC by random forest | AUC by logistic regression | Maximum AUC |
| Prolactin (PRL) | 0.61 | 0.63 | 0.63 |
| Tetranectin | 0.56 | 0.64 | 0.64 |
| Carcinoembryonic Antigen Related Cell Adhesion Molecule 1 (CEACAM1) | 0.61 | 0.64 | 0.64 |
| 6Ckine | 0.59 | 0.63 | 0.63 |
| Serum Amyloid P Component (SAP) | 0.61 | 0.62 | 0.62 |
| Complement Factor H Related Protein 1 (CFHR1) | 0.43 | 0.64 | 0.64 |
| Chemokine CC-4 (HCC-4) | 0.59 | 0.64 | 0.64 |
| Complement C3 (C3) | 0.59 | 0.64 | 0.64 |
| Alpha Fetoprotein (AFP) | 0.57 | 0.66 | 0.66 |
| Angiopoietin 1 (ANG-1) | 0.59 | 0.64 | 0.64 |
| Interleukin 18 (IL18) | 0.62 | 0.66 | 0.66 |
| Gelsolin | 0.66 | 0.66 | 0.66 |
| Tenascin C (TN-C) | 0.58 | 0.62 | 0.62 |
| Vitronectin | 0.59 | 0.65 | 0.65 |
| Beta 2 Microglobulin (B2M) | 0.56 | 0.64 | 0.64 |
| Pancreatic Secretory Trypsin Inhibitor (TATI) | 0.59 | 0.64 | 0.64 |
| Matrix Metalloproteinase 3 (MMP3) | 0.64 | 0.64 | 0.64 |
| Omentin | 0.51 | 0.64 | 0.64 |
| Interleukin 18 Binding Protein (IL 18bp) | 0.63 | 0.64 | 0.64 |
| Apolipoprotein D (ApoD) | 0.67 | 0.63 | 0.67 |
| Monocyte Chemotactic Protein 4 (MCP-4) | 0.46 | 0.64 | 0.64 |
| Apolipoprotein E (Apo-E) | 0.57 | 0.64 | 0.64 |
| ST2 | 0.57 | 0.64 | 0.64 |
| Thrombospondin 1 | 0.58 | 0.64 | 0.64 |
| Gastric Inhibitory Polypeptide (GIP) | 0.55 | 0.65 | 0.65 |
| Matrix Metalloproteinase 7 (MMP7) | 0.67 | 0.62 | 0.67 |
| Intercellular Adhesion Molecule 1 (ICAM-1) | 0.57 | 0.64 | 0.64 |
| Dickkopf Related Protein 1 (DKK1) | 0.54 | 0.64 | 0.64 |

TABLE 11

| 2 Biomarker Multivariate Analysis. Combination of Immunoglobulin E (IgE) and Analyte 2 | | | |
|---|---|---|---|
| Analyte 2 | AUC by random forest | AUC by logistic regression | Maximum AUC |
| Macrophage Inflammatory Protein 3 beta (MIP3beta) | 0.54 | 0.63 | 0.63 |
| Vascular Cell Adhesion Molecule 1 (VCAM1) | 0.54 | 0.67 | 0.67 |
| Macrophage Derived Chemokine (MDC) | 0.48 | 0.64 | 0.64 |
| Vascular Endothelial Growth Factor (VEGF) | 0.46 | 0.65 | 0.65 |
| Ficolin 3 | 0.51 | 0.64 | 0.64 |
| Immunoglobulin A (IgA) | 0.51 | 0.66 | 0.66 |
| Factor VII | 0.63 | 0.65 | 0.65 |
| Interleukin 6 Receptor (IL6R) | 0.53 | 0.61 | 0.61 |
| Receptor for Advanced Glycosylation End Products (RAGE) | 0.56 | 0.63 | 0.63 |
| Fibulin 1C (FIB1C) | 0.55 | 0.63 | 0.63 |
| Interferon Inducble T Cell Alpha Chemoattractant (ITAC) | 0.60 | 0.58 | 0.60 |
| Growth Hormone (GH) | 0.52 | 0.66 | 0.66 |
| Heparin Binding EGF Like Growth Factor (HBEGF) | 0.52 | 0.61 | 0.61 |
| Neuronal Cell Adhesion Molecule (NrCAM) | 0.61 | 0.63 | 0.63 |
| Growth Regulated Alpha Protein (GROalpha) | 0.56 | 0.64 | 0.64 |
| Growth Differentiation Factor 15 (GDF15) | 0.55 | 0.60 | 0.60 |
| Mast Stem Cell Growth Factor Receptor (SCFR) | 0.52 | 0.63 | 0.63 |
| Cadherin 1 (Ecad) | 0.54 | 0.60 | 0.60 |
| Angiogenin | 0.48 | 0.63 | 0.63 |
| Sortilin | 0.49 | 0.62 | 0.62 |
| Alpha 1 Antitrypsin (AAT) | 0.56 | 0.60 | 0.60 |
| Immunoglobulin M (IgM) | 0.57 | 0.62 | 0.62 |
| Pulmonary and Activation Regulated Chemokine (PARC) | 0.65 | 0.64 | 0.65 |
| Pulmonary Surfactant Associated Protein D (SP-D) | 0.50 | 0.60 | 0.60 |
| B Cell Activating Factor (BAFF) | 0.61 | 0.64 | 0.64 |
| Adrenomedullin (ADM) | 0.55 | 0.69 | 0.69 |
| Pigment Epithelium Derived Factor (PEDF) | 0.63 | 0.69 | 0.69 |
| Interleukin 1 Receptor Antagonist (IL1ra) | 0.51 | 0.65 | 0.65 |
| Thyrosine Binding Globulin (TBG) | 0.58 | 0.66 | 0.66 |
| Microalbumin | 0.59 | 0.61 | 0.61 |
| Leptin | 0.56 | 0.66 | 0.66 |
| Eotaxin 2 | 0.62 | 0.62 | 0.62 |
| Insulin like Growth Factor Binding Protein 2 (IGFBP2) | 0.59 | 0.62 | 0.62 |

TABLE 11-continued

2 Biomarker Multivariate Analysis. Combination of Immunoglobulin E (IgE) and Analyte 2

| Analyte 2 | AUC by random forest | AUC by logistic regression | Maximum AUC |
|---|---|---|---|
| Resistin | 0.52 | 0.59 | 0.59 |
| Cathepsin D | 0.57 | 0.67 | 0.67 |
| E-Selectin | 0.55 | 0.66 | 0.66 |
| YKL40 | 0.62 | 0.58 | 0.62 |
| Interleukin 22 (IL22) | 0.54 | 0.59 | 0.59 |
| Cacinoembryonic Antigen (CEA) | 0.51 | 0.60 | 0.60 |
| Interleukin 8 (IL8) | 0.62 | 0.59 | 0.62 |
| Cancer Antigen 15-3 (CA 15-3) | 0.53 | 0.60 | 0.60 |
| Leptin Receptor (LeptinR) | 0.59 | 0.66 | 0.66 |
| Insulin | 0.55 | 0.68 | 0.68 |
| Monocyte Chemotactic Protein 1 (MCP1) | 0.56 | 0.63 | 0.63 |
| Prolactin (PRL) | 0.54 | 0.63 | 0.63 |
| Tetranectin | 0.50 | 0.59 | 0.59 |
| Carcinoembryonic Antigen Related Cell Adhesion Molecule 1 (CEACAM1) | 0.50 | 0.61 | 0.61 |
| 6Ckine | 0.62 | 0.66 | 0.66 |
| Serum Amyloid P Component (SAP) | 0.57 | 0.65 | 0.65 |
| Complement Factor H Related Protein 1 (CFHR1) | 0.52 | 0.59 | 0.59 |
| Chemokine CC-4 (HCC-4) | 0.66 | 0.59 | 0.66 |
| Complement C3 (C3) | 0.59 | 0.60 | 0.60 |
| Alpha Fetoprotein (AFP) | 0.56 | 0.59 | 0.59 |
| Angiopoietin 1 (ANG-1) | 0.54 | 0.62 | 0.62 |
| Interleukin 18 (IL18) | 0.64 | 0.68 | 0.68 |
| Gelsolin | 0.56 | 0.60 | 0.60 |
| Tenascin C (TN-C) | 0.51 | 0.61 | 0.61 |
| Vitronectin | 0.68 | 0.60 | 0.68 |
| Beta 2 Microglobulin (B2M) | 0.61 | 0.63 | 0.63 |
| Pancreatic Secretory Trypsin Inhibitor (TATI) | 0.57 | 0.58 | 0.58 |
| Matrix Metalloproteinase 3 (MMP3) | 0.62 | 0.62 | 0.62 |
| Omentin | 0.52 | 0.62 | 0.62 |
| Interleukin 18 Binding Protein (IL 18bp) | 0.65 | 0.65 | 0.65 |
| Apolipoprotein D (ApoD) | 0.64 | 0.65 | 0.65 |
| Monoctye Chemotactic Protein 4 (MCP-4) | 0.54 | 0.58 | 0.58 |
| Apolipoprotein E (Apo-E) | 0.59 | 0.64 | 0.64 |
| ST2 | 0.59 | 0.59 | 0.59 |
| Thrombospondin 1 | 0.56 | 0.58 | 0.58 |
| Gastric Inhibitory Polypeptide (GIP) | 0.57 | 0.64 | 0.64 |
| Matrix Metalloproteinase 7 (MMP7) | 0.64 | 0.62 | 0.64 |
| Intercellular Adhesion Molecule 1 (ICAM-1) | 0.57 | 0.59 | 0.59 |
| Dickkopf Related Protein 1 (DKK1) | 0.51 | 0.57 | 0.57 |

TABLE 12

2 Biomarker Multivariate Analysis. Combination of Macrophage Inflammatory Protein 3 beta (MIP3beta) and Analyte 2

| Analyte 2 | AUC by random forest | AUC by logistic regression | Maximum AUC |
|---|---|---|---|
| Vascular Cell Adhesion Molecule 1 (VCAM1) | 0.60 | 0.65 | 0.65 |
| Macrophage Derived Chemokine (MDC) | 0.57 | 0.65 | 0.65 |
| Vascular Endothelial Growth Factor (VEGF) | 0.57 | 0.65 | 0.65 |
| Ficolin 3 | 0.63 | 0.66 | 0.66 |
| Immunoglobulin A (IgA) | 0.50 | 0.63 | 0.63 |
| Factor VII | 0.61 | 0.61 | 0.61 |
| Interleukin 6 Receptor (IL6R) | 0.59 | 0.65 | 0.65 |
| Receptor for Advanced Glycosylation End Products (RAGE) | 0.63 | 0.66 | 0.66 |
| Fibulin 1C (FIB1C) | 0.61 | 0.64 | 0.64 |
| Interferon Inducble T Cell Alpha Chemoattractant (ITAC) | 0.57 | 0.62 | 0.62 |
| Growth Hormone (GH) | 0.56 | 0.65 | 0.65 |
| Heparin Binding EGF Like Growth Factor (HBEGF) | 0.61 | 0.62 | 0.62 |
| Neuronal Cell Adhesion Molecule (NrCAM) | 0.57 | 0.63 | 0.63 |
| Growth Regulated Alpha Protein (GROalpha) | 0.58 | 0.62 | 0.62 |
| Growth Differentiation Factor 15 (GDF15) | 0.60 | 0.63 | 0.63 |
| Mast Stem Cell Growth Factor Receptor (SCFR) | 0.47 | 0.67 | 0.67 |
| Cadherin 1 (Ecad) | 0.69 | 0.63 | 0.69 |
| Angiogenin | 0.60 | 0.64 | 0.64 |
| Sortilin | 0.60 | 0.62 | 0.62 |
| Alpha 1 Antitrypsin (AAT) | 0.61 | 0.64 | 0.64 |
| Immunoglobulin M (IgM) | 0.48 | 0.64 | 0.64 |

TABLE 12-continued

2 Biomarker Multivariate Analysis. Combination of Macrophage Inflammatory Protein 3 beta (MIP3beta) and Analyte 2

| Analyte 2 | AUC by random forest | AUC by logistic regression | Maximum AUC |
|---|---|---|---|
| Pulmonary and Activation Regulated Chemokine (PARC) | 0.60 | 0.64 | 0.64 |
| Pulmonary Surfactant Associated Protein D (SP-D) | 0.58 | 0.63 | 0.63 |
| B Cell Activating Factor (BAFF) | 0.63 | 0.64 | 0.64 |
| Adrenomedullin (ADM) | 0.55 | 0.67 | 0.67 |
| Pigment Epithelium Derived Factor (PEDF) | 0.60 | 0.66 | 0.66 |
| Interleukin 1 Receptor Antagonist (IL1ra) | 0.63 | 0.62 | 0.63 |
| Thyrosine Binding Globulin (TBG) | 0.57 | 0.64 | 0.64 |
| Microalbumin | 0.59 | 0.63 | 0.63 |
| Leptin | 0.52 | 0.65 | 0.65 |
| Eotaxin 2 | 0.61 | 0.64 | 0.64 |
| Insulin like Growth Factor Binding Protein 2 (IGFBP2) | 0.56 | 0.63 | 0.63 |
| Resistin | 0.52 | 0.62 | 0.62 |
| Cathepsin D | 0.56 | 0.65 | 0.65 |
| E-Selectin | 0.60 | 0.64 | 0.64 |
| YKL40 | 0.48 | 0.63 | 0.63 |
| Interleukin 22 (IL22) | 0.56 | 0.63 | 0.63 |
| Cacinoembryonic Antigen (CEA) | 0.58 | 0.61 | 0.61 |
| Interleukin 8 (IL8) | 0.62 | 0.62 | 0.62 |
| Cancer Antigen 15-3 (CA 15-3) | 0.54 | 0.64 | 0.64 |
| Leptin Receptor (LeptinR) | 0.54 | 0.66 | 0.66 |
| Insulin | 0.57 | 0.65 | 0.65 |
| Monocyte Chemotactic Protein 1 (MCP1) | 0.60 | 0.62 | 0.62 |
| Prolactin (PRL) | 0.48 | 0.64 | 0.64 |
| Tetranectin | 0.53 | 0.62 | 0.62 |
| Carcinoembryonic Antigen Related Cell Adhesion Molecule 1 (CEACAM1) | 0.56 | 0.64 | 0.64 |
| 6Ckine | 0.55 | 0.63 | 0.63 |
| Serum Amyloid P Component (SAP) | 0.58 | 0.63 | 0.63 |
| Complement Factor H Related Protein 1 (CFHR1) | 0.63 | 0.62 | 0.63 |
| Chemokine CC-4 (HCC-4) | 0.57 | 0.62 | 0.62 |
| Complement C3 (C3) | 0.63 | 0.61 | 0.63 |
| Alpha Fetoprotein (AFP) | 0.59 | 0.63 | 0.63 |
| Angiopoietin 1 (ANG-1) | 0.59 | 0.63 | 0.63 |
| Interleukin 18 (IL18) | 0.58 | 0.65 | 0.65 |
| Gelsolin | 0.57 | 0.63 | 0.63 |
| Tenascin C (TN-C) | 0.52 | 0.63 | 0.63 |
| Vitronectin | 0.62 | 0.61 | 0.62 |
| Beta 2 Microglobulin (B2M) | 0.53 | 0.63 | 0.63 |
| Pancreatic Secretory Trypsin Inhibitor (TATI) | 0.54 | 0.62 | 0.62 |
| Matrix Metalloproteinase 3 (MMP3) | 0.61 | 0.63 | 0.63 |
| Omentin | 0.53 | 0.61 | 0.61 |
| Interleukin 18 Binding Protein (IL 18bp) | 0.58 | 0.62 | 0.62 |
| Apolipoprotein D (ApoD) | 0.62 | 0.62 | 0.62 |
| Monoctye Chemotactic Protein 4 (MCP-4) | 0.53 | 0.62 | 0.62 |
| Apolipoprotein E (Apo-E) | 0.48 | 0.63 | 0.63 |
| ST2 | 0.59 | 0.63 | 0.63 |
| Thrombospondin 1 | 0.58 | 0.62 | 0.62 |
| Gastric Inhibitory Polypeptide (GIP) | 0.60 | 0.64 | 0.64 |
| Matrix Metalloproteinase 7 (MMP7) | 0.58 | 0.62 | 0.62 |
| Intercellular Adhesion Molecule 1 (ICAM-1) | 0.60 | 0.62 | 0.62 |
| Dickkopf Related Protein 1 (DKK1) | 0.51 | 0.61 | 0.61 |

TABLE 13

2 Biomarker Multivariate Analysis. Combination of Vascular Cell Adhesion Molecule 1 (VCAM1) and Analyte 2

| Analyte 2 | AUC by random forest | AUC by logistic regression | Maximum AUC |
|---|---|---|---|
| Macrophage Derived Chemokine (MDC) | 0.59 | 0.66 | 0.66 |
| Vascular Endothelial Growth Factor (VEGF) | 0.46 | 0.66 | 0.66 |
| Ficolin 3 | 0.56 | 0.66 | 0.66 |
| Immunoglobulin A (IgA) | 0.56 | 0.66 | 0.66 |
| Factor VII | 0.67 | 0.66 | 0.67 |
| Interleukin 6 Receptor (IL6R) | 0.46 | 0.66 | 0.66 |
| Receptor for Advanced Glycosylation End Products (RAGE) | 0.61 | 0.69 | 0.69 |
| Fibulin 1C (FIB1C) | 0.56 | 0.63 | 0.63 |
| Interferon Inducble T Cell Alpha Chemoattractant (ITAC) | 0.65 | 0.61 | 0.65 |

TABLE 13-continued

2 Biomarker Multivariate Analysis. Combination of Vascular Cell Adhesion
Molecule 1 (VCAM1) and Analyte 2

| Analyte 2 | AUC by random forest | AUC by logistic regression | Maximum AUC |
|---|---|---|---|
| Growth Hormone (GH) | 0.55 | 0.66 | 0.66 |
| Heparin Binding EGF Like Growth Factor (HBEGF) | 0.55 | 0.62 | 0.62 |
| Neuronal Cell Adhesion Molecule (NrCAM) | 0.67 | 0.65 | 0.67 |
| Growth Regulated Alpha Protein (GROalpha) | 0.67 | 0.62 | 0.67 |
| Growth Differentiation Factor 15 (GDF15) | 0.64 | 0.62 | 0.64 |
| Mast Stem Cell Growth Factor Receptor (SCFR) | 0.50 | 0.66 | 0.66 |
| Cadherin 1 (Ecad) | 0.64 | 0.62 | 0.64 |
| Angiogenin | 0.54 | 0.63 | 0.63 |
| Sortilin | 0.57 | 0.62 | 0.62 |
| Alpha 1 Antitrypsin (AAT) | 0.50 | 0.64 | 0.64 |
| Immunoglobulin M (IgM) | 0.61 | 0.62 | 0.62 |
| Pulmonary and Activation Regulated Chemokine (PARC) | 0.58 | 0.64 | 0.64 |
| Pulmonary Surfactant Associated Protein D (SP-D) | 0.53 | 0.60 | 0.60 |
| B Cell Activating Factor (BAFF) | 0.71 | 0.66 | 0.71 |
| Adrenomedullin (ADM) | 0.62 | 0.67 | 0.67 |
| Pigment Epithelium Derived Factor (PEDF) | 0.63 | 0.66 | 0.66 |
| Interleukin 1 Receptor Antagonist (IL1ra) | 0.59 | 0.66 | 0.66 |
| Thyrosine Binding Globulin (TBG) | 0.52 | 0.63 | 0.63 |
| Microalbumin | 0.64 | 0.66 | 0.66 |
| Leptin | 0.56 | 0.68 | 0.68 |
| Eotaxin 2 | 0.67 | 0.62 | 0.67 |
| Insulin like Growth Factor Binding Protein 2 (IGFBP2) | 0.57 | 0.62 | 0.62 |
| Resistin | 0.56 | 0.63 | 0.63 |
| Cathepsin D | 0.54 | 0.64 | 0.64 |
| E-Selectin | 0.57 | 0.67 | 0.67 |
| YKL40 | 0.55 | 0.62 | 0.62 |
| Interleukin 22 (IL22) | 0.50 | 0.63 | 0.63 |
| Cacinoembryonic Antigen (CEA) | 0.57 | 0.63 | 0.63 |
| Interleukin 8 (IL8) | 0.63 | 0.62 | 0.63 |
| Cancer Antigen 15-3 (CA 15-3) | 0.52 | 0.62 | 0.62 |
| Leptin Receptor (LeptinR) | 0.50 | 0.65 | 0.65 |
| Insulin | 0.52 | 0.65 | 0.65 |
| Monocyte Chemotactic Protein 1 (MCP1) | 0.55 | 0.64 | 0.64 |
| Prolactin (PRL) | 0.53 | 0.64 | 0.64 |
| Tetranectin | 0.52 | 0.62 | 0.62 |
| Carcinoembryonic Antigen Related Cell Adhesion Molecule 1 (CEACAM1) | 0.57 | 0.65 | 0.65 |
| 6Ckine | 0.56 | 0.65 | 0.65 |
| Serum Amyloid P Component (SAP) | 0.57 | 0.64 | 0.64 |
| Complement Factor H Related Protein 1 (CFHR1) | 0.50 | 0.62 | 0.62 |
| Chemokine CC-4 (HCC-4) | 0.58 | 0.63 | 0.63 |
| Complement C3 (C3) | 0.62 | 0.61 | 0.62 |
| Alpha Fetoprotein (AFP) | 0.46 | 0.66 | 0.66 |
| Angiopoietin 1 (ANG-1) | 0.57 | 0.62 | 0.62 |
| Interleukin 18 (IL18) | 0.67 | 0.67 | 0.67 |
| Gelsolin | 0.59 | 0.62 | 0.62 |
| Tenascin C (TN-C) | 0.55 | 0.64 | 0.64 |
| Vitronectin | 0.62 | 0.62 | 0.62 |
| Beta 2 Microglobulin (B2M) | 0.57 | 0.62 | 0.62 |
| Pancreatic Secretory Trypsin Inhibitor (TATI) | 0.55 | 0.62 | 0.62 |
| Matrix Metalloproteinase 3 (MMP3) | 0.64 | 0.65 | 0.65 |
| Omentin | 0.59 | 0.62 | 0.62 |
| Interleukin 18 Binding Protein (IL 18bp) | 0.65 | 0.63 | 0.65 |
| Apolipoprotein D (ApoD) | 0.69 | 0.63 | 0.69 |
| Monoctye Chemotactic Protein 4 (MCP-4) | 0.49 | 0.63 | 0.63 |
| Apolipoprotein E (Apo-E) | 0.47 | 0.65 | 0.65 |
| ST2 | 0.61 | 0.62 | 0.62 |
| Thrombospondin 1 | 0.56 | 0.62 | 0.62 |
| Gastric Inhibitory Polypeptide (GIP) | 0.58 | 0.64 | 0.64 |
| Matrix Metalloproteinase 7 (MMP7) | 0.57 | 0.64 | 0.64 |
| Intercellular Adhesion Molecule 1 (ICAM-1) | 0.55 | 0.62 | 0.62 |
| Dickkopf Related Protein 1 (DKK1) | 0.53 | 0.63 | 0.63 |

TABLE 14

2 Biomarker Multivariate Analysis. Combination of Macrophage Derived Chemokine (MDC) and Analyte 2

| Analyte 2 | AUC by random forest | AUC by logistic regression | Maximum AUC |
|---|---|---|---|
| Vascular Endothelial Growth Factor (VEGF) | 0.57 | 0.66 | 0.66 |
| Ficolin 3 | 0.52 | 0.66 | 0.66 |
| Immunoglobulin A (IgA) | 0.50 | 0.64 | 0.64 |
| Factor VII | 0.58 | 0.63 | 0.63 |
| Interleukin 6 Receptor (IL6R) | 0.49 | 0.64 | 0.64 |
| Receptor for Advanced Glycosylation End Products (RAGE) | 0.57 | 0.66 | 0.66 |
| Fibulin 1C (FIB1C) | 0.54 | 0.63 | 0.63 |
| Interferon Inducble T Cell Alpha Chemoattractant (ITAC) | 0.62 | 0.62 | 0.62 |
| Growth Hormone (GH) | 0.56 | 0.63 | 0.63 |
| Heparin Binding EGF Like Growth Factor (HBEGF) | 0.51 | 0.63 | 0.63 |
| Neuronal Cell Adhesion Molecule (NrCAM) | 0.62 | 0.66 | 0.66 |
| Growth Regulated Alpha Protein (GROalpha) | 0.63 | 0.62 | 0.63 |
| Growth Differentiation Factor 15 (GDF15) | 0.57 | 0.64 | 0.64 |
| Mast Stem Cell Growth Factor Receptor (SCFR) | 0.53 | 0.65 | 0.65 |
| Cadherin 1 (Ecad) | 0.59 | 0.63 | 0.63 |
| Angiogenin | 0.57 | 0.64 | 0.64 |
| Sortilin | 0.57 | 0.64 | 0.64 |
| Alpha 1 Antitrypsin (AAT) | 0.54 | 0.65 | 0.65 |
| Immunoglobulin M (IgM) | 0.59 | 0.64 | 0.64 |
| Pulmonary and Activation Regulated Chemokine (PARC) | 0.57 | 0.66 | 0.66 |
| Pulmonary Surfactant Associated Protein D (SP-D) | 0.54 | 0.63 | 0.63 |
| B Cell Activating Factor (BAFF) | 0.56 | 0.65 | 0.65 |
| Adrenomedullin (ADM) | 0.62 | 0.67 | 0.67 |
| Pigment Epithelium Derived Factor (PEDF) | 0.60 | 0.66 | 0.66 |
| Interleukin 1 Receptor Antagonist (IL1ra) | 0.54 | 0.63 | 0.63 |
| Thyrosine Binding Globulin (TBG) | 0.54 | 0.63 | 0.63 |
| Microalbumin | 0.57 | 0.64 | 0.64 |
| Leptin | 0.53 | 0.64 | 0.64 |
| Eotaxin 2 | 0.61 | 0.63 | 0.63 |
| Insulin like Growth Factor Binding Protein 2 (IGFBP2) | 0.55 | 0.63 | 0.63 |
| Resistin | 0.53 | 0.62 | 0.62 |
| Cathepsin D | 0.53 | 0.65 | 0.65 |
| E-Selectin | 0.53 | 0.66 | 0.66 |
| YKL40 | 0.55 | 0.63 | 0.63 |
| Interleukin 22 (IL22) | 0.49 | 0.62 | 0.62 |
| Cacinoembryonic Antigen (CEA) | 0.57 | 0.62 | 0.62 |
| Interleukin 8 (IL8) | 0.62 | 0.64 | 0.64 |
| Cancer Antigen 15-3 (CA 15-3) | 0.52 | 0.63 | 0.63 |
| Leptin Receptor (LeptinR) | 0.53 | 0.63 | 0.63 |
| Insulin | 0.61 | 0.63 | 0.63 |
| Monocyte Chemotactic Protein 1 (MCP1) | 0.55 | 0.63 | 0.63 |
| Prolactin (PRL) | 0.53 | 0.65 | 0.65 |
| Tetranectin | 0.49 | 0.63 | 0.63 |
| Carcinoembryonic Antigen Related Cell Adhesion Molecule 1 (CEACAM1) | 0.57 | 0.64 | 0.64 |
| 6Ckine | 0.59 | 0.64 | 0.64 |
| Serum Amyloid P Component (SAP) | 0.65 | 0.63 | 0.65 |
| Complement Factor H Related Protein 1 (CFHR1) | 0.57 | 0.62 | 0.62 |
| Chemokine CC-4 (HCC-4) | 0.56 | 0.63 | 0.63 |
| Complement C3 (C3) | 0.56 | 0.63 | 0.63 |
| Alpha Fetoprotein (AFP) | 0.49 | 0.64 | 0.64 |
| Angiopoietin 1 (ANG-1) | 0.60 | 0.63 | 0.63 |
| Interleukin 18 (IL18) | 0.62 | 0.66 | 0.66 |
| Gelsolin | 0.54 | 0.63 | 0.63 |
| Tenascin C (TN-C) | 0.56 | 0.64 | 0.64 |
| Vitronectin | 0.56 | 0.62 | 0.62 |
| Beta 2 Microglobulin (B2M) | 0.58 | 0.63 | 0.63 |
| Pancreatic Secretory Trypsin Inhibitor (TATI) | 0.49 | 0.63 | 0.63 |
| Matrix Metalloproteinase 3 (MMP3) | 0.59 | 0.64 | 0.64 |
| Omentin | 0.51 | 0.63 | 0.63 |
| Interleukin 18 Binding Protein (IL 18bp) | 0.62 | 0.64 | 0.64 |
| Apolipoprotein D (ApoD) | 0.62 | 0.62 | 0.62 |
| Monoctye Chemotactic Protein 4 (MCP-4) | 0.55 | 0.63 | 0.63 |
| Apolipoprotein E (Apo-E) | 0.62 | 0.65 | 0.65 |
| ST2 | 0.53 | 0.63 | 0.63 |
| Thrombospondin 1 | 0.62 | 0.62 | 0.62 |
| Gastric Inhibitory Polypeptide (GIP) | 0.52 | 0.64 | 0.64 |
| Matrix Metalloproteinase 7 (MMP7) | 0.61 | 0.63 | 0.63 |
| Intercellular Adhesion Molecule 1 (ICAM-1) | 0.56 | 0.63 | 0.63 |
| Dickkopf Related Protein 1 (DKK1) | 0.52 | 0.63 | 0.63 |

TABLE 15

2 Biomarker Multivariate Analysis. Combination of Vascular Endothelial Growth Factor (VEGF) and Analyte 2

| Analyte 2 | AUC by random forest | AUC by logistic regression | Maximum AUC |
|---|---|---|---|
| Ficolin 3 | 0.53 | 0.65 | 0.65 |
| Immunoglobulin A (IgA) | 0.53 | 0.64 | 0.64 |
| Factor VII | 0.61 | 0.63 | 0.63 |
| Interleukin 6 Receptor (IL6R) | 0.52 | 0.63 | 0.63 |
| Receptor for Advanced Glycosylation End Products (RAGE) | 0.53 | 0.66 | 0.66 |
| Fibulin 1C (FIB1C) | 0.56 | 0.62 | 0.62 |
| Interferon Inducble T Cell Alpha Chemoattractant (ITAC) | 0.49 | 0.60 | 0.60 |
| Growth Hormone (GH) | 0.50 | 0.64 | 0.64 |
| Heparin Binding EGF Like Growth Factor (HBEGF) | 0.53 | 0.63 | 0.63 |
| Neuronal Cell Adhesion Molecule (NrCAM) | 0.57 | 0.64 | 0.64 |
| Growth Regulated Alpha Protein (GROalpha) | 0.55 | 0.60 | 0.60 |
| Growth Differentiation Factor 15 (GDF15) | 0.53 | 0.62 | 0.62 |
| Mast Stem Cell Growth Factor Receptor (SCFR) | 0.59 | 0.64 | 0.64 |
| Cadherin 1 (Ecad) | 0.55 | 0.61 | 0.61 |
| Angiogenin | 0.62 | 0.62 | 0.62 |
| Sortilin | 0.54 | 0.62 | 0.62 |
| Alpha 1 Antitrypsin (AAT) | 0.50 | 0.61 | 0.61 |
| Immunoglobulin M (IgM) | 0.51 | 0.61 | 0.61 |
| Pulmonary and Activation Regulated Chemokine (PARC) | 0.53 | 0.67 | 0.67 |
| Pulmonary Surfactant Associated Protein D (SP-D) | 0.52 | 0.60 | 0.60 |
| B Cell Activating Factor (BAFF) | 0.60 | 0.65 | 0.65 |
| Adrenomedullin (ADM) | 0.57 | 0.66 | 0.66 |
| Pigment Epithelium Derived Factor (PEDF) | 0.53 | 0.67 | 0.67 |
| Interleukin 1 Receptor Antagonist (IL1ra) | 0.55 | 0.61 | 0.61 |
| Thyrosine Binding Globulin (TBG) | 0.52 | 0.66 | 0.66 |
| Microalbumin | 0.62 | 0.63 | 0.63 |
| Leptin | 0.59 | 0.63 | 0.63 |
| Eotaxin 2 | 0.62 | 0.63 | 0.63 |
| Insulin like Growth Factor Binding Protein 2 (IGFBP2) | 0.52 | 0.62 | 0.62 |
| Resistin | 0.52 | 0.62 | 0.62 |
| Cathepsin D | 0.51 | 0.67 | 0.67 |
| E-Selectin | 0.54 | 0.67 | 0.67 |
| YKL40 | 0.52 | 0.61 | 0.61 |
| Interleukin 22 (IL22) | 0.57 | 0.66 | 0.66 |
| Cacinoembryonic Antigen (CEA) | 0.49 | 0.62 | 0.62 |
| Interleukin 8 (IL8) | 0.57 | 0.60 | 0.60 |
| Cancer Antigen 15-3 (CA 15-3) | 0.59 | 0.61 | 0.61 |
| Leptin Receptor (LeptinR) | 0.50 | 0.62 | 0.62 |
| Insulin | 0.58 | 0.64 | 0.64 |
| Monocyte Chemotactic Protein 1 (MCP1) | 0.54 | 0.64 | 0.64 |
| Prolactin (PRL) | 0.55 | 0.61 | 0.61 |
| Tetranectin | 0.54 | 0.60 | 0.60 |
| Carcinoembryonic Antigen Related Cell Adhesion Molecule 1 (CEACAM1) | 0.51 | 0.61 | 0.61 |
| 6Ckine | 0.51 | 0.65 | 0.65 |
| Serum Amyloid P Component (SAP) | 0.58 | 0.64 | 0.64 |
| Complement Factor H Related Protein 1 (CFHR1) | 0.52 | 0.60 | 0.60 |
| Chemokine CC-4 (HCC-4) | 0.48 | 0.60 | 0.60 |
| Complement C3 (C3) | 0.48 | 0.60 | 0.60 |
| Alpha Fetoprotein (AFP) | 0.57 | 0.63 | 0.63 |
| Angiopoietin 1 (ANG-1) | 0.51 | 0.60 | 0.60 |
| Interleukin 18 (IL18) | 0.55 | 0.66 | 0.66 |
| Gelsolin | 0.52 | 0.61 | 0.61 |
| Tenascin C (TN-C) | 0.52 | 0.60 | 0.60 |
| Vitronectin | 0.51 | 0.62 | 0.62 |
| Beta 2 Microglobulin (B2M) | 0.53 | 0.63 | 0.63 |
| Pancreatic Secretory Trypsin Inhibitor (TATI) | 0.58 | 0.61 | 0.61 |
| Matrix Metalloproteinase 3 (MMP3) | 0.52 | 0.64 | 0.64 |
| Omentin | 0.60 | 0.60 | 0.60 |
| Interleukin 18 Binding Protein (IL 18bp) | 0.58 | 0.62 | 0.62 |
| Apolipoprotein D (ApoD) | 0.56 | 0.62 | 0.62 |
| Monoctye Chemotactic Protein 4 (MCP-4) | 0.57 | 0.61 | 0.61 |
| Apolipoprotein E (Apo-E) | 0.52 | 0.64 | 0.64 |
| ST2 | 0.53 | 0.61 | 0.61 |
| Thrombospondin 1 | 0.56 | 0.60 | 0.60 |
| Gastric Inhibitory Polypeptide (GIP) | 0.55 | 0.65 | 0.65 |
| Matrix Metalloproteinase 7 (MMP7) | 0.52 | 0.62 | 0.62 |
| Intercellular Adhesion Molecule 1 (ICAM-1) | 0.48 | 0.61 | 0.61 |
| Dickkopf Related Protein 1 (DKK1) | 0.55 | 0.61 | 0.61 |

TABLE 16

| 2 Biomarker Multivariate Analysis. Combination of Ficolin 3 and Analyte 2 | | | |
|---|---|---|---|
| Analyte 2 | AUC by random forest | AUC by logistic regression | Maximum AUC |
| Immunoglobulin A (IgA) | 0.56 | 0.62 | 0.62 |
| Factor VII | 0.58 | 0.62 | 0.62 |
| Interleukin 6 Receptor (IL6R) | 0.53 | 0.64 | 0.64 |
| Receptor for Advanced Glycosylation End Products (RAGE) | 0.58 | 0.64 | 0.64 |
| Fibulin 1C (FIB1C) | 0.59 | 0.64 | 0.64 |
| Interferon Inducble T Cell Alpha Chemoattractant (ITAC) | 0.51 | 0.61 | 0.61 |
| Growth Hormone (GH) | 0.53 | 0.64 | 0.64 |
| Heparin Binding EGF Like Growth Factor (HBEGF) | 0.52 | 0.61 | 0.61 |
| Neuronal Cell Adhesion Molecule (NrCAM) | 0.54 | 0.64 | 0.64 |
| Growth Regulated Alpha Protein (GROalpha) | 0.53 | 0.62 | 0.62 |
| Growth Differentiation Factor 15 (GDF15) | 0.50 | 0.62 | 0.62 |
| Mast Stem Cell Growth Factor Receptor (SCFR) | 0.55 | 0.65 | 0.65 |
| Cadherin 1 (Ecad) | 0.62 | 0.61 | 0.62 |
| Angiogenin | 0.54 | 0.63 | 0.63 |
| Sortilin | 0.50 | 0.61 | 0.61 |
| Alpha 1 Antitrypsin (AAT) | 0.51 | 0.60 | 0.60 |
| Immunoglobulin M (IgM) | 0.57 | 0.63 | 0.63 |
| Pulmonary and Activation Regulated Chemokine (PARC) | 0.57 | 0.64 | 0.64 |
| Pulmonary Surfactant Associated Protein D (SP-D) | 0.57 | 0.61 | 0.61 |
| B Cell Activating Factor (BAFF) | 0.52 | 0.65 | 0.65 |
| Adrenomedullin (ADM) | 0.56 | 0.66 | 0.66 |
| Pigment Epithelium Derived Factor (PEDF) | 0.57 | 0.65 | 0.65 |
| Interleukin 1 Receptor Antagonist (IL1ra) | 0.56 | 0.64 | 0.64 |
| Thyrosine Binding Globulin (TBG) | 0.59 | 0.62 | 0.62 |
| Microalbumin | 0.60 | 0.62 | 0.62 |
| Leptin | 0.51 | 0.65 | 0.65 |
| Eotaxin 2 | 0.54 | 0.62 | 0.62 |
| Insulin like Growth Factor Binding Protein 2 (IGFBP2) | 0.57 | 0.60 | 0.60 |
| Resistin | 0.47 | 0.62 | 0.62 |
| Cathepsin D | 0.57 | 0.65 | 0.65 |
| E-Selectin | 0.47 | 0.65 | 0.65 |
| YKL40 | 0.52 | 0.62 | 0.62 |
| Interleukin 22 (IL22) | 0.55 | 0.61 | 0.61 |
| Cacinoembryonic Antigen (CEA) | 0.49 | 0.61 | 0.61 |
| Interleukin 8 (IL8) | 0.57 | 0.62 | 0.62 |
| Cancer Antigen 15-3 (CA 15-3) | 0.61 | 0.61 | 0.61 |
| Leptin Receptor (LeptinR) | 0.55 | 0.63 | 0.63 |
| Insulin | 0.54 | 0.63 | 0.63 |
| Monocyte Chemotactic Protein 1 (MCP1) | 0.57 | 0.64 | 0.64 |
| Prolactin (PRL) | 0.62 | 0.62 | 0.62 |
| Tetranectin | 0.56 | 0.61 | 0.61 |
| Carcinoembryonic Antigen Related Cell Adhesion Molecule 1 (CEACAM1) | 0.50 | 0.63 | 0.63 |
| 6Ckine | 0.49 | 0.66 | 0.66 |
| Serum Amyloid P Component (SAP) | 0.53 | 0.61 | 0.61 |
| Complement Factor H Related Protein 1 (CFHR1) | 0.54 | 0.62 | 0.62 |
| Chemokine CC-4 (HCC-4) | 0.57 | 0.62 | 0.62 |
| Complement C3 (C3) | 0.54 | 0.61 | 0.61 |
| Alpha Fetoprotein (AFP) | 0.57 | 0.65 | 0.65 |
| Angiopoietin 1 (ANG-1) | 0.51 | 0.63 | 0.63 |
| Interleukin 18 (IL18) | 0.54 | 0.66 | 0.66 |
| Gelsolin | 0.40 | 0.62 | 0.62 |
| Tenascin C (TN-C) | 0.50 | 0.62 | 0.62 |
| Vitronectin | 0.48 | 0.61 | 0.61 |
| Beta 2 Microglobulin (B2M) | 0.49 | 0.62 | 0.62 |
| Pancreatic Secretory Trypsin Inhibitor (TATI) | 0.53 | 0.61 | 0.61 |
| Matrix Metalloproteinase 3 (MMP3) | 0.65 | 0.64 | 0.65 |
| Omentin | 0.59 | 0.62 | 0.62 |
| Interleukin 18 Binding Protein (IL 18bp) | 0.55 | 0.64 | 0.64 |
| Apolipoprotein D (ApoD) | 0.49 | 0.61 | 0.61 |
| Monoctye Chemotactic Protein 4 (MCP-4) | 0.58 | 0.61 | 0.61 |
| Apolipoprotein E (Apo-E) | 0.49 | 0.63 | 0.63 |
| ST2 | 0.50 | 0.61 | 0.61 |
| Thrombospondin 1 | 0.58 | 0.61 | 0.61 |
| Gastric Inhibitory Polypeptide (GIP) | 0.56 | 0.62 | 0.62 |
| Matrix Metalloproteinase 7 (MMP7) | 0.50 | 0.61 | 0.61 |
| Intercellular Adhesion Molecule 1 (ICAM-1) | 0.50 | 0.62 | 0.62 |
| Dickkopf Related Protein 1 (DKK1) | 0.51 | 0.61 | 0.61 |

TABLE 17

2 Biomarker Multivariate Analysis. Combination of Immunoglobulin A (IgA) and Analyte 2

| Analyte 2 | AUC by random forest | AUC by logistic regression | Maximum AUC |
|---|---|---|---|
| Factor VII | 0.55 | 0.62 | 0.62 |
| Interleukin 6 Receptor (IL6R) | 0.55 | 0.63 | 0.63 |
| Receptor for Advanced Glycosylation End Products (RAGE) | 0.47 | 0.63 | 0.63 |
| Fibulin 1C (FIB1C) | 0.58 | 0.62 | 0.62 |
| Interferon Inducble T Cell Alpha Chemoattractant (ITAC) | 0.52 | 0.59 | 0.59 |
| Growth Hormone (GH) | 0.61 | 0.60 | 0.61 |
| Heparin Binding EGF Like Growth Factor (HBEGF) | 0.54 | 0.60 | 0.60 |
| Neuronal Cell Adhesion Molecule (NrCAM) | 0.50 | 0.63 | 0.63 |
| Growth Regulated Alpha Protein (GROalpha) | 0.50 | 0.60 | 0.60 |
| Growth Differentiation Factor 15 (GDF15) | 0.51 | 0.59 | 0.59 |
| Mast Stem Cell Growth Factor Receptor (SCFR) | 0.56 | 0.63 | 0.63 |
| Cadherin 1 (Ecad) | 0.47 | 0.59 | 0.59 |
| Angiogenin | 0.47 | 0.61 | 0.61 |
| Sortilin | 0.56 | 0.59 | 0.59 |
| Alpha 1 Antitrypsin (AAT) | 0.51 | 0.59 | 0.59 |
| Immunoglobulin M (IgM) | 0.55 | 0.62 | 0.62 |
| Pulmonary and Activation Regulated Chemokine (PARC) | 0.53 | 0.63 | 0.63 |
| Pulmonary Surfactant Associated Protein D (SP-D) | 0.58 | 0.59 | 0.59 |
| B Cell Activating Factor (BAFF) | 0.48 | 0.61 | 0.61 |
| Adrenomedullin (ADM) | 0.49 | 0.63 | 0.63 |
| Pigment Epithelium Derived Factor (PEDF) | 0.52 | 0.67 | 0.67 |
| Interleukin 1 Receptor Antagonist (IL1ra) | 0.57 | 0.62 | 0.62 |
| Thyrosine Binding Globulin (TBG) | 0.62 | 0.61 | 0.62 |
| Microalbumin | 0.53 | 0.62 | 0.62 |
| Leptin | 0.52 | 0.63 | 0.63 |
| Eotaxin 2 | 0.56 | 0.59 | 0.59 |
| Insulin like Growth Factor Binding Protein 2 (IGFBP2) | 0.49 | 0.61 | 0.61 |
| Resistin | 0.56 | 0.60 | 0.60 |
| Cathepsin D | 0.58 | 0.64 | 0.64 |
| E-Selectin | 0.44 | 0.68 | 0.68 |
| YKL40 | 0.54 | 0.59 | 0.59 |
| Interleukin 22 (IL22) | 0.66 | 0.60 | 0.66 |
| Cacinoembryonic Antigen (CEA) | 0.57 | 0.62 | 0.62 |
| Interleukin 8 (IL8) | 0.54 | 0.59 | 0.59 |
| Cancer Antigen 15-3 (CA 15-3) | 0.66 | 0.60 | 0.66 |
| Leptin Receptor (LeptinR) | 0.54 | 0.60 | 0.60 |
| Insulin | 0.53 | 0.63 | 0.63 |
| Monocyte Chemotactic Protein 1 (MCP1) | 0.56 | 0.62 | 0.62 |
| Prolactin (PRL) | 0.53 | 0.61 | 0.61 |
| Tetranectin | 0.63 | 0.59 | 0.63 |
| Carcinoembryonic Antigen Related Cell Adhesion Molecule 1 (CEACAM1) | 0.63 | 0.60 | 0.63 |
| 6Ckine | 0.53 | 0.61 | 0.61 |
| Serum Amyloid P Component (SAP) | 0.55 | 0.60 | 0.60 |
| Complement Factor H Related Protein 1 (CFHR1) | 0.49 | 0.58 | 0.58 |
| Chemokine CC-4 (HCC-4) | 0.60 | 0.59 | 0.60 |
| Complement C3 (C3) | 0.53 | 0.58 | 0.58 |
| Alpha Fetoprotein (AFP) | 0.57 | 0.61 | 0.61 |
| Angiopoietin 1 (ANG-1) | 0.57 | 0.60 | 0.60 |
| Interleukin 18 (IL18) | 0.52 | 0.64 | 0.64 |
| Gelsolin | 0.53 | 0.60 | 0.60 |
| Tenascin C (TN-C) | 0.55 | 0.58 | 0.58 |
| Vitronectin | 0.53 | 0.57 | 0.57 |
| Beta 2 Microglobulin (B2M) | 0.48 | 0.60 | 0.60 |
| Pancreatic Secretory Trypsin Inhibitor (TATI) | 0.60 | 0.58 | 0.60 |
| Matrix Metalloproteinase 3 (MMP3) | 0.53 | 0.61 | 0.61 |
| Omentin | 0.62 | 0.59 | 0.62 |
| Interleukin 18 Binding Protein (IL 18bp) | 0.62 | 0.62 | 0.62 |
| Apolipoprotein D (ApoD) | 0.55 | 0.58 | 0.58 |
| Monoctye Chemotactic Protein 4 (MCP-4) | 0.65 | 0.59 | 0.65 |
| Apolipoprotein E (Apo-E) | 0.56 | 0.61 | 0.61 |
| ST2 | 0.57 | 0.58 | 0.58 |
| Thrombospondin 1 | 0.56 | 0.58 | 0.58 |
| Gastric Inhibitory Polypeptide (GIP) | 0.62 | 0.63 | 0.63 |
| Matrix Metalloproteinase 7 (MMP7) | 0.55 | 0.59 | 0.59 |
| Intercellular Adhesion Molecule 1 (ICAM-1) | 0.58 | 0.59 | 0.59 |
| Dickkopf Related Protein 1 (DKK1) | 0.51 | 0.59 | 0.59 |

TABLE 18

| 2 Biomarker Multivariate Analysis. Combination of Factor VII and Analyte 2 | | | |
|---|---|---|---|
| Analyte 2 | AUC by random forest | AUC by logistic regression | Maximum AUC |
| Interleukin 6 Receptor (IL6R) | 0.59 | 0.61 | 0.61 |
| Receptor for Advanced Glycosylation End Products (RAGE) | 0.65 | 0.64 | 0.65 |
| Fibulin 1C (FIB1C) | 0.53 | 0.60 | 0.60 |
| Interferon Inducble T Cell Alpha Chemoattractant (ITAC) | 0.46 | 0.60 | 0.60 |
| Growth Hormone (GH) | 0.60 | 0.59 | 0.60 |
| Heparin Binding EGF Like Growth Factor (HBEGF) | 0.55 | 0.60 | 0.60 |
| Neuronal Cell Adhesion Molecule (NrCAM) | 0.62 | 0.62 | 0.62 |
| Growth Regulated Alpha Protein (GROalpha) | 0.54 | 0.60 | 0.60 |
| Growth Differentiation Factor 15 (GDF15) | 0.63 | 0.59 | 0.63 |
| Mast Stem Cell Growth Factor Receptor (SCFR) | 0.53 | 0.62 | 0.62 |
| Cadherin 1 (Ecad) | 0.74 | 0.59 | 0.74 |
| Angiogenin | 0.64 | 0.60 | 0.64 |
| Sortilin | 0.56 | 0.59 | 0.59 |
| Alpha 1 Antitrypsin (AAT) | 0.56 | 0.60 | 0.60 |
| Immunoglobulin M (IgM) | 0.63 | 0.62 | 0.63 |
| Pulmonary and Activation Regulated Chemokine (PARC) | 0.59 | 0.60 | 0.60 |
| Pulmonary Surfactant Associated Protein D (SP-D) | 0.68 | 0.59 | 0.68 |
| B Cell Activating Factor (BAFF) | 0.57 | 0.63 | 0.63 |
| Adrenomedullin (ADM) | 0.58 | 0.66 | 0.66 |
| Pigment Epithelium Derived Factor (PEDF) | 0.56 | 0.65 | 0.65 |
| Interleukin 1 Receptor Antagonist (IL1ra) | 0.52 | 0.61 | 0.61 |
| Thyrosine Binding Globulin (TBG) | 0.55 | 0.59 | 0.59 |
| Microalbumin | 0.65 | 0.62 | 0.65 |
| Leptin | 0.57 | 0.62 | 0.62 |
| Eotaxin 2 | 0.67 | 0.60 | 0.67 |
| Insulin like Growth Factor Binding Protein 2 (IGFBP2) | 0.51 | 0.59 | 0.59 |
| Resistin | 0.55 | 0.59 | 0.59 |
| Cathepsin D | 0.48 | 0.63 | 0.63 |
| E-Selectin | 0.59 | 0.65 | 0.65 |
| YKL40 | 0.55 | 0.57 | 0.57 |
| Interleukin 22 (IL22) | 0.53 | 0.60 | 0.60 |
| Cacinoembryonic Antigen (CEA) | 0.67 | 0.58 | 0.67 |
| Interleukin 8 (IL8) | 0.60 | 0.58 | 0.60 |
| Cancer Antigen 15-3 (CA 15-3) | 0.54 | 0.59 | 0.59 |
| Leptin Receptor (LeptinR) | 0.66 | 0.64 | 0.66 |
| Insulin | 0.64 | 0.60 | 0.64 |
| Monocyte Chemotactic Protein 1 (MCP1) | 0.56 | 0.61 | 0.61 |
| Prolactin (PRL) | 0.47 | 0.58 | 0.58 |
| Tetranectin | 0.57 | 0.57 | 0.57 |
| Carcinoembryonic Antigen Related Cell Adhesion Molecule 1 (CEACAM1) | 0.58 | 0.64 | 0.64 |
| 6Ckine | 0.53 | 0.62 | 0.62 |
| Serum Amyloid P Component (SAP) | 0.54 | 0.60 | 0.60 |
| Complement Factor H Related Protein 1 (CFHR1) | 0.56 | 0.59 | 0.59 |
| Chemokine CC-4 (HCC-4) | 0.58 | 0.58 | 0.58 |
| Complement C3 (C3) | 0.53 | 0.58 | 0.58 |
| Alpha Fetoprotein (AFP) | 0.57 | 0.62 | 0.62 |
| Angiopoietin 1 (ANG-1) | 0.56 | 0.58 | 0.58 |
| Interleukin 18 (IL18) | 0.64 | 0.63 | 0.64 |
| Gelsolin | 0.57 | 0.58 | 0.58 |
| Tenascin C (TN-C) | 0.52 | 0.60 | 0.60 |
| Vitronectin | 0.59 | 0.58 | 0.59 |
| Beta 2 Microglobulin (B2M) | 0.52 | 0.59 | 0.59 |
| Pancreatic Secretory Trypsin Inhibitor (TATI) | 0.53 | 0.58 | 0.58 |
| Matrix Metalloproteinase 3 (MMP3) | 0.62 | 0.60 | 0.62 |
| Omentin | 0.51 | 0.57 | 0.57 |
| Interleukin 18 Binding Protein (IL 18bp) | 0.60 | 0.60 | 0.60 |
| Apolipoprotein D (ApoD) | 0.65 | 0.58 | 0.65 |
| Monoctye Chemotactic Protein 4 (MCP-4) | 0.57 | 0.59 | 0.59 |
| Apolipoprotein E (Apo-E) | 0.59 | 0.63 | 0.63 |
| ST2 | 0.62 | 0.58 | 0.62 |
| Thrombospondin 1 | 0.59 | 0.58 | 0.59 |
| Gastric Inhibitory Polypeptide (GIP) | 0.64 | 0.59 | 0.64 |
| Matrix Metalloproteinase 7 (MMP7) | 0.61 | 0.61 | 0.61 |
| Intercellular Adhesion Molecule 1 (ICAM-1) | 0.55 | 0.58 | 0.58 |
| Dickkopf Related Protein 1 (DKK1) | 0.58 | 0.58 | 0.58 |

TABLE 19

2 Biomarker Multivariate Analysis. Combination of Interleukin 6 Receptor (IL6R) and Analyte 2

| Analyte 2 | AUC by random forest | AUC by logistic regression | Maximum AUC |
|---|---|---|---|
| Receptor for Advanced Glycosylation End Products (RAGE) | 0.56 | 0.64 | 0.64 |
| Fibulin 1C (FIB1C) | 0.54 | 0.59 | 0.59 |
| Interferon Inducble T Cell Alpha Chemoattractant (ITAC) | 0.55 | 0.57 | 0.57 |
| Growth Hormone (GH) | 0.57 | 0.62 | 0.62 |
| Heparin Binding EGF Like Growth Factor (HBEGF) | 0.61 | 0.60 | 0.61 |
| Neuronal Cell Adhesion Molecule (NrCAM) | 0.50 | 0.64 | 0.64 |
| Growth Regulated Alpha Protein (GROalpha) | 0.54 | 0.42 | 0.54 |
| Growth Differentiation Factor 15 (GDF15) | 0.57 | 0.60 | 0.60 |
| Mast Stem Cell Growth Factor Receptor (SCFR) | 0.59 | 0.62 | 0.62 |
| Cadherin 1 (Ecad) | 0.56 | 0.58 | 0.58 |
| Angiogenin | 0.57 | 0.61 | 0.61 |
| Sortilin | 0.57 | 0.61 | 0.61 |
| Alpha 1 Antitrypsin (AAT) | 0.54 | 0.59 | 0.59 |
| Immunoglobulin M (IgM) | 0.51 | 0.59 | 0.59 |
| Pulmonary and Activation Regulated Chemokine (PARC) | 0.66 | 0.65 | 0.66 |
| Pulmonary Surfactant Associated Protein D (SP-D) | 0.52 | 0.58 | 0.58 |
| B Cell Activating Factor (BAFF) | 0.56 | 0.60 | 0.60 |
| Adrenomedullin (ADM) | 0.52 | 0.65 | 0.65 |
| Pigment Epithelium Derived Factor (PEDF) | 0.58 | 0.69 | 0.69 |
| Interleukin 1 Receptor Antagonist (IL1ra) | 0.51 | 0.66 | 0.66 |
| Thyrosine Binding Globulin (TBG) | 0.55 | 0.60 | 0.60 |
| Microalbumin | 0.59 | 0.59 | 0.59 |
| Leptin | 0.54 | 0.64 | 0.64 |
| Eotaxin 2 | 0.67 | 0.58 | 0.67 |
| Insulin like Growth Factor Binding Protein 2 (IGFBP2) | 0.51 | 0.60 | 0.60 |
| Resistin | 0.49 | 0.61 | 0.61 |
| Cathepsin D | 0.56 | 0.66 | 0.66 |
| E-Selectin | 0.54 | 0.66 | 0.66 |
| YKL40 | 0.58 | 0.58 | 0.58 |
| Interleukin 22 (IL22) | 0.52 | 0.62 | 0.62 |
| Cacinoembryonic Antigen (CEA) | 0.54 | 0.60 | 0.60 |
| Interleukin 8 (IL8) | 0.58 | 0.58 | 0.58 |
| Cancer Antigen 15-3 (CA 15-3) | 0.60 | 0.58 | 0.60 |
| Leptin Receptor (LeptinR) | 0.57 | 0.59 | 0.59 |
| Insulin | 0.48 | 0.63 | 0.63 |
| Monocyte Chemotactic Protein 1 (MCP1) | 0.58 | 0.62 | 0.62 |
| Prolactin (PRL) | 0.60 | 0.59 | 0.60 |
| Tetranectin | 0.61 | 0.59 | 0.61 |
| Carcinoembryonic Antigen Related Cell Adhesion Molecule 1 (CEACAM1) | 0.58 | 0.58 | 0.58 |
| 6Ckine | 0.52 | 0.63 | 0.63 |
| Serum Amyloid P Component (SAP) | 0.56 | 0.61 | 0.61 |
| Complement Factor H Related Protein 1 (CFHR1) | 0.49 | 0.58 | 0.58 |
| Chemokine CC-4 (HCC-4) | 0.56 | 0.58 | 0.58 |
| Complement C3 (C3) | 0.59 | 0.59 | 0.59 |
| Alpha Fetoprotein (AFP) | 0.49 | 0.60 | 0.60 |
| Angiopoietin 1 (ANG-1) | 0.49 | 0.58 | 0.58 |
| Interleukin 18 (IL18) | 0.50 | 0.66 | 0.66 |
| Gelsolin | 0.56 | 0.60 | 0.60 |
| Tenascin C (TN-C) | 0.49 | 0.59 | 0.59 |
| Vitronectin | 0.56 | 0.59 | 0.59 |
| Beta 2 Microglobulin (B2M) | 0.60 | 0.60 | 0.60 |
| Pancreatic Secretory Trypsin Inhibitor (TATI) | 0.55 | 0.58 | 0.58 |
| Matrix Metalloproteinase 3 (MMP3) | 0.58 | 0.60 | 0.60 |
| Omentin | 0.65 | 0.58 | 0.65 |
| Interleukin 18 Binding Protein (IL 18bp) | 0.50 | 0.62 | 0.62 |
| Apolipoprotein D (ApoD) | 0.60 | 0.58 | 0.60 |
| Monoctye Chemotactic Protein 4 (MCP-4) | 0.60 | 0.58 | 0.60 |
| Apolipoprotein E (Apo-E) | 0.51 | 0.62 | 0.62 |
| ST2 | 0.53 | 0.58 | 0.58 |
| Thrombospondin 1 | 0.51 | 0.59 | 0.59 |
| Gastric Inhibitory Polypeptide (GIP) | 0.50 | 0.60 | 0.60 |
| Matrix Metalloproteinase 7 (MMP7) | 0.55 | 0.60 | 0.60 |
| Intercellular Adhesion Molecule 1 (ICAM-1) | 0.53 | 0.60 | 0.60 |
| Dickkopf Related Protein 1 (DKK1) | 0.54 | 0.62 | 0.62 |

TABLE 20

2 Biomarker Multivariate Analysis. Combination of Receptor for Advanced Glycosylation End Products (RAGE) and Analyte 2

| Analyte 2 | AUC by random forest | AUC by logistic regression | Maximum AUC |
|---|---|---|---|
| Fibulin 1C (FIB1C) | 0.50 | 0.65 | 0.65 |
| Interferon Inducble T Cell Alpha Chemoattractant (ITAC) | 0.61 | 0.61 | 0.61 |
| Growth Hormone (GH) | 0.58 | 0.62 | 0.62 |
| Heparin Binding EGF Like Growth Factor (HBEGF) | 0.54 | 0.63 | 0.63 |
| Neuronal Cell Adhesion Molecule (NrCAM) | 0.60 | 0.62 | 0.62 |
| Growth Regulated Alpha Protein (GROalpha) | 0.60 | 0.63 | 0.63 |
| Growth Differentation Factor 15 (GDF15) | 0.46 | 0.62 | 0.62 |
| Mast Stem Cell Growth Factor Receptor (SCFR) | 0.53 | 0.66 | 0.66 |
| Cadherin 1 (Ecad) | 0.59 | 0.63 | 0.63 |
| Angiogenin | 0.55 | 0.61 | 0.61 |
| Sortilin | 0.58 | 0.63 | 0.63 |
| Alpha 1 Antitrypsin (AAT) | 0.51 | 0.63 | 0.63 |
| Immunoglobulin M (IgM) | 0.58 | 0.60 | 0.60 |
| Pulmonary and Activation Regulated Chemokine (PARC) | 0.52 | 0.65 | 0.65 |
| Pulmonary Surfactant Associated Protein D (SP-D) | 0.55 | 0.61 | 0.61 |
| B Cell Activating Factor (BAFF) | 0.55 | 0.61 | 0.61 |
| Adrenomedullin (ADM) | 0.57 | 0.65 | 0.65 |
| Pigment Epithelium Derived Factor (PEDF) | 0.57 | 0.69 | 0.69 |
| Interleukin 1 Receptor Antagonist (IL1ra) | 0.49 | 0.65 | 0.65 |
| Thyrosine Binding Globulin (TBG) | 0.47 | 0.63 | 0.63 |
| Microalbumin | 0.55 | 0.61 | 0.61 |
| Leptin | 0.53 | 0.64 | 0.64 |
| Eotaxin 2 | 0.63 | 0.62 | 0.63 |
| Insulin like Growth Factor Binding Protein 2 (IGFBP2) | 0.59 | 0.61 | 0.61 |
| Resistin | 0.59 | 0.62 | 0.62 |
| Cathepsin D | 0.52 | 0.67 | 0.67 |
| E-Selectin | 0.56 | 0.66 | 0.66 |
| YKL40 | 0.54 | 0.62 | 0.62 |
| Interleukin 22 (IL22) | 0.55 | 0.64 | 0.64 |
| Cacinoembryonic Antigen (CEA) | 0.50 | 0.62 | 0.62 |
| Interleukin 8 (IL8) | 0.62 | 0.62 | 0.62 |
| Cancer Antigen 15-3 (CA 15-3) | 0.52 | 0.63 | 0.63 |
| Leptin Receptor (LeptinR) | 0.55 | 0.63 | 0.63 |
| Insulin | 0.55 | 0.64 | 0.64 |
| Monocyte Chemotactic Protein 1 (MCP1) | 0.58 | 0.67 | 0.67 |
| Prolactin (PRL) | 0.53 | 0.61 | 0.61 |
| Tetranectin | 0.53 | 0.61 | 0.61 |
| Carcinoembryonic Antigen Related Cell Adhesion Molecule 1 (CEACAM1) | 0.51 | 0.62 | 0.62 |
| 6Ckine | 0.48 | 0.63 | 0.63 |
| Serum Amyloid P Component (SAP) | 0.58 | 0.62 | 0.62 |
| Complement Factor H Related Protein 1 (CFHR1) | 0.51 | 0.61 | 0.61 |
| Chemokine CC-4 (HCC-4) | 0.46 | 0.61 | 0.61 |
| Complement C3 (C3) | 0.58 | 0.61 | 0.61 |
| Alpha Fetoprotein (AFP) | 0.59 | 0.65 | 0.65 |
| Angiopoietin 1 (ANG-1) | 0.63 | 0.60 | 0.63 |
| Interleukin 18 (IL18) | 0.59 | 0.65 | 0.65 |
| Gelsolin | 0.57 | 0.64 | 0.64 |
| Tenascin C (TN-C) | 0.49 | 0.62 | 0.62 |
| Vitronectin | 0.59 | 0.61 | 0.61 |
| Beta 2 Microglobulin (B2M) | 0.64 | 0.64 | 0.64 |
| Pancreatic Secretory Trypsin Inhibitor (TATI) | 0.49 | 0.62 | 0.62 |
| Matrix Metalloproteinase 3 (MMP3) | 0.65 | 0.63 | 0.65 |
| Omentin | 0.53 | 0.61 | 0.61 |
| Interleukin 18 Binding Protein (IL 18bp) | 0.66 | 0.64 | 0.66 |
| Apolipoprotein D (ApoD) | 0.64 | 0.62 | 0.64 |
| Monoctye Chemotactic Protein 4 (MCP-4) | 0.50 | 0.62 | 0.62 |
| Apolipoprotein E (Apo-E) | 0.61 | 0.66 | 0.66 |
| ST2 | 0.55 | 0.61 | 0.61 |
| Thrombospondin 1 | 0.60 | 0.62 | 0.62 |
| Gastric Inhibitory Polypeptide (GIP) | 0.56 | 0.64 | 0.64 |
| Matrix Metalloproteinase 7 (MMP7) | 0.56 | 0.62 | 0.62 |
| Intercellular Adhesion Molecule 1 (ICAM-1) | 0.48 | 0.62 | 0.62 |
| Dickkopf Related Protein 1 (DKK1) | 0.55 | 0.63 | 0.63 |

TABLE 21

2 Biomarker Multivariate Analysis. Combination of Fibulin 1C (FIB1C) and Analyte 2

| Analyte 2 | AUC by random forest | AUC by logistic regression | Maximum AUC |
|---|---|---|---|
| Interferon Inducble T Cell Alpha Chemoattractant (ITAC) | 0.59 | 0.56 | 0.59 |
| Growth Hormone (GH) | 0.55 | 0.63 | 0.63 |
| Heparin Binding EGF Like Growth Factor (HBEGF) | 0.52 | 0.57 | 0.57 |
| Neuronal Cell Adhesion Molecule (NrCAM) | 0.55 | 0.64 | 0.64 |
| Growth Regulated Alpha Protein (GROalpha) | 0.52 | 0.58 | 0.58 |
| Growth Differentiation Factor 15 (GDF15) | 0.57 | 0.58 | 0.58 |
| Mast Stem Cell Growth Factor Receptor (SCFR) | 0.53 | 0.59 | 0.59 |
| Cadherin 1 (Ecad) | 0.54 | 0.57 | 0.57 |
| Angiogenin | 0.47 | 0.58 | 0.58 |
| Sortilin | 0.55 | 0.58 | 0.58 |
| Alpha 1 Antitrypsin (AAT) | 0.52 | 0.56 | 0.56 |
| Immunoglobulin M (IgM) | 0.56 | 0.56 | 0.56 |
| Pulmonary and Activation Regulated Chemokine (PARC) | 0.58 | 0.62 | 0.62 |
| Pulmonary Surfactant Associated Protein D (SP-D) | 0.49 | 0.57 | 0.57 |
| B Cell Activating Factor (BAFF) | 0.57 | 0.61 | 0.61 |
| Adrenomedullin (ADM) | 0.56 | 0.64 | 0.64 |
| Pigment Epithelium Derived Factor (PEDF) | 0.50 | 0.65 | 0.65 |
| Interleukin 1 Receptor Antagonist (IL1ra) | 0.50 | 0.60 | 0.60 |
| Thyrosine Binding Globulin (TBG) | 0.48 | 0.61 | 0.61 |
| Microalbumin | 0.59 | 0.58 | 0.59 |
| Leptin | 0.56 | 0.60 | 0.60 |
| Eotaxin 2 | 0.61 | 0.58 | 0.61 |
| Insulin like Growth Factor Binding Protein 2 (IGFBP2) | 0.50 | 0.58 | 0.58 |
| Resistin | 0.48 | 0.58 | 0.58 |
| Cathepsin D | 0.52 | 0.63 | 0.63 |
| E-Selectin | 0.51 | 0.64 | 0.64 |
| YKL40 | 0.57 | 0.57 | 0.57 |
| Interleukin 22 (IL22) | 0.61 | 0.59 | 0.61 |
| Cacinoembryonic Antigen (CEA) | 0.49 | 0.57 | 0.57 |
| Interleukin 8 (IL8) | 0.53 | 0.58 | 0.58 |
| Cancer Antigen 15-3 (CA 15-3) | 0.52 | 0.57 | 0.57 |
| Leptin Receptor (LeptinR) | 0.58 | 0.59 | 0.59 |
| Insulin | 0.53 | 0.66 | 0.66 |
| Monocyte Chemotactic Protein 1 (MCP1) | 0.58 | 0.60 | 0.60 |
| Prolactin (PRL) | 0.51 | 0.62 | 0.62 |
| Tetranectin | 0.48 | 0.57 | 0.57 |
| Carcinoembryonic Antigen Related Cell Adhesion Molecule 1 (CEACAM1) | 0.54 | 0.58 | 0.58 |
| 6Ckine | 0.55 | 0.62 | 0.62 |
| Serum Amyloid P Component (SAP) | 0.57 | 0.61 | 0.61 |
| Complement Factor H Related Protein 1 (CFHR1) | 0.50 | 0.58 | 0.58 |
| Chemokine CC-4 (HCC-4) | 0.53 | 0.58 | 0.58 |
| Complement C3 (C3) | 0.63 | 0.44 | 0.63 |
| Alpha Fetoprotein (AFP) | 0.57 | 0.58 | 0.58 |
| Angiopoietin 1 (ANG-1) | 0.57 | 0.57 | 0.57 |
| Interleukin 18 (IL18) | 0.47 | 0.63 | 0.63 |
| Gelsolin | 0.55 | 0.57 | 0.57 |
| Tenascin C (TN-C) | 0.49 | 0.46 | 0.49 |
| Vitronectin | 0.53 | 0.56 | 0.56 |
| Beta 2 Microglobulin (B2M) | 0.58 | 0.58 | 0.58 |
| Pancreatic Secretory Trypsin Inhibitor (TATI) | 0.53 | 0.57 | 0.57 |
| Matrix Metalloproteinase 3 (MMP3) | 0.66 | 0.57 | 0.66 |
| Omentin | 0.59 | 0.58 | 0.59 |
| Interleukin 18 Binding Protein (IL 18bp) | 0.53 | 0.61 | 0.61 |
| Apolipoprotein D (ApoD) | 0.57 | 0.58 | 0.58 |
| Monoctye Chemotactic Protein 4 (MCP-4) | 0.50 | 0.58 | 0.58 |
| Apolipoprotein E (Apo-E) | 0.50 | 0.61 | 0.61 |
| ST2 | 0.58 | 0.56 | 0.58 |
| Thrombospondin 1 | 0.57 | 0.57 | 0.57 |
| Gastric Inhibitory Polypeptide (GIP) | 0.52 | 0.61 | 0.61 |
| Matrix Metalloproteinase 7 (MMP7) | 0.55 | 0.61 | 0.61 |
| Intercellular Adhesion Molecule 1 (ICAM-1) | 0.53 | 0.57 | 0.57 |
| Dickkopf Related Protein 1 (DKK1) | 0.50 | 0.56 | 0.56 |

TABLE 22

2 Biomarker Multivariate Analysis. Combination of Interferon Inducble
T Cell Alpha Chemoattractant (ITAC) and Analyte 2

| Analyte 2 | AUC by random forest | AUC by logistic regression | Maximum AUC |
|---|---|---|---|
| Growth Hormone (GH) | 0.55 | 0.59 | 0.59 |
| Heparin Binding EGF Like Growth Factor (HBEGF) | 0.50 | 0.54 | 0.54 |
| Neuronal Cell Adhesion Molecule (NrCAM) | 0.61 | 0.56 | 0.61 |
| Growth Regulated Alpha Protein (GROalpha) | 0.44 | 0.53 | 0.53 |
| Growth Differentation Factor 15 (GDF15) | 0.61 | 0.51 | 0.61 |
| Mast Stem Cell Growth Factor Receptor (SCFR) | 0.54 | 0.60 | 0.60 |
| Cadherin 1 (Ecad) | 0.54 | 0.50 | 0.54 |
| Angiogenin | 0.53 | 0.57 | 0.57 |
| Sortilin | 0.53 | 0.47 | 0.53 |
| Alpha 1 Antitrypsin (AAT) | 0.59 | 0.55 | 0.59 |
| Immunoglobulin M (IgM) | 0.56 | 0.47 | 0.56 |
| Pulmonary and Activation Regulated Chemokine (PARC) | 0.61 | 0.59 | 0.61 |
| Pulmonary Surfactant Associated Protein D (SP-D) | 0.57 | 0.55 | 0.57 |
| B Cell Activating Factor (BAFF) | 0.58 | 0.59 | 0.59 |
| Adrenomedullin (ADM) | 0.60 | 0.61 | 0.61 |
| Pigment Epithelium Derived Factor (PEDF) | 0.67 | 0.65 | 0.67 |
| Interleukin 1 Receptor Antagonist (IL1ra) | 0.50 | 0.59 | 0.59 |
| Thyrosine Binding Globulin (TBG) | 0.54 | 0.60 | 0.60 |
| Microalbumin | 0.65 | 0.46 | 0.65 |
| Leptin | 0.47 | 0.60 | 0.60 |
| Eotaxin 2 | 0.58 | 0.54 | 0.58 |
| Insulin like Growth Factor Binding Protein 2 (IGFBP2) | 0.56 | 0.56 | 0.56 |
| Resistin | 0.53 | 0.54 | 0.54 |
| Cathepsin D | 0.56 | 0.63 | 0.63 |
| E-Selectin | 0.60 | 0.63 | 0.63 |
| YKL40 | 0.58 | 0.49 | 0.58 |
| Interleukin 22 (IL22) | 0.55 | 0.56 | 0.56 |
| Cacinoembryonic Antigen (CEA) | 0.51 | 0.54 | 0.54 |
| Interleukin 8 (IL8) | 0.45 | 0.56 | 0.56 |
| Cancer Antigen 15-3 (CA 15-3) | 0.49 | 0.53 | 0.53 |
| Leptin Receptor (LeptinR) | 0.51 | 0.58 | 0.58 |
| Insulin | 0.48 | 0.60 | 0.60 |
| Monocyte Chemotactic Protein 1 (MCP1) | 0.58 | 0.58 | 0.58 |
| Prolactin (PRL) | 0.51 | 0.54 | 0.54 |
| Tetranectin | 0.55 | 0.51 | 0.55 |
| Carcinoembryonic Antigen Related Cell Adhesion Molecule 1 (CEACAM1) | 0.52 | 0.56 | 0.56 |
| 6Ckine | 0.55 | 0.60 | 0.60 |
| Serum Amyloid P Component (SAP) | 0.54 | 0.59 | 0.59 |
| Complement Factor H Related Protein 1 (CFHR1) | 0.50 | 0.56 | 0.56 |
| Chemokine CC-4 (HCC-4) | 0.58 | 0.53 | 0.58 |
| Complement C3 (C3) | 0.60 | 0.53 | 0.60 |
| Alpha Fetoprotein (AFP) | 0.44 | 0.53 | 0.53 |
| Angiopoietin 1 (ANG-1) | 0.51 | 0.51 | 0.51 |
| Interleukin 18 (IL18) | 0.55 | 0.63 | 0.63 |
| Gelsolin | 0.61 | 0.54 | 0.61 |
| Tenascin C (TN-C) | 0.59 | 0.53 | 0.59 |
| Vitronectin | 0.51 | 0.49 | 0.51 |
| Beta 2 Microglobulin (B2M) | 0.58 | 0.55 | 0.58 |
| Pancreatic Secretory Trypsin Inhibitor (TATI) | 0.57 | 0.57 | 0.57 |
| Matrix Metalloproteinase 3 (MMP3) | 0.60 | 0.57 | 0.60 |
| Omentin | 0.58 | 0.50 | 0.58 |
| Interleukin 18 Binding Protein (IL 18bp) | 0.62 | 0.58 | 0.62 |
| Apolipoprotein D (ApoD) | 0.60 | 0.56 | 0.60 |
| Monoctye Chemotactic Protein 4 (MCP-4) | 0.52 | 0.49 | 0.52 |
| Apolipoprotein E (Apo-E) | 0.61 | 0.60 | 0.61 |
| ST2 | 0.49 | 0.55 | 0.55 |
| Thrombospondin 1 | 0.54 | 0.52 | 0.54 |
| Gastric Inhibitory Polypeptide (GIP) | 0.51 | 0.58 | 0.58 |
| Matrix Metalloproteinase 7 (MMP7) | 0.63 | 0.57 | 0.63 |
| Intercellular Adhesion Molecule 1 (ICAM-1) | 0.54 | 0.50 | 0.54 |
| Dickkopf Related Protein 1 (DKK1) | 0.51 | 0.50 | 0.51 |

TABLE 23

2 Biomarker Multivariate Analysis. Combination of Growth Hormone (GH) and Analyte 2

| Analyte 2 | AUC by random forest | AUC by logistic regression | Maximum AUC |
|---|---|---|---|
| Heparin Binding EGF Like Growth Factor (HBEGF) | 0.52 | 0.59 | 0.59 |
| Neuronal Cell Adhesion Molecule (NrCAM) | 0.52 | 0.65 | 0.65 |
| Growth Regulated Alpha Protein (GROalpha) | 0.56 | 0.57 | 0.57 |
| Growth Differentiation Factor 15 (GDF15) | 0.56 | 0.65 | 0.65 |
| Mast Stem Cell Growth Factor Receptor (SCFR) | 0.58 | 0.62 | 0.62 |
| Cadherin 1 (Ecad) | 0.53 | 0.60 | 0.60 |
| Angiogenin | 0.52 | 0.61 | 0.61 |
| Sortilin | 0.52 | 0.57 | 0.57 |
| Alpha 1 Antitrypsin (AAT) | 0.48 | 0.57 | 0.57 |
| Immunoglobulin M (IgM) | 0.58 | 0.59 | 0.59 |
| Pulmonary and Activation Regulated Chemokine (PARC) | 0.58 | 0.65 | 0.65 |
| Pulmonary Surfactant Associated Protein D (SP-D) | 0.57 | 0.61 | 0.61 |
| B Cell Activating Factor (BAFF) | 0.50 | 0.61 | 0.61 |
| Adrenomedullin (ADM) | 0.55 | 0.64 | 0.64 |
| Pigment Epithelium Derived Factor (PEDF) | 0.52 | 0.65 | 0.65 |
| Interleukin 1 Receptor Antagonist (IL1ra) | 0.54 | 0.59 | 0.59 |
| Thyrosine Binding Globulin (TBG) | 0.58 | 0.61 | 0.61 |
| Microalbumin | 0.56 | 0.58 | 0.58 |
| Leptin | 0.56 | 0.62 | 0.62 |
| Eotaxin 2 | 0.50 | 0.60 | 0.60 |
| Insulin like Growth Factor Binding Protein 2 (IGFBP2) | 0.54 | 0.62 | 0.62 |
| Resistin | 0.56 | 0.59 | 0.59 |
| Cathepsin D | 0.58 | 0.65 | 0.65 |
| E-Selectin | 0.49 | 0.64 | 0.64 |
| YKL40 | 0.50 | 0.60 | 0.60 |
| Interleukin 22 (IL22) | 0.63 | 0.62 | 0.63 |
| Cacinoembryonic Antigen (CEA) | 0.61 | 0.63 | 0.63 |
| Interleukin 8 (IL8) | 0.54 | 0.61 | 0.61 |
| Cancer Antigen 15-3 (CA 15-3) | 0.61 | 0.61 | 0.61 |
| Leptin Receptor (LeptinR) | 0.54 | 0.60 | 0.60 |
| Insulin | 0.57 | 0.62 | 0.62 |
| Monocyte Chemotactic Protein 1 (MCP1) | 0.54 | 0.62 | 0.62 |
| Prolactin (PRL) | 0.59 | 0.61 | 0.61 |
| Tetranectin | 0.47 | 0.62 | 0.62 |
| Carcinoembryonic Antigen Related Cell Adhesion Molecule 1 (CEACAM1) | 0.50 | 0.60 | 0.60 |
| 6Ckine | 0.54 | 0.60 | 0.60 |
| Serum Amyloid P Component (SAP) | 0.54 | 0.61 | 0.61 |
| Complement Factor H Related Protein 1 (CFHR1) | 0.56 | 0.60 | 0.60 |
| Chemokine CC-4 (HCC-4) | 0.54 | 0.59 | 0.59 |
| Complement C3 (C3) | 0.58 | 0.60 | 0.60 |
| Alpha Fetoprotein (AFP) | 0.49 | 0.63 | 0.63 |
| Angiopoietin 1 (ANG-1) | 0.57 | 0.61 | 0.61 |
| Interleukin 18 (IL18) | 0.50 | 0.64 | 0.64 |
| Gelsolin | 0.61 | 0.64 | 0.64 |
| Tenascin C (TN-C) | 0.55 | 0.60 | 0.60 |
| Vitronectin | 0.52 | 0.58 | 0.58 |
| Beta 2 Microglobulin (B2M) | 0.52 | 0.59 | 0.59 |
| Pancreatic Secretory Trypsin Inhibitor (TATI) | 0.50 | 0.58 | 0.58 |
| Matrix Metalloproteinase 3 (MMP3) | 0.51 | 0.60 | 0.60 |
| Omentin | 0.62 | 0.59 | 0.62 |
| Interleukin 18 Binding Protein (IL 18bp) | 0.54 | 0.64 | 0.64 |
| Apolipoprotein D (ApoD) | 0.58 | 0.60 | 0.60 |
| Monoctye Chemotactic Protein 4 (MCP-4) | 0.53 | 0.61 | 0.61 |
| Apolipoprotein E (Apo-E) | 0.55 | 0.61 | 0.61 |
| ST2 | 0.55 | 0.60 | 0.60 |
| Thrombospondin 1 | 0.52 | 0.59 | 0.59 |
| Gastric Inhibitory Polypeptide (GIP) | 0.60 | 0.61 | 0.61 |
| Matrix Metalloproteinase 7 (MMP7) | 0.52 | 0.57 | 0.57 |
| Intercellular Adhesion Molecule 1 (ICAM-1) | 0.55 | 0.57 | 0.57 |
| Dickkopf Related Protein 1 (DKK1) | 0.55 | 0.59 | 0.59 |

TABLE 24

2 Biomarker Multivariate Analysis. Combination of Heparin Binding EGF Like Growth Factor (HBEGF) and Analyte 2

| Analyte 2 | AUC by random forest | AUC by logistic regression | Maximum AUC |
|---|---|---|---|
| Neuronal Cell Adhesion Molecule (NrCAM) | 0.58 | 0.59 | 0.59 |
| Growth Regulated Alpha Protein (GROalpha) | 0.48 | 0.58 | 0.58 |
| Growth Differentiation Factor 15 (GDF15) | 0.63 | 0.57 | 0.63 |
| Mast Stem Cell Growth Factor Receptor (SCFR) | 0.55 | 0.61 | 0.61 |
| Cadherin 1 (Ecad) | 0.59 | 0.56 | 0.59 |
| Angiogenin | 0.46 | 0.57 | 0.57 |
| Sortilin | 0.48 | 0.53 | 0.53 |
| Alpha 1 Antitrypsin (AAT) | 0.53 | 0.56 | 0.56 |
| Immunoglobulin M (IgM) | 0.55 | 0.56 | 0.56 |
| Pulmonary and Activation Regulated Chemokine (PARC) | 0.56 | 0.59 | 0.59 |
| Pulmonary Surfactant Associated Protein D (SP-D) | 0.55 | 0.54 | 0.55 |
| B Cell Activating Factor (BAFF) | 0.56 | 0.61 | 0.61 |
| Adrenomedullin (ADM) | 0.49 | 0.63 | 0.63 |
| Pigment Epithelium Derived Factor (PEDF) | 0.49 | 0.65 | 0.65 |
| Interleukin 1 Receptor Antagonist (IL1ra) | 0.55 | 0.60 | 0.60 |
| Thyrosine Binding Globulin (TBG) | 0.47 | 0.60 | 0.60 |
| Microalbumin | 0.51 | 0.59 | 0.59 |
| Leptin | 0.55 | 0.60 | 0.60 |
| Eotaxin 2 | 0.52 | 0.56 | 0.56 |
| Insulin like Growth Factor Binding Protein 2 (IGFBP2) | 0.52 | 0.58 | 0.58 |
| Resistin | 0.49 | 0.54 | 0.54 |
| Cathepsin D | 0.54 | 0.62 | 0.62 |
| E-Selectin | 0.51 | 0.63 | 0.63 |
| YKL40 | 0.50 | 0.53 | 0.53 |
| Interleukin 22 (IL22) | 0.63 | 0.58 | 0.63 |
| Cacinoembryonic Antigen (CEA) | 0.51 | 0.57 | 0.57 |
| Interleukin 8 (IL8) | 0.62 | 0.54 | 0.62 |
| Cancer Antigen 15-3 (CA 15-3) | 0.56 | 0.59 | 0.59 |
| Leptin Receptor (LeptinR) | 0.50 | 0.60 | 0.60 |
| Insulin | 0.53 | 0.59 | 0.59 |
| Monocyte Chemotactic Protein 1 (MCP1) | 0.51 | 0.58 | 0.58 |
| Prolactin (PRL) | 0.60 | 0.57 | 0.60 |
| Tetranectin | 0.54 | 0.53 | 0.54 |
| Carcinoembryonic Antigen Related Cell Adhesion Molecule 1 (CEACAM1) | 0.59 | 0.60 | 0.60 |
| 6Ckine | 0.53 | 0.60 | 0.60 |
| Serum Amyloid P Component (SAP) | 0.51 | 0.58 | 0.58 |
| Complement Factor H Related Protein 1 (CFHR1) | 0.49 | 0.53 | 0.53 |
| Chemokine CC-4 (HCC-4) | 0.48 | 0.52 | 0.52 |
| Complement C3 (C3) | 0.51 | 0.53 | 0.53 |
| Alpha Fetoprotein (AFP) | 0.50 | 0.59 | 0.59 |
| Angiopoietin 1 (ANG-1) | 0.46 | 0.58 | 0.58 |
| Interleukin 18 (IL18) | 0.64 | 0.65 | 0.65 |
| Gelsolin | 0.49 | 0.56 | 0.56 |
| Tenascin C (TN-C) | 0.53 | 0.55 | 0.55 |
| Vitronectin | 0.50 | 0.53 | 0.53 |
| Beta 2 Microglobulin (B2M) | 0.48 | 0.57 | 0.57 |
| Pancreatic Secretory Trypsin Inhibitor (TATI) | 0.51 | 0.53 | 0.53 |
| Matrix Metalloproteinase 3 (MMP3) | 0.55 | 0.55 | 0.55 |
| Omentin | 0.53 | 0.54 | 0.54 |
| Interleukin 18 Binding Protein (IL 18bp) | 0.51 | 0.59 | 0.59 |
| Apolipoprotein D (ApoD) | 0.59 | 0.57 | 0.59 |
| Monoctye Chemotactic Protein 4 (MCP-4) | 0.48 | 0.54 | 0.54 |
| Apolipoprotein E (Apo-E) | 0.59 | 0.61 | 0.61 |
| ST2 | 0.56 | 0.53 | 0.56 |
| Thrombospondin 1 | 0.53 | 0.53 | 0.53 |
| Gastric Inhibitory Polypeptide (GIP) | 0.53 | 0.59 | 0.59 |
| Matrix Metalloproteinase 7 (MMP7) | 0.56 | 0.57 | 0.57 |
| Intercellular Adhesion Molecule 1 (ICAM-1) | 0.54 | 0.54 | 0.54 |
| Dickkopf Related Protein 1 (DKK1) | 0.57 | 0.53 | 0.57 |

TABLE 25

2 Biomarker Multivariate Analysis. Combination of Neuronal Cell Adhesion Molecule (NrCAM) and Analyte 2

| Analyte 2 | AUC by random forest | AUC by logistic regression | Maximum AUC |
|---|---|---|---|
| Growth Regulated Alpha Protein (GROalpha) | 0.48 | 0.59 | 0.59 |
| Growth Differentiation Factor 15 (GDF15) | 0.59 | 0.62 | 0.62 |

TABLE 25-continued

2 Biomarker Multivariate Analysis. Combination of Neuronal
Cell Adhesion Molecule (NrCAM) and Analyte 2

| Analyte 2 | AUC by random forest | AUC by logistic regression | Maximum AUC |
|---|---|---|---|
| Mast Stem Cell Growth Factor Receptor (SCFR) | 0.51 | 0.64 | 0.64 |
| Cadherin 1 (Ecad) | 0.56 | 0.63 | 0.63 |
| Angiogenin | 0.56 | 0.62 | 0.62 |
| Sortilin | 0.56 | 0.61 | 0.61 |
| Alpha 1 Antitrypsin (AAT) | 0.58 | 0.64 | 0.64 |
| Immunoglobulin M (IgM) | 0.50 | 0.59 | 0.59 |
| Pulmonary and Activation Regulated Chemokine (PARC) | 0.56 | 0.64 | 0.64 |
| Pulmonary Surfactant Associated Protein D (SP-D) | 0.50 | 0.62 | 0.62 |
| B Cell Activating Factor (BAFF) | 0.58 | 0.61 | 0.61 |
| Adrenomedullin (ADM) | 0.61 | 0.63 | 0.63 |
| Pigment Epithelium Derived Factor (PEDF) | 0.61 | 0.69 | 0.69 |
| Interleukin 1 Receptor Antagonist (IL1ra) | 0.57 | 0.63 | 0.63 |
| Thyrosine Binding Globulin (TBG) | 0.63 | 0.60 | 0.63 |
| Microalbumin | 0.58 | 0.62 | 0.62 |
| Leptin | 0.56 | 0.64 | 0.64 |
| Eotaxin 2 | 0.67 | 0.61 | 0.67 |
| Insulin like Growth Factor Binding Protein 2 (IGFBP2) | 0.53 | 0.59 | 0.59 |
| Resistin | 0.45 | 0.62 | 0.62 |
| Cathepsin D | 0.54 | 0.65 | 0.65 |
| E-Selectin | 0.63 | 0.69 | 0.69 |
| YKL40 | 0.60 | 0.60 | 0.60 |
| Interleukin 22 (IL22) | 0.51 | 0.62 | 0.62 |
| Cacinoembryonic Antigen (CEA) | 0.53 | 0.64 | 0.64 |
| Interleukin 8 (IL8) | 0.60 | 0.63 | 0.63 |
| Cancer Antigen 15-3 (CA 15-3) | 0.57 | 0.62 | 0.62 |
| Leptin Receptor (LeptinR) | 0.58 | 0.63 | 0.63 |
| Insulin | 0.58 | 0.63 | 0.63 |
| Monocyte Chemotactic Protein 1 (MCP1) | 0.62 | 0.66 | 0.66 |
| Prolactin (PRL) | 0.52 | 0.62 | 0.62 |
| Tetranectin | 0.54 | 0.59 | 0.59 |
| Carcinoembryonic Antigen Related Cell Adhesion Molecule 1 (CEACAM1) | 0.54 | 0.61 | 0.61 |
| 6Ckine | 0.62 | 0.61 | 0.62 |
| Serum Amyloid P Component (SAP) | 0.46 | 0.61 | 0.61 |
| Complement Factor H Related Protein 1 (CFHR1) | 0.54 | 0.60 | 0.60 |
| Chemokine CC-4 (HCC-4) | 0.53 | 0.59 | 0.59 |
| Complement C3 (C3) | 0.63 | 0.59 | 0.63 |
| Alpha Fetoprotein (AFP) | 0.56 | 0.63 | 0.63 |
| Angiopoietin 1 (ANG-1) | 0.57 | 0.61 | 0.61 |
| Interleukin 18 (IL18) | 0.58 | 0.66 | 0.66 |
| Gelsolin | 0.58 | 0.60 | 0.60 |
| Tenascin C (TN-C) | 0.53 | 0.60 | 0.60 |
| Vitronectin | 0.63 | 0.57 | 0.63 |
| Beta 2 Microglobulin (B2M) | 0.62 | 0.62 | 0.62 |
| Pancreatic Secretory Trypsin Inhibitor (TATI) | 0.55 | 0.60 | 0.60 |
| Matrix Metalloproteinase 3 (MMP3) | 0.62 | 0.63 | 0.63 |
| Omentin | 0.52 | 0.60 | 0.60 |
| Interleukin 18 Binding Protein (IL 18bp) | 0.56 | 0.64 | 0.64 |
| Apolipoprotein D (ApoD) | 0.59 | 0.61 | 0.61 |
| Monoctye Chemotactic Protein 4 (MCP-4) | 0.56 | 0.60 | 0.60 |
| Apolipoprotein E (Apo-E) | 0.59 | 0.61 | 0.61 |
| ST2 | 0.58 | 0.61 | 0.61 |
| Thrombospondin 1 | 0.55 | 0.60 | 0.60 |
| Gastric Inhibitory Polypeptide (GIP) | 0.55 | 0.63 | 0.63 |
| Matrix Metalloproteinase 7 (MMP7) | 0.55 | 0.62 | 0.62 |
| Intercellular Adhesion Molecule 1 (ICAM-1) | 0.62 | 0.60 | 0.62 |
| Dickkopf Related Protein 1 (DKK1) | 0.52 | 0.60 | 0.60 |

TABLE 26

2 Biomarker Multivariate Analysis. Combination of Growth
Regulated Alpha Protein (GROalpha) and Analyte 2

| Analyte 2 | AUC by random forest | AUC by logistic regression | Maximum AUC |
|---|---|---|---|
| Growth Differentiation Factor 15 (GDF15) | 0.60 | 0.56 | 0.60 |
| Mast Stem Cell Growth Factor Receptor (SCFR) | 0.54 | 0.58 | 0.58 |
| Cadherin 1 (Ecad) | 0.63 | 0.56 | 0.63 |
| Angiogenin | 0.52 | 0.58 | 0.58 |
| Sortilin | 0.49 | 0.57 | 0.57 |

TABLE 26-continued

2 Biomarker Multivariate Analysis. Combination of Growth
Regulated Alpha Protein (GROalpha) and Analyte 2

| Analyte 2 | AUC by random forest | AUC by logistic regression | Maximum AUC |
|---|---|---|---|
| Alpha 1 Antitrypsin (AAT) | 0.56 | 0.54 | 0.56 |
| Immunoglobulin M (IgM) | 0.60 | 0.53 | 0.60 |
| Pulmonary and Activation Regulated Chemokine (PARC) | 0.58 | 0.62 | 0.62 |
| Pulmonary Surfactant Associated Protein D (SP-D) | 0.54 | 0.53 | 0.54 |
| B Cell Activating Factor (BAFF) | 0.57 | 0.59 | 0.59 |
| Adrenomedullin (ADM) | 0.53 | 0.64 | 0.64 |
| Pigment Epithelium Derived Factor (PEDF) | 0.66 | 0.67 | 0.67 |
| Interleukin 1 Receptor Antagonist (IL1ra) | 0.46 | 0.60 | 0.60 |
| Thyrosine Binding Globulin (TBG) | 0.61 | 0.61 | 0.61 |
| Microalbumin | 0.62 | 0.56 | 0.62 |
| Leptin | 0.59 | 0.62 | 0.62 |
| Eotaxin 2 | 0.64 | 0.58 | 0.64 |
| Insulin like Growth Factor Binding Protein 2 (IGFBP2) | 0.49 | 0.57 | 0.57 |
| Resistin | 0.52 | 0.54 | 0.54 |
| Cathepsin D | 0.55 | 0.62 | 0.62 |
| E-Selectin | 0.54 | 0.64 | 0.64 |
| YKL40 | 0.48 | 0.56 | 0.56 |
| Interleukin 22 (IL22) | 0.50 | 0.57 | 0.57 |
| Cacinoembryonic Antigen (CEA) | 0.49 | 0.55 | 0.55 |
| Interleukin 8 (IL8) | 0.59 | 0.54 | 0.59 |
| Cancer Antigen 15-3 (CA 15-3) | 0.56 | 0.53 | 0.56 |
| Leptin Receptor (LeptinR) | 0.56 | 0.61 | 0.61 |
| Insulin | 0.45 | 0.62 | 0.62 |
| Monocyte Chemotactic Protein 1 (MCP1) | 0.59 | 0.60 | 0.60 |
| Prolactin (PRL) | 0.53 | 0.54 | 0.54 |
| Tetranectin | 0.50 | 0.46 | 0.50 |
| Carcinoembryonic Antigen Related Cell Adhesion Molecule 1 (CEACAM1) | 0.45 | 0.56 | 0.56 |
| 6Ckine | 0.55 | 0.63 | 0.63 |
| Serum Amyloid P Component (SAP) | 0.59 | 0.61 | 0.61 |
| Complement Factor H Related Protein 1 (CFHR1) | 0.51 | 0.56 | 0.56 |
| Chemokine CC-4 (HCC-4) | 0.52 | 0.55 | 0.55 |
| Complement C3 (C3) | 0.60 | 0.56 | 0.60 |
| Alpha Fetoprotein (AFP) | 0.52 | 0.56 | 0.56 |
| Angiopoietin 1 (ANG-1) | 0.50 | 0.54 | 0.54 |
| Interleukin 18 (IL18) | 0.65 | 0.63 | 0.65 |
| Gelsolin | 0.45 | 0.55 | 0.55 |
| Tenascin C (TN-C) | 0.53 | 0.54 | 0.54 |
| Vitronectin | 0.65 | 0.46 | 0.65 |
| Beta 2 Microglobulin (B2M) | 0.59 | 0.55 | 0.59 |
| Pancreatic Secretory Trypsin Inhibitor (TATI) | 0.55 | 0.47 | 0.55 |
| Matrix Metalloproteinase 3 (MMP3) | 0.60 | 0.56 | 0.60 |
| Omentin | 0.54 | 0.48 | 0.54 |
| Interleukin 18 Binding Protein (IL 18bp) | 0.66 | 0.58 | 0.66 |
| Apolipoprotein D (ApoD) | 0.60 | 0.54 | 0.60 |
| Monoctye Chemotactic Protein 4 (MCP-4) | 0.50 | 0.55 | 0.55 |
| Apolipoprotein E (Apo-E) | 0.58 | 0.60 | 0.60 |
| ST2 | 0.63 | 0.47 | 0.63 |
| Thrombospondin 1 | 0.53 | 0.54 | 0.54 |
| Gastric Inhibitory Polypeptide (GIP) | 0.50 | 0.59 | 0.59 |
| Matrix Metalloproteinase 7 (MMP7) | 0.62 | 0.58 | 0.62 |
| Intercellular Adhesion Molecule 1 (ICAM-1) | 0.55 | 0.52 | 0.55 |
| Dickkopf Related Protein 1 (DKK1) | 0.52 | 0.53 | 0.53 |

TABLE 27

2 Biomarker Multivariate Analysis. Combination of Growth
Differentiation Factor 15 (GDF15) and Analyte 2

| Analyte 2 | AUC by random forest | AUC by logistic regression | Maximum AUC |
|---|---|---|---|
| Mast Stem Cell Growth Factor Receptor (SCFR) | 0.52 | 0.61 | 0.61 |
| Cadherin 1 (Ecad) | 0.71 | 0.54 | 0.71 |
| Angiogenin | 0.53 | 0.59 | 0.59 |
| Sortilin | 0.58 | 0.54 | 0.58 |
| Alpha 1 Antitrypsin (AAT) | 0.64 | 0.56 | 0.64 |
| Immunoglobulin M (IgM) | 0.61 | 0.54 | 0.61 |
| Pulmonary and Activation Regulated Chemokine (PARC) | 0.63 | 0.59 | 0.63 |
| Pulmonary Surfactant Associated Protein D (SP-D) | 0.52 | 0.54 | 0.54 |
| B Cell Activating Factor (BAFF) | 0.56 | 0.58 | 0.58 |

TABLE 27-continued

2 Biomarker Multivariate Analysis. Combination of Growth Differentiation Factor 15 (GDF15) and Analyte 2

| Analyte 2 | AUC by random forest | AUC by logistic regression | Maximum AUC |
|---|---|---|---|
| Adrenomedullin (ADM) | 0.57 | 0.63 | 0.63 |
| Pigment Epithelium Derived Factor (PEDF) | 0.62 | 0.65 | 0.65 |
| Interleukin 1 Receptor Antagonist (IL1ra) | 0.57 | 0.59 | 0.59 |
| Thyrosine Binding Globulin (TBG) | 0.61 | 0.60 | 0.61 |
| Microalbumin | 0.65 | 0.45 | 0.65 |
| Leptin | 0.62 | 0.61 | 0.62 |
| Eotaxin 2 | 0.64 | 0.58 | 0.64 |
| Insulin like Growth Factor Binding Protein 2 (IGFBP2) | 0.66 | 0.57 | 0.66 |
| Resistin | 0.55 | 0.57 | 0.57 |
| Cathepsin D | 0.49 | 0.62 | 0.62 |
| E-Selectin | 0.53 | 0.64 | 0.64 |
| YKL40 | 0.48 | 0.54 | 0.54 |
| Interleukin 22 (IL22) | 0.59 | 0.58 | 0.59 |
| Cacinoembryonic Antigen (CEA) | 0.54 | 0.57 | 0.57 |
| Interleukin 8 (IL8) | 0.58 | 0.46 | 0.58 |
| Cancer Antigen 15-3 (CA 15-3) | 0.64 | 0.54 | 0.64 |
| Leptin Receptor (LeptinR) | 0.57 | 0.60 | 0.60 |
| Insulin | 0.52 | 0.64 | 0.64 |
| Monocyte Chemotactic Protein 1 (MCP1) | 0.64 | 0.59 | 0.64 |
| Prolactin (PRL) | 0.52 | 0.56 | 0.56 |
| Tetranectin | 0.59 | 0.54 | 0.59 |
| Carcinoembryonic Antigen Related Cell Adhesion Molecule 1 (CEACAM1) | 0.59 | 0.57 | 0.59 |
| 6Ckine | 0.55 | 0.60 | 0.60 |
| Serum Amyloid P Component (SAP) | 0.56 | 0.59 | 0.59 |
| Complement Factor H Related Protein 1 (CFHR1) | 0.57 | 0.47 | 0.57 |
| Chemokine CC-4 (HCC-4) | 0.58 | 0.55 | 0.58 |
| Complement C3 (C3) | 0.69 | 0.54 | 0.69 |
| Alpha Fetoprotein (AFP) | 0.52 | 0.61 | 0.61 |
| Angiopoietin 1 (ANG-1) | 0.59 | 0.56 | 0.59 |
| Interleukin 18 (IL18) | 0.60 | 0.62 | 0.62 |
| Gelsolin | 0.52 | 0.55 | 0.55 |
| Tenascin C (TN-C) | 0.47 | 0.55 | 0.55 |
| Vitronectin | 0.47 | 0.54 | 0.54 |
| Beta 2 Microglobulin (B2M) | 0.56 | 0.55 | 0.56 |
| Pancreatic Secretory Trypsin Inhibitor (TATI) | 0.49 | 0.46 | 0.49 |
| Matrix Metalloproteinase 3 (MMP3) | 0.61 | 0.55 | 0.61 |
| Omentin | 0.50 | 0.56 | 0.56 |
| Interleukin 18 Binding Protein (IL 18bp) | 0.54 | 0.58 | 0.58 |
| Apolipoprotein D (ApoD) | 0.62 | 0.56 | 0.62 |
| Monoctye Chemotactic Protein 4 (MCP-4) | 0.53 | 0.57 | 0.57 |
| Apolipoprotein E (Apo-E) | 0.59 | 0.60 | 0.60 |
| ST2 | 0.59 | 0.55 | 0.59 |
| Thrombospondin 1 | 0.56 | 0.52 | 0.56 |
| Gastric Inhibitory Polypeptide (GIP) | 0.55 | 0.59 | 0.59 |
| Matrix Metalloproteinase 7 (MMP7) | 0.60 | 0.57 | 0.60 |
| Intercellular Adhesion Molecule 1 (ICAM-1) | 0.53 | 0.54 | 0.54 |
| Dickkopf Related Protein 1 (DKK1) | 0.49 | 0.55 | 0.55 |

TABLE 28

2 Biomarker Multivariate Analysis. Combination of Mast Stem Cell Growth Factor Receptor (SCFR) and Analyte 2

| Analyte 2 | AUC by random forest | AUC by logistic regression | Maximum AUC |
|---|---|---|---|
| Cadherin 1 (Ecad) | 0.59 | 0.60 | 0.60 |
| Angiogenin | 0.57 | 0.62 | 0.62 |
| Sortilin | 0.49 | 0.60 | 0.60 |
| Alpha 1 Antitrypsin (AAT) | 0.51 | 0.61 | 0.61 |
| Immunoglobulin M (IgM) | 0.59 | 0.59 | 0.59 |
| Pulmonary and Activation Regulated Chemokine (PARC) | 0.50 | 0.66 | 0.66 |
| Pulmonary Surfactant Associated Protein D (SP-D) | 0.57 | 0.59 | 0.59 |
| B Cell Activating Factor (BAFF) | 0.53 | 0.63 | 0.63 |
| Adrenomedullin (ADM) | 0.53 | 0.68 | 0.68 |
| Pigment Epithelium Derived Factor (PEDF) | 0.50 | 0.70 | 0.70 |
| Interleukin 1 Receptor Antagonist (IL1ra) | 0.50 | 0.67 | 0.67 |
| Thyrosine Binding Globulin (TBG) | 0.58 | 0.63 | 0.63 |
| Microalbumin | 0.63 | 0.62 | 0.63 |
| Leptin | 0.52 | 0.68 | 0.68 |

TABLE 28-continued

2 Biomarker Multivariate Analysis. Combination of Mast Stem Cell Growth Factor Receptor (SCFR) and Analyte 2

| Analyte 2 | AUC by random forest | AUC by logistic regression | Maximum AUC |
|---|---|---|---|
| Eotaxin 2 | 0.57 | 0.62 | 0.62 |
| Insulin like Growth Factor Binding Protein 2 (IGFBP2) | 0.56 | 0.62 | 0.62 |
| Resistin | 0.59 | 0.61 | 0.61 |
| Cathepsin D | 0.49 | 0.67 | 0.67 |
| E-Selectin | 0.57 | 0.67 | 0.67 |
| YKL40 | 0.53 | 0.60 | 0.60 |
| Interleukin 22 (IL22) | 0.50 | 0.62 | 0.62 |
| Cacinoembryonic Antigen (CEA) | 0.58 | 0.59 | 0.59 |
| Interleukin 8 (IL8) | 0.60 | 0.59 | 0.60 |
| Cancer Antigen 15-3 (CA 15-3) | 0.57 | 0.59 | 0.59 |
| Leptin Receptor (LeptinR) | 0.52 | 0.62 | 0.62 |
| Insulin | 0.52 | 0.68 | 0.68 |
| Monocyte Chemotactic Protein 1 (MCP1) | 0.56 | 0.62 | 0.62 |
| Prolactin (PRL) | 0.63 | 0.61 | 0.63 |
| Tetranectin | 0.54 | 0.59 | 0.59 |
| Carcinoembryonic Antigen Related Cell Adhesion Molecule 1 (CEACAM1) | 0.50 | 0.63 | 0.63 |
| 6Ckine | 0.61 | 0.65 | 0.65 |
| Serum Amyloid P Component (SAP) | 0.52 | 0.66 | 0.66 |
| Complement Factor H Related Protein 1 (CFHR1) | 0.49 | 0.60 | 0.60 |
| Chemokine CC-4 (HCC-4) | 0.51 | 0.60 | 0.60 |
| Complement C3 (C3) | 0.53 | 0.63 | 0.63 |
| Alpha Fetoprotein (AFP) | 0.61 | 0.62 | 0.62 |
| Angiopoietin 1 (ANG-1) | 0.52 | 0.60 | 0.60 |
| Interleukin 18 (IL18) | 0.53 | 0.68 | 0.68 |
| Gelsolin | 0.54 | 0.60 | 0.60 |
| Tenascin C (TN-C) | 0.46 | 0.60 | 0.60 |
| Vitronectin | 0.52 | 0.61 | 0.61 |
| Beta 2 Microglobulin (B2M) | 0.48 | 0.62 | 0.62 |
| Pancreatic Secretory Trypsin Inhibitor (TATI) | 0.59 | 0.60 | 0.60 |
| Matrix Metalloproteinase 3 (MMP3) | 0.60 | 0.61 | 0.61 |
| Omentin | 0.69 | 0.60 | 0.69 |
| Interleukin 18 Binding Protein (IL 18bp) | 0.52 | 0.66 | 0.66 |
| Apolipoprotein D (ApoD) | 0.59 | 0.62 | 0.62 |
| Monoctye Chemotactic Protein 4 (MCP-4) | 0.63 | 0.60 | 0.63 |
| Apolipoprotein E (Apo-E) | 0.48 | 0.65 | 0.65 |
| ST2 | 0.53 | 0.60 | 0.60 |
| Thrombospondin 1 | 0.53 | 0.59 | 0.59 |
| Gastric Inhibitory Polypeptide (GIP) | 0.54 | 0.65 | 0.65 |
| Matrix Metalloproteinase 7 (MMP7) | 0.54 | 0.61 | 0.61 |
| Intercellular Adhesion Molecule 1 (ICAM-1) | 0.57 | 0.59 | 0.59 |
| Dickkopf Related Protein 1 (DKK1) | 0.56 | 0.61 | 0.61 |

TABLE 29

2 Biomarker Multivariate Analysis. Combination of Cadherin 1 (Ecad) and Analyte 2

| Analyte 2 | AUC by random forest | AUC by logistic regression | Maximum AUC |
|---|---|---|---|
| Angiogenin | 0.50 | 0.58 | 0.58 |
| Sortilin | 0.54 | 0.55 | 0.55 |
| Alpha 1 Antitrypsin (AAT) | 0.44 | 0.54 | 0.54 |
| Immunoglobulin M (IgM) | 0.60 | 0.48 | 0.60 |
| Pulmonary and Activation Regulated Chemokine (PARC) | 0.64 | 0.60 | 0.64 |
| Pulmonary Surfactant Associated Protein D (SP-D) | 0.56 | 0.51 | 0.56 |
| B Cell Activating Factor (BAFF) | 0.60 | 0.60 | 0.60 |
| Adrenomedullin (ADM) | 0.59 | 0.63 | 0.63 |
| Pigment Epithelium Derived Factor (PEDF) | 0.68 | 0.64 | 0.68 |
| Interleukin 1 Receptor Antagonist (IL1ra) | 0.58 | 0.60 | 0.60 |
| Thyrosine Binding Globulin (TBG) | 0.54 | 0.60 | 0.60 |
| Microalbumin | 0.59 | 0.55 | 0.59 |
| Leptin | 0.61 | 0.61 | 0.61 |
| Eotaxin 2 | 0.65 | 0.57 | 0.65 |
| Insulin like Growth Factor Binding Protein 2 (IGFBP2) | 0.51 | 0.57 | 0.57 |
| Resistin | 0.59 | 0.57 | 0.59 |
| Cathepsin D | 0.59 | 0.62 | 0.62 |
| E-Selectin | 0.49 | 0.63 | 0.63 |
| YKL40 | 0.58 | 0.55 | 0.58 |
| Interleukin 22 (IL22) | 0.59 | 0.56 | 0.59 |
| Cacinoembryonic Antigen (CEA) | 0.64 | 0.54 | 0.64 |

TABLE 29-continued

2 Biomarker Multivariate Analysis. Combination of Cadherin 1 (Ecad) and Analyte 2

| Analyte 2 | AUC by random forest | AUC by logistic regression | Maximum AUC |
|---|---|---|---|
| Interleukin 8 (IL8) | 0.67 | 0.53 | 0.67 |
| Cancer Antigen 15-3 (CA 15-3) | 0.52 | 0.46 | 0.52 |
| Leptin Receptor (LeptinR) | 0.62 | 0.58 | 0.62 |
| Insulin | 0.58 | 0.63 | 0.63 |
| Monocyte Chemotactic Protein 1 (MCP1) | 0.70 | 0.59 | 0.70 |
| Prolactin (PRL) | 0.53 | 0.55 | 0.55 |
| Tetranectin | 0.57 | 0.54 | 0.57 |
| Carcinoembryonic Antigen Related Cell Adhesion Molecule 1 (CEACAM1) | 0.55 | 0.57 | 0.57 |
| 6Ckine | 0.55 | 0.62 | 0.62 |
| Serum Amyloid P Component (SAP) | 0.58 | 0.57 | 0.58 |
| Complement Factor H Related Protein 1 (CFHR1) | 0.54 | 0.55 | 0.55 |
| Chemokine CC-4 (HCC-4) | 0.57 | 0.53 | 0.57 |
| Complement C3 (C3) | 0.66 | 0.52 | 0.66 |
| Alpha Fetoprotein (AFP) | 0.54 | 0.58 | 0.58 |
| Angiopoietin 1 (ANG-1) | 0.63 | 0.56 | 0.63 |
| Interleukin 18 (IL18) | 0.58 | 0.63 | 0.63 |
| Gelsolin | 0.60 | 0.54 | 0.60 |
| Tenascin C (TN-C) | 0.56 | 0.54 | 0.56 |
| Vitronectin | 0.65 | 0.47 | 0.65 |
| Beta 2 Microglobulin (B2M) | 0.55 | 0.56 | 0.56 |
| Pancreatic Secretory Trypsin Inhibitor (TATI) | 0.58 | 0.54 | 0.58 |
| Matrix Metalloproteinase 3 (MMP3) | 0.70 | 0.55 | 0.70 |
| Omentin | 0.56 | 0.57 | 0.57 |
| Interleukin 18 Binding Protein (IL 18bp) | 0.54 | 0.58 | 0.58 |
| Apolipoprotein D (ApoD) | 0.60 | 0.57 | 0.60 |
| Monoctye Chemotactic Protein 4 (MCP-4) | 0.56 | 0.57 | 0.57 |
| Apolipoprotein E (Apo-E) | 0.54 | 0.60 | 0.60 |
| ST2 | 0.60 | 0.57 | 0.60 |
| Thrombospondin 1 | 0.61 | 0.53 | 0.61 |
| Gastric Inhibitory Polypeptide (GIP) | 0.53 | 0.60 | 0.60 |
| Matrix Metalloproteinase 7 (MMP7) | 0.54 | 0.55 | 0.55 |
| Intercellular Adhesion Molecule 1 (ICAM-1) | 0.56 | 0.53 | 0.56 |
| Dickkopf Related Protein 1 (DKK1) | 0.58 | 0.48 | 0.58 |

TABLE 30

2 Biomarker Multivariate Analysis. Combination of Angiogenin and Analyte 2

| Analyte 2 | AUC by random forest | AUC by logistic regression | Maximum AUC |
|---|---|---|---|
| Sortilin | 0.53 | 0.58 | 0.58 |
| Alpha 1 Antitrypsin (AAT) | 0.52 | 0.58 | 0.58 |
| Immunoglobulin M (IgM) | 0.56 | 0.58 | 0.58 |
| Pulmonary and Activation Regulated Chemokine (PARC) | 0.62 | 0.63 | 0.63 |
| Pulmonary Surfactant Associated Protein D (SP-D) | 0.53 | 0.58 | 0.58 |
| B Cell Activating Factor (BAFF) | 0.52 | 0.59 | 0.59 |
| Adrenomedullin (ADM) | 0.52 | 0.62 | 0.62 |
| Pigment Epithelium Derived Factor (PEDF) | 0.62 | 0.65 | 0.65 |
| Interleukin 1 Receptor Antagonist (IL1ra) | 0.50 | 0.61 | 0.61 |
| Thyrosine Binding Globulin (TBG) | 0.47 | 0.60 | 0.60 |
| Microalbumin | 0.57 | 0.59 | 0.59 |
| Leptin | 0.64 | 0.62 | 0.64 |
| Eotaxin 2 | 0.60 | 0.60 | 0.60 |
| Insulin like Growth Factor Binding Protein 2 (IGFBP2) | 0.56 | 0.57 | 0.57 |
| Resistin | 0.53 | 0.59 | 0.59 |
| Cathepsin D | 0.54 | 0.62 | 0.62 |
| E-Selectin | 0.63 | 0.64 | 0.64 |
| YKL40 | 0.57 | 0.58 | 0.58 |
| Interleukin 22 (IL22) | 0.44 | 0.60 | 0.60 |
| Cacinoembryonic Antigen (CEA) | 0.50 | 0.59 | 0.59 |
| Interleukin 8 (IL8) | 0.52 | 0.58 | 0.58 |
| Cancer Antigen 15-3 (CA 15-3) | 0.61 | 0.58 | 0.61 |
| Leptin Receptor (LeptinR) | 0.50 | 0.61 | 0.61 |
| Insulin | 0.55 | 0.64 | 0.64 |
| Monocyte Chemotactic Protein 1 (MCP1) | 0.47 | 0.60 | 0.60 |
| Prolactin (PRL) | 0.54 | 0.57 | 0.57 |
| Tetranectin | 0.54 | 0.58 | 0.58 |
| Carcinoembryonic Antigen Related Cell Adhesion Molecule 1 (CEACAM1) | 0.56 | 0.59 | 0.59 |
| 6Ckine | 0.50 | 0.62 | 0.62 |

TABLE 30-continued

| 2 Biomarker Multivariate Analysis. Combination of Angiogenin and Analyte 2 | | | |
|---|---|---|---|
| Analyte 2 | AUC by random forest | AUC by logistic regression | Maximum AUC |
| Serum Amyloid P Component (SAP) | 0.57 | 0.59 | 0.59 |
| Complement Factor H Related Protein 1 (CFHR1) | 0.53 | 0.59 | 0.59 |
| Chemokine CC-4 (HCC-4) | 0.57 | 0.58 | 0.58 |
| Complement C3 (C3) | 0.61 | 0.55 | 0.61 |
| Alpha Fetoprotein (AFP) | 0.50 | 0.63 | 0.63 |
| Angiopoietin 1 (ANG-1) | 0.57 | 0.57 | 0.57 |
| Interleukin 18 (IL18) | 0.59 | 0.64 | 0.64 |
| Gelsolin | 0.52 | 0.58 | 0.58 |
| Tenascin C (TN-C) | 0.52 | 0.58 | 0.58 |
| Vitronectin | 0.50 | 0.56 | 0.56 |
| Beta 2 Microglobulin (B2M) | 0.57 | 0.58 | 0.58 |
| Pancreatic Secretory Trypsin Inhibitor (TATI) | 0.53 | 0.58 | 0.58 |
| Matrix Metalloproteinase 3 (MMP3) | 0.59 | 0.58 | 0.59 |
| Omentin | 0.58 | 0.58 | 0.58 |
| Interleukin 18 Binding Protein (IL 18bp) | 0.54 | 0.60 | 0.60 |
| Apolipoprotein D (ApoD) | 0.64 | 0.57 | 0.64 |
| Monoctye Chemotactic Protein 4 (MCP-4) | 0.57 | 0.58 | 0.58 |
| Apolipoprotein E (Apo-E) | 0.50 | 0.63 | 0.63 |
| ST2 | 0.51 | 0.58 | 0.58 |
| Thrombospondin 1 | 0.50 | 0.58 | 0.58 |
| Gastric Inhibitory Polypeptide (GIP) | 0.62 | 0.61 | 0.62 |
| Matrix Metalloproteinase 7 (MMP7) | 0.53 | 0.58 | 0.58 |
| Intercellular Adhesion Molecule 1 (ICAM-1) | 0.52 | 0.57 | 0.57 |
| Dickkopf Related Protein 1 (DKK1) | 0.55 | 0.57 | 0.57 |

TABLE 31

| 2 Biomarker Multivariate Analysis. Combination of Sortilin and Analyte 2 | | | |
|---|---|---|---|
| Analyte 2 | AUC by random forest | AUC by logistic regression | Maximum AUC |
| Alpha 1 Antitrypsin (AAT) | 0.60 | 0.55 | 0.60 |
| Immunoglobulin M (IgM) | 0.56 | 0.45 | 0.56 |
| Pulmonary and Activation Regulated Chemokine (PARC) | 0.53 | 0.59 | 0.59 |
| Pulmonary Surfactant Associated Protein D (SP-D) | 0.55 | 0.53 | 0.55 |
| B Cell Activating Factor (BAFF) | 0.50 | 0.58 | 0.58 |
| Adrenomedullin (ADM) | 0.60 | 0.64 | 0.64 |
| Pigment Epithelium Derived Factor (PEDF) | 0.60 | 0.65 | 0.65 |
| Interleukin 1 Receptor Antagonist (IL1ra) | 0.47 | 0.58 | 0.58 |
| Thyrosine Binding Globulin (TBG) | 0.48 | 0.59 | 0.59 |
| Microalbumin | 0.58 | 0.58 | 0.58 |
| Leptin | 0.51 | 0.59 | 0.59 |
| Eotaxin 2 | 0.62 | 0.57 | 0.62 |
| Insulin like Growth Factor Binding Protein 2 (IGFBP2) | 0.55 | 0.58 | 0.58 |
| Resistin | 0.51 | 0.58 | 0.58 |
| Cathepsin D | 0.51 | 0.62 | 0.62 |
| E-Selectin | 0.49 | 0.64 | 0.64 |
| YKL40 | 0.52 | 0.54 | 0.54 |
| Interleukin 22 (IL22) | 0.56 | 0.58 | 0.58 |
| Cacinoembryonic Antigen (CEA) | 0.54 | 0.56 | 0.56 |
| Interleukin 8 (IL8) | 0.56 | 0.53 | 0.56 |
| Cancer Antigen 15-3 (CA 15-3) | 0.47 | 0.60 | 0.60 |
| Leptin Receptor (LeptinR) | 0.54 | 0.62 | 0.62 |
| Insulin | 0.52 | 0.61 | 0.61 |
| Monocyte Chemotactic Protein 1 (MCP1) | 0.60 | 0.58 | 0.60 |
| Prolactin (PRL) | 0.47 | 0.57 | 0.57 |
| Tetranectin | 0.43 | 0.53 | 0.53 |
| Carcinoembryonic Antigen Related Cell Adhesion Molecule 1 (CEACAM1) | 0.49 | 0.59 | 0.59 |
| 6Ckine | 0.55 | 0.60 | 0.60 |
| Serum Amyloid P Component (SAP) | 0.50 | 0.58 | 0.58 |
| Complement Factor H Related Protein 1 (CFHR1) | 0.58 | 0.53 | 0.58 |
| Chemokine CC-4 (HCC-4) | 0.54 | 0.54 | 0.54 |
| Complement C3 (C3) | 0.52 | 0.54 | 0.54 |
| Alpha Fetoprotein (AFP) | 0.55 | 0.61 | 0.61 |
| Angiopoietin 1 (ANG-1) | 0.50 | 0.57 | 0.57 |
| Interleukin 18 (IL18) | 0.55 | 0.63 | 0.63 |
| Gelsolin | 0.56 | 0.47 | 0.56 |
| Tenascin C (TN-C) | 0.48 | 0.53 | 0.53 |
| Vitronectin | 0.53 | 0.53 | 0.53 |
| Beta 2 Microglobulin (B2M) | 0.52 | 0.56 | 0.56 |

TABLE 31-continued

2 Biomarker Multivariate Analysis. Combination of Sortilin and Analyte 2

| Analyte 2 | AUC by random forest | AUC by logistic regression | Maximum AUC |
|---|---|---|---|
| Pancreatic Secretory Trypsin Inhibitor (TATI) | 0.55 | 0.53 | 0.55 |
| Matrix Metalloproteinase 3 (MMP3) | 0.57 | 0.56 | 0.57 |
| Omentin | 0.59 | 0.55 | 0.59 |
| Interleukin 18 Binding Protein (IL 18bp) | 0.55 | 0.58 | 0.58 |
| Apolipoprotein D (ApoD) | 0.60 | 0.58 | 0.60 |
| Monoctye Chemotactic Protein 4 (MCP-4) | 0.57 | 0.53 | 0.57 |
| Apolipoprotein E (Apo-E) | 0.52 | 0.60 | 0.60 |
| ST2 | 0.52 | 0.54 | 0.54 |
| Thrombospondin 1 | 0.57 | 0.53 | 0.57 |
| Gastric Inhibitory Polypeptide (GIP) | 0.49 | 0.58 | 0.58 |
| Matrix Metalloproteinase 7 (MMP7) | 0.51 | 0.57 | 0.57 |
| Intercellular Adhesion Molecule 1 (ICAM-1) | 0.54 | 0.54 | 0.54 |
| Dickkopf Related Protein 1 (DKK1) | 0.59 | 0.47 | 0.59 |

TABLE 32

2 Biomarker Multivariate Analysis. Combination of Alpha 1 Antitrypsin (AAT) and Analyte 2

| Analyte 2 | AUC by random forest | AUC by logistic regression | Maximum AUC |
|---|---|---|---|
| Immunoglobulin M (IgM) | 0.50 | 0.57 | 0.57 |
| Pulmonary and Activation Regulated Chemokine (PARC) | 0.62 | 0.63 | 0.63 |
| Pulmonary Surfactant Associated Protein D (SP-D) | 0.50 | 0.45 | 0.50 |
| B Cell Activating Factor (BAFF) | 0.60 | 0.61 | 0.61 |
| Adrenomedullin (ADM) | 0.55 | 0.65 | 0.65 |
| Pigment Epithelium Derived Factor (PEDF) | 0.64 | 0.66 | 0.66 |
| Interleukin 1 Receptor Antagonist (IL1ra) | 0.49 | 0.65 | 0.65 |
| Thyrosine Binding Globulin (TBG) | 0.55 | 0.63 | 0.63 |
| Microalbumin | 0.59 | 0.59 | 0.59 |
| Leptin | 0.54 | 0.64 | 0.64 |
| Eotaxin 2 | 0.58 | 0.59 | 0.59 |
| Insulin like Growth Factor Binding Protein 2 (IGFBP2) | 0.57 | 0.60 | 0.60 |
| Resistin | 0.58 | 0.58 | 0.58 |
| Cathepsin D | 0.54 | 0.65 | 0.65 |
| E-Selectin | 0.51 | 0.65 | 0.65 |
| YKL40 | 0.54 | 0.54 | 0.54 |
| Interleukin 22 (IL22) | 0.49 | 0.56 | 0.56 |
| Cacinoembryonic Antigen (CEA) | 0.51 | 0.57 | 0.57 |
| Interleukin 8 (IL8) | 0.56 | 0.55 | 0.56 |
| Cancer Antigen 15-3 (CA 15-3) | 0.56 | 0.57 | 0.57 |
| Leptin Receptor (LeptinR) | 0.50 | 0.59 | 0.59 |
| Insulin | 0.52 | 0.58 | 0.58 |
| Monocyte Chemotactic Protein 1 (MCP1) | 0.51 | 0.60 | 0.60 |
| Prolactin (PRL) | 0.53 | 0.57 | 0.57 |
| Tetranectin | 0.51 | 0.56 | 0.56 |
| Carcinoembryonic Antigen Related Cell Adhesion Molecule 1 (CEACAM1) | 0.55 | 0.59 | 0.59 |
| 6Ckine | 0.52 | 0.63 | 0.63 |
| Serum Amyloid P Component (SAP) | 0.57 | 0.62 | 0.62 |
| Complement Factor H Related Protein 1 (CFHR1) | 0.50 | 0.55 | 0.55 |
| Chemokine CC-4 (HCC-4) | 0.57 | 0.55 | 0.57 |
| Complement C3 (C3) | 0.53 | 0.58 | 0.58 |
| Alpha Fetoprotein (AFP) | 0.54 | 0.58 | 0.58 |
| Angiopoietin 1 (ANG-1) | 0.59 | 0.56 | 0.59 |
| Interleukin 18 (IL18) | 0.63 | 0.62 | 0.63 |
| Gelsolin | 0.67 | 0.56 | 0.67 |
| Tenascin C (TN-C) | 0.51 | 0.57 | 0.57 |
| Vitronectin | 0.50 | 0.56 | 0.56 |
| Beta 2 Microglobulin (B2M) | 0.57 | 0.44 | 0.57 |
| Pancreatic Secretory Trypsin Inhibitor (TATI) | 0.54 | 0.56 | 0.56 |
| Matrix Metalloproteinase 3 (MMP3) | 0.60 | 0.56 | 0.60 |
| Omentin | 0.54 | 0.56 | 0.56 |
| Interleukin 18 Binding Protein (IL 18bp) | 0.49 | 0.58 | 0.58 |
| Apolipoprotein D (ApoD) | 0.60 | 0.57 | 0.60 |
| Monoctye Chemotactic Protein 4 (MCP-4) | 0.52 | 0.55 | 0.55 |
| Apolipoprotein E (Apo-E) | 0.59 | 0.62 | 0.62 |
| ST2 | 0.51 | 0.55 | 0.55 |
| Thrombospondin 1 | 0.65 | 0.54 | 0.65 |
| Gastric Inhibitory Polypeptide (GIP) | 0.56 | 0.58 | 0.58 |
| Matrix Metalloproteinase 7 (MMP7) | 0.62 | 0.59 | 0.62 |
| Intercellular Adhesion Molecule 1 (ICAM-1) | 0.58 | 0.57 | 0.58 |
| Dickkopf Related Protein 1 (DKK1) | 0.49 | 0.54 | 0.54 |

TABLE 33

2 Biomarker Multivariate Analysis. Combination of Immunoglobulin M (IgM) and Analyte 2

| Analyte 2 | AUC by random forest | AUC by logistic regression | Maximum AUC |
|---|---|---|---|
| Pulmonary and Activation Regulated Chemokine (PARC) | 0.64 | 0.60 | 0.64 |
| Pulmonary Surfactant Associated Protein D (SP-D) | 0.55 | 0.46 | 0.55 |
| B Cell Activating Factor (BAFF) | 0.60 | 0.58 | 0.60 |
| Adrenomedullin (ADM) | 0.56 | 0.63 | 0.63 |
| Pigment Epithelium Derived Factor (PEDF) | 0.56 | 0.66 | 0.66 |
| Interleukin 1 Receptor Antagonist (IL1ra) | 0.48 | 0.62 | 0.62 |
| Thyrosine Binding Globulin (TBG) | 0.54 | 0.59 | 0.59 |
| Microalbumin | 0.67 | 0.57 | 0.67 |
| Leptin | 0.57 | 0.64 | 0.64 |
| Eotaxin 2 | 0.60 | 0.56 | 0.60 |
| Insulin like Growth Factor Binding Protein 2 (IGFBP2) | 0.69 | 0.57 | 0.69 |
| Resistin | 0.56 | 0.58 | 0.58 |
| Cathepsin D | 0.51 | 0.63 | 0.63 |
| E-Selectin | 0.55 | 0.63 | 0.63 |
| YKL40 | 0.48 | 0.54 | 0.54 |
| Interleukin 22 (IL22) | 0.52 | 0.58 | 0.58 |
| Cacinoembryonic Antigen (CEA) | 0.53 | 0.56 | 0.56 |

TABLE 33-continued

2 Biomarker Multivariate Analysis. Combination of Immunoglobulin M (IgM) and Analyte 2

| Analyte 2 | AUC by random forest | AUC by logistic regression | Maximum AUC |
|---|---|---|---|
| Interleukin 8 (IL8) | 0.55 | 0.54 | 0.55 |
| Cancer Antigen 15-3 (CA 15-3) | 0.57 | 0.56 | 0.57 |
| Leptin Receptor (LeptinR) | 0.58 | 0.58 | 0.58 |
| Insulin | 0.67 | 0.65 | 0.67 |
| Monocyte Chemotactic Protein 1 (MCP1) | 0.59 | 0.61 | 0.61 |
| Prolactin (PRL) | 0.52 | 0.56 | 0.56 |
| Tetranectin | 0.51 | 0.53 | 0.53 |
| Carcinoembryonic Antigen Related Cell Adhesion Molecule 1 (CEACAM1) | 0.56 | 0.58 | 0.58 |
| 6Ckine | 0.60 | 0.63 | 0.63 |
| Serum Amyloid P Component (SAP) | 0.65 | 0.61 | 0.65 |
| Complement Factor H Related Protein 1 (CFHR1) | 0.51 | 0.54 | 0.54 |
| Chemokine CC-4 (HCC-4) | 0.55 | 0.55 | 0.55 |
| Complement C3 (C3) | 0.66 | 0.56 | 0.66 |
| Alpha Fetoprotein (AFP) | 0.58 | 0.57 | 0.58 |
| Angiopoietin 1 (ANG-1) | 0.62 | 0.54 | 0.62 |
| Interleukin 18 (IL18) | 0.60 | 0.66 | 0.66 |
| Gelsolin | 0.68 | 0.46 | 0.68 |
| Tenascin C (TN-C) | 0.62 | 0.54 | 0.62 |
| Vitronectin | 0.53 | 0.54 | 0.54 |
| Beta 2 Microglobulin (B2M) | 0.60 | 0.56 | 0.60 |
| Pancreatic Secretory Trypsin Inhibitor (TATI) | 0.56 | 0.47 | 0.56 |
| Matrix Metalloproteinase 3 (MMP3) | 0.64 | 0.55 | 0.64 |
| Omentin | 0.54 | 0.47 | 0.54 |
| Interleukin 18 Binding Protein (IL 18bp) | 0.62 | 0.58 | 0.62 |
| Apolipoprotein D (ApoD) | 0.70 | 0.59 | 0.70 |
| Monoctye Chemotactic Protein 4 (MCP-4) | 0.52 | 0.54 | 0.54 |
| Apolipoprotein E (Apo-E) | 0.60 | 0.62 | 0.62 |
| ST2 | 0.46 | 0.54 | 0.54 |
| Thrombospondin 1 | 0.52 | 0.55 | 0.55 |
| Gastric Inhibitory Polypeptide (GIP) | 0.56 | 0.60 | 0.60 |
| Matrix Metalloproteinase 7 (MMP7) | 0.58 | 0.58 | 0.58 |
| Intercellular Adhesion Molecule 1 (ICAM-1) | 0.56 | 0.54 | 0.56 |
| Dickkopf Related Protein 1 (DKK1) | 0.55 | 0.55 | 0.55 |

TABLE 34

2 Biomarker Multivariate Analysis. Combination of Pulmonary and Activation Regulated Chemokine (PARC) and Analyte 2

| Analyte 2 | AUC by random forest | AUC by logistic regression | Maximum AUC |
|---|---|---|---|
| Pulmonary Surfactant Associated Protein D (SP-D) | 0.52 | 0.60 | 0.60 |
| B Cell Activating Factor (BAFF) | 0.63 | 0.62 | 0.63 |
| Adrenomedullin (ADM) | 0.55 | 0.63 | 0.63 |
| Pigment Epithelium Derived Factor (PEDF) | 0.54 | 0.67 | 0.67 |
| Interleukin 1 Receptor Antagonist (IL1ra) | 0.58 | 0.62 | 0.62 |
| Thyrosine Binding Globulin (TBG) | 0.59 | 0.62 | 0.62 |
| Microalbumin | 0.60 | 0.61 | 0.61 |
| Leptin | 0.52 | 0.63 | 0.63 |
| Eotaxin 2 | 0.64 | 0.61 | 0.64 |
| Insulin like Growth Factor Binding Protein 2 (IGFBP2) | 0.59 | 0.61 | 0.61 |
| Resistin | 0.53 | 0.61 | 0.61 |
| Cathepsin D | 0.52 | 0.62 | 0.62 |
| E-Selectin | 0.50 | 0.65 | 0.65 |
| YKL40 | 0.61 | 0.59 | 0.61 |
| Interleukin 22 (IL22) | 0.49 | 0.62 | 0.62 |
| Cacinoembryonic Antigen (CEA) | 0.55 | 0.61 | 0.61 |
| Interleukin 8 (IL8) | 0.57 | 0.59 | 0.59 |
| Cancer Antigen 15-3 (CA 15-3) | 0.48 | 0.61 | 0.61 |
| Leptin Receptor (LeptinR) | 0.57 | 0.62 | 0.62 |
| Insulin | 0.59 | 0.64 | 0.64 |
| Monocyte Chemotactic Protein 1 (MCP1) | 0.55 | 0.62 | 0.62 |
| Prolactin (PRL) | 0.55 | 0.62 | 0.62 |
| Tetranectin | 0.48 | 0.60 | 0.60 |
| Carcinoembryonic Antigen Related Cell Adhesion Molecule 1 (CEACAM1) | 0.53 | 0.62 | 0.62 |
| 6Ckine | 0.50 | 0.63 | 0.63 |
| Serum Amyloid P Component (SAP) | 0.53 | 0.62 | 0.62 |
| Complement Factor H Related Protein 1 (CFHR1) | 0.64 | 0.42 | 0.64 |
| Chemokine CC-4 (HCC-4) | 0.57 | 0.59 | 0.59 |
| Complement C3 (C3) | 0.62 | 0.60 | 0.62 |
| Alpha Fetoprotein (AFP) | 0.57 | 0.63 | 0.63 |
| Angiopoietin 1 (ANG-1) | 0.58 | 0.61 | 0.61 |
| Interleukin 18 (IL18) | 0.60 | 0.65 | 0.65 |
| Gelsolin | 0.60 | 0.61 | 0.61 |
| Tenascin C (TN-C) | 0.51 | 0.61 | 0.61 |
| Vitronectin | 0.54 | 0.60 | 0.60 |
| Beta 2 Microglobulin (B2M) | 0.60 | 0.60 | 0.60 |
| Pancreatic Secretory Trypsin Inhibitor (TATI) | 0.56 | 0.59 | 0.59 |
| Matrix Metalloproteinase 3 (MMP3) | 0.64 | 0.62 | 0.64 |
| Omentin | 0.51 | 0.59 | 0.59 |
| Interleukin 18 Binding Protein (IL 18bp) | 0.54 | 0.61 | 0.61 |
| Apolipoprotein D (ApoD) | 0.70 | 0.60 | 0.70 |
| Monoctye Chemotactic Protein 4 (MCP-4) | 0.53 | 0.59 | 0.59 |
| Apolipoprotein E (Apo-E) | 0.57 | 0.64 | 0.64 |
| ST2 | 0.60 | 0.59 | 0.60 |
| Thrombospondin 1 | 0.60 | 0.59 | 0.60 |
| Gastric Inhibitory Polypeptide (GIP) | 0.58 | 0.63 | 0.63 |
| Matrix Metalloproteinase 7 (MMP7) | 0.59 | 0.61 | 0.61 |
| Intercellular Adhesion Molecule 1 (ICAM-1) | 0.47 | 0.59 | 0.59 |
| Dickkopf Related Protein 1 (DKK1) | 0.55 | 0.59 | 0.59 |

TABLE 35

2 Biomarker Multivariate Analysis. Combination of Pulmonary Surfactant Associated Protein D (SP-D) and Analyte 2

| Analyte 2 | AUC by random forest | AUC by logistic regression | Maximum AUC |
|---|---|---|---|
| B Cell Activating Factor (BAFF) | 0.55 | 0.58 | 0.58 |
| Adrenomedullin (ADM) | 0.52 | 0.62 | 0.62 |
| Pigment Epithelium Derived Factor (PEDF) | 0.64 | 0.65 | 0.65 |
| Interleukin 1 Receptor Antagonist (IL1ra) | 0.52 | 0.59 | 0.59 |
| Thyrosine Binding Globulin (TBG) | 0.63 | 0.59 | 0.63 |
| Microalbumin | 0.58 | 0.45 | 0.58 |
| Leptin | 0.50 | 0.61 | 0.61 |
| Eotaxin 2 | 0.62 | 0.55 | 0.62 |
| Insulin like Growth Factor Binding Protein 2 (IGFBP2) | 0.50 | 0.56 | 0.56 |
| Resistin | 0.55 | 0.56 | 0.56 |
| Cathepsin D | 0.53 | 0.62 | 0.62 |
| E-Selectin | 0.50 | 0.64 | 0.64 |
| YKL40 | 0.58 | 0.51 | 0.58 |
| Interleukin 22 (IL22) | 0.54 | 0.56 | 0.56 |
| Cacinoembryonic Antigen (CEA) | 0.56 | 0.54 | 0.56 |

TABLE 35-continued

2 Biomarker Multivariate Analysis. Combination of Pulmonary Surfactant Associated Protein D (SP-D) and Analyte 2

| Analyte 2 | AUC by random forest | AUC by logistic regression | Maximum AUC |
|---|---|---|---|
| Interleukin 8 (IL8) | 0.55 | 0.50 | 0.55 |
| Cancer Antigen 15-3 (CA 15-3) | 0.57 | 0.55 | 0.57 |
| Leptin Receptor (LeptinR) | 0.55 | 0.57 | 0.57 |
| Insulin | 0.50 | 0.62 | 0.62 |
| Monocyte Chemotactic Protein 1 (MCP1) | 0.55 | 0.59 | 0.59 |
| Prolactin (PRL) | 0.52 | 0.55 | 0.55 |
| Tetranectin | 0.56 | 0.51 | 0.56 |
| Carcinoembryonic Antigen Related Cell Adhesion Molecule 1 (CEACAM1) | 0.55 | 0.57 | 0.57 |
| 6Ckine | 0.51 | 0.61 | 0.61 |
| Serum Amyloid P Component (SAP) | 0.53 | 0.57 | 0.57 |
| Complement Factor H Related Protein 1 (CFHR1) | 0.53 | 0.50 | 0.53 |
| Chemokine CC-4 (HCC-4) | 0.50 | 0.52 | 0.52 |
| Complement C3 (C3) | 0.46 | 0.52 | 0.52 |
| Alpha Fetoprotein (AFP) | 0.58 | 0.55 | 0.58 |
| Angiopoietin 1 (ANG-1) | 0.53 | 0.54 | 0.54 |
| Interleukin 18 (IL18) | 0.56 | 0.65 | 0.65 |
| Gelsolin | 0.53 | 0.47 | 0.53 |
| Tenascin C (TN-C) | 0.54 | 0.54 | 0.54 |
| Vitronectin | 0.60 | 0.50 | 0.60 |
| Beta 2 Microglobulin (B2M) | 0.50 | 0.56 | 0.56 |
| Pancreatic Secretory Trypsin Inhibitor (TATI) | 0.52 | 0.52 | 0.52 |
| Matrix Metalloproteinase 3 (MMP3) | 0.54 | 0.55 | 0.55 |
| Omentin | 0.70 | 0.51 | 0.70 |
| Interleukin 18 Binding Protein (IL 18bp) | 0.50 | 0.59 | 0.59 |
| Apolipoprotein D (ApoD) | 0.54 | 0.55 | 0.55 |
| Monoctye Chemotactic Protein 4 (MCP-4) | 0.55 | 0.53 | 0.55 |
| Apolipoprotein E (Apo-E) | 0.48 | 0.60 | 0.60 |
| ST2 | 0.50 | 0.52 | 0.52 |
| Thrombospondin 1 | 0.56 | 0.51 | 0.56 |
| Gastric Inhibitory Polypeptide (GIP) | 0.54 | 0.59 | 0.59 |
| Matrix Metalloproteinase 7 (MMP7) | 0.50 | 0.56 | 0.56 |
| Intercellular Adhesion Molecule 1 (ICAM-1) | 0.63 | 0.52 | 0.63 |
| Dickkopf Related Protein 1 (DKK1) | 0.59 | 0.53 | 0.59 |

TABLE 36

2 Biomarker Multivariate Analysis. Combination of B Cell Activating Factor (BAFF) and Analyte 2

| Analyte 2 | AUC by random forest | AUC by logistic regression | Maximum AUC |
|---|---|---|---|
| Adrenomedullin (ADM) | 0.58 | 0.64 | 0.64 |
| Pigment Epithelium Derived Factor (PEDF) | 0.54 | 0.67 | 0.67 |
| Interleukin 1 Receptor Antagonist (IL1ra) | 0.47 | 0.62 | 0.62 |
| Thyrosine Binding Globulin (TBG) | 0.49 | 0.59 | 0.59 |
| Microalbumin | 0.61 | 0.57 | 0.61 |
| Leptin | 0.46 | 0.61 | 0.61 |
| Eotaxin 2 | 0.64 | 0.59 | 0.64 |
| Insulin like Growth Factor Binding Protein 2 (IGFBP2) | 0.50 | 0.60 | 0.60 |
| Resistin | 0.51 | 0.62 | 0.62 |
| Cathepsin D | 0.60 | 0.64 | 0.64 |
| E-Selectin | 0.50 | 0.66 | 0.66 |
| YKL40 | 0.60 | 0.58 | 0.60 |
| Interleukin 22 (IL22) | 0.55 | 0.60 | 0.60 |
| Cacinoembryonic Antigen (CEA) | 0.57 | 0.60 | 0.60 |
| Interleukin 8 (IL8) | 0.61 | 0.59 | 0.61 |
| Cancer Antigen 15-3 (CA 15-3) | 0.51 | 0.59 | 0.59 |
| Leptin Receptor (LeptinR) | 0.50 | 0.60 | 0.60 |
| Insulin | 0.58 | 0.65 | 0.65 |
| Monocyte Chemotactic Protein 1 (MCP1) | 0.50 | 0.62 | 0.62 |
| Prolactin (PRL) | 0.53 | 0.59 | 0.59 |
| Tetranectin | 0.56 | 0.59 | 0.59 |
| Carcinoembryonic Antigen Related Cell Adhesion Molecule 1 (CEACAM1) | 0.48 | 0.57 | 0.57 |
| 6Ckine | 0.53 | 0.63 | 0.63 |
| Serum Amyloid P Component (SAP) | 0.55 | 0.61 | 0.61 |
| Complement Factor H Related Protein 1 (CFHR1) | 0.54 | 0.58 | 0.58 |
| Chemokine CC-4 (HCC-4) | 0.60 | 0.58 | 0.60 |
| Complement C3 (C3) | 0.59 | 0.59 | 0.59 |
| Alpha Fetoprotein (AFP) | 0.50 | 0.63 | 0.63 |
| Angiopoietin 1 (ANG-1) | 0.57 | 0.59 | 0.59 |
| Interleukin 18 (IL18) | 0.47 | 0.65 | 0.65 |
| Gelsolin | 0.57 | 0.62 | 0.62 |
| Tenascin C (TN-C) | 0.55 | 0.60 | 0.60 |
| Vitronectin | 0.59 | 0.58 | 0.59 |
| Beta 2 Microglobulin (B2M) | 0.49 | 0.61 | 0.61 |
| Pancreatic Secretory Trypsin Inhibitor (TATI) | 0.56 | 0.58 | 0.58 |
| Matrix Metalloproteinase 3 (MMP3) | 0.61 | 0.61 | 0.61 |
| Omentin | 0.57 | 0.58 | 0.58 |
| Interleukin 18 Binding Protein (IL 18bp) | 0.60 | 0.61 | 0.61 |
| Apolipoprotein D (ApoD) | 0.63 | 0.58 | 0.63 |
| Monoctye Chemotactic Protein 4 (MCP-4) | 0.44 | 0.59 | 0.59 |
| Apolipoprotein E (Apo-E) | 0.56 | 0.64 | 0.64 |
| ST2 | 0.54 | 0.58 | 0.58 |
| Thrombospondin 1 | 0.58 | 0.58 | 0.58 |
| Gastric Inhibitory Polypeptide (GIP) | 0.50 | 0.63 | 0.63 |
| Matrix Metalloproteinase 7 (MMP7) | 0.57 | 0.59 | 0.59 |
| Intercellular Adhesion Molecule 1 (ICAM-1) | 0.53 | 0.58 | 0.58 |
| Dickkopf Related Protein 1 (DKK1) | 0.53 | 0.59 | 0.59 |

TABLE 37

2 Biomarker Multivariate Analysis. Combination of Adrenomedullin (ADM) and Analyte 2

| Analyte 2 | AUC by random forest | AUC by logistic regression | Maximum AUC |
|---|---|---|---|
| Pigment Epithelium Derived Factor (PEDF) | 0.57 | 0.66 | 0.66 |
| Interleukin 1 Receptor Antagonist (IL1ra) | 0.51 | 0.63 | 0.63 |
| Thyrosine Binding Globulin (TBG) | 0.58 | 0.63 | 0.63 |
| Microalbumin | 0.63 | 0.63 | 0.63 |
| Leptin | 0.51 | 0.62 | 0.62 |
| Eotaxin 2 | 0.61 | 0.63 | 0.63 |
| Insulin like Growth Factor Binding Protein 2 (IGFBP2) | 0.42 | 0.61 | 0.61 |
| Resistin | 0.48 | 0.63 | 0.63 |
| Cathepsin D | 0.50 | 0.65 | 0.65 |
| E-Selectin | 0.55 | 0.70 | 0.70 |
| YKL40 | 0.56 | 0.62 | 0.62 |
| Interleukin 22 (IL22) | 0.48 | 0.63 | 0.63 |
| Cacinoembryonic Antigen (CEA) | 0.64 | 0.64 | 0.64 |
| Interleukin 8 (IL8) | 0.61 | 0.62 | 0.62 |
| Cancer Antigen 15-3 (CA 15-3) | 0.48 | 0.63 | 0.63 |
| Leptin Receptor (LeptinR) | 0.55 | 0.63 | 0.63 |
| Insulin | 0.51 | 0.64 | 0.64 |

TABLE 37-continued

2 Biomarker Multivariate Analysis. Combination of Adrenomedullin (ADM) and Analyte 2

| Analyte 2 | AUC by random forest | AUC by logistic regression | Maximum AUC |
|---|---|---|---|
| Monocyte Chemotactic Protein 1 (MCP1) | 0.56 | 0.66 | 0.66 |
| Prolactin (PRL) | 0.55 | 0.62 | 0.62 |
| Tetranectin | 0.55 | 0.63 | 0.63 |
| Carcinoembryonic Antigen Related Cell Adhesion Molecule 1 (CEACAM1) | 0.56 | 0.61 | 0.61 |
| 6Ckine | 0.51 | 0.65 | 0.65 |
| Serum Amyloid P Component (SAP) | 0.47 | 0.61 | 0.61 |
| Complement Factor H Related Protein 1 (CFHR1) | 0.49 | 0.63 | 0.63 |
| Chemokine CC-4 (HCC-4) | 0.52 | 0.61 | 0.61 |
| Complement C3 (C3) | 0.55 | 0.62 | 0.62 |
| Alpha Fetoprotein (AFP) | 0.54 | 0.65 | 0.65 |
| Angiopoietin 1 (ANG-1) | 0.51 | 0.62 | 0.62 |
| Interleukin 18 (IL18) | 0.55 | 0.66 | 0.66 |
| Gelsolin | 0.57 | 0.63 | 0.63 |
| Tenascin C (TN-C) | 0.46 | 0.62 | 0.62 |
| Vitronectin | 0.58 | 0.62 | 0.62 |
| Beta 2 Microglobulin (B2M) | 0.59 | 0.62 | 0.62 |
| Pancreatic Secretory Trypsin Inhibitor (TATI) | 0.47 | 0.63 | 0.63 |
| Matrix Metalloproteinase 3 (MMP3) | 0.65 | 0.64 | 0.65 |
| Omentin | 0.54 | 0.63 | 0.63 |
| Interleukin 18 Binding Protein (IL 18bp) | 0.60 | 0.65 | 0.65 |
| Apolipoprotein D (ApoD) | 0.57 | 0.62 | 0.62 |
| Monoctye Chemotactic Protein 4 (MCP-4) | 0.55 | 0.62 | 0.62 |
| Apolipoprotein E (Apo-E) | 0.54 | 0.64 | 0.64 |
| ST2 | 0.53 | 0.62 | 0.62 |
| Thrombospondin 1 | 0.52 | 0.62 | 0.62 |
| Gastric Inhibitory Polypeptide (GIP) | 0.58 | 0.63 | 0.63 |
| Matrix Metalloproteinase 7 (MMP7) | 0.51 | 0.64 | 0.64 |
| Intercellular Adhesion Molecule 1 (ICAM-1) | 0.54 | 0.63 | 0.63 |
| Dickkopf Related Protein 1 (DKK1) | 0.48 | 0.62 | 0.62 |

TABLE 38

2 Biomarker Multivariate Analysis. Combination of Pigment Epithelium Derived Factor (PEDF) and Analyte 2

| Analyte 2 | AUC by random forest | AUC by logistic regression | Maximum AUC |
|---|---|---|---|
| Interleukin 1 Receptor Antagonist (IL1ra) | 0.53 | 0.64 | 0.64 |
| Thyrosine Binding Globulin (TBG) | 0.51 | 0.64 | 0.64 |
| Microalbumin | 0.66 | 0.66 | 0.66 |
| Leptin | 0.53 | 0.64 | 0.64 |
| Eotaxin 2 | 0.69 | 0.64 | 0.69 |
| Insulin like Growth Factor Binding Protein 2 (IGFBP2) | 0.47 | 0.64 | 0.64 |
| Resistin | 0.53 | 0.64 | 0.64 |
| Cathepsin D | 0.56 | 0.67 | 0.67 |
| E-Selectin | 0.51 | 0.67 | 0.67 |
| YKL40 | 0.56 | 0.65 | 0.65 |
| Interleukin 22 (IL22) | 0.57 | 0.65 | 0.65 |
| Cacinoembryonic Antigen (CEA) | 0.52 | 0.65 | 0.65 |
| Interleukin 8 (IL8) | 0.45 | 0.64 | 0.64 |
| Cancer Antigen 15-3 (CA 15-3) | 0.60 | 0.66 | 0.66 |
| Leptin Receptor (LeptinR) | 0.53 | 0.65 | 0.65 |
| Insulin | 0.55 | 0.64 | 0.64 |
| Monocyte Chemotactic Protein 1 (MCP1) | 0.61 | 0.66 | 0.66 |
| Prolactin (PRL) | 0.56 | 0.64 | 0.64 |
| Tetranectin | 0.56 | 0.65 | 0.65 |
| Carcinoembryonic Antigen Related Cell Adhesion Molecule 1 (CEACAM1) | 0.55 | 0.67 | 0.67 |
| 6Ckine | 0.56 | 0.66 | 0.66 |
| Serum Amyloid P Component (SAP) | 0.51 | 0.64 | 0.64 |
| Complement Factor H Related Protein 1 (CFHR1) | 0.55 | 0.65 | 0.65 |
| Chemokine CC-4 (HCC-4) | 0.58 | 0.64 | 0.64 |
| Complement C3 (C3) | 0.60 | 0.65 | 0.65 |
| Alpha Fetoprotein (AFP) | 0.52 | 0.68 | 0.68 |
| Angiopoietin 1 (ANG-1) | 0.60 | 0.64 | 0.64 |
| Interleukin 18 (IL18) | 0.51 | 0.66 | 0.66 |
| Gelsolin | 0.58 | 0.65 | 0.65 |
| Tenascin C (TN-C) | 0.55 | 0.66 | 0.66 |
| Vitronectin | 0.50 | 0.65 | 0.65 |
| Beta 2 Microglobulin (B2M) | 0.60 | 0.65 | 0.65 |
| Pancreatic Secretory Trypsin Inhibitor (TATI) | 0.64 | 0.64 | 0.64 |
| Matrix Metalloproteinase 3 (MMP3) | 0.54 | 0.65 | 0.65 |
| Omentin | 0.53 | 0.64 | 0.64 |
| Interleukin 18 Binding Protein (IL 18bp) | 0.59 | 0.65 | 0.65 |
| Apolipoprotein D (ApoD) | 0.60 | 0.64 | 0.64 |
| Monoctye Chemotactic Protein 4 (MCP-4) | 0.49 | 0.65 | 0.65 |
| Apolipoprotein E (Apo-E) | 0.53 | 0.64 | 0.64 |
| ST2 | 0.56 | 0.64 | 0.64 |
| Thrombospondin 1 | 0.55 | 0.64 | 0.64 |
| Gastric Inhibitory Polypeptide (GIP) | 0.55 | 0.65 | 0.65 |
| Matrix Metalloproteinase 7 (MMP7) | 0.59 | 0.65 | 0.65 |
| Intercellular Adhesion Molecule 1 (ICAM-1) | 0.51 | 0.64 | 0.64 |
| Dickkopf Related Protein 1 (DKK1) | 0.50 | 0.65 | 0.65 |

TABLE 39

2 Biomarker Multivariate Analysis. Combination of Interleukin 1 Receptor Antagonist (IL1ra) and Analyte 2

| Analyte 2 | AUC by random forest | AUC by logistic regression | Maximum AUC |
|---|---|---|---|
| Thyrosine Binding Globulin (TBG) | 0.55 | 0.61 | 0.61 |
| Microalbumin | 0.56 | 0.62 | 0.62 |
| Leptin | 0.56 | 0.61 | 0.61 |
| Eotaxin 2 | 0.59 | 0.60 | 0.60 |
| Insulin like Growth Factor Binding Protein 2 (IGFBP2) | 0.54 | 0.61 | 0.61 |
| Resistin | 0.54 | 0.58 | 0.58 |
| Cathepsin D | 0.59 | 0.64 | 0.64 |
| E-Selectin | 0.53 | 0.67 | 0.67 |
| YKL40 | 0.53 | 0.59 | 0.59 |
| Interleukin 22 (IL22) | 0.52 | 0.62 | 0.62 |
| Cacinoembryonic Antigen (CEA) | 0.53 | 0.62 | 0.62 |
| Interleukin 8 (IL8) | 0.56 | 0.58 | 0.58 |
| Cancer Antigen 15-3 (CA 15-3) | 0.59 | 0.61 | 0.61 |
| Leptin Receptor (LeptinR) | 0.51 | 0.61 | 0.61 |
| Insulin | 0.55 | 0.61 | 0.61 |
| Monocyte Chemotactic Protein 1 (MCP1) | 0.52 | 0.63 | 0.63 |
| Prolactin (PRL) | 0.55 | 0.61 | 0.61 |
| Tetranectin | 0.56 | 0.59 | 0.59 |
| Carcinoembryonic Antigen Related Cell Adhesion Molecule 1 (CEACAM1) | 0.50 | 0.63 | 0.63 |
| 6Ckine | 0.54 | 0.60 | 0.60 |
| Serum Amyloid P Component (SAP) | 0.51 | 0.60 | 0.60 |
| Complement Factor H Related Protein 1 (CFHR1) | 0.61 | 0.58 | 0.61 |

TABLE 39-continued

2 Biomarker Multivariate Analysis. Combination of Interleukin 1 Receptor Antagonist (IL1ra) and Analyte 2

| Analyte 2 | AUC by random forest | AUC by logistic regression | Maximum AUC |
|---|---|---|---|
| Chemokine CC-4 (HCC-4) | 0.57 | 0.58 | 0.58 |
| Complement C3 (C3) | 0.58 | 0.58 | 0.58 |
| Alpha Fetoprotein (AFP) | 0.49 | 0.62 | 0.62 |
| Angiopoietin 1 (ANG-1) | 0.53 | 0.59 | 0.59 |
| Interleukin 18 (IL18) | 0.53 | 0.62 | 0.62 |
| Gelsolin | 0.62 | 0.59 | 0.62 |
| Tenascin C (TN-C) | 0.52 | 0.59 | 0.59 |
| Vitronectin | 0.55 | 0.59 | 0.59 |
| Beta 2 Microglobulin (B2M) | 0.49 | 0.59 | 0.59 |
| Pancreatic Secretory Trypsin Inhibitor (TATI) | 0.51 | 0.58 | 0.58 |
| Matrix Metalloproteinase 3 (MMP3) | 0.56 | 0.59 | 0.59 |
| Omentin | 0.63 | 0.59 | 0.63 |
| Interleukin 18 Binding Protein (IL 18bp) | 0.49 | 0.59 | 0.59 |
| Apolipoprotein D (ApoD) | 0.68 | 0.59 | 0.68 |
| Monoctye Chemotactic Protein 4 (MCP-4) | 0.53 | 0.59 | 0.59 |
| Apolipoprotein E (Apo-E) | 0.53 | 0.62 | 0.62 |
| ST2 | 0.55 | 0.58 | 0.58 |
| Thrombospondin 1 | 0.51 | 0.59 | 0.59 |
| Gastric Inhibitory Polypeptide (GIP) | 0.58 | 0.62 | 0.62 |
| Matrix Metalloproteinase 7 (MMP7) | 0.57 | 0.62 | 0.62 |
| Intercellular Adhesion Molecule 1 (ICAM-1) | 0.50 | 0.58 | 0.58 |
| Dickkopf Related Protein 1 (DKK1) | 0.54 | 0.59 | 0.59 |

TABLE 40

2 Biomarker Multivariate Analysis. Combination of Thyrosine Binding Globulin (TBG) and Analyte 2

| Analyte 2 | AUC by random forest | AUC by logistic regression | Maximum AUC |
|---|---|---|---|
| Microalbumin | 0.48 | 0.59 | 0.59 |
| Leptin | 0.60 | 0.60 | 0.60 |
| Eotaxin 2 | 0.55 | 0.61 | 0.61 |
| Insulin like Growth Factor Binding Protein 2 (IGFBP2) | 0.59 | 0.58 | 0.59 |
| Resistin | 0.49 | 0.58 | 0.58 |
| Cathepsin D | 0.56 | 0.63 | 0.63 |
| E-Selectin | 0.50 | 0.65 | 0.65 |
| YKL40 | 0.54 | 0.58 | 0.58 |
| Interleukin 22 (IL22) | 0.58 | 0.60 | 0.60 |
| Cacinoembryonic Antigen (CEA) | 0.54 | 0.62 | 0.62 |
| Interleukin 8 (IL8) | 0.47 | 0.58 | 0.58 |
| Cancer Antigen 15-3 (CA 15-3) | 0.60 | 0.59 | 0.60 |
| Leptin Receptor (LeptinR) | 0.53 | 0.62 | 0.62 |
| Insulin | 0.56 | 0.61 | 0.61 |
| Monocyte Chemotactic Protein 1 (MCP1) | 0.53 | 0.61 | 0.61 |
| Prolactin (PRL) | 0.59 | 0.58 | 0.59 |
| Tetranectin | 0.51 | 0.59 | 0.59 |
| Carcinoembryonic Antigen Related Cell Adhesion Molecule 1 (CEACAM1) | 0.56 | 0.61 | 0.61 |
| 6Ckine | 0.50 | 0.61 | 0.61 |
| Serum Amyloid P Component (SAP) | 0.53 | 0.58 | 0.58 |
| Complement Factor H Related Protein 1 (CFHR1) | 0.58 | 0.59 | 0.59 |
| Chemokine CC-4 (HCC-4) | 0.56 | 0.58 | 0.58 |
| Complement C3 (C3) | 0.51 | 0.58 | 0.58 |
| Alpha Fetoprotein (AFP) | 0.53 | 0.59 | 0.59 |
| Angiopoietin 1 (ANG-1) | 0.53 | 0.59 | 0.59 |
| Interleukin 18 (IL18) | 0.56 | 0.62 | 0.62 |
| Gelsolin | 0.58 | 0.60 | 0.60 |
| Tenascin C (TN-C) | 0.58 | 0.59 | 0.59 |
| Vitronectin | 0.51 | 0.58 | 0.58 |
| Beta 2 Microglobulin (B2M) | 0.52 | 0.58 | 0.58 |
| Pancreatic Secretory Trypsin Inhibitor (TATI) | 0.55 | 0.60 | 0.60 |
| Matrix Metalloproteinase 3 (MMP3) | 0.54 | 0.59 | 0.59 |
| Omentin | 0.60 | 0.59 | 0.60 |
| Interleukin 18 Binding Protein (IL 18bp) | 0.52 | 0.60 | 0.60 |
| Apolipoprotein D (ApoD) | 0.54 | 0.58 | 0.58 |
| Monoctye Chemotactic Protein 4 (MCP-4) | 0.49 | 0.60 | 0.60 |
| Apolipoprotein E (Apo-E) | 0.54 | 0.61 | 0.61 |
| ST2 | 0.54 | 0.58 | 0.58 |
| Thrombospondin 1 | 0.53 | 0.59 | 0.59 |
| Gastric Inhibitory Polypeptide (GIP) | 0.55 | 0.59 | 0.59 |
| Matrix Metalloproteinase 7 (MMP7) | 0.55 | 0.60 | 0.60 |
| Intercellular Adhesion Molecule 1 (ICAM-1) | 0.51 | 0.58 | 0.58 |
| Dickkopf Related Protein 1 (DKK1) | 0.59 | 0.59 | 0.59 |

TABLE 41

2 Biomarker Multivariate Analysis. Combination of Microalbumin and Analyte 2

| Analyte 2 | AUC by random forest | AUC by logistic regression | Maximum AUC |
|---|---|---|---|
| Leptin | 0.60 | 0.61 | 0.61 |
| Eotaxin 2 | 0.61 | 0.55 | 0.61 |
| Insulin like Growth Factor Binding Protein 2 (IGFBP2) | 0.63 | 0.57 | 0.63 |
| Resistin | 0.54 | 0.59 | 0.59 |
| Cathepsin D | 0.64 | 0.65 | 0.65 |
| E-Selectin | 0.58 | 0.65 | 0.65 |
| YKL40 | 0.57 | 0.56 | 0.57 |
| Interleukin 22 (IL22) | 0.50 | 0.59 | 0.59 |
| Cacinoembryonic Antigen (CEA) | 0.59 | 0.57 | 0.59 |
| Interleukin 8 (IL8) | 0.60 | 0.45 | 0.60 |
| Cancer Antigen 15-3 (CA 15-3) | 0.54 | 0.58 | 0.58 |
| Leptin Receptor (LeptinR) | 0.55 | 0.58 | 0.58 |
| Insulin | 0.65 | 0.59 | 0.65 |
| Monocyte Chemotactic Protein 1 (MCP1) | 0.58 | 0.61 | 0.61 |
| Prolactin (PRL) | 0.50 | 0.56 | 0.56 |
| Tetranectin | 0.55 | 0.57 | 0.57 |
| Carcinoembryonic Antigen Related Cell Adhesion Molecule 1 (CEACAM1) | 0.56 | 0.57 | 0.57 |
| 6Ckine | 0.63 | 0.62 | 0.63 |
| Serum Amyloid P Component (SAP) | 0.65 | 0.60 | 0.65 |
| Complement Factor H Related Protein 1 (CFHR1) | 0.55 | 0.45 | 0.55 |
| Chemokine CC-4 (HCC-4) | 0.62 | 0.45 | 0.62 |
| Complement C3 (C3) | 0.64 | 0.56 | 0.64 |
| Alpha Fetoprotein (AFP) | 0.53 | 0.58 | 0.58 |
| Angiopoietin 1 (ANG-1) | 0.57 | 0.44 | 0.57 |
| Interleukin 18 (IL18) | 0.64 | 0.63 | 0.64 |
| Gelsolin | 0.65 | 0.60 | 0.65 |
| Tenascin C (TN-C) | 0.57 | 0.58 | 0.58 |
| Vitronectin | 0.59 | 0.56 | 0.59 |
| Beta 2 Microglobulin (B2M) | 0.59 | 0.56 | 0.59 |
| Pancreatic Secretory Trypsin Inhibitor (TATI) | 0.51 | 0.45 | 0.51 |
| Matrix Metalloproteinase 3 (MMP3) | 0.64 | 0.59 | 0.64 |
| Omentin | 0.56 | 0.44 | 0.56 |
| Interleukin 18 Binding Protein (IL 18bp) | 0.58 | 0.59 | 0.59 |
| Apolipoprotein D (ApoD) | 0.66 | 0.57 | 0.66 |

TABLE 41-continued

2 Biomarker Multivariate Analysis. Combination of Microalbumin and Analyte 2

| Analyte 2 | AUC by random forest | AUC by logistic regression | Maximum AUC |
|---|---|---|---|
| Monoctye Chemotactic Protein 4 (MCP-4) | 0.57 | 0.45 | 0.57 |
| Apolipoprotein E (Apo-E) | 0.58 | 0.63 | 0.63 |
| ST2 | 0.57 | 0.45 | 0.57 |
| Thrombospondin 1 | 0.61 | 0.58 | 0.61 |
| Gastric Inhibitory Polypeptide (GIP) | 0.61 | 0.59 | 0.61 |
| Matrix Metalloproteinase 7 (MMP7) | 0.63 | 0.56 | 0.63 |
| Intercellular Adhesion Molecule 1 (ICAM-1) | 0.60 | 0.56 | 0.60 |
| Dickkopf Related Protein 1 (DKK1) | 0.57 | 0.58 | 0.58 |

TABLE 42

2 Biomarker Multivariate Analysis. Combination of Leptin and Analyte 2

| Analyte 2 | AUC by random forest | AUC by logistic regression | Maximum AUC |
|---|---|---|---|
| Eotaxin 2 | 0.55 | 0.61 | 0.61 |
| Insulin like Growth Factor Binding Protein 2 (IGFBP2) | 0.60 | 0.60 | 0.60 |
| Resistin | 0.60 | 0.60 | 0.60 |
| Cathepsin D | 0.55 | 0.65 | 0.65 |
| E-Selectin | 0.53 | 0.67 | 0.67 |
| YKL40 | 0.56 | 0.60 | 0.60 |
| Interleukin 22 (IL22) | 0.48 | 0.61 | 0.61 |
| Cacinoembryonic Antigen (CEA) | 0.52 | 0.61 | 0.61 |
| Interleukin 8 (IL8) | 0.51 | 0.60 | 0.60 |
| Cancer Antigen 15-3 (CA 15-3) | 0.46 | 0.62 | 0.62 |
| Leptin Receptor (LeptinR) | 0.52 | 0.61 | 0.61 |
| Insulin | 0.51 | 0.63 | 0.63 |
| Monocyte Chemotactic Protein 1 (MCP1) | 0.61 | 0.63 | 0.63 |
| Prolactin (PRL) | 0.54 | 0.60 | 0.60 |
| Tetranectin | 0.61 | 0.60 | 0.61 |
| Carcinoembryonic Antigen Related Cell Adhesion Molecule 1 (CEACAM1) | 0.52 | 0.62 | 0.62 |
| 6Ckine | 0.50 | 0.62 | 0.62 |
| Serum Amyloid P Component (SAP) | 0.55 | 0.60 | 0.60 |
| Complement Factor H Related Protein 1 (CFHR1) | 0.48 | 0.61 | 0.61 |
| Chemokine CC-4 (HCC-4) | 0.60 | 0.60 | 0.60 |
| Complement C3 (C3) | 0.50 | 0.60 | 0.60 |
| Alpha Fetoprotein (AFP) | 0.51 | 0.64 | 0.64 |
| Angiopoietin 1 (ANG-1) | 0.58 | 0.60 | 0.60 |
| Interleukin 18 (IL18) | 0.54 | 0.64 | 0.64 |
| Gelsolin | 0.63 | 0.61 | 0.63 |
| Tenascin C (TN-C) | 0.51 | 0.60 | 0.60 |
| Vitronectin | 0.55 | 0.60 | 0.60 |
| Beta 2 Microglobulin (B2M) | 0.47 | 0.60 | 0.60 |
| Pancreatic Secretory Trypsin Inhibitor (TATI) | 0.56 | 0.60 | 0.60 |
| Matrix Metalloproteinase 3 (MMP3) | 0.57 | 0.61 | 0.61 |
| Omentin | 0.56 | 0.60 | 0.60 |
| Interleukin 18 Binding Protein (IL 18bp) | 0.53 | 0.63 | 0.63 |
| Apolipoprotein D (ApoD) | 0.63 | 0.60 | 0.63 |
| Monoctye Chemotactic Protein 4 (MCP-4) | 0.56 | 0.60 | 0.60 |
| Apolipoprotein E (Apo-E) | 0.58 | 0.63 | 0.63 |
| ST2 | 0.48 | 0.59 | 0.59 |
| Thrombospondin 1 | 0.52 | 0.59 | 0.59 |
| Gastric Inhibitory Polypeptide (GIP) | 0.52 | 0.63 | 0.63 |
| Matrix Metalloproteinase 7 (MMP7) | 0.52 | 0.60 | 0.60 |
| Intercellular Adhesion Molecule 1 (ICAM-1) | 0.47 | 0.61 | 0.61 |
| Dickkopf Related Protein 1 (DKK1) | 0.55 | 0.60 | 0.60 |

TABLE 43

2 Biomarker Multivariate Analysis. Combination of Eotaxin 2 and Analyte 2

| Analyte 2 | AUC by random forest | AUC by logistic regression | Maximum AUC |
|---|---|---|---|
| Insulin like Growth Factor Binding Protein 2 (IGFBP2) | 0.70 | 0.58 | 0.70 |
| Resistin | 0.59 | 0.55 | 0.59 |
| Cathepsin D | 0.63 | 0.62 | 0.63 |
| E-Selectin | 0.60 | 0.63 | 0.63 |
| YKL40 | 0.58 | 0.57 | 0.58 |
| Interleukin 22 (IL22) | 0.53 | 0.60 | 0.60 |
| Cacinoembryonic Antigen (CEA) | 0.62 | 0.57 | 0.62 |
| Interleukin 8 (IL8) | 0.60 | 0.58 | 0.60 |
| Cancer Antigen 15-3 (CA 15-3) | 0.51 | 0.56 | 0.56 |
| Leptin Receptor (LeptinR) | 0.53 | 0.60 | 0.60 |
| Insulin | 0.69 | 0.60 | 0.69 |
| Monocyte Chemotactic Protein 1 (MCP1) | 0.56 | 0.59 | 0.59 |
| Prolactin (PRL) | 0.62 | 0.57 | 0.62 |
| Tetranectin | 0.62 | 0.59 | 0.62 |
| Carcinoembryonic Antigen Related Cell Adhesion Molecule 1 (CEACAM1) | 0.61 | 0.57 | 0.61 |
| 6Ckine | 0.60 | 0.61 | 0.61 |
| Serum Amyloid P Component (SAP) | 0.62 | 0.59 | 0.62 |
| Complement Factor H Related Protein 1 (CFHR1) | 0.56 | 0.57 | 0.57 |
| Chemokine CC-4 (HCC-4) | 0.55 | 0.56 | 0.56 |
| Complement C3 (C3) | 0.64 | 0.53 | 0.64 |
| Alpha Fetoprotein (AFP) | 0.60 | 0.55 | 0.60 |
| Angiopoietin 1 (ANG-1) | 0.53 | 0.55 | 0.55 |
| Interleukin 18 (IL18) | 0.61 | 0.64 | 0.64 |
| Gelsolin | 0.62 | 0.57 | 0.62 |
| Tenascin C (TN-C) | 0.52 | 0.56 | 0.56 |
| Vitronectin | 0.58 | 0.56 | 0.58 |
| Beta 2 Microglobulin (B2M) | 0.63 | 0.56 | 0.63 |
| Pancreatic Secretory Trypsin Inhibitor (TATI) | 0.60 | 0.58 | 0.60 |
| Matrix Metalloproteinase 3 (MMP3) | 0.65 | 0.56 | 0.65 |
| Omentin | 0.52 | 0.56 | 0.56 |
| Interleukin 18 Binding Protein (IL 18bp) | 0.63 | 0.58 | 0.63 |
| Apolipoprotein D (ApoD) | 0.65 | 0.58 | 0.65 |
| Monoctye Chemotactic Protein 4 (MCP-4) | 0.52 | 0.56 | 0.56 |
| Apolipoprotein E (Apo-E) | 0.59 | 0.61 | 0.61 |
| ST2 | 0.54 | 0.57 | 0.57 |
| Thrombospondin 1 | 0.61 | 0.57 | 0.61 |
| Gastric Inhibitory Polypeptide (GIP) | 0.53 | 0.58 | 0.58 |
| Matrix Metalloproteinase 7 (MMP7) | 0.61 | 0.56 | 0.61 |
| Intercellular Adhesion Molecule 1 (ICAM-1) | 0.66 | 0.47 | 0.66 |
| Dickkopf Related Protein 1 (DKK1) | 0.60 | 0.57 | 0.60 |

TABLE 44

2 Biomarker Multivariate Analysis. Combination of Insulin like Growth Factor Binding Protein 2 (IGFBP2) and Analyte 2

| Analyte 2 | AUC by random forest | AUC by logistic regression | Maximum AUC |
|---|---|---|---|
| Resistin | 0.50 | 0.59 | 0.59 |
| Cathepsin D | 0.52 | 0.62 | 0.62 |
| E-Selectin | 0.54 | 0.64 | 0.64 |
| YKL40 | 0.51 | 0.57 | 0.57 |
| Interleukin 22 (IL22) | 0.51 | 0.60 | 0.60 |
| Cacinoembryonic Antigen (CEA) | 0.50 | 0.58 | 0.58 |
| Interleukin 8 (IL8) | 0.55 | 0.57 | 0.57 |
| Cancer Antigen 15-3 (CA 15-3) | 0.52 | 0.57 | 0.57 |
| Leptin Receptor (LeptinR) | 0.52 | 0.59 | 0.59 |
| Insulin | 0.57 | 0.60 | 0.60 |
| Monocyte Chemotactic Protein 1 (MCP1) | 0.59 | 0.61 | 0.61 |

TABLE 44-continued

2 Biomarker Multivariate Analysis. Combination of Insulin like Growth Factor Binding Protein 2 (IGFBP2) and Analyte 2

| Analyte 2 | AUC by random forest | AUC by logistic regression | Maximum AUC |
|---|---|---|---|
| Prolactin (PRL) | 0.52 | 0.56 | 0.56 |
| Tetranectin | 0.52 | 0.56 | 0.56 |
| Carcinoembryonic Antigen Related Cell Adhesion Molecule 1 (CEACAM1) | 0.53 | 0.58 | 0.58 |
| 6Ckine | 0.52 | 0.61 | 0.61 |
| Serum Amyloid P Component (SAP) | 0.54 | 0.58 | 0.58 |
| Complement Factor H Related Protein 1 (CFHR1) | 0.52 | 0.55 | 0.55 |
| Chemokine CC-4 (HCC-4) | 0.55 | 0.57 | 0.57 |
| Complement C3 (C3) | 0.63 | 0.57 | 0.63 |
| Alpha Fetoprotein (AFP) | 0.54 | 0.59 | 0.59 |
| Angiopoietin 1 (ANG-1) | 0.58 | 0.55 | 0.58 |
| Interleukin 18 (IL18) | 0.56 | 0.63 | 0.63 |
| Gelsolin | 0.59 | 0.57 | 0.59 |
| Tenascin C (TN-C) | 0.55 | 0.59 | 0.59 |
| Vitronectin | 0.54 | 0.57 | 0.57 |
| Beta 2 Microglobulin (B2M) | 0.60 | 0.57 | 0.60 |
| Pancreatic Secretory Trypsin Inhibitor (TATI) | 0.53 | 0.56 | 0.56 |
| Matrix Metalloproteinase 3 (MMP3) | 0.62 | 0.58 | 0.62 |
| Omentin | 0.49 | 0.57 | 0.57 |
| Interleukin 18 Binding Protein (IL 18bp) | 0.60 | 0.59 | 0.60 |
| Apolipoprotein D (ApoD) | 0.61 | 0.57 | 0.61 |
| Monoctye Chemotactic Protein 4 (MCP-4) | 0.57 | 0.57 | 0.57 |
| Apolipoprotein E (Apo-E) | 0.53 | 0.61 | 0.61 |
| ST2 | 0.56 | 0.55 | 0.56 |
| Thrombospondin 1 | 0.55 | 0.55 | 0.55 |
| Gastric Inhibitory Polypeptide (GIP) | 0.62 | 0.59 | 0.62 |
| Matrix Metalloproteinase 7 (MMP7) | 0.58 | 0.56 | 0.58 |
| Intercellular Adhesion Molecule 1 (ICAM-1) | 0.54 | 0.58 | 0.58 |
| Dickkopf Related Protein 1 (DKK1) | 0.49 | 0.58 | 0.58 |

TABLE 45

2 Biomarker Multivariate Analysis. Combination of Resistin and Analyte 2

| Analyte 2 | AUC by random forest | AUC by logistic regression | Maximum AUC |
|---|---|---|---|
| Cathepsin D | 0.56 | 0.63 | 0.63 |
| E-Selectin | 0.56 | 0.64 | 0.64 |
| YKL40 | 0.55 | 0.45 | 0.55 |
| Interleukin 22 (IL22) | 0.51 | 0.57 | 0.57 |
| Cacinoembryonic Antigen (CEA) | 0.48 | 0.57 | 0.57 |
| Interleukin 8 (IL8) | 0.53 | 0.54 | 0.54 |
| Cancer Antigen 15-3 (CA 15-3) | 0.56 | 0.59 | 0.59 |
| Leptin Receptor (LeptinR) | 0.45 | 0.59 | 0.59 |
| Insulin | 0.51 | 0.64 | 0.64 |
| Monocyte Chemotactic Protein 1 (MCP1) | 0.53 | 0.60 | 0.60 |
| Prolactin (PRL) | 0.55 | 0.58 | 0.58 |
| Tetranectin | 0.49 | 0.55 | 0.55 |
| Carcinoembryonic Antigen Related Cell Adhesion Molecule 1 (CEACAM1) | 0.48 | 0.59 | 0.59 |
| 6Ckine | 0.58 | 0.60 | 0.60 |
| Serum Amyloid P Component (SAP) | 0.54 | 0.58 | 0.58 |
| Complement Factor H Related Protein 1 (CFHR1) | 0.59 | 0.55 | 0.59 |
| Chemokine CC-4 (HCC-4) | 0.51 | 0.46 | 0.51 |
| Complement C3 (C3) | 0.58 | 0.46 | 0.58 |
| Alpha Fetoprotein (AFP) | 0.61 | 0.61 | 0.61 |
| Angiopoietin 1 (ANG-1) | 0.51 | 0.60 | 0.60 |
| Interleukin 18 (IL18) | 0.51 | 0.63 | 0.63 |
| Gelsolin | 0.54 | 0.57 | 0.57 |
| Tenascin C (TN-C) | 0.52 | 0.57 | 0.57 |
| Vitronectin | 0.53 | 0.47 | 0.53 |
| Beta 2 Microglobulin (B2M) | 0.52 | 0.57 | 0.57 |
| Pancreatic Secretory Trypsin Inhibitor (TATI) | 0.52 | 0.45 | 0.52 |
| Matrix Metalloproteinase 3 (MMP3) | 0.51 | 0.56 | 0.56 |
| Omentin | 0.54 | 0.55 | 0.55 |
| Interleukin 18 Binding Protein (IL 18bp) | 0.59 | 0.60 | 0.60 |
| Apolipoprotein D (ApoD) | 0.57 | 0.57 | 0.57 |
| Monoctye Chemotactic Protein 4 (MCP-4) | 0.54 | 0.55 | 0.55 |
| Apolipoprotein E (Apo-E) | 0.51 | 0.61 | 0.61 |
| ST2 | 0.51 | 0.54 | 0.54 |
| Thrombospondin 1 | 0.51 | 0.55 | 0.55 |
| Gastric Inhibitory Polypeptide (GIP) | 0.54 | 0.62 | 0.62 |
| Matrix Metalloproteinase 7 (MMP7) | 0.51 | 0.58 | 0.58 |
| Intercellular Adhesion Molecule 1 (ICAM-1) | 0.57 | 0.56 | 0.57 |
| Dickkopf Related Protein 1 (DKK1) | 0.56 | 0.45 | 0.56 |

TABLE 46

2 Biomarker Multivariate Analysis. Combination of Cathepsin D and Analyte 2

| Analyte 2 | AUC by random forest | AUC by logistic regression | Maximum AUC |
|---|---|---|---|
| E-Selectin | 0.55 | 0.67 | 0.67 |
| YKL40 | 0.49 | 0.62 | 0.62 |
| Interleukin 22 (IL22) | 0.51 | 0.65 | 0.65 |
| Cacinoembryonic Antigen (CEA) | 0.61 | 0.63 | 0.63 |
| Interleukin 8 (IL8) | 0.59 | 0.63 | 0.63 |
| Cancer Antigen 15-3 (CA 15-3) | 0.55 | 0.62 | 0.62 |
| Leptin Receptor (LeptinR) | 0.57 | 0.64 | 0.64 |
| Insulin | 0.62 | 0.63 | 0.63 |
| Monocyte Chemotactic Protein 1 (MCP1) | 0.49 | 0.64 | 0.64 |
| Prolactin (PRL) | 0.54 | 0.63 | 0.63 |
| Tetranectin | 0.54 | 0.63 | 0.63 |
| Carcinoembryonic Antigen Related Cell Adhesion Molecule 1 (CEACAM1) | 0.54 | 0.64 | 0.64 |
| 6Ckine | 0.56 | 0.63 | 0.63 |
| Serum Amyloid P Component (SAP) | 0.52 | 0.63 | 0.63 |
| Complement Factor H Related Protein 1 (CFHR1) | 0.49 | 0.63 | 0.63 |
| Chemokine CC-4 (HCC-4) | 0.54 | 0.62 | 0.62 |
| Complement C3 (C3) | 0.49 | 0.62 | 0.62 |
| Alpha Fetoprotein (AFP) | 0.57 | 0.66 | 0.66 |
| Angiopoietin 1 (ANG-1) | 0.54 | 0.62 | 0.62 |
| Interleukin 18 (IL18) | 0.54 | 0.67 | 0.67 |
| Gelsolin | 0.57 | 0.63 | 0.63 |
| Tenascin C (TN-C) | 0.50 | 0.63 | 0.63 |
| Vitronectin | 0.49 | 0.63 | 0.63 |
| Beta 2 Microglobulin (B2M) | 0.60 | 0.63 | 0.63 |
| Pancreatic Secretory Trypsin Inhibitor (TATI) | 0.52 | 0.62 | 0.62 |
| Matrix Metalloproteinase 3 (MMP3) | 0.57 | 0.62 | 0.62 |
| Omentin | 0.60 | 0.62 | 0.62 |
| Interleukin 18 Binding Protein (IL 18bp) | 0.51 | 0.63 | 0.63 |
| Apolipoprotein D (ApoD) | 0.59 | 0.62 | 0.62 |
| Monocyte Chemotactic Protein 4 (MCP-4) | 0.50 | 0.62 | 0.62 |
| Apolipoprotein E (Apo-E) | 0.55 | 0.64 | 0.64 |
| ST2 | 0.53 | 0.62 | 0.62 |
| Thrombospondin 1 | 0.56 | 0.62 | 0.62 |
| Gastric Inhibitory Polypeptide (GIP) | 0.48 | 0.63 | 0.63 |
| Matrix Metalloproteinase 7 (MMP7) | 0.53 | 0.63 | 0.63 |

TABLE 46-continued

2 Biomarker Multivariate Analysis. Combination of Cathepsin D and Analyte 2

| Analyte 2 | AUC by random forest | AUC by logistic regression | Maximum AUC |
|---|---|---|---|
| Intercellular Adhesion Molecule 1 (ICAM-1) | 0.53 | 0.62 | 0.62 |
| Dickkopf Related Protein 1 (DKK1) | 0.55 | 0.63 | 0.63 |

TABLE 47

2 Biomarker Multivariate Analysis. Combination of E-Selectin and Analyte 2

| Analyte 2 | AUC by random forest | AUC by logistic regression | Maximum AUC |
|---|---|---|---|
| YKL40 | 0.46 | 0.63 | 0.63 |
| Interleukin 22 (IL22) | 0.55 | 0.65 | 0.65 |
| Cacinoembryonic Antigen (CEA) | 0.52 | 0.63 | 0.63 |
| Interleukin 8 (IL8) | 0.55 | 0.64 | 0.64 |
| Cancer Antigen 15-3 (CA 15-3) | 0.55 | 0.66 | 0.66 |
| Leptin Receptor (LeptinR) | 0.52 | 0.65 | 0.65 |
| Insulin | 0.59 | 0.66 | 0.66 |
| Monocyte Chemotactic Protein 1 (MCP1) | 0.51 | 0.65 | 0.65 |
| Prolactin (PRL) | 0.55 | 0.64 | 0.64 |
| Tetranectin | 0.55 | 0.64 | 0.64 |
| Carcinoembryonic Antigen Related Cell Adhesion Molecule 1 (CEACAM1) | 0.58 | 0.67 | 0.67 |
| 6Ckine | 0.53 | 0.66 | 0.66 |
| Serum Amyloid P Component (SAP) | 0.54 | 0.65 | 0.65 |
| Complement Factor H Related Protein 1 (CFHR1) | 0.49 | 0.63 | 0.63 |
| Chemokine CC-4 (HCC-4) | 0.49 | 0.63 | 0.63 |
| Complement C3 (C3) | 0.49 | 0.63 | 0.63 |
| Alpha Fetoprotein (AFP) | 0.50 | 0.67 | 0.67 |
| Angiopoietin 1 (ANG-1) | 0.49 | 0.63 | 0.63 |
| Interleukin 18 (IL18) | 0.51 | 0.66 | 0.66 |
| Gelsolin | 0.60 | 0.64 | 0.64 |
| Tenascin C (TN-C) | 0.49 | 0.63 | 0.63 |
| Vitronectin | 0.51 | 0.64 | 0.64 |
| Beta 2 Microglobulin (B2M) | 0.54 | 0.64 | 0.64 |
| Pancreatic Secretory Trypsin Inhibitor (TATI) | 0.56 | 0.63 | 0.63 |
| Matrix Metalloproteinase 3 (MMP3) | 0.59 | 0.65 | 0.65 |
| Omentin | 0.58 | 0.63 | 0.63 |
| Interleukin 18 Binding Protein (IL 18bp) | 0.50 | 0.64 | 0.64 |
| Apolipoprotein D (ApoD) | 0.62 | 0.65 | 0.65 |
| Monoctye Chemotactic Protein 4 (MCP-4) | 0.59 | 0.63 | 0.63 |
| Apolipoprotein E (Apo-E) | 0.55 | 0.65 | 0.65 |
| ST2 | 0.56 | 0.64 | 0.64 |
| Thrombospondin 1 | 0.49 | 0.64 | 0.64 |
| Gastric Inhibitory Polypeptide (GIP) | 0.51 | 0.66 | 0.66 |
| Matrix Metalloproteinase 7 (MMP7) | 0.56 | 0.64 | 0.64 |
| Intercellular Adhesion Molecule 1 (ICAM-1) | 0.52 | 0.63 | 0.63 |
| Dickkopf Related Protein 1 (DKK1) | 0.54 | 0.64 | 0.64 |

TABLE 48

2 Biomarker Multivariate Analysis. Combination of YKL40 and Analyte 2

| Analyte 2 | AUC by random forest | AUC by logistic regression | Maximum AUC |
|---|---|---|---|
| Interleukin 22 (IL22) | 0.58 | 0.55 | 0.58 |
| Cacinoembryonic Antigen (CEA) | 0.49 | 0.55 | 0.55 |
| Interleukin 8 (IL8) | 0.52 | 0.52 | 0.52 |
| Cancer Antigen 15-3 (CA 15-3) | 0.61 | 0.55 | 0.61 |
| Leptin Receptor (LeptinR) | 0.52 | 0.59 | 0.59 |
| Insulin | 0.58 | 0.61 | 0.61 |
| Monocyte Chemotactic Protein 1 (MCP1) | 0.49 | 0.58 | 0.58 |
| Prolactin (PRL) | 0.55 | 0.58 | 0.58 |
| Tetranectin | 0.53 | 0.53 | 0.53 |
| Carcinoembryonic Antigen Related Cell Adhesion Molecule 1 (CEACAM1) | 0.54 | 0.57 | 0.57 |
| 6Ckine | 0.56 | 0.60 | 0.60 |
| Serum Amyloid P Component (SAP) | 0.55 | 0.57 | 0.57 |
| Complement Factor H Related Protein 1 (CFHR1) | 0.58 | 0.52 | 0.58 |
| Chemokine CC-4 (HCC-4) | 0.48 | 0.50 | 0.50 |
| Complement C3 (C3) | 0.51 | 0.51 | 0.51 |
| Alpha Fetoprotein (AFP) | 0.55 | 0.44 | 0.55 |
| Angiopoietin 1 (ANG-1) | 0.55 | 0.55 | 0.55 |
| Interleukin 18 (IL18) | 0.62 | 0.63 | 0.63 |
| Gelsolin | 0.51 | 0.53 | 0.53 |
| Tenascin C (TN-C) | 0.52 | 0.52 | 0.52 |
| Vitronectin | 0.52 | 0.49 | 0.52 |
| Beta 2 Microglobulin (B2M) | 0.58 | 0.56 | 0.58 |
| Pancreatic Secretory Trypsin Inhibitor (TATI) | 0.55 | 0.52 | 0.55 |
| Matrix Metalloproteinase 3 (MMP3) | 0.60 | 0.54 | 0.60 |
| Omentin | 0.56 | 0.52 | 0.56 |
| Interleukin 18 Binding Protein (IL 18bp) | 0.52 | 0.58 | 0.58 |
| Apolipoprotein D (ApoD) | 0.62 | 0.56 | 0.62 |
| Monoctye Chemotactic Protein 4 (MCP-4) | 0.57 | 0.55 | 0.57 |
| Apolipoprotein E (Apo-E) | 0.55 | 0.60 | 0.60 |
| ST2 | 0.53 | 0.52 | 0.53 |
| Thrombospondin 1 | 0.53 | 0.50 | 0.53 |
| Gastric Inhibitory Polypeptide (GIP) | 0.46 | 0.59 | 0.59 |
| Matrix Metalloproteinase 7 (MMP7) | 0.54 | 0.56 | 0.56 |
| Intercellular Adhesion Molecule 1 (ICAM-1) | 0.59 | 0.49 | 0.59 |
| Dickkopf Related Protein 1 (DKK1) | 0.60 | 0.49 | 0.60 |

TABLE 49

2 Biomarker Multivariate Analysis. Combination of Interleukin 22 (IL22) and Analyte 2

| Analyte 2 | AUC by random forest | AUC by logistic regression | Maximum AUC |
|---|---|---|---|
| Cacinoembryonic Antigen (CEA) | 0.63 | 0.58 | 0.63 |
| Interleukin 8 (IL8) | 0.56 | 0.57 | 0.57 |
| Cancer Antigen 15-3 (CA 15-3) | 0.67 | 0.59 | 0.67 |
| Leptin Receptor (LeptinR) | 0.53 | 0.60 | 0.60 |
| Insulin | 0.55 | 0.61 | 0.61 |
| Monocyte Chemotactic Protein 1 (MCP1) | 0.54 | 0.60 | 0.60 |
| Prolactin (PRL) | 0.51 | 0.60 | 0.60 |
| Tetranectin | 0.57 | 0.58 | 0.58 |
| Carcinoembryonic Antigen Related Cell Adhesion Molecule 1 (CEACAM1) | 0.59 | 0.59 | 0.59 |
| 6Ckine | 0.55 | 0.62 | 0.62 |
| Serum Amyloid P Component (SAP) | 0.52 | 0.60 | 0.60 |
| Complement Factor H Related Protein 1 (CFHR1) | 0.53 | 0.59 | 0.59 |
| Chemokine CC-4 (HCC-4) | 0.52 | 0.57 | 0.57 |
| Complement C3 (C3) | 0.53 | 0.57 | 0.57 |
| Alpha Fetoprotein (AFP) | 0.52 | 0.57 | 0.57 |
| Angiopoietin 1 (ANG-1) | 0.51 | 0.58 | 0.58 |
| Interleukin 18 (IL18) | 0.49 | 0.64 | 0.64 |

TABLE 49-continued

2 Biomarker Multivariate Analysis. Combination of Interleukin 22 (IL22) and Analyte 2

| Analyte 2 | AUC by random forest | AUC by logistic regression | Maximum AUC |
|---|---|---|---|
| Gelsolin | 0.53 | 0.57 | 0.57 |
| Tenascin C (TN-C) | 0.52 | 0.43 | 0.52 |
| Vitronectin | 0.49 | 0.56 | 0.56 |
| Beta 2 Microglobulin (B2M) | 0.53 | 0.57 | 0.57 |
| Pancreatic Secretory Trypsin Inhibitor (TATI) | 0.56 | 0.56 | 0.56 |
| Matrix Metalloproteinase 3 (MMP3) | 0.52 | 0.58 | 0.58 |
| Omentin | 0.67 | 0.57 | 0.67 |
| Interleukin 18 Binding Protein (IL 18bp) | 0.52 | 0.60 | 0.60 |
| Apolipoprotein D (ApoD) | 0.56 | 0.57 | 0.57 |
| Monoctye Chemotactic Protein 4 (MCP-4) | 0.58 | 0.57 | 0.58 |
| Apolipoprotein E (Apo-E) | 0.56 | 0.62 | 0.62 |
| ST2 | 0.54 | 0.57 | 0.57 |
| Thrombospondin 1 | 0.54 | 0.57 | 0.57 |
| Gastric Inhibitory Polypeptide (GIP) | 0.52 | 0.60 | 0.60 |
| Matrix Metalloproteinase 7 (MMP7) | 0.53 | 0.57 | 0.57 |
| Intercellular Adhesion Molecule 1 (ICAM-1) | 0.70 | 0.57 | 0.70 |
| Dickkopf Related Protein 1 (DKK1) | 0.56 | 0.58 | 0.58 |

TABLE 50

2 Biomarker Multivariate Analysis. Combination of Carcinoembryonic Antigen (CEA) and Analyte 2

| Analyte 2 | AUC by random forest | AUC by logistic regression | Maximum AUC |
|---|---|---|---|
| Interleukin 8 (IL8) | 0.51 | 0.56 | 0.56 |
| Cancer Antigen 15-3 (CA 15-3) | 0.62 | 0.56 | 0.62 |
| Leptin Receptor (LeptinR) | 0.59 | 0.59 | 0.59 |
| Insulin | 0.50 | 0.64 | 0.64 |
| Monocyte Chemotactic Protein 1 (MCP1) | 0.49 | 0.59 | 0.59 |
| Prolactin (PRL) | 0.62 | 0.59 | 0.62 |
| Tetranectin | 0.55 | 0.56 | 0.56 |
| Carcinoembryonic Antigen Related Cell Adhesion Molecule 1 (CEACAM1) | 0.52 | 0.57 | 0.57 |
| 6Ckine | 0.53 | 0.61 | 0.61 |
| Serum Amyloid P Component (SAP) | 0.52 | 0.58 | 0.58 |
| Complement Factor H Related Protein 1 (CFHR1) | 0.51 | 0.56 | 0.56 |
| Chemokine CC-4 (HCC-4) | 0.51 | 0.54 | 0.54 |
| Complement C3 (C3) | 0.58 | 0.56 | 0.58 |
| Alpha Fetoprotein (AFP) | 0.65 | 0.63 | 0.65 |
| Angiopoietin 1 (ANG-1) | 0.52 | 0.57 | 0.57 |
| Interleukin 18 (IL18) | 0.59 | 0.63 | 0.63 |
| Gelsolin | 0.50 | 0.57 | 0.57 |
| Tenascin C (TN-C) | 0.57 | 0.45 | 0.57 |
| Vitronectin | 0.59 | 0.56 | 0.59 |
| Beta 2 Microglobulin (B2M) | 0.49 | 0.56 | 0.56 |
| Pancreatic Secretory Trypsin Inhibitor (TATI) | 0.61 | 0.56 | 0.61 |
| Matrix Metalloproteinase 3 (MMP3) | 0.58 | 0.45 | 0.58 |
| Omentin | 0.63 | 0.57 | 0.63 |
| Interleukin 18 Binding Protein (IL 18bp) | 0.57 | 0.58 | 0.58 |
| Apolipoprotein D (ApoD) | 0.58 | 0.56 | 0.58 |
| Monoctye Chemotactic Protein 4 (MCP-4) | 0.45 | 0.56 | 0.56 |
| Apolipoprotein E (Apo-E) | 0.56 | 0.62 | 0.62 |
| ST2 | 0.50 | 0.58 | 0.58 |
| Thrombospondin 1 | 0.52 | 0.55 | 0.55 |
| Gastric Inhibitory Polypeptide (GIP) | 0.54 | 0.59 | 0.59 |
| Matrix Metalloproteinase 7 (MMP7) | 0.48 | 0.58 | 0.58 |

TABLE 50-continued

2 Biomarker Multivariate Analysis. Combination of Carcinoembryonic Antigen (CEA) and Analyte 2

| Analyte 2 | AUC by random forest | AUC by logistic regression | Maximum AUC |
|---|---|---|---|
| Intercellular Adhesion Molecule 1 (ICAM-1) | 0.59 | 0.55 | 0.59 |
| Dickkopf Related Protein 1 (DKK1) | 0.54 | 0.46 | 0.54 |

TABLE 51

2 Biomarker Multivariate Analysis. Combination of Interleukin 8 (IL8) and Analyte 2

| Analyte 2 | AUC by random forest | AUC by logistic regression | Maximum AUC |
|---|---|---|---|
| Cancer Antigen 15-3 (CA 15-3) | 0.52 | 0.54 | 0.54 |
| Leptin Receptor (LeptinR) | 0.60 | 0.59 | 0.60 |
| Insulin | 0.55 | 0.61 | 0.61 |
| Monocyte Chemotactic Protein 1 (MCP1) | 0.58 | 0.59 | 0.59 |
| Prolactin (PRL) | 0.52 | 0.56 | 0.56 |
| Tetranectin | 0.58 | 0.52 | 0.58 |
| Carcinoembryonic Antigen Related Cell Adhesion Molecule 1 (CEACAM1) | 0.57 | 0.57 | 0.57 |
| 6Ckine | 0.54 | 0.61 | 0.61 |
| Serum Amyloid P Component (SAP) | 0.42 | 0.58 | 0.58 |
| Complement Factor H Related Protein 1 (CFHR1) | 0.60 | 0.50 | 0.60 |
| Chemokine CC-4 (HCC-4) | 0.54 | 0.50 | 0.54 |
| Complement C3 (C3) | 0.61 | 0.52 | 0.61 |
| Alpha Fetoprotein (AFP) | 0.53 | 0.57 | 0.57 |
| Angiopoietin 1 (ANG-1) | 0.59 | 0.54 | 0.59 |
| Interleukin 18 (IL18) | 0.52 | 0.63 | 0.63 |
| Gelsolin | 0.61 | 0.46 | 0.61 |
| Tenascin C (TN-C) | 0.50 | 0.53 | 0.53 |
| Vitronectin | 0.47 | 0.50 | 0.50 |
| Beta 2 Microglobulin (B2M) | 0.62 | 0.56 | 0.62 |
| Pancreatic Secretory Trypsin Inhibitor (TATI) | 0.56 | 0.55 | 0.56 |
| Matrix Metalloproteinase 3 (MMP3) | 0.60 | 0.54 | 0.60 |
| Omentin | 0.55 | 0.52 | 0.55 |
| Interleukin 18 Binding Protein (IL 18bp) | 0.57 | 0.58 | 0.58 |
| Apolipoprotein D (ApoD) | 0.64 | 0.55 | 0.64 |
| Monoctye Chemotactic Protein 4 (MCP-4) | 0.52 | 0.54 | 0.54 |
| Apolipoprotein E (Apo-E) | 0.62 | 0.60 | 0.62 |
| ST2 | 0.63 | 0.49 | 0.63 |
| Thrombospondin 1 | 0.54 | 0.53 | 0.54 |
| Gastric Inhibitory Polypeptide (GIP) | 0.56 | 0.59 | 0.59 |
| Matrix Metalloproteinase 7 (MMP7) | 0.51 | 0.56 | 0.56 |
| Intercellular Adhesion Molecule 1 (ICAM-1) | 0.56 | 0.50 | 0.56 |
| Dickkopf Related Protein 1 (DKK1) | 0.57 | 0.48 | 0.57 |

TABLE 52

2 Biomarker Multivariate Analysis. Combination of Cancer Antigen 15-3 (CA 15-3) and Analyte 2

| Analyte 2 | AUC by random forest | AUC by logistic regression | Maximum AUC |
|---|---|---|---|
| Leptin Receptor (LeptinR) | 0.59 | 0.58 | 0.59 |
| Insulin | 0.62 | 0.61 | 0.62 |
| Monocyte Chemotactic Protein 1 (MCP1) | 0.52 | 0.61 | 0.61 |
| Prolactin (PRL) | 0.67 | 0.57 | 0.67 |
| Tetranectin | 0.61 | 0.54 | 0.61 |

TABLE 52-continued

2 Biomarker Multivariate Analysis. Combination of Cancer Antigen 15-3 (CA 15-3) and Analyte 2

| Analyte 2 | AUC by random forest | AUC by logistic regression | Maximum AUC |
|---|---|---|---|
| Carcinoembryonic Antigen Related Cell Adhesion Molecule 1 (CEACAM1) | 0.56 | 0.58 | 0.58 |
| 6Ckine | 0.49 | 0.63 | 0.63 |
| Serum Amyloid P Component (SAP) | 0.50 | 0.59 | 0.59 |
| Complement Factor H Related Protein 1 (CFHR1) | 0.51 | 0.54 | 0.54 |
| Chemokine CC-4 (HCC-4) | 0.61 | 0.54 | 0.61 |
| Complement C3 (C3) | 0.46 | 0.57 | 0.57 |
| Alpha Fetoprotein (AFP) | 0.61 | 0.59 | 0.61 |
| Angiopoietin 1 (ANG-1) | 0.59 | 0.56 | 0.59 |
| Interleukin 18 (IL18) | 0.55 | 0.65 | 0.65 |
| Gelsolin | 0.52 | 0.55 | 0.55 |
| Tenascin C (TN-C) | 0.56 | 0.55 | 0.56 |
| Vitronectin | 0.56 | 0.55 | 0.56 |
| Beta 2 Microglobulin (B2M) | 0.50 | 0.56 | 0.56 |
| Pancreatic Secretory Trypsin Inhibitor (TATI) | 0.55 | 0.55 | 0.55 |
| Matrix Metalloproteinase 3 (MMP3) | 0.47 | 0.56 | 0.56 |
| Omentin | 0.60 | 0.53 | 0.60 |
| Interleukin 18 Binding Protein (IL 18bp) | 0.55 | 0.58 | 0.58 |
| Apolipoprotein D (ApoD) | 0.55 | 0.55 | 0.55 |
| Monocyte Chemotactic Protein 4 (MCP-4) | 0.59 | 0.55 | 0.59 |
| Apolipoprotein E (Apo-E) | 0.56 | 0.61 | 0.61 |
| ST2 | 0.51 | 0.54 | 0.54 |
| Thrombospondin 1 | 0.56 | 0.55 | 0.56 |
| Gastric Inhibitory Polypeptide (GIP) | 0.69 | 0.60 | 0.69 |
| Matrix Metalloproteinase 7 (MMP7) | 0.54 | 0.57 | 0.57 |
| Intercellular Adhesion Molecule 1 (ICAM-1) | 0.61 | 0.55 | 0.61 |
| Dickkopf Related Protein 1 (DKK1) | 0.67 | 0.55 | 0.67 |

TABLE 53

2 Biomarker Multivariate Analysis. Combination of Leptin Receptor (LeptinR) and Analyte 2

| Analyte 2 | AUC by random forest | AUC by logistic regression | Maximum AUC |
|---|---|---|---|
| Insulin | 0.55 | 0.62 | 0.62 |
| Monocyte Chemotactic Protein 1 (MCP1) | 0.55 | 0.61 | 0.61 |
| Prolactin (PRL) | 0.64 | 0.58 | 0.64 |
| Tetranectin | 0.58 | 0.58 | 0.58 |
| Carcinoembryonic Antigen Related Cell Adhesion Molecule 1 (CEACAM1) | 0.55 | 0.59 | 0.59 |
| 6Ckine | 0.58 | 0.61 | 0.61 |
| Serum Amyloid P Component (SAP) | 0.47 | 0.60 | 0.60 |
| Complement Factor H Related Protein 1 (CFHR1) | 0.55 | 0.58 | 0.58 |
| Chemokine CC-4 (HCC-4) | 0.51 | 0.60 | 0.60 |
| Complement C3 (C3) | 0.55 | 0.60 | 0.60 |
| Alpha Fetoprotein (AFP) | 0.52 | 0.59 | 0.59 |
| Angiopoietin 1 (ANG-1) | 0.56 | 0.58 | 0.58 |
| Interleukin 18 (IL18) | 0.58 | 0.64 | 0.64 |
| Gelsolin | 0.48 | 0.59 | 0.59 |
| Tenascin C (TN-C) | 0.57 | 0.59 | 0.59 |
| Vitronectin | 0.57 | 0.60 | 0.60 |
| Beta 2 Microglobulin (B2M) | 0.58 | 0.58 | 0.58 |
| Pancreatic Secretory Trypsin Inhibitor (TATI) | 0.55 | 0.58 | 0.58 |
| Matrix Metalloproteinase 3 (MMP3) | 0.52 | 0.60 | 0.60 |
| Omentin | 0.55 | 0.58 | 0.58 |
| Interleukin 18 Binding Protein (IL 18bp) | 0.53 | 0.61 | 0.61 |
| Apolipoprotein D (ApoD) | 0.60 | 0.60 | 0.60 |
| Monoctye Chemotactic Protein 4 (MCP-4) | 0.54 | 0.58 | 0.58 |
| Apolipoprotein E (Apo-E) | 0.53 | 0.64 | 0.64 |
| ST2 | 0.59 | 0.58 | 0.59 |
| Thrombospondin 1 | 0.62 | 0.57 | 0.62 |
| Gastric Inhibitory Polypeptide (GIP) | 0.54 | 0.61 | 0.61 |
| Matrix Metalloproteinase 7 (MMP7) | 0.53 | 0.59 | 0.59 |
| Intercellular Adhesion Molecule 1 (ICAM-1) | 0.51 | 0.60 | 0.60 |
| Dickkopf Related Protein 1 (DKK1) | 0.59 | 0.61 | 0.61 |

TABLE 54

2 Biomarker Multivariate Analysis. Combination of Insulin and Analyte 2

| Analyte 2 | AUC by random forest | AUC by logistic regression | Maximum AUC |
|---|---|---|---|
| Monocyte Chemotactic Protein 1 (MCP1) | 0.53 | 0.62 | 0.62 |
| Prolactin (PRL) | 0.58 | 0.63 | 0.63 |
| Tetranectin | 0.56 | 0.61 | 0.61 |
| Carcinoembryonic Antigen Related Cell Adhesion Molecule 1 (CEACAM1) | 0.49 | 0.64 | 0.64 |
| 6Ckine | 0.53 | 0.61 | 0.61 |
| Serum Amyloid P Component (SAP) | 0.54 | 0.59 | 0.59 |
| Complement Factor H Related Protein 1 (CFHR1) | 0.53 | 0.62 | 0.62 |
| Chemokine CC-4 (HCC-4) | 0.53 | 0.60 | 0.60 |
| Complement C3 (C3) | 0.59 | 0.60 | 0.60 |
| Alpha Fetoprotein (AFP) | 0.50 | 0.60 | 0.60 |
| Angiopoietin 1 (ANG-1) | 0.58 | 0.63 | 0.63 |
| Interleukin 18 (IL18) | 0.56 | 0.64 | 0.64 |
| Gelsolin | 0.63 | 0.64 | 0.64 |
| Tenascin C (TN-C) | 0.55 | 0.57 | 0.57 |
| Vitronectin | 0.56 | 0.60 | 0.60 |
| Beta 2 Microglobulin (B2M) | 0.48 | 0.61 | 0.61 |
| Pancreatic Secretory Trypsin Inhibitor (TATI) | 0.52 | 0.61 | 0.61 |
| Matrix Metalloproteinase 3 (MMP3) | 0.55 | 0.58 | 0.58 |
| Omentin | 0.47 | 0.60 | 0.60 |
| Interleukin 18 Binding Protein (IL 18 bp) | 0.52 | 0.60 | 0.60 |
| Apolipoprotein D (ApoD) | 0.60 | 0.62 | 0.62 |
| Monocyte Chemotactic Protein 4 (MCP-4) | 0.49 | 0.63 | 0.63 |
| Apolipoprotein E (Apo-E) | 0.53 | 0.60 | 0.60 |
| ST2 | 0.54 | 0.60 | 0.60 |
| Thrombospondin 1 | 0.56 | 0.62 | 0.62 |
| Gastric Inhibitory Polypeptide (GIP) | 0.53 | 0.64 | 0.64 |
| Matrix Metalloproteinase 7 (MMP7) | 0.61 | 0.64 | 0.64 |
| Intercellular Adhesion Molecule 1 (ICAM-1) | 0.48 | 0.62 | 0.62 |
| Dickkopf Related Protein 1 (DKK1) | 0.52 | 0.58 | 0.58 |

TABLE 55

2 Biomarker Multivariate Analysis. Combination of Monocyte Chemotactic Protein 1 (MCP1) and Analyte 2

| Analyte 2 | AUC by random forest | AUC by logistic regression | Maximum AUC |
|---|---|---|---|
| Prolactin (PRL) | 0.50 | 0.60 | 0.60 |
| Tetranectin | 0.57 | 0.60 | 0.60 |

TABLE 55-continued

2 Biomarker Multivariate Analysis. Combination of Monocyte Chemotactic Protein 1 (MCP1) and Analyte 2

| Analyte 2 | AUC by random forest | AUC by logistic regression | Maximum AUC |
|---|---|---|---|
| Carcinoembryonic Antigen Related Cell Adhesion Molecule 1 (CEACAM1) | 0.62 | 0.62 | 0.62 |
| 6Ckine | 0.52 | 0.63 | 0.63 |
| Serum Amyloid P Component (SAP) | 0.58 | 0.60 | 0.60 |
| Complement Factor H Related Protein 1 (CFHR1) | 0.56 | 0.58 | 0.58 |
| Chemokine CC-4 (HCC-4) | 0.53 | 0.58 | 0.58 |
| Complement C3 (C3) | 0.59 | 0.59 | 0.59 |
| Alpha Fetoprotein (AFP) | 0.52 | 0.62 | 0.62 |
| Angiopoietin 1 (ANG-1) | 0.61 | 0.59 | 0.61 |
| Interleukin 18 (IL18) | 0.59 | 0.65 | 0.65 |
| Gelsolin | 0.63 | 0.61 | 0.63 |
| Tenascin C (TN-C) | 0.56 | 0.56 | 0.56 |
| Vitronectin | 0.62 | 0.58 | 0.62 |
| Beta 2 Microglobulin (B2M) | 0.56 | 0.60 | 0.60 |
| Pancreatic Secretory Trypsin Inhibitor (TATI) | 0.50 | 0.58 | 0.58 |
| Matrix Metalloproteinase 3 (MMP3) | 0.56 | 0.60 | 0.60 |
| Omentin | 0.51 | 0.57 | 0.57 |
| Interleukin 18 Binding Protein (IL 18 bp) | 0.53 | 0.61 | 0.61 |
| Apolipoprotein D (ApoD) | 0.64 | 0.59 | 0.64 |
| Monoctye Chemotactic Protein 4 (MCP-4) | 0.52 | 0.58 | 0.58 |
| Apolipoprotein E (Apo-E) | 0.59 | 0.62 | 0.62 |
| ST2 | 0.58 | 0.58 | 0.58 |
| Thrombospondin 1 | 0.58 | 0.58 | 0.58 |
| Gastric Inhibitory Polypeptide (GIP) | 0.50 | 0.61 | 0.61 |
| Matrix Metalloproteinase 7 (MMP7) | 0.55 | 0.60 | 0.60 |
| Intercellular Adhesion Molecule 1 (ICAM-1) | 0.53 | 0.59 | 0.59 |
| Dickkopf Related Protein 1 (DKK1) | 0.52 | 0.58 | 0.58 |

TABLE 56

2 Biomarker Multivariate Analysis. Combination of Prolactin (PRL) and Analyte 2

| Analyte 2 | AUC by random forest | AUC by logistic regression | Maximum AUC |
|---|---|---|---|
| Tetranectin | 0.47 | 0.57 | 0.57 |
| Carcinoembryonic Antigen Related Cell Adhesion Molecule 1 (CEACAM1) | 0.54 | 0.58 | 0.58 |
| 6Ckine | 0.52 | 0.60 | 0.60 |
| Serum Amyloid P Component (SAP) | 0.49 | 0.59 | 0.59 |
| Complement Factor H Related Protein 1 (CFHR1) | 0.57 | 0.56 | 0.57 |
| Chemokine CC-4 (HCC-4) | 0.52 | 0.55 | 0.55 |
| Complement C3 (C3) | 0.47 | 0.55 | 0.55 |
| Alpha Fetoprotein (AFP) | 0.57 | 0.59 | 0.59 |
| Angiopoietin 1 (ANG-1) | 0.54 | 0.54 | 0.54 |
| Interleukin 18 (IL18) | 0.53 | 0.63 | 0.63 |
| Gelsolin | 0.49 | 0.59 | 0.59 |
| Tenascin C (TN-C) | 0.55 | 0.56 | 0.56 |
| Vitronectin | 0.51 | 0.54 | 0.54 |
| Beta 2 Microglobulin (B2M) | 0.52 | 0.55 | 0.55 |
| Pancreatic Secretory Trypsin Inhibitor (TATI) | 0.57 | 0.57 | 0.57 |
| Matrix Metalloproteinase 3 (MMP3) | 0.51 | 0.57 | 0.57 |
| Omentin | 0.71 | 0.55 | 0.71 |
| Interleukin 18 Binding Protein (IL 18 bp) | 0.46 | 0.60 | 0.60 |
| Apolipoprotein D (ApoD) | 0.56 | 0.56 | 0.56 |
| Monoctye Chemotactic Protein 4 (MCP-4) | 0.62 | 0.57 | 0.62 |
| Apolipoprotein E (Apo-E) | 0.53 | 0.61 | 0.61 |
| ST2 | 0.53 | 0.56 | 0.56 |
| Thrombospondin 1 | 0.47 | 0.56 | 0.56 |
| Gastric Inhibitory Polypeptide (GIP) | 0.52 | 0.64 | 0.64 |
| Matrix Metalloproteinase 7 (MMP7) | 0.55 | 0.54 | 0.55 |
| Intercellular Adhesion Molecule 1 (ICAM-1) | 0.62 | 0.46 | 0.62 |
| Dickkopf Related Protein 1 (DKK1) | 0.62 | 0.56 | 0.62 |

TABLE 57

2 Biomarker Multivariate Analysis. Combination of Tetranectin and Analyte 2

| Analyte 2 | AUC by random forest | AUC by logistic regression | Maximum AUC |
|---|---|---|---|
| Carcinoembryonic Antigen Related Cell Adhesion Molecule 1 (CEACAM1) | 0.50 | 0.58 | 0.58 |
| 6Ckine | 0.54 | 0.61 | 0.61 |
| Serum Amyloid P Component (SAP) | 0.51 | 0.58 | 0.58 |
| Complement Factor H Related Protein 1 (CFHR1) | 0.49 | 0.49 | 0.49 |
| Chemokine CC-4 (HCC-4) | 0.54 | 0.49 | 0.54 |
| Complement C3 (C3) | 0.54 | 0.52 | 0.54 |
| Alpha Fetoprotein (AFP) | 0.54 | 0.58 | 0.58 |
| Angiopoietin 1 (ANG-1) | 0.54 | 0.47 | 0.54 |
| Interleukin 18 (IL18) | 0.56 | 0.63 | 0.63 |
| Gelsolin | 0.56 | 0.47 | 0.56 |
| Tenascin C (TN-C) | 0.59 | 0.52 | 0.59 |
| Vitronectin | 0.49 | 0.50 | 0.50 |
| Beta 2 Microglobulin (B2M) | 0.50 | 0.58 | 0.58 |
| Pancreatic Secretory Trypsin Inhibitor (TATI) | 0.60 | 0.51 | 0.60 |
| Matrix Metalloproteinase 3 (MMP3) | 0.55 | 0.56 | 0.56 |
| Omentin | 0.49 | 0.52 | 0.52 |
| Interleukin 18 Binding Protein (IL 18 bp) | 0.53 | 0.58 | 0.58 |
| Apolipoprotein D (ApoD) | 0.58 | 0.57 | 0.58 |
| Monoctye Chemotactic Protein 4 (MCP-4) | 0.58 | 0.56 | 0.58 |
| Apolipoprotein E (Apo-E) | 0.56 | 0.60 | 0.60 |
| ST2 | 0.46 | 0.53 | 0.53 |
| Thrombospondin 1 | 0.49 | 0.52 | 0.52 |
| Gastric Inhibitory Polypeptide (GIP) | 0.55 | 0.59 | 0.59 |
| Matrix Metalloproteinase 7 (MMP7) | 0.46 | 0.56 | 0.56 |
| Intercellular Adhesion Molecule 1 (ICAM-1) | 0.63 | 0.49 | 0.63 |
| Dickkopf Related Protein 1 (DKK1) | 0.59 | 0.48 | 0.59 |

TABLE 58

2 Biomarker Multivariate Analysis. Combination of Carcinoembryonic Antigen Related Cell Adhesion Molecule 1 (CEACAM1) and Analyte 2

| Analyte 2 | AUC by random forest | AUC by logistic regression | Maximum AUC |
|---|---|---|---|
| 6Ckine | 0.57 | 0.61 | 0.61 |
| Serum Amyloid P Component (SAP) | 0.55 | 0.60 | 0.60 |
| Complement Factor H Related Protein 1 (CFHR1) | 0.55 | 0.56 | 0.56 |
| Chemokine CC-4 (HCC-4) | 0.56 | 0.57 | 0.57 |
| Complement C3 (C3) | 0.59 | 0.58 | 0.59 |
| Alpha Fetoprotein (AFP) | 0.56 | 0.59 | 0.59 |
| Angiopoietin 1 (ANG-1) | 0.51 | 0.44 | 0.51 |
| Interleukin 18 (IL18) | 0.60 | 0.66 | 0.66 |
| Gelsolin | 0.58 | 0.60 | 0.60 |

TABLE 58-continued

2 Biomarker Multivariate Analysis. Combination of
Carcinoembryonic Antigen Related Cell Adhesion
Molecule 1 (CEACAM1) and Analyte 2

| Analyte 2 | AUC by random forest | AUC by logistic regression | Maximum AUC |
|---|---|---|---|
| Tenascin C (TN-C) | 0.53 | 0.57 | 0.57 |
| Vitronectin | 0.55 | 0.58 | 0.58 |
| Beta 2 Microglobulin (B2M) | 0.55 | 0.59 | 0.59 |
| Pancreatic Secretory Trypsin Inhibitor (TATI) | 0.53 | 0.56 | 0.56 |
| Matrix Metalloproteinase 3 (MMP3) | 0.60 | 0.61 | 0.61 |
| Omentin | 0.54 | 0.57 | 0.57 |
| Interleukin 18 Binding Protein (IL 18bp) | 0.59 | 0.62 | 0.62 |
| Apolipoprotein D (ApoD) | 0.57 | 0.58 | 0.58 |
| Monoctye Chemotactic Protein 4 (MCP-4) | 0.56 | 0.57 | 0.57 |
| Apolipoprotein E (Apo-E) | 0.63 | 0.65 | 0.65 |
| ST2 | 0.55 | 0.57 | 0.57 |
| Thrombospondin 1 | 0.49 | 0.57 | 0.57 |
| Gastric Inhibitory Polypeptide (GIP) | 0.53 | 0.62 | 0.62 |
| Matrix Metalloproteinase 7 (MMP7) | 0.51 | 0.58 | 0.58 |
| Intercellular Adhesion Molecule 1 (ICAM-1) | 0.57 | 0.58 | 0.58 |
| Dickkopf Related Protein 1 (DKK1) | 0.49 | 0.59 | 0.59 |

TABLE 59

2 Biomarker Multivariate Analysis.
Combination of 6Ckine and Analyte 2

| Analyte 2 | AUC by random forest | AUC by logistic regression | Maximum AUC |
|---|---|---|---|
| Serum Amyloid P Component (SAP) | 0.57 | 0.61 | 0.61 |
| Complement Factor H Related Protein 1 (CFHR1) | 0.57 | 0.60 | 0.60 |
| Chemokine CC-4 (HCC-4) | 0.48 | 0.61 | 0.61 |
| Complement C3 (C3) | 0.56 | 0.60 | 0.60 |
| Alpha Fetoprotein (AFP) | 0.56 | 0.61 | 0.61 |
| Angiopoietin 1 (ANG-1) | 0.52 | 0.61 | 0.61 |
| Interleukin 18 (IL18) | 0.47 | 0.64 | 0.64 |
| Gelsolin | 0.55 | 0.60 | 0.60 |
| Tenascin C (TN-C) | 0.54 | 0.62 | 0.62 |
| Vitronectin | 0.63 | 0.61 | 0.63 |
| Beta 2 Microglobulin (B2M) | 0.52 | 0.61 | 0.61 |
| Pancreatic Secretory Trypsin Inhibitor (TATI) | 0.54 | 0.61 | 0.61 |
| Matrix Metalloproteinase 3 (MMP3) | 0.62 | 0.60 | 0.62 |
| Omentin | 0.56 | 0.60 | 0.60 |
| Interleukin 18 Binding Protein (IL 18bp) | 0.49 | 0.61 | 0.61 |
| Apolipoprotein D (ApoD) | 0.58 | 0.61 | 0.61 |
| Monoctye Chemotactic Protein 4 (MCP-4) | 0.52 | 0.60 | 0.60 |
| Apolipoprotein E (Apo-E) | 0.46 | 0.62 | 0.62 |
| ST2 | 0.58 | 0.61 | 0.61 |
| Thrombospondin 1 | 0.54 | 0.60 | 0.60 |
| Gastric Inhibitory Polypeptide (GIP) | 0.51 | 0.62 | 0.62 |
| Matrix Metalloproteinase 7 (MMP7) | 0.54 | 0.61 | 0.61 |
| Intercellular Adhesion Molecule 1 (ICAM-1) | 0.55 | 0.61 | 0.61 |
| Dickkopf Related Protein 1 (DKK1) | 0.56 | 0.59 | 0.59 |

TABLE 60

2 Biomarker Multivariate Analysis. Combination of
Serum Amyloid P Component (SAP) and Analyte 2

| Analyte 2 | AUC by random forest | AUC by logistic regression | Maximum AUC |
|---|---|---|---|
| Complement Factor H Related Protein 1 (CFHR1) | 0.53 | 0.59 | 0.59 |
| Chemokine CC-4 (HCC-4) | 0.50 | 0.57 | 0.57 |
| Complement C3 (C3) | 0.61 | 0.57 | 0.61 |
| Alpha Fetoprotein (AFP) | 0.55 | 0.61 | 0.61 |
| Angiopoietin 1 (ANG-1) | 0.61 | 0.58 | 0.61 |
| Interleukin 18 (IL18) | 0.48 | 0.62 | 0.62 |
| Gelsolin | 0.56 | 0.60 | 0.60 |
| Tenascin C (TN-C) | 0.54 | 0.59 | 0.59 |
| Vitronectin | 0.54 | 0.58 | 0.58 |
| Beta 2 Microglobulin (B2M) | 0.53 | 0.57 | 0.57 |
| Pancreatic Secretory Trypsin Inhibitor (TATI) | 0.52 | 0.58 | 0.58 |
| Matrix Metalloproteinase 3 (MMP3) | 0.55 | 0.59 | 0.59 |
| Omentin | 0.50 | 0.57 | 0.57 |
| Interleukin 18 Binding Protein (IL 18bp) | 0.56 | 0.60 | 0.60 |
| Apolipoprotein D (ApoD) | 0.61 | 0.58 | 0.61 |
| Monoctye Chemotactic Protein 4 (MCP-4) | 0.49 | 0.58 | 0.58 |
| Apolipoprotein E (Apo-E) | 0.60 | 0.62 | 0.62 |
| ST2 | 0.55 | 0.57 | 0.57 |
| Thrombospondin 1 | 0.55 | 0.57 | 0.57 |
| Gastric Inhibitory Polypeptide (GIP) | 0.52 | 0.60 | 0.60 |
| Matrix Metalloproteinase 7 (MMP7) | 0.58 | 0.58 | 0.58 |
| Intercellular Adhesion Molecule 1 (ICAM-1) | 0.50 | 0.58 | 0.58 |
| Dickkopf Related Protein 1 (DKK1) | 0.51 | 0.59 | 0.59 |

TABLE 61

2 Biomarker Multivariate Analysis. Combination of Complement
Factor H Related Protein 1 (CFHR1) and Analyte 2

| Analyte 2 | AUC by random forest | AUC by logistic regression | Maximum AUC |
|---|---|---|---|
| Chemokine CC-4 (HCC-4) | 0.52 | 0.50 | 0.52 |
| Complement C3 (C3) | 0.55 | 0.48 | 0.55 |
| Alpha Fetoprotein (AFP) | 0.50 | 0.57 | 0.57 |
| Angiopoietin 1 (ANG-1) | 0.58 | 0.54 | 0.58 |
| Interleukin 18 (IL18) | 0.55 | 0.64 | 0.64 |
| Gelsolin | 0.56 | 0.46 | 0.56 |
| Tenascin C (TN-C) | 0.50 | 0.53 | 0.53 |
| Vitronectin | 0.57 | 0.50 | 0.57 |
| Beta 2 Microglobulin (B2M) | 0.53 | 0.45 | 0.53 |
| Pancreatic Secretory Trypsin Inhibitor (TATI) | 0.56 | 0.50 | 0.56 |
| Matrix Metalloproteinase 3 (MMP3) | 0.62 | 0.54 | 0.62 |
| Omentin | 0.62 | 0.54 | 0.62 |
| Interleukin 18 Binding Protein (IL 18bp) | 0.45 | 0.58 | 0.58 |
| Apolipoprotein D (ApoD) | 0.55 | 0.54 | 0.55 |
| Monoctye Chemotactic Protein 4 (MCP-4) | 0.49 | 0.54 | 0.54 |
| Apolipoprotein E (Apo-E) | 0.56 | 0.60 | 0.60 |
| ST2 | 0.57 | 0.52 | 0.57 |
| Thrombospondin 1 | 0.56 | 0.53 | 0.56 |
| Gastric Inhibitory Polypeptide (GIP) | 0.52 | 0.59 | 0.59 |
| Matrix Metalloproteinase 7 (MMP7) | 0.49 | 0.56 | 0.56 |
| Intercellular Adhesion Molecule 1 (ICAM-1) | 0.60 | 0.51 | 0.60 |
| Dickkopf Related Protein 1 (DKK1) | 0.48 | 0.49 | 0.49 |

TABLE 62

2 Biomarker Multivariate Analysis. Combination of Chemokine CC-4 (HCC-4) and Analyte 2

| Analyte 2 | AUC by random forest | AUC by logistic regression | Maximum AUC |
|---|---|---|---|
| Complement C3 (C3) | 0.55 | 0.51 | 0.55 |
| Alpha Fetoprotein (AFP) | 0.47 | 0.53 | 0.53 |
| Angiopoietin 1 (ANG-1) | 0.56 | 0.53 | 0.56 |
| Interleukin 18 (IL18) | 0.56 | 0.63 | 0.63 |
| Gelsolin | 0.56 | 0.54 | 0.56 |
| Tenascin C (TN-C) | 0.49 | 0.54 | 0.54 |
| Vitronectin | 0.61 | 0.51 | 0.61 |
| Beta 2 Microglobulin (B2M) | 0.50 | 0.56 | 0.56 |
| Pancreatic Secretory Trypsin Inhibitor (TATI) | 0.58 | 0.51 | 0.58 |
| Matrix Metalloproteinase 3 (MMP3) | 0.58 | 0.55 | 0.58 |
| Omentin | 0.54 | 0.53 | 0.54 |
| Interleukin 18 Binding Protein (IL 18bp) | 0.51 | 0.58 | 0.58 |
| Apolipoprotein D (ApoD) | 0.59 | 0.55 | 0.59 |
| Monoctye Chemotactic Protein 4 (MCP-4) | 0.51 | 0.48 | 0.51 |
| Apolipoprotein E (Apo-E) | 0.50 | 0.60 | 0.60 |
| ST2 | 0.54 | 0.51 | 0.54 |
| Thrombospondin 1 | 0.54 | 0.51 | 0.54 |
| Gastric Inhibitory Polypeptide (GIP) | 0.52 | 0.60 | 0.60 |
| Matrix Metalloproteinase 7 (MMP7) | 0.57 | 0.56 | 0.57 |
| Intercellular Adhesion Molecule 1 (ICAM-1) | 0.60 | 0.51 | 0.60 |
| Dickkopf Related Protein 1 (DKK1) | 0.50 | 0.49 | 0.50 |

TABLE 63

2 Biomarker Multivariate Analysis. Combination of Complement C3 (C3) and Analyte 2

| Analyte 2 | AUC by random forest | AUC by logistic regression | Maximum AUC |
|---|---|---|---|
| Alpha Fetoprotein (AFP) | 0.55 | 0.57 | 0.57 |
| Angiopoietin 1 (ANG-1) | 0.54 | 0.55 | 0.55 |
| Interleukin 18 (IL18) | 0.52 | 0.62 | 0.62 |
| Gelsolin | 0.64 | 0.54 | 0.64 |
| Tenascin C (TN-C) | 0.54 | 0.55 | 0.55 |
| Vitronectin | 0.47 | 0.51 | 0.51 |
| Beta 2 Microglobulin (B2M) | 0.58 | 0.54 | 0.58 |
| Pancreatic Secretory Trypsin Inhibitor (TATI) | 0.49 | 0.51 | 0.51 |
| Matrix Metalloproteinase 3 (MMP3) | 0.56 | 0.57 | 0.57 |
| Omentin | 0.52 | 0.53 | 0.53 |
| Interleukin 18 Binding Protein (IL 18 bp) | 0.55 | 0.58 | 0.58 |
| Apolipoprotein D (ApoD) | 0.70 | 0.56 | 0.70 |
| Monoctye Chemotactic Protein 4 (MCP-4) | 0.53 | 0.54 | 0.54 |
| Apolipoprotein E (Apo-E) | 0.59 | 0.61 | 0.61 |
| ST2 | 0.52 | 0.51 | 0.52 |
| Thrombospondin 1 | 0.66 | 0.49 | 0.66 |
| Gastric Inhibitory Polypeptide (GIP) | 0.56 | 0.59 | 0.59 |
| Matrix Metalloproteinase 7 (MMP7) | 0.63 | 0.56 | 0.63 |
| Intercellular Adhesion Molecule 1 (ICAM-1) | 0.57 | 0.52 | 0.57 |
| Dickkopf Related Protein 1 (DKK1) | 0.51 | 0.53 | 0.53 |

TABLE 64

2 Biomarker Multivariate Analysis. Combination of Alpha Fetoprotein (AFP) and Analyte 2

| Analyte 2 | AUC by random forest | AUC by logistic regression | Maximum AUC |
|---|---|---|---|
| Angiopoietin 1 (ANG-1) | 0.50 | 0.55 | 0.55 |
| Interleukin 18 (IL18) | 0.48 | 0.66 | 0.66 |
| Gelsolin | 0.61 | 0.60 | 0.61 |
| Tenascin C (TN-C) | 0.52 | 0.56 | 0.56 |
| Vitronectin | 0.52 | 0.57 | 0.57 |
| Beta 2 Microglobulin (B2M) | 0.55 | 0.59 | 0.59 |
| Pancreatic Secretory Trypsin Inhibitor (TATI) | 0.56 | 0.54 | 0.56 |
| Matrix Metalloproteinase 3 (MMP3) | 0.49 | 0.57 | 0.57 |
| Omentin | 0.54 | 0.56 | 0.56 |
| Interleukin 18 Binding Protein (IL 18bp) | 0.55 | 0.62 | 0.62 |
| Apolipoprotein D (ApoD) | 0.59 | 0.46 | 0.59 |
| Monoctye Chemotactic Protein 4 (MCP-4) | 0.57 | 0.56 | 0.57 |
| Apolipoprotein E (Apo-E) | 0.60 | 0.63 | 0.63 |
| ST2 | 0.54 | 0.55 | 0.55 |
| Thrombospondin 1 | 0.52 | 0.55 | 0.55 |
| Gastric Inhibitory Polypeptide (GIP) | 0.59 | 0.58 | 0.59 |
| Matrix Metalloproteinase 7 (MMP7) | 0.53 | 0.61 | 0.61 |
| Intercellular Adhesion Molecule 1 (ICAM-1) | 0.52 | 0.56 | 0.56 |
| Dickkopf Related Protein 1 (DKK1) | 0.60 | 0.56 | 0.60 |

TABLE 65

2 Biomarker Multivariate Analysis. Combination of Angiopoietin 1 (ANG-1) and Analyte 2

| Analyte 2 | AUC by random forest | AUC by logistic regression | Maximum AUC |
|---|---|---|---|
| Interleukin 18 (IL18) | 0.62 | 0.62 | 0.62 |
| Gelsolin | 0.58 | 0.55 | 0.58 |
| Tenascin C (TN-C) | 0.58 | 0.56 | 0.58 |
| Vitronectin | 0.56 | 0.54 | 0.56 |
| Beta 2 Microglobulin (B2M) | 0.50 | 0.57 | 0.57 |
| Pancreatic Secretory Trypsin Inhibitor (TATI) | 0.55 | 0.54 | 0.55 |
| Matrix Metalloproteinase 3 (MMP3) | 0.56 | 0.55 | 0.56 |
| Omentin | 0.59 | 0.54 | 0.59 |
| Interleukin 18 Binding Protein (IL 18bp) | 0.59 | 0.56 | 0.59 |
| Apolipoprotein D (ApoD) | 0.62 | 0.56 | 0.62 |
| Monoctye Chemotactic Protein 4 (MCP-4) | 0.55 | 0.57 | 0.57 |
| Apolipoprotein E (Apo-E) | 0.49 | 0.60 | 0.60 |
| ST2 | 0.61 | 0.54 | 0.61 |
| Thrombospondin 1 | 0.59 | 0.54 | 0.59 |
| Gastric Inhibitory Polypeptide (GIP) | 0.50 | 0.59 | 0.59 |
| Matrix Metalloproteinase 7 (MMP7) | 0.62 | 0.58 | 0.62 |
| Intercellular Adhesion Molecule 1 (ICAM-1) | 0.52 | 0.52 | 0.52 |
| Dickkopf Related Protein 1 (DKK1) | 0.53 | 0.56 | 0.56 |

TABLE 66

2 Biomarker Multivariate Analysis. Combination of Interleukin 18 (IL18) and Analyte 2

| Analyte 2 | AUC by random forest | AUC by logistic regression | Maximum AUC |
|---|---|---|---|
| Gelsolin | 0.47 | 0.63 | 0.63 |
| Tenascin C (TN-C) | 0.56 | 0.65 | 0.65 |
| Vitronectin | 0.56 | 0.63 | 0.63 |
| Beta 2 Microglobulin (B2M) | 0.50 | 0.62 | 0.62 |

TABLE 66-continued

2 Biomarker Multivariate Analysis. Combination of
Interleukin 18 (IL18) and Analyte 2

| Analyte 2 | AUC by random forest | AUC by logistic regression | Maximum AUC |
|---|---|---|---|
| Pancreatic Secretory Trypsin Inhibitor (TATI) | 0.57 | 0.63 | 0.63 |
| Matrix Metalloproteinase 3 (MMP3) | 0.60 | 0.63 | 0.63 |
| Omentin | 0.54 | 0.63 | 0.63 |
| Interleukin 18 Binding Protein (IL 18bp) | 0.58 | 0.61 | 0.61 |
| Apolipoprotein D (ApoD) | 0.59 | 0.63 | 0.63 |
| Monoctye Chemotactic Protein 4 (MCP-4) | 0.48 | 0.64 | 0.64 |
| Apolipoprotein E (Apo-E) | 0.51 | 0.64 | 0.64 |
| ST2 | 0.55 | 0.63 | 0.63 |
| Thrombospondin 1 | 0.55 | 0.63 | 0.63 |
| Gastric Inhibitory Polypeptide (GIP) | 0.53 | 0.63 | 0.63 |
| Matrix Metalloproteinase 7 (MMP7) | 0.59 | 0.63 | 0.63 |
| Intercellular Adhesion Molecule 1 (ICAM-1) | 0.57 | 0.63 | 0.63 |
| Dickkopf Related Protein 1 (DKK1) | 0.54 | 0.63 | 0.63 |

TABLE 67

2 Biomarker Multivariate Analysis.
Combination of Gelsolin and Analyte 2

| Analyte 2 | AUC by random forest | AUC by logistic regression | Maximum AUC |
|---|---|---|---|
| Tenascin C (TN-C) | 0.48 | 0.46 | 0.48 |
| Vitronectin | 0.55 | 0.55 | 0.55 |
| Beta 2 Microglobulin (B2M) | 0.45 | 0.58 | 0.58 |
| Pancreatic Secretory Trypsin Inhibitor (TATI) | 0.51 | 0.46 | 0.51 |
| Matrix Metalloproteinase 3 (MMP3) | 0.68 | 0.57 | 0.68 |
| Omentin | 0.53 | 0.56 | 0.56 |
| Interleukin 18 Binding Protein (IL 18bp) | 0.58 | 0.60 | 0.60 |
| Apolipoprotein D (ApoD) | 0.62 | 0.56 | 0.62 |
| Monoctye Chemotactic Protein 4 (MCP-4) | 0.46 | 0.56 | 0.56 |
| Apolipoprotein E (Apo-E) | 0.51 | 0.61 | 0.61 |
| ST2 | 0.56 | 0.47 | 0.56 |
| Thrombospondin 1 | 0.57 | 0.54 | 0.57 |
| Gastric Inhibitory Polypeptide (GIP) | 0.51 | 0.61 | 0.61 |
| Matrix Metalloproteinase 7 (MMP7) | 0.60 | 0.56 | 0.60 |
| Intercellular Adhesion Molecule 1 (ICAM-1) | 0.50 | 0.54 | 0.54 |
| Dickkopf Related Protein 1 (DKK1) | 0.54 | 0.54 | 0.54 |

TABLE 68

2 Biomarker Multivariate Analysis.
Combination of Tenascin C (TN-C) and Analyte 2

| Analyte 2 | AUC by random forest | AUC by logistic regression | Maximum AUC |
|---|---|---|---|
| Vitronectin | 0.59 | 0.54 | 0.59 |
| Beta 2 Microglobulin (B2M) | 0.56 | 0.56 | 0.56 |
| Pancreatic Secretory Trypsin Inhibitor (TATI) | 0.57 | 0.52 | 0.57 |
| Matrix Metalloproteinase 3 (MMP3) | 0.51 | 0.56 | 0.56 |
| Omentin | 0.57 | 0.54 | 0.57 |
| Interleukin 18 Binding Protein (IL 18bp) | 0.53 | 0.57 | 0.57 |
| Apolipoprotein D (ApoD) | 0.65 | 0.54 | 0.65 |
| Monoctye Chemotactic Protein 4 (MCP-4) | 0.52 | 0.53 | 0.53 |
| Apolipoprotein E (Apo-E) | 0.51 | 0.62 | 0.62 |
| ST2 | 0.50 | 0.53 | 0.53 |
| Thrombospondin 1 | 0.60 | 0.49 | 0.60 |
| Gastric Inhibitory Polypeptide (GIP) | 0.54 | 0.59 | 0.59 |
| Matrix Metalloproteinase 7 (MMP7) | 0.51 | 0.56 | 0.56 |
| Intercellular Adhesion Molecule 1 (ICAM-1) | 0.59 | 0.47 | 0.59 |
| Dickkopf Related Protein 1 (DKK1) | 0.53 | 0.48 | 0.53 |

TABLE 69

2 Biomarker Multivariate Analysis. Combination
of Vitronectin and Analyte 2

| Analyte 2 | AUC by random forest | AUC by logistic regression | Maximum AUC |
|---|---|---|---|
| Beta 2 Microglobulin (B2M) | 0.62 | 0.55 | 0.62 |
| Pancreatic Secretory Trypsin Inhibitor (TATI) | 0.55 | 0.50 | 0.55 |
| Matrix Metalloproteinase 3 (MMP3) | 0.53 | 0.56 | 0.56 |
| Omentin | 0.55 | 0.48 | 0.55 |
| Interleukin 18 Binding Protein (IL 18 bp) | 0.58 | 0.57 | 0.58 |
| Apolipoprotein D (ApoD) | 0.69 | 0.55 | 0.69 |
| Monoctye Chemotactic Protein 4 (MCP-4) | 0.53 | 0.51 | 0.53 |
| Apolipoprotein E (Apo-E) | 0.55 | 0.60 | 0.60 |
| ST2 | 0.53 | 0.50 | 0.53 |
| Thrombospondin 1 | 0.52 | 0.49 | 0.52 |
| Gastric Inhibitory Polypeptide (GIP) | 0.54 | 0.58 | 0.58 |
| Matrix Metalloproteinase 7 (MMP7) | 0.54 | 0.57 | 0.57 |
| Intercellular Adhesion Molecule 1 (ICAM-1) | 0.45 | 0.48 | 0.48 |
| Dickkopf Related Protein 1 (DKK1) | 0.49 | 0.48 | 0.49 |

TABLE 70

2 Biomarker Multivariate Analysis. Combination of
Beta 2 Microglobulin (B2M) and Analyte 2

| Analyte 2 | AUC by random forest | AUC by logistic regression | Maximum AUC |
|---|---|---|---|
| Pancreatic Secretory Trypsin Inhibitor (TATI) | 0.53 | 0.56 | 0.56 |
| Matrix Metalloproteinase 3 (MMP3) | 0.60 | 0.57 | 0.60 |
| Omentin | 0.52 | 0.56 | 0.56 |
| Interleukin 18 Binding Protein (IL 18 bp) | 0.52 | 0.58 | 0.58 |
| Apolipoprotein D (ApoD) | 0.66 | 0.57 | 0.66 |
| Monoctye Chemotactic Protein 4 (MCP-4) | 0.66 | 0.55 | 0.66 |
| Apolipoprotein E (Apo-E) | 0.49 | 0.60 | 0.60 |
| ST2 | 0.53 | 0.56 | 0.56 |
| Thrombospondin 1 | 0.54 | 0.55 | 0.55 |
| Gastric Inhibitory Polypeptide (GIP) | 0.51 | 0.59 | 0.59 |
| Matrix Metalloproteinase 7 (MMP7) | 0.51 | 0.58 | 0.58 |
| Intercellular Adhesion Molecule 1 (ICAM-1) | 0.51 | 0.56 | 0.56 |
| Dickkopf Related Protein 1 (DKK1) | 0.56 | 0.56 | 0.56 |

TABLE 71

2 Biomarker Multivariate Analysis. Combination of Pancreatic Secretory Trypsin Inhibitor (TATI) and Analyte 2

| Analyte 2 | AUC by random forest | AUC by logistic regression | Maximum AUC |
|---|---|---|---|
| Matrix Metalloproteinase 3 (MMP3) | 0.60 | 0.54 | 0.60 |
| Omentin | 0.58 | 0.51 | 0.58 |
| Interleukin 18 Binding Protein (IL 18 bp) | 0.55 | 0.57 | 0.57 |
| Apolipoprotein D (ApoD) | 0.56 | 0.54 | 0.56 |
| Monoctye Chemotactic Protein 4 (MCP-4) | 0.58 | 0.48 | 0.58 |
| Apolipoprotein E (Apo-E) | 0.58 | 0.60 | 0.60 |
| ST2 | 0.55 | 0.49 | 0.55 |
| Thrombospondin 1 | 0.50 | 0.53 | 0.53 |
| Gastric Inhibitory Polypeptide (GIP) | 0.54 | 0.58 | 0.58 |
| Matrix Metalloproteinase 7 (MMP7) | 0.50 | 0.55 | 0.55 |
| Intercellular Adhesion Molecule 1 (ICAM-1) | 0.61 | 0.49 | 0.61 |
| Dickkopf Related Protein 1 (DKK1) | 0.52 | 0.50 | 0.52 |

TABLE 72

2 Biomarker Multivariate Analysis. Combination of Matrix Metalloproteinase 3 (MMP3) and Analyte 2

| Analyte 2 | AUC by random forest | AUC by logistic regression | Maximum AUC |
|---|---|---|---|
| Omentin | 0.57 | 0.55 | 0.57 |
| Interleukin 18 Binding Protein (IL 18 bp) | 0.62 | 0.59 | 0.62 |
| Apolipoprotein D (ApoD) | 0.69 | 0.57 | 0.69 |
| Monoctye Chemotactic Protein 4 (MCP-4) | 0.52 | 0.55 | 0.55 |
| Apolipoprotein E (Apo-E) | 0.56 | 0.60 | 0.60 |
| ST2 | 0.61 | 0.54 | 0.61 |
| Thrombospondin 1 | 0.67 | 0.54 | 0.67 |
| Gastric Inhibitory Polypeptide (GIP) | 0.52 | 0.57 | 0.57 |
| Matrix Metalloproteinase 7 (MMP7) | 0.64 | 0.58 | 0.64 |
| Intercellular Adhesion Molecule 1 (ICAM-1) | 0.51 | 0.55 | 0.55 |
| Dickkopf Related Protein 1 (DKK1) | 0.54 | 0.56 | 0.56 |

TABLE 73

2 Biomarker Multivariate Analysis. Combination of Omentin and Analyte 2

| Analyte 2 | AUC by random forest | AUC by logistic regression | Maximum AUC |
|---|---|---|---|
| Interleukin 18 Binding Protein (IL 18 bp) | 0.54 | 0.58 | 0.58 |
| Apolipoprotein D (ApoD) | 0.55 | 0.56 | 0.56 |
| Monoctye Chemotactic Protein 4 (MCP-4) | 0.69 | 0.52 | 0.69 |
| Apolipoprotein E (Apo-E) | 0.54 | 0.60 | 0.60 |
| ST2 | 0.56 | 0.48 | 0.56 |
| Thrombospondin 1 | 0.51 | 0.50 | 0.51 |
| Gastric Inhibitory Polypeptide (GIP) | 0.66 | 0.57 | 0.66 |
| Matrix Metalloproteinase 7 (MMP7) | 0.51 | 0.56 | 0.56 |
| Intercellular Adhesion Molecule 1 (ICAM-1) | 0.60 | 0.48 | 0.60 |
| Dickkopf Related Protein 1 (DKK1) | 0.66 | 0.48 | 0.66 |

TABLE 74

2 Biomarker Multivariate Analysis. Combination of Interleukin 18 Binding Protein (IL 18 bp) and Analyte 2

| Analyte 2 | AUC by random forest | AUC by logistic regression | Maximum AUC |
|---|---|---|---|
| Apolipoprotein D (ApoD) | 0.63 | 0.58 | 0.63 |
| Monoctye Chemotactic Protein 4 (MCP-4) | 0.53 | 0.58 | 0.58 |
| Apolipoprotein E (Apo-E) | 0.52 | 0.61 | 0.61 |
| ST2 | 0.57 | 0.58 | 0.58 |
| Thrombospondin 1 | 0.65 | 0.58 | 0.65 |
| Gastric Inhibitory Polypeptide (GIP) | 0.52 | 0.61 | 0.61 |
| Matrix Metalloproteinase 7 (MMP7) | 0.55 | 0.60 | 0.60 |
| Intercellular Adhesion Molecule 1 (ICAM-1) | 0.51 | 0.57 | 0.57 |
| Dickkopf Related Protein 1 (DKK1) | 0.53 | 0.59 | 0.59 |

TABLE 75

2 Biomarker Multivariate Analysis. Combination of Apolipoprotein D (ApoD) and Analyte 2

| Analyte 2 | AUC by random forest | AUC by logistic regression | Maximum AUC |
|---|---|---|---|
| Monoctye Chemotactic Protein 4 (MCP-4) | 0.59 | 0.56 | 0.59 |
| Apolipoprotein E (Apo-E) | 0.61 | 0.60 | 0.61 |
| ST2 | 0.59 | 0.55 | 0.59 |
| Thrombospondin 1 | 0.62 | 0.54 | 0.62 |
| Gastric Inhibitory Polypeptide (GIP) | 0.58 | 0.59 | 0.59 |
| Matrix Metalloproteinase 7 (MMP7) | 0.65 | 0.57 | 0.65 |
| Intercellular Adhesion Molecule 1 (ICAM-1) | 0.56 | 0.55 | 0.56 |
| Dickkopf Related Protein 1 (DKK1) | 0.55 | 0.55 | 0.55 |

TABLE 76

2 Biomarker Multivariate Analysis. Combination of Monocyte Chemotactic Protein 4 (MCP-4) and Analyte 2

| Analyte 2 | AUC by random forest | AUC by logistic regression | Maximum AUC |
|---|---|---|---|
| Apolipoprotein E (Apo-E) | 0.51 | 0.61 | 0.61 |
| ST2 | 0.54 | 0.54 | 0.54 |
| Thrombospondin 1 | 0.57 | 0.51 | 0.57 |
| Gastric Inhibitory Polypeptide (GIP) | 0.54 | 0.60 | 0.60 |
| Matrix Metalloproteinase 7 (MMP7) | 0.51 | 0.55 | 0.55 |
| Intercellular Adhesion Molecule 1 (ICAM-1) | 0.53 | 0.52 | 0.53 |
| Dickkopf Related Protein 1 (DKK1) | 0.60 | 0.52 | 0.60 |

TABLE 77

2 Biomarker Multivariate Analysis. Combination of Apolipoprotein E (Apo-E) and Analyte 2

| Analyte 2 | AUC by random forest | AUC by logistic regression | Maximum AUC |
|---|---|---|---|
| ST2 | 0.56 | 0.60 | 0.60 |
| Thrombospondin 1 | 0.51 | 0.60 | 0.60 |
| Gastric Inhibitory Polypeptide (GIP) | 0.53 | 0.61 | 0.61 |
| Matrix Metalloproteinase 7 (MMP7) | 0.48 | 0.61 | 0.61 |
| Intercellular Adhesion Molecule 1 (ICAM-1) | 0.58 | 0.61 | 0.61 |
| Dickkopf Related Protein 1 (DKK1) | 0.52 | 0.61 | 0.61 |

TABLE 78

2 Biomarker Multivariate Analysis. Combination of ST2 and Analyte 2

| Analyte 2 | AUC by random forest | AUC by logistic regression | Maximum AUC |
|---|---|---|---|
| Thrombospondin 1 | 0.56 | 0.53 | 0.56 |
| Gastric Inhibitory Polypeptide (GIP) | 0.57 | 0.59 | 0.59 |
| Matrix Metalloproteinase 7 (MMP7) | 0.49 | 0.56 | 0.56 |
| Intercellular Adhesion Molecule 1 (ICAM-1) | 0.54 | 0.50 | 0.54 |
| Dickkopf Related Protein 1 (DKK1) | 0.47 | 0.50 | 0.50 |

TABLE 79

2 Biomarker Multivariate Analysis. Combination of Thrombospondin 1 and Analyte 2

| Analyte 2 | AUC by random forest | AUC by logistic regression | Maximum AUC |
|---|---|---|---|
| Gastric Inhibitory Polypeptide (GIP) | 0.52 | 0.57 | 0.57 |
| Matrix Metalloproteinase 7 (MMP7) | 0.54 | 0.56 | 0.56 |
| Intercellular Adhesion Molecule 1 (ICAM-1) | 0.56 | 0.54 | 0.56 |
| Dickkopf Related Protein 1 (DKK1) | 0.53 | 0.49 | 0.53 |

TABLE 80

2 Biomarker Multivariate Analysis. Combination of Gastric Inhibitory Polypeptide (GIP) and Analyte 2

| Analyte 2 | AUC by random forest | AUC by logistic regression | Maximum AUC |
|---|---|---|---|
| Matrix Metalloproteinase 7 (MMP7) | 0.54 | 0.61 | 0.61 |
| Intercellular Adhesion Molecule 1 (ICAM-1) | 0.67 | 0.58 | 0.67 |
| Dickkopf Related Protein 1 (DKK1) | 0.51 | 0.57 | 0.57 |

TABLE 81

2 Biomarker Multivariate Analysis. Combination of Matrix Metalloproteinase 7 (MMP7) and Analyte 2

| Analyte 2 | AUC by random forest | AUC by logistic regression | Maximum AUC |
|---|---|---|---|
| Intercellular Adhesion Molecule 1 (ICAM-1) | 0.48 | 0.56 | 0.56 |
| Dickkopf Related Protein 1 (DKK1) | 0.53 | 0.55 | 0.55 |

TABLE 82

2 Biomarker Multivariate Analysis. Combination of Intercellular Adhesion Molecule 1 (ICAM-1) and Analyte 2

| Analyte 2 | AUC by random forest | AUC by logistic regression | Maximum AUC |
|---|---|---|---|
| Dickkopf Related Protein 1 (DKK1) | 0.67 | 0.54 | 0.67 |

TABLE 83

Multivariate Analysis of 10, 20, 40, 60, or 80 analytes using various methods

| Method | Analytes | Total Number of Analytes | Mean AUC |
|---|---|---|---|
| Random Forest | Set 1, 2, 3, 4, and 5 | 80 | 0.761 |
| Random Forest | Set 1, 2, 3, and 4 | 60 | 0.79 |
| Random Forest | Set 1, 2, and 3 | 40 | 0.845 |
| Random Forest | Set 1 and 2 | 20 | 0.857 |
| Random Forest | Set 1 | 10 | 0.797 |
| Gradient Boosting | Set 1, 2, 3, 4, and 5 | 80 | 0.795 |
| Gradient Boosting | Set 1, 2, 3, and 4 | 60 | 0.827 |
| Gradient Boosting | Set 1, 2, and 3 | 40 | 0.873 |
| Gradient Boosting | Set 1 and 2 | 20 | 0.859 |
| Gradient Boosting | Set 1 | 10 | 0.785 |
| LASSO | Set 1, 2, 3, 4, and 5 | 80 | 0.819 |
| LASSO | Set 1, 2, 3, and 4 | 60 | 0.829 |
| LASSO | Set 1, 2, and 3 | 40 | 0.817 |
| LASSO | Set 1 and 2 | 20 | 0.816 |
| LASSO | Set 1 | 10 | 0.754 |

The invention claimed is:

1. A method for assessing multiple sclerosis activity in an individual, the method comprising:
    obtaining a dataset comprising quantitative expression values for a plurality of biomarkers from a test sample from the individual, wherein the plurality of biomarkers comprise each of the biomarkers shown in a first set and a second set,
        wherein the first set comprises MDC, VEGF, Ficolin 3, IgA, Factor VII, IL6R, RAGE, FIB1C, ITAC, and GH, and
        wherein the second set comprises IGFBP2, Resistin, Cathepsin D, E-Selectin, YKL40, IL22, IL8, CA 15-3, LeptinR, MCP1, PRL, Tetranectin, CEACAM1, 6Ckine, SAP, CFHR1, HCC-4, and C3,
    applying a predictive model to expression values of the biomarkers of the first set and the second set to generate a score;
    determining a presence of multiple sclerosis activity, wherein the presence of multiple sclerosis activity is one of presence of multiple sclerosis or presence of an exacerbated state in the individual based on the score, and
    administering a therapeutic to the individual to reduce the determined presence of multiple sclerosis activity, wherein the therapeutic comprises one or more of corticosteroids, plasma exchange, ocrelizumab, IFN-β, Glatiramer acetate, anti-VLA4, dimethyl fumarate, teriflunomide, fingolimod, anti-CD52 antibody, methotrexate, cladribine, simvastatin, and cyclophosphamide.

2. The method of claim 1, wherein the presence of multiple sclerosis activity in the individual is presence of an exacerbated state wherein a performance of the predictive model is characterized by an area under the curve (AUC) ranging from 0.60 to 0.99, and wherein determining the presence of multiple sclerosis activity in the individual based on the score comprises comparing the generated score to a distribution of scores, the distribution of scores corresponding to individuals previously diagnosed with multiple sclerosis that have been clinically classified as being in one of a state of quiescence or exacerbation; and classifying the individual as being in one of the state of quiescence or exacerbation based on the comparison.

3. The method of claim 1, wherein the dataset comprises quantitative expression values for forty or more biomarkers.

4. The method of claim 1, wherein the dataset comprises quantitative expression values for sixty or more biomarkers.

5. The method of any one of claim 1, wherein performance of the predictive model is characterized by an area under the curve (AUC) ranging from 0.60 to 0.99, from 0.70 to 0.99, or from 0.80 to 0.99.

6. The method of any one of claim 1, wherein the step of obtaining the dataset comprises carrying out a multiplex immunoassay on the test sample from the individual.

7. The method of any one of claim 1, wherein obtaining the dataset from the test sample comprises obtaining the test sample and processing the test sample to experimentally determine the dataset.

8. The method of any one of claim 1, wherein the quantitative expression values for the plurality of biomarkers are adjusted based on at least one of age and gender of the individual.

9. The method of any one of claim 1, wherein determining a presence of multiple sclerosis activity comprises determining presence of an exacerbated state of multiple sclerosis in the individual.

10. The method of any one of claim 1, wherein determining a presence of multiple sclerosis activity comprises diagnosing the individual with multiple sclerosis.

11. The method of any one of claim 1, wherein determining a presence of multiple sclerosis activity in the individual based on the score comprises:
   comparing the generated score to a distribution of scores, the distribution of scores corresponding to individuals that have been previously classified in one of a plurality of categories of multiple sclerosis activity.

* * * * *